(12) United States Patent
Harris et al.

(10) Patent No.: US 11,376,083 B2
(45) Date of Patent: Jul. 5, 2022

(54) DETERMINING ROBOTIC SURGICAL ASSEMBLY COUPLING STATUS

(71) Applicant: Ethicon LLC, Guaynabo, PR (US)

(72) Inventors: Jason L. Harris, Lebanon, OH (US); Frederick E. Shelton, IV, Hillsboro, OH (US); Chad E. Eckert, Milford, OH (US); Joshua P. Morgan, Loveland, OH (US); Nicholas M. Morgan, Loveland, OH (US)

(73) Assignee: Cilag GmbH International, Zug (CH)

( * ) Notice: Subject to any disclaimer, the term of this patent is extended or adjusted under 35 U.S.C. 154(b) by 209 days.

(21) Appl. No.: 16/454,757

(22) Filed: Jun. 27, 2019

(65) Prior Publication Data

US 2020/0405406 A1     Dec. 31, 2020

(51) Int. Cl.
*A61B 34/30*     (2016.01)
*A61B 90/50*     (2016.01)
(Continued)

(52) U.S. Cl.
CPC .............. *A61B 34/30* (2016.02); *A61B 90/50* (2016.02); *A61B 90/361* (2016.02);
(Continued)

(58) Field of Classification Search
CPC .................. A61B 34/30; A61B 90/50; A61B 2017/00199; A61B 2017/00477; A61B 2090/0808; A61B 2017/00221; A61B 2017/00119; A61B 2017/00411; A61B 90/361; A61B 2560/0443; A61B 18/14; A61B 17/320068; A61B 2018/00017; A61B 2018/00029; A61B 2217/005; A61B 2217/007; A61B 2034/102; A61B 2090/372; A61B 90/53; A61B 2034/2059; A61B 2034/2048; A61B 2090/371; A61B 2017/00017; A61B 2017/00115;
(Continued)

(56) References Cited

U.S. PATENT DOCUMENTS 5,383,860 A    1/1995 Lau
5,662,615 A    9/1997 Blake, III
(Continued)

OTHER PUBLICATIONS

IEEE Std 802.3-2012 (Revision of IEEE Std 802.3-2008, published Dec. 28, 2012.

(Continued)

*Primary Examiner* — Richard G Louis

(57) ABSTRACT

Various connection detection assemblies for a robotic surgical assembly are disclosed. The robotic surgical assembly can include a carriage, a carriage housing releasably connectable to the carriage, a motor housing configured to house a motor pack for driving the surgical instrument, wherein the motor housing is releasable connectable to the carriage housing, and an interface module configured to releasably secure the robotic surgical assembly to the surgical instrument. The robotic surgical assembly can also include a series of interconnections defined by mating portions of the carriage, the carriage housing, the motor housing, and the interface module. A control circuit configured to detect a fully engaged configuration of the mating portions based on the interconnections.

9 Claims, 72 Drawing Sheets

(51) Int. Cl.
  *A61B 17/00* (2006.01)
  *A61B 90/00* (2016.01)
(52) U.S. Cl.
  CPC .............. *A61B 2017/00119* (2013.01); *A61B 2017/00199* (2013.01); *A61B 2017/00411* (2013.01); *A61B 2017/00477* (2013.01); *A61B 2090/0808* (2016.02); *A61B 2560/0443* (2013.01)
(58) Field of Classification Search
  CPC ........... A61B 2017/00398; A61B 2017/00473; A61B 2017/07257; A61B 2017/07285; A61B 2017/2927; A61B 2090/064; A61B 2090/066; A61B 46/10; A61B 46/40
  See application file for complete search history.

(56) References Cited

U.S. PATENT DOCUMENTS

| | | | |
|---|---|---|---|
| 5,980,493 A | 11/1999 | Smith et al. | |
| 6,537,290 B2 | 3/2003 | Adams et al. | |
| 7,134,587 B2 | 11/2006 | Schwemberger et al. | |
| 7,955,322 B2 | 6/2011 | Devengenzo et al. | |
| 7,982,776 B2 | 7/2011 | Dunki-Jacobs et al. | |
| 7,995,045 B2 | 8/2011 | Dunki-Jacobs | |
| 8,054,184 B2 | 11/2011 | Cline et al. | |
| 8,070,731 B2 | 12/2011 | Wenchell et al. | |
| 8,197,446 B2 | 6/2012 | Beardsley | |
| 8,348,126 B2 | 1/2013 | Olson et al. | |
| 8,491,533 B2 | 7/2013 | Parihar et al. | |
| 8,613,727 B2 | 12/2013 | Hart et al. | |
| 8,616,431 B2 | 12/2013 | Timm et al. | |
| 8,628,529 B2 | 1/2014 | Aldridge et al. | |
| 8,828,023 B2 | 9/2014 | Neff et al. | |
| 8,912,746 B2 | 12/2014 | Reid et al. | |
| 9,060,775 B2 | 6/2015 | Wiener et al. | |
| 9,072,535 B2 | 7/2015 | Shelton, IV et al. | |
| 9,072,536 B2 | 7/2015 | Shelton, IV et al. | |
| 9,106,270 B2 | 8/2015 | Puterbaugh et al. | |
| 9,107,684 B2 | 8/2015 | Ma | |
| 9,204,879 B2 | 12/2015 | Shelton, IV | |
| 9,345,481 B2 | 5/2016 | Hall et al. | |
| 9,526,407 B2 | 12/2016 | Hoeg et al. | |
| 9,561,038 B2 | 2/2017 | Shelton, IV et al. | |
| 9,572,552 B1 | 2/2017 | Bodor et al. | |
| 9,597,104 B2 | 3/2017 | Nicholas et al. | |
| 9,649,110 B2 | 5/2017 | Parihar et al. | |
| 9,757,128 B2 | 9/2017 | Baber et al. | |
| 9,763,661 B2 | 9/2017 | Zergiebel et al. | |
| 9,820,740 B2 | 11/2017 | Zemlok et al. | |
| 9,888,942 B1 | 2/2018 | Savage et al. | |
| 9,937,626 B2 | 4/2018 | Rockrohr | |
| 9,987,008 B2 | 6/2018 | Scirica et al. | |
| 10,098,527 B2 | 10/2018 | Weisenburgh, II et al. | |
| 10,164,466 B2 | 12/2018 | Calderoni | |
| 10,166,080 B2 | 1/2019 | Balicki et al. | |
| 10,166,082 B1 | 1/2019 | Hariri et al. | |
| 10,172,687 B2 | 1/2019 | Garbus et al. | |
| 10,179,413 B2 | 1/2019 | Rockrohr | |
| 10,213,266 B2 | 2/2019 | Zemlok et al. | |
| 10,231,775 B2 | 3/2019 | Shelton, IV et al. | |
| 10,251,672 B2 | 4/2019 | Meglan | |
| 10,258,359 B2 | 4/2019 | Kapadia | |
| 10,321,964 B2 | 6/2019 | Grover et al. | |
| 10,376,338 B2 | 8/2019 | Taylor et al. | |
| 10,390,895 B2 | 8/2019 | Henderson et al. | |
| 10,398,517 B2 | 9/2019 | Eckert et al. | |
| 10,420,620 B2 | 9/2019 | Rockrohr | |
| 10,426,516 B2 | 10/2019 | Racenet et al. | |
| 10,507,068 B2 | 12/2019 | Kopp et al. | |
| 10,517,686 B2 | 12/2019 | Vokrot et al. | |
| 10,537,351 B2 | 1/2020 | Shelton, IV et al. | |
| 10,548,504 B2 | 2/2020 | Shelton, IV et al. | |
| 10,561,470 B2 | 2/2020 | Hourtash et al. | |
| 10,588,706 B2 | 3/2020 | Limon | |
| 10,624,691 B2 | 4/2020 | Wiener et al. | |
| 10,639,111 B2 | 5/2020 | Kopp | |
| 10,653,489 B2 | 5/2020 | Kopp | |
| 10,667,877 B2 | 6/2020 | Kapadia | |
| 10,675,104 B2 | 6/2020 | Kapadia | |
| 10,716,639 B2 | 7/2020 | Kapadia et al. | |
| 10,736,219 B2 | 8/2020 | Seow et al. | |
| 10,743,872 B2 | 8/2020 | Leimbach et al. | |
| 10,751,087 B2 | 8/2020 | Morgan et al. | |
| 10,765,484 B2 | 9/2020 | Bonutti et al. | |
| 10,772,688 B2 | 9/2020 | Peine et al. | |
| 10,779,849 B2 | 9/2020 | Shelton, IV et al. | |
| 10,779,897 B2 | 9/2020 | Rockrohr | |
| 10,779,900 B2 | 9/2020 | Pedros et al. | |
| 10,799,304 B2 | 10/2020 | Kapadia et al. | |
| 10,806,454 B2 | 10/2020 | Kopp | |
| 10,813,703 B2 | 10/2020 | Swayze et al. | |
| 10,849,700 B2 | 12/2020 | Kopp et al. | |
| 10,881,399 B2 | 1/2021 | Shelton, IV et al. | |
| 10,893,884 B2 | 1/2021 | Stoddard et al. | |
| 10,898,280 B2 | 1/2021 | Kopp | |
| 10,912,616 B2 | 2/2021 | Dachs, II et al. | |
| 10,932,772 B2 | 3/2021 | Shelton, IV et al. | |
| 10,959,788 B2 | 3/2021 | Grover et al. | |
| 10,980,610 B2 | 4/2021 | Rosenberg et al. | |
| 11,013,569 B2 | 5/2021 | Shelton, IV et al. | |
| 11,026,764 B2 | 6/2021 | Kopp | |
| 11,045,265 B2 | 6/2021 | Seow et al. | |
| 11,058,504 B2 | 7/2021 | Blanco et al. | |
| 11,090,125 B2 | 8/2021 | Peine et al. | |
| 11,109,866 B2 | 9/2021 | Shelton, IV et al. | |
| 11,160,623 B2 | 11/2021 | Hagn | |
| 2002/0072736 A1 | 6/2002 | Tierney et al. | |
| 2006/0069306 A1 | 3/2006 | Banik et al. | |
| 2006/0135978 A1 | 6/2006 | Franer | |
| 2007/0078395 A1 | 4/2007 | Valaie | |
| 2008/0064921 A1* | 3/2008 | Larkin | A61B 1/04 600/104 |
| 2011/0230719 A1 | 9/2011 | Katakura et al. | |
| 2011/0306840 A1 | 12/2011 | Allen et al. | |
| 2012/0132018 A1 | 5/2012 | Tang et al. | |
| 2012/0238827 A1 | 9/2012 | Berry et al. | |
| 2013/0331730 A1 | 12/2013 | Fenech et al. | |
| 2014/0066944 A1* | 3/2014 | Taylor | B25J 15/0466 606/103 |
| 2014/0263552 A1 | 9/2014 | Hall et al. | |
| 2014/0343569 A1 | 11/2014 | Turner | |
| 2016/0015261 A1 | 1/2016 | Kishi et al. | |
| 2016/0361127 A1* | 12/2016 | Dachs, II | A61B 46/10 |
| 2017/0188802 A1 | 7/2017 | Lawrence et al. | |
| 2017/0202591 A1 | 7/2017 | Shelton, IV et al. | |
| 2017/0224428 A1 | 8/2017 | Kopp | |
| 2017/0296213 A1 | 10/2017 | Swensgard et al. | |
| 2018/0296286 A1 | 10/2018 | Peine et al. | |
| 2019/0000478 A1 | 1/2019 | Messerly et al. | |
| 2019/0053866 A1 | 2/2019 | Seow et al. | |
| 2019/0059986 A1 | 2/2019 | Shelton, IV et al. | |
| 2019/0104919 A1 | 4/2019 | Shelton, IV et al. | |
| 2019/0133703 A1 | 5/2019 | Seow et al. | |
| 2019/0183596 A1 | 6/2019 | Dachs, II | |
| 2019/0200844 A1 | 7/2019 | Shelton, IV et al. | |
| 2019/0200981 A1 | 7/2019 | Harris et al. | |
| 2019/0201045 A1 | 7/2019 | Yates et al. | |
| 2019/0201046 A1 | 7/2019 | Shelton, IV et al. | |
| 2019/0201047 A1 | 7/2019 | Yates et al. | |
| 2019/0201120 A1 | 7/2019 | Shelton, IV et al. | |
| 2019/0201136 A1 | 7/2019 | Shelton, IV et al. | |
| 2019/0201137 A1 | 7/2019 | Shelton, IV et al. | |
| 2019/0201594 A1 | 7/2019 | Shelton, IV et al. | |
| 2019/0206562 A1 | 7/2019 | Shelton, IV et al. | |
| 2019/0206563 A1 | 7/2019 | Shelton, IV et al. | |
| 2019/0206564 A1 | 7/2019 | Shelton, IV et al. | |
| 2019/0206569 A1 | 7/2019 | Shelton, IV et al. | |
| 2019/0208641 A1 | 7/2019 | Yates et al. | |
| 2019/0298471 A1 | 10/2019 | Holop | |
| 2019/0321112 A1 | 10/2019 | Cecil | |
| 2020/0214776 A1* | 7/2020 | Hingwe | A61B 34/35 |
| 2020/0315715 A1 | 10/2020 | Rockrohr et al. | |

(56) References Cited

U.S. PATENT DOCUMENTS

| | | |
|---|---|---|
| 2020/0405375 A1 | 12/2020 | Shelton, IV et al. |
| 2020/0405401 A1 | 12/2020 | Shelton, IV et al. |
| 2020/0405403 A1 | 12/2020 | Shelton, IV et al. |
| 2020/0405404 A1 | 12/2020 | Shelton, IV et al. |
| 2020/0405405 A1 | 12/2020 | Shelton, IV et al. |
| 2020/0405407 A1 | 12/2020 | Shelton, IV et al. |
| 2020/0405408 A1 | 12/2020 | Shelton, IV et al. |
| 2020/0405414 A1 | 12/2020 | Shelton, IV et al. |
| 2020/0405415 A1 | 12/2020 | Shelton, IV et al. |
| 2020/0405416 A1 | 12/2020 | Shelton, IV et al. |
| 2020/0405417 A1 | 12/2020 | Shelton, IV et al. |
| 2020/0405421 A1 | 12/2020 | Luck |
| 2020/0405422 A1 | 12/2020 | Shelton, IV et al. |
| 2021/0212777 A1 | 7/2021 | Cheng |

OTHER PUBLICATIONS

"ATM-MPLS Network Interworking Version 2.0, af-aic-0178.001" ATM Standard, The ATM Forum Technical Committee, published Aug. 2003.

* cited by examiner

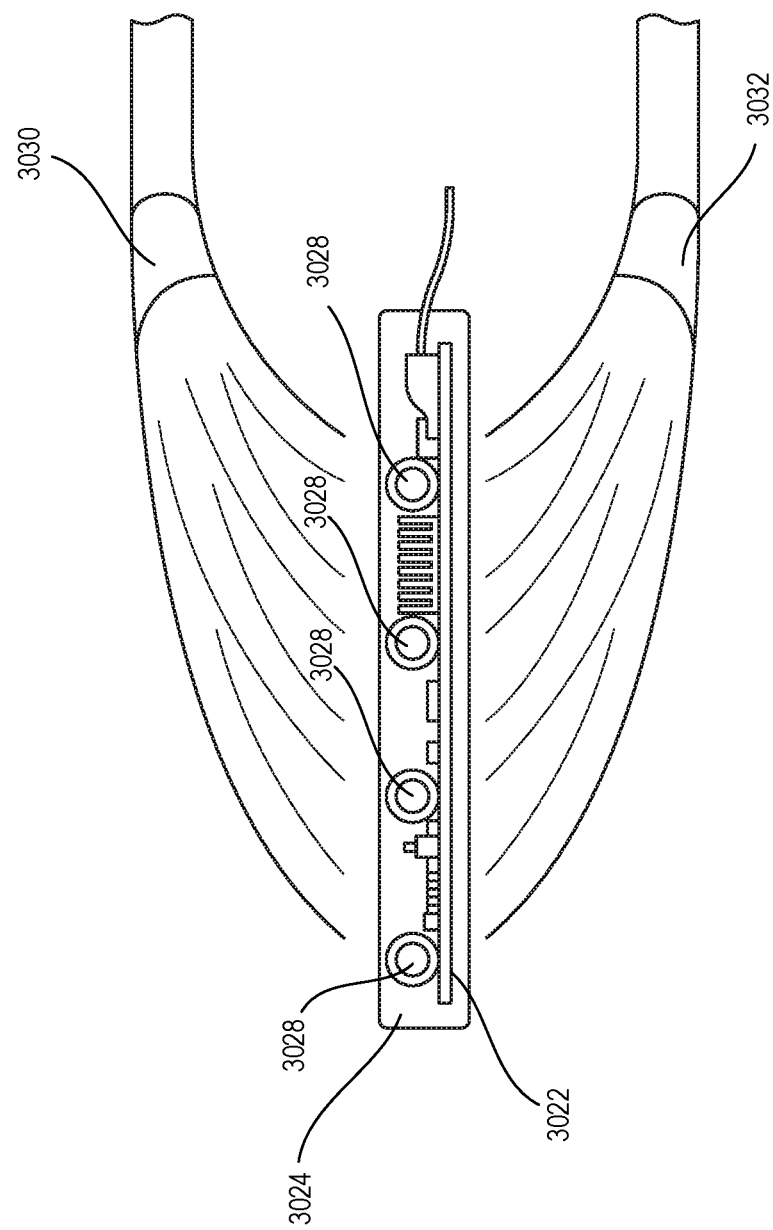

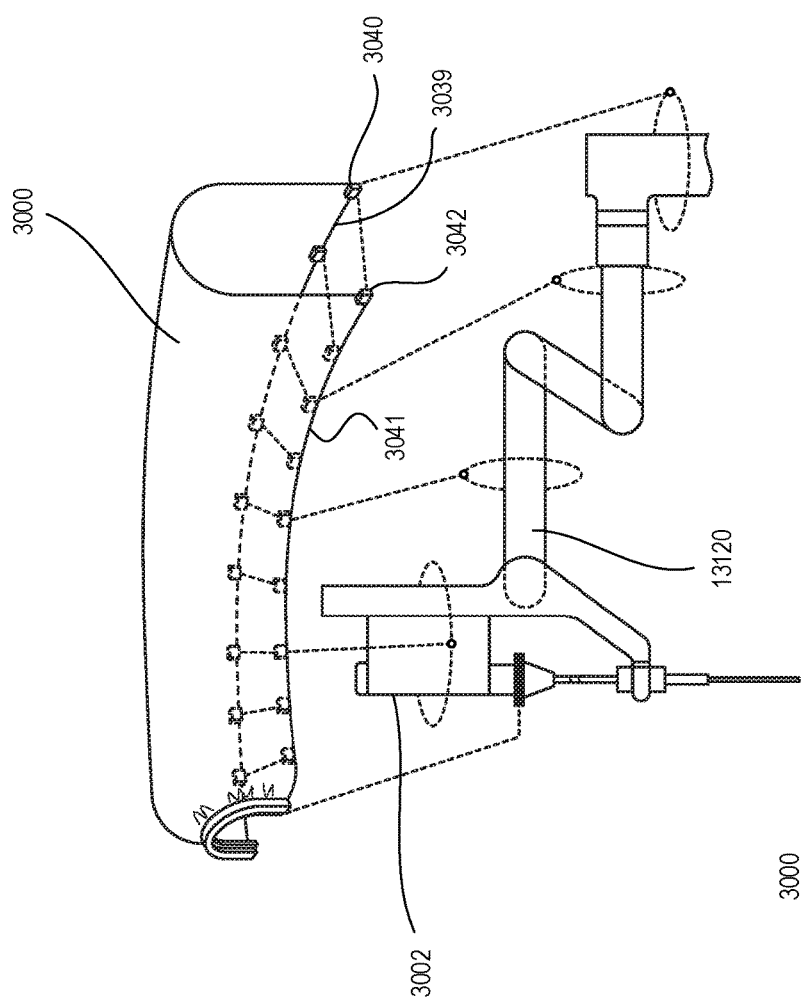
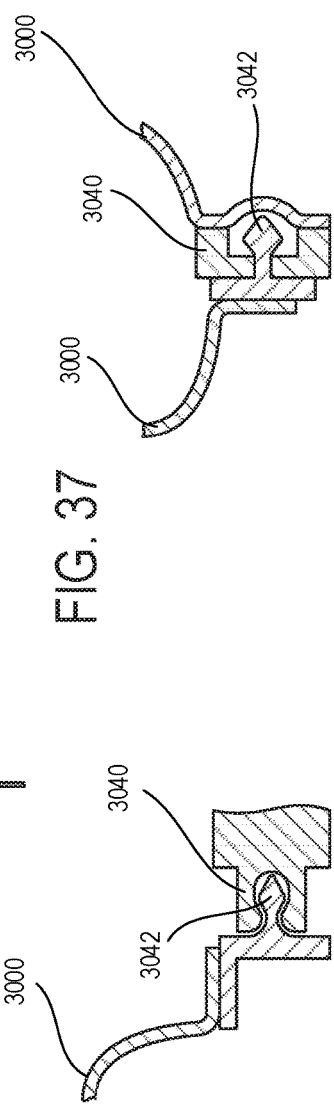
FIG. 37
FIG. 38B
FIG. 38A

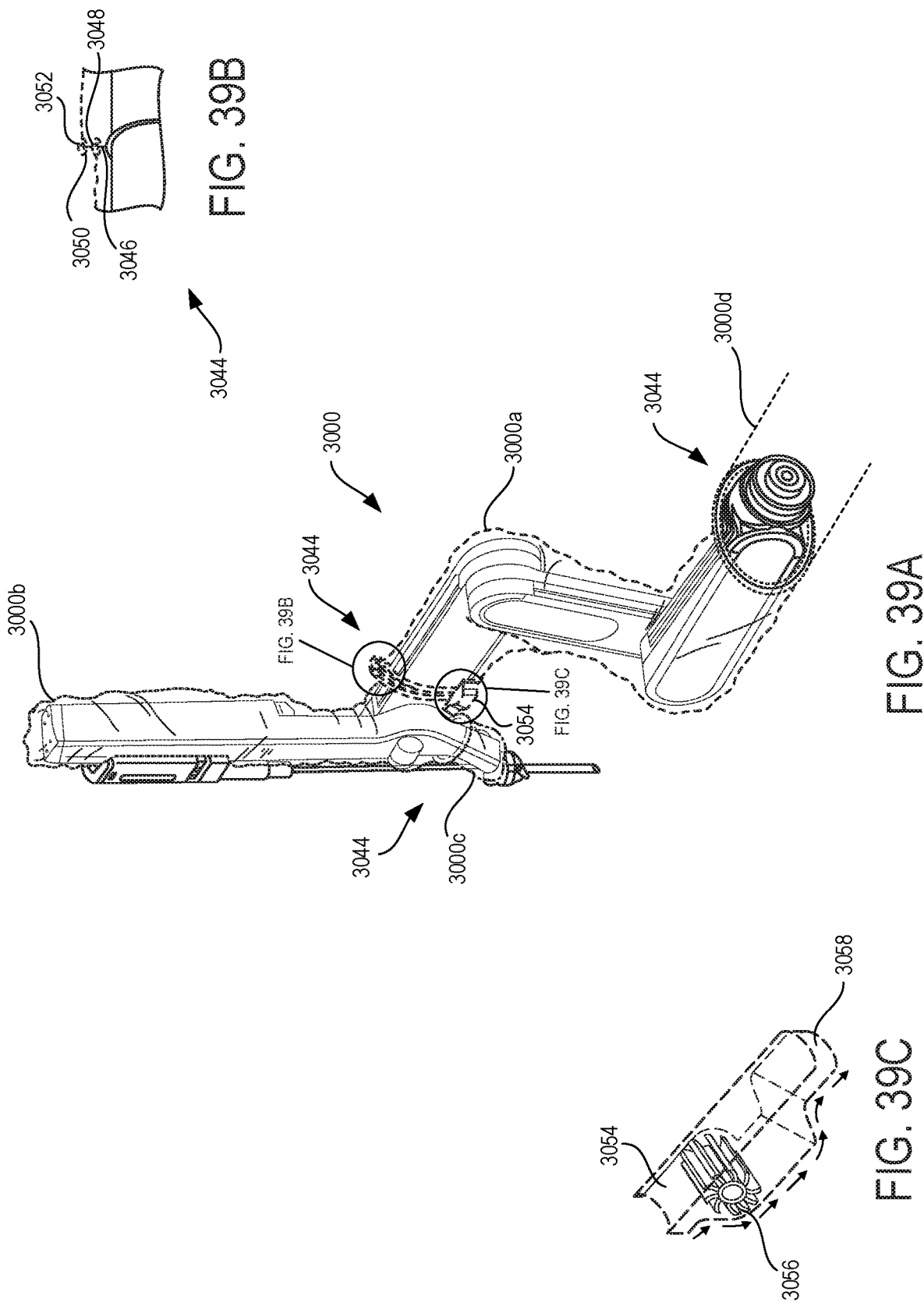

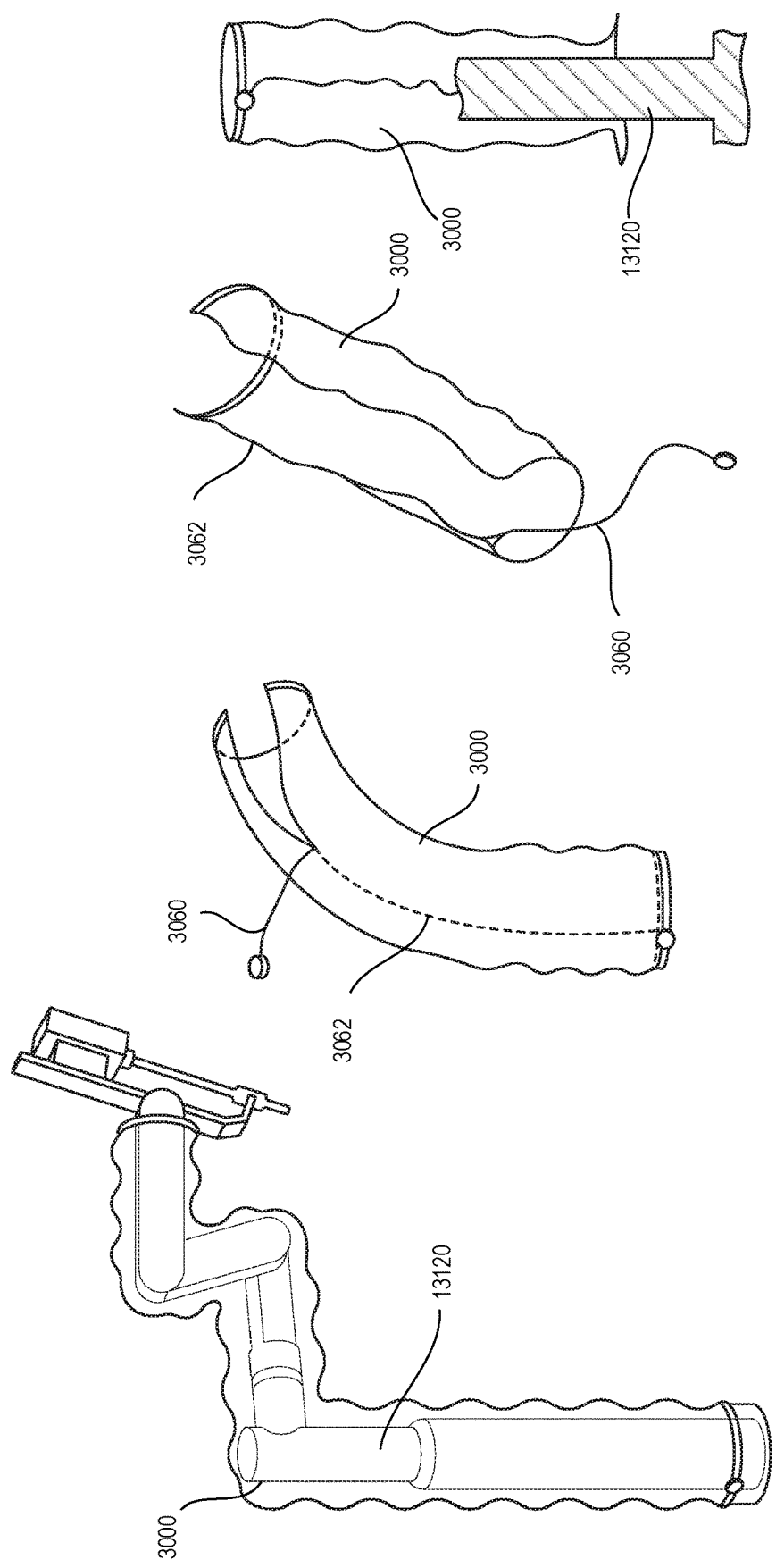

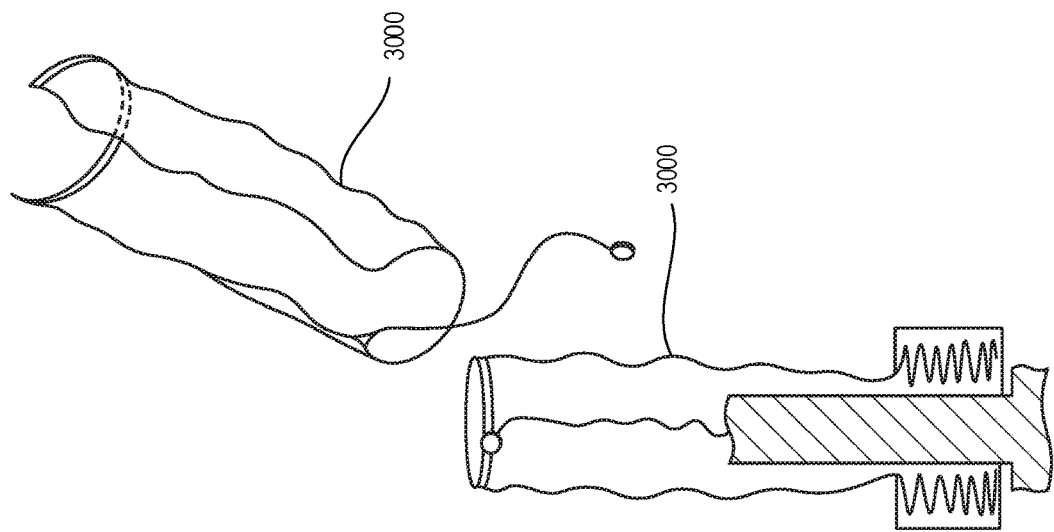
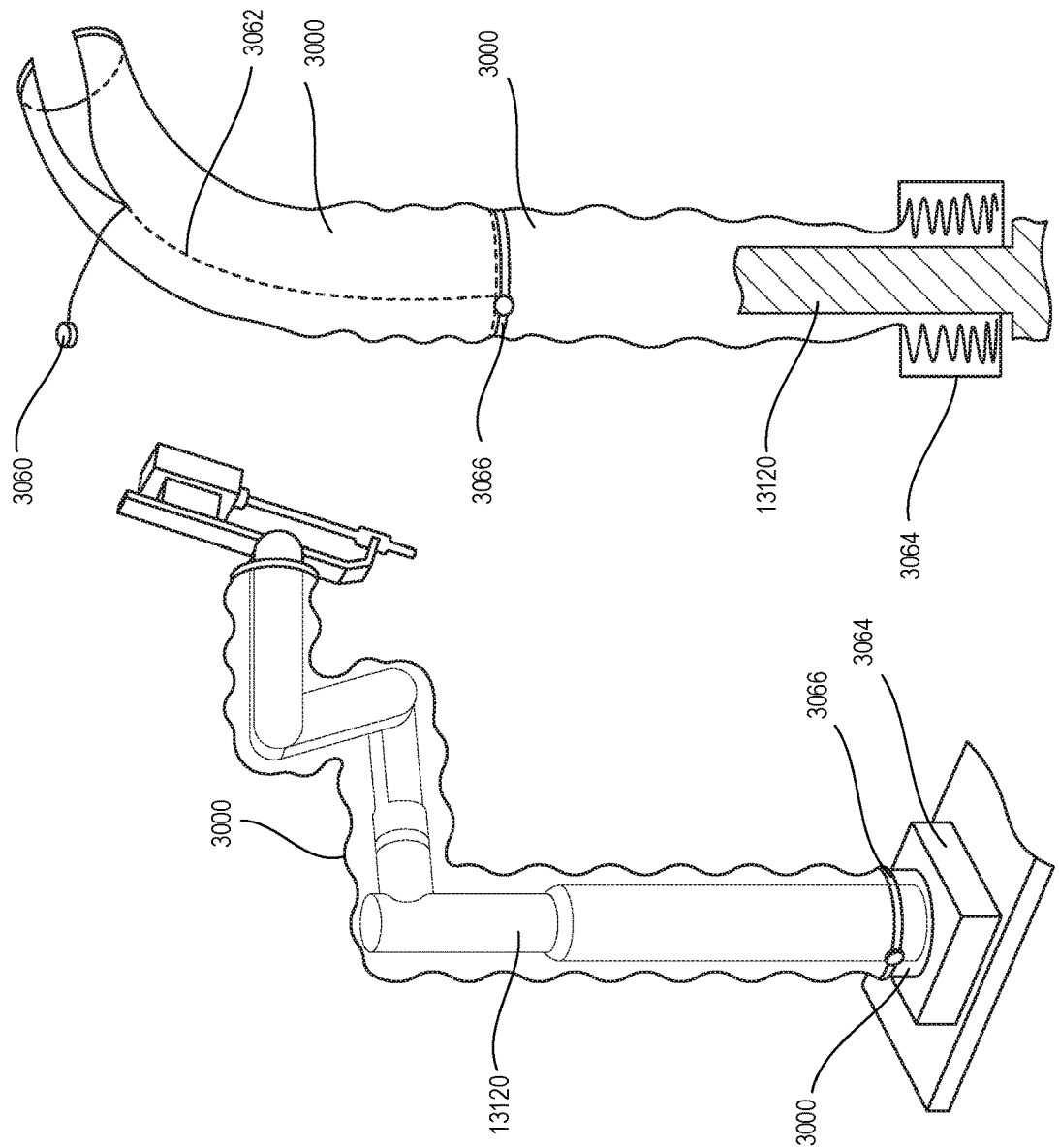

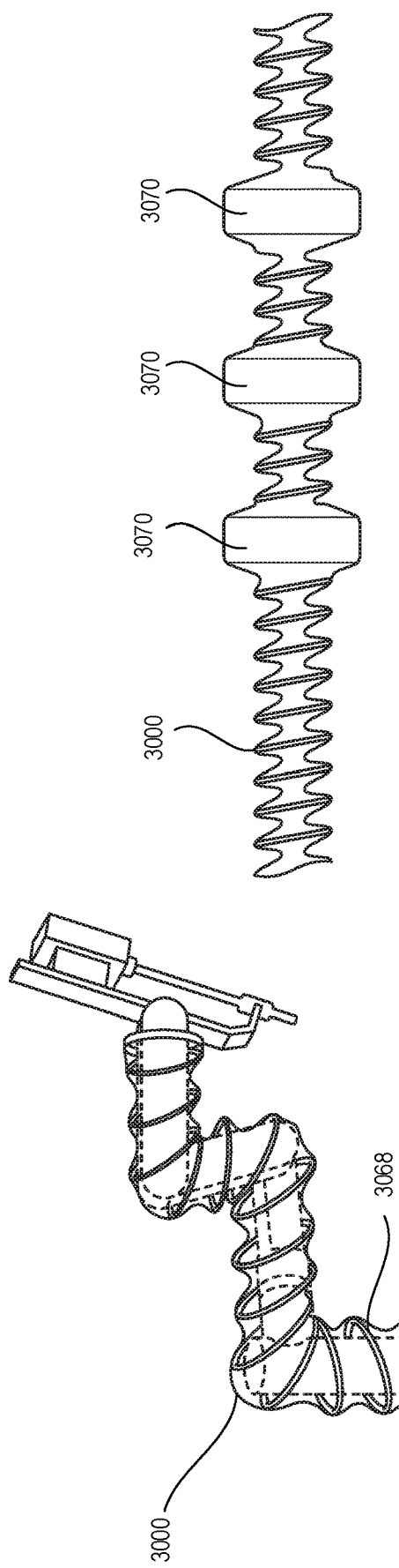
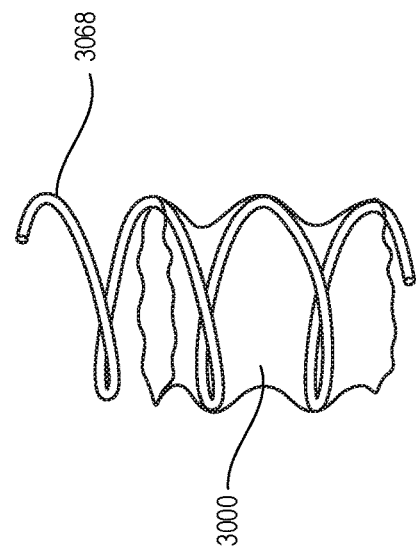
FIG. 44
FIG. 43B
FIG. 43A

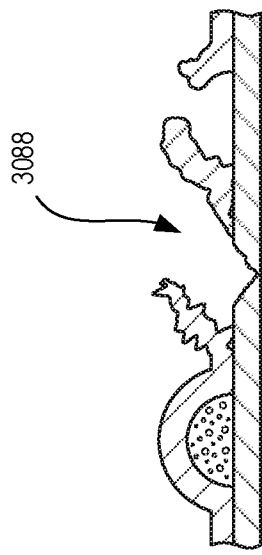
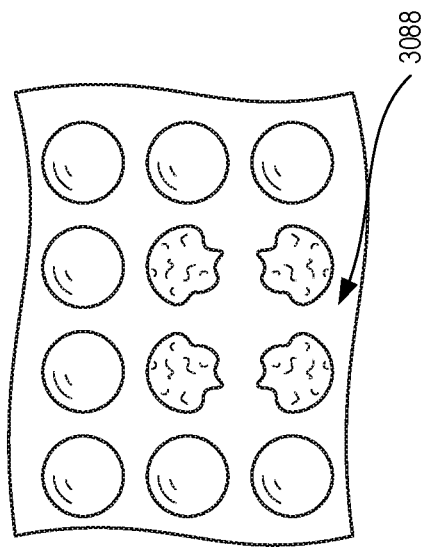
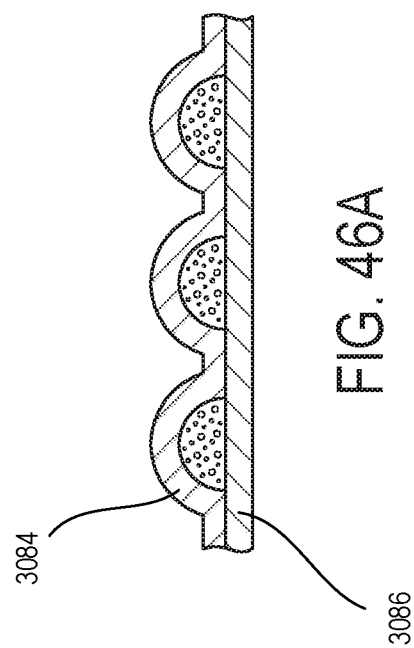
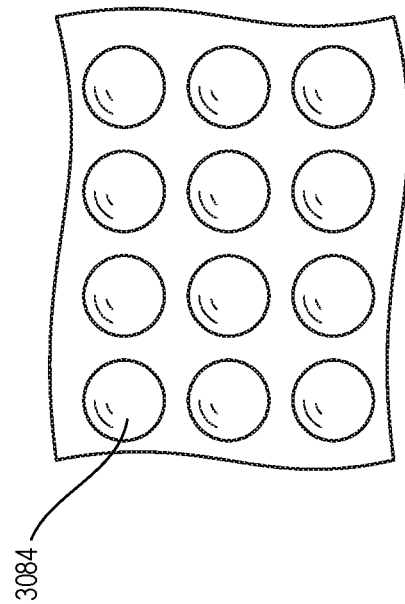
FIG. 46A
FIG. 46B
FIG. 46C
FIG. 46D

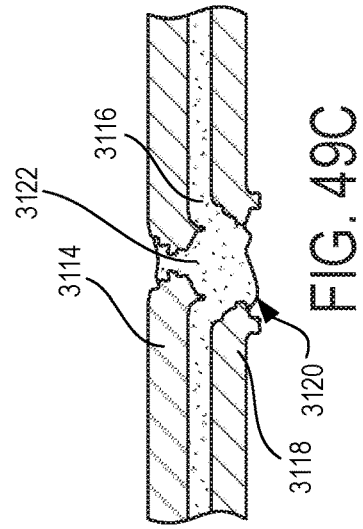
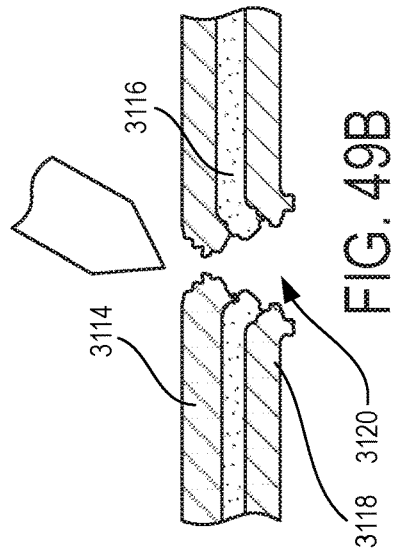
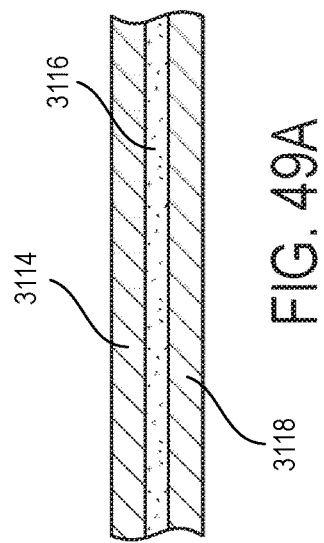

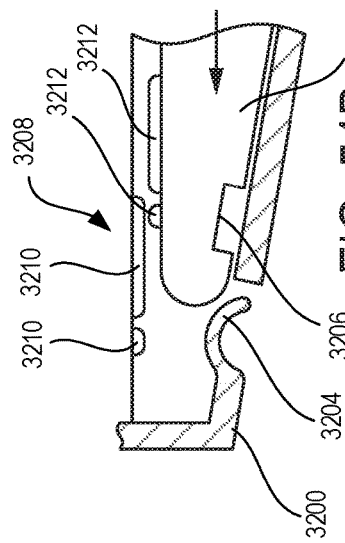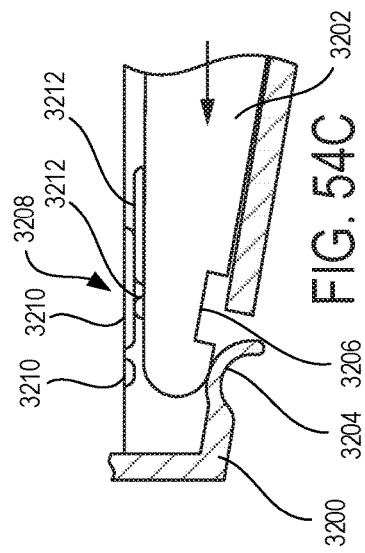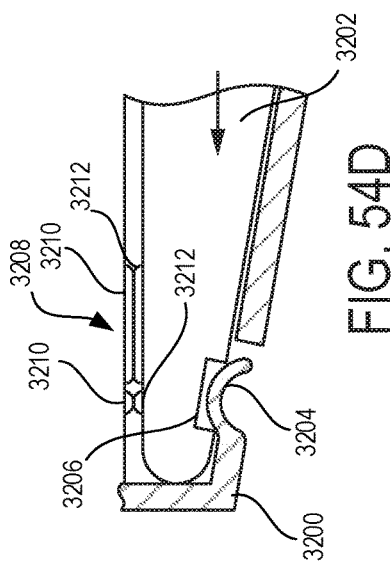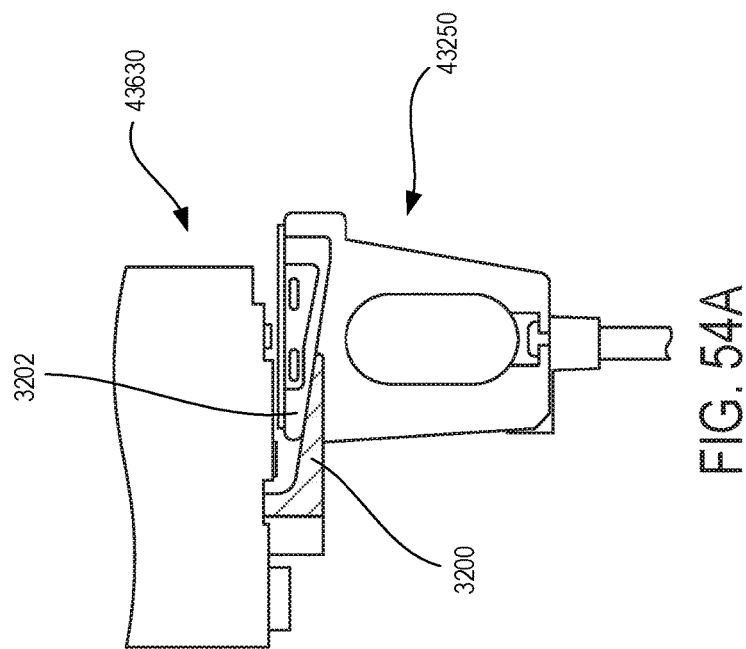

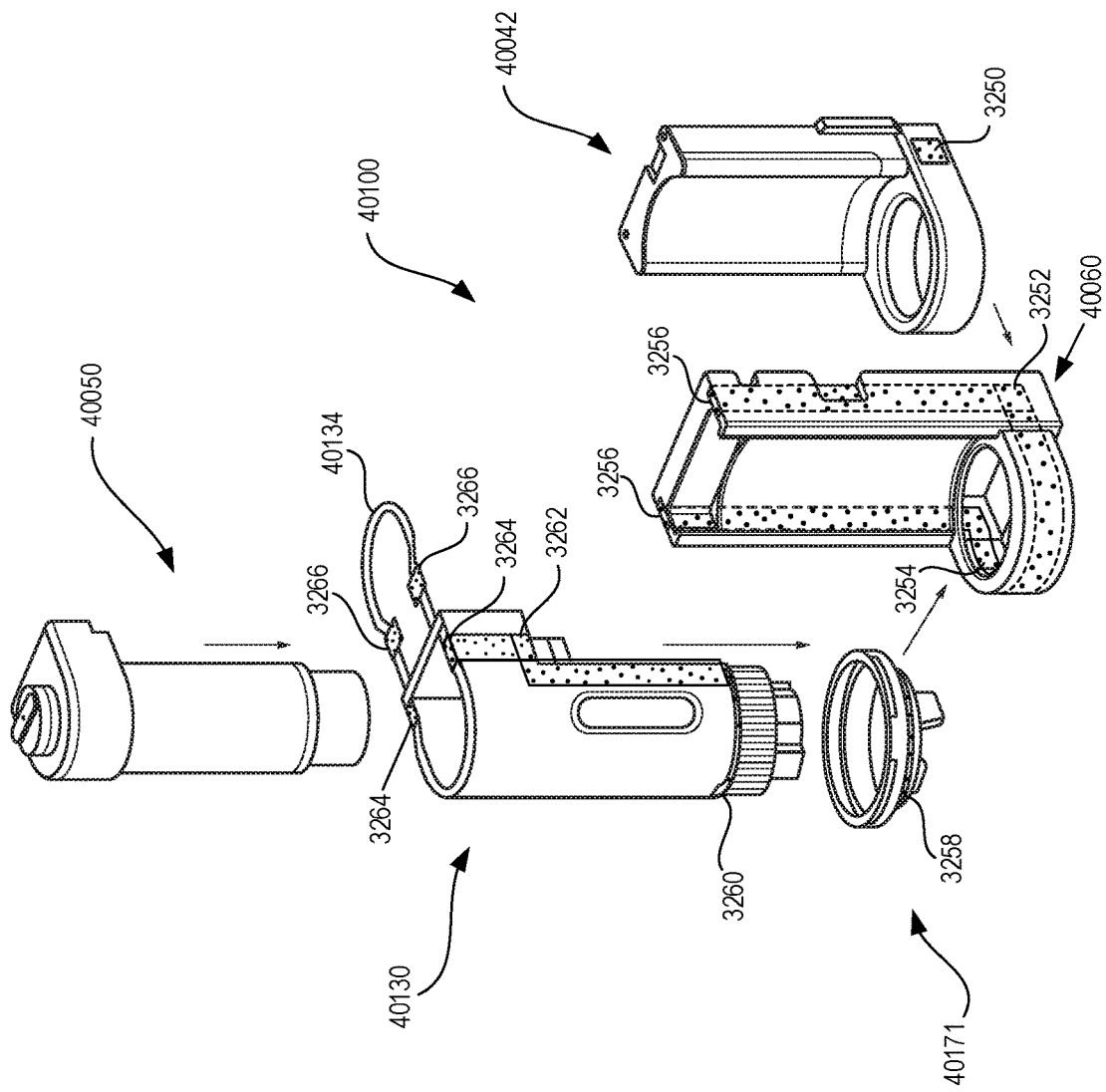

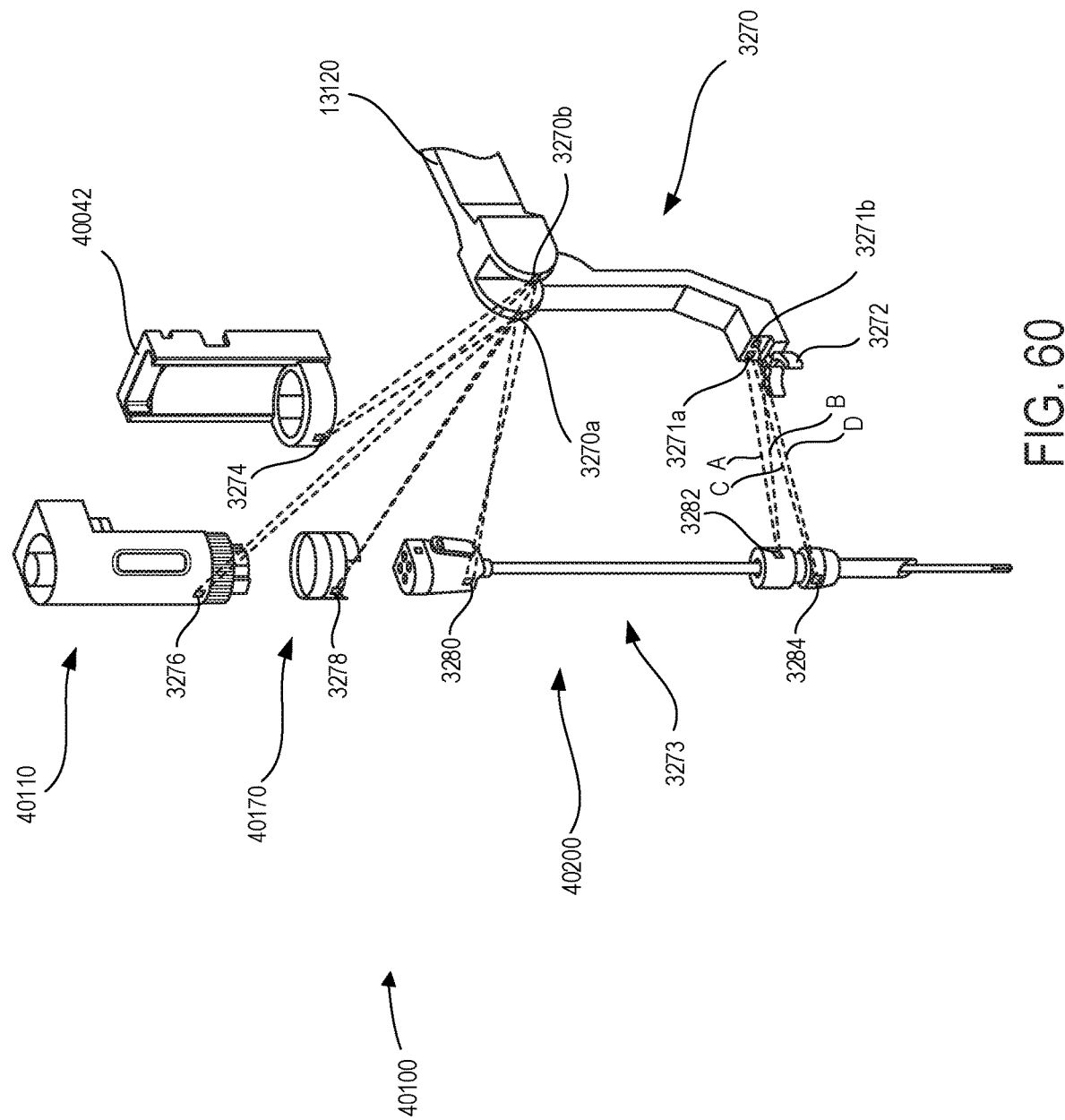

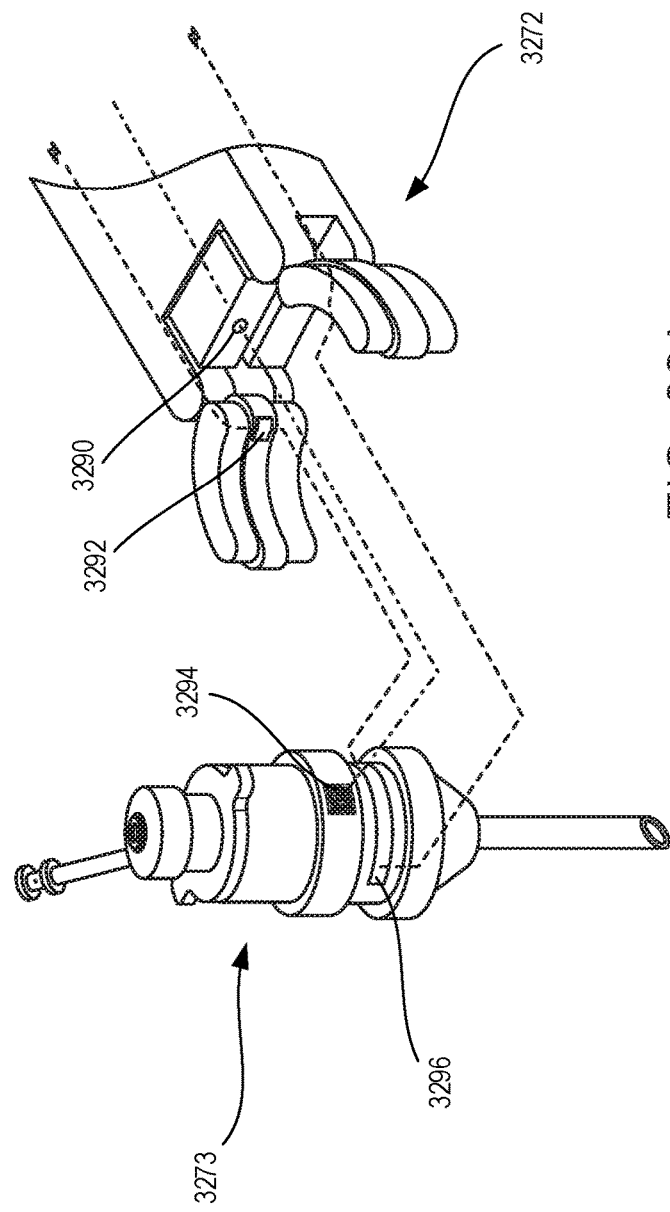
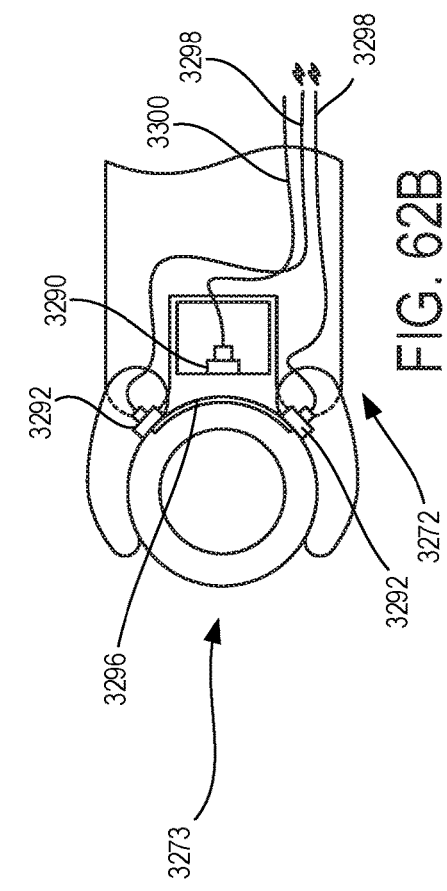
FIG. 62A
FIG. 62B

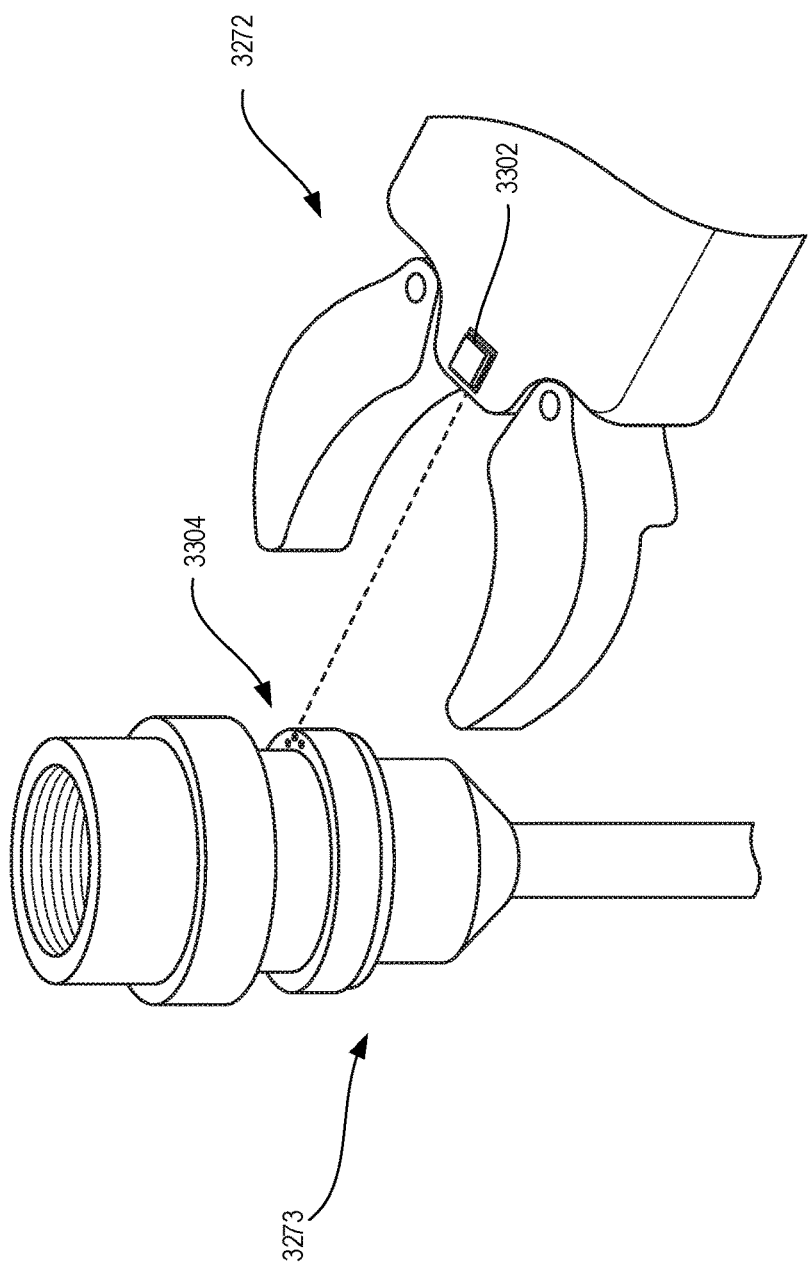

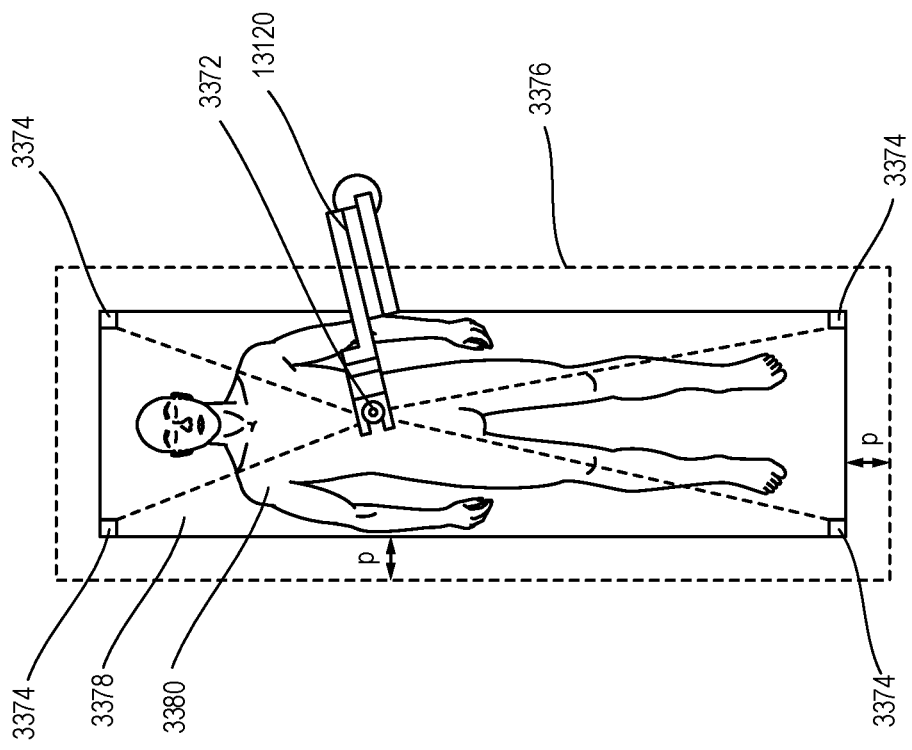
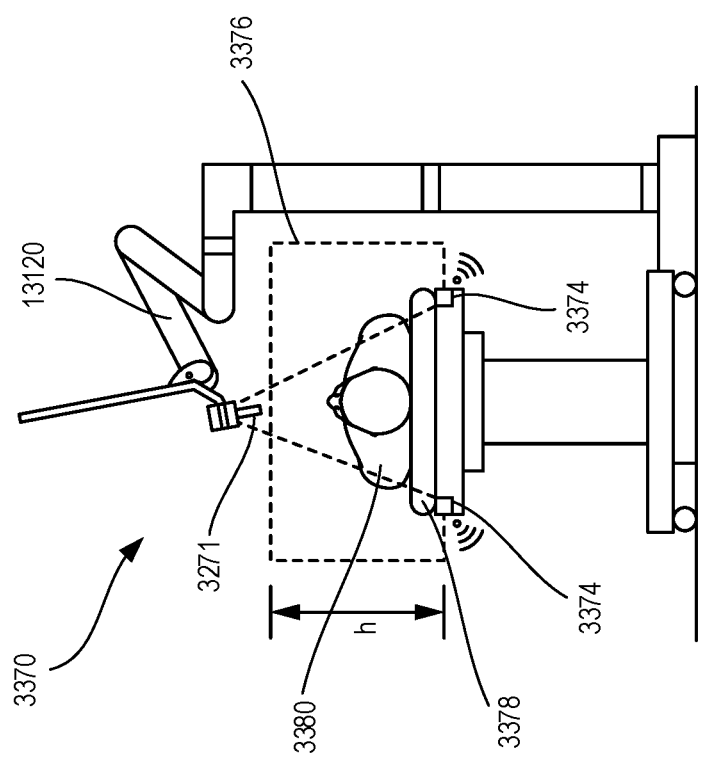

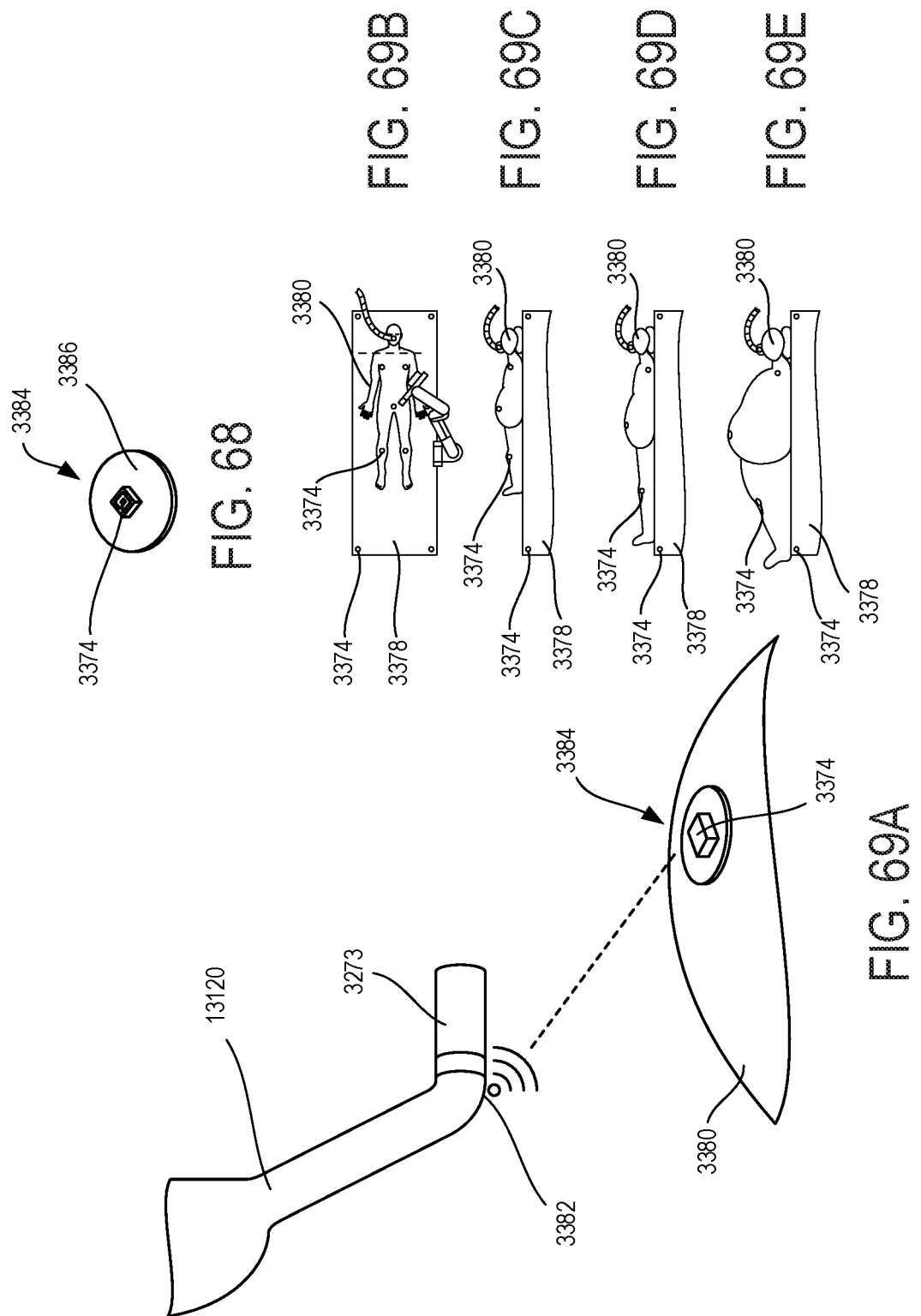

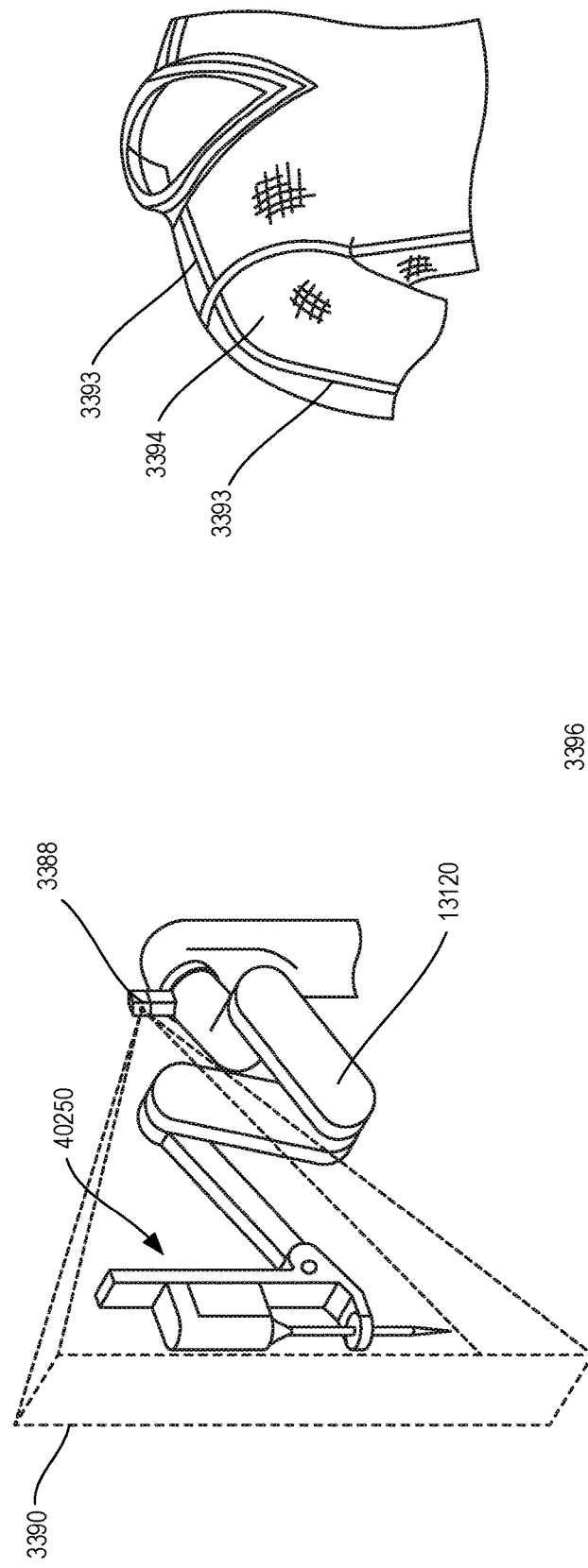
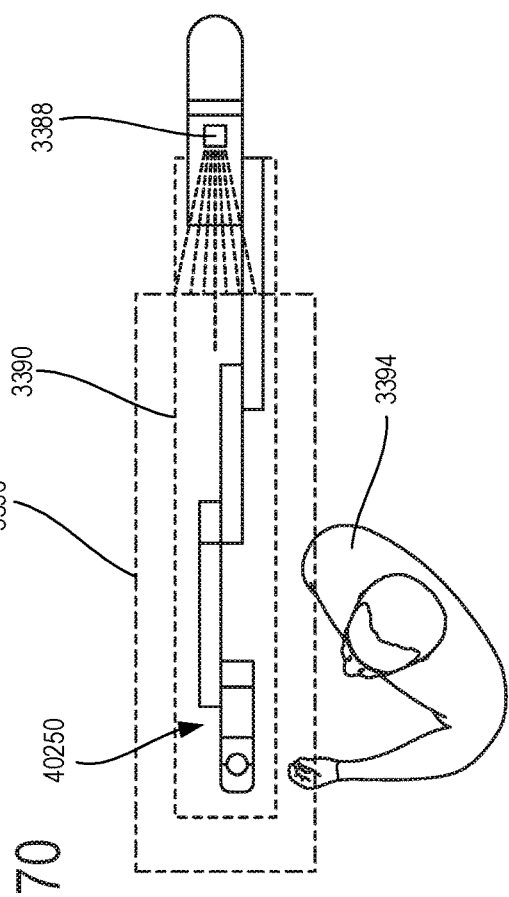
FIG. 70
FIG. 71
FIG. 72

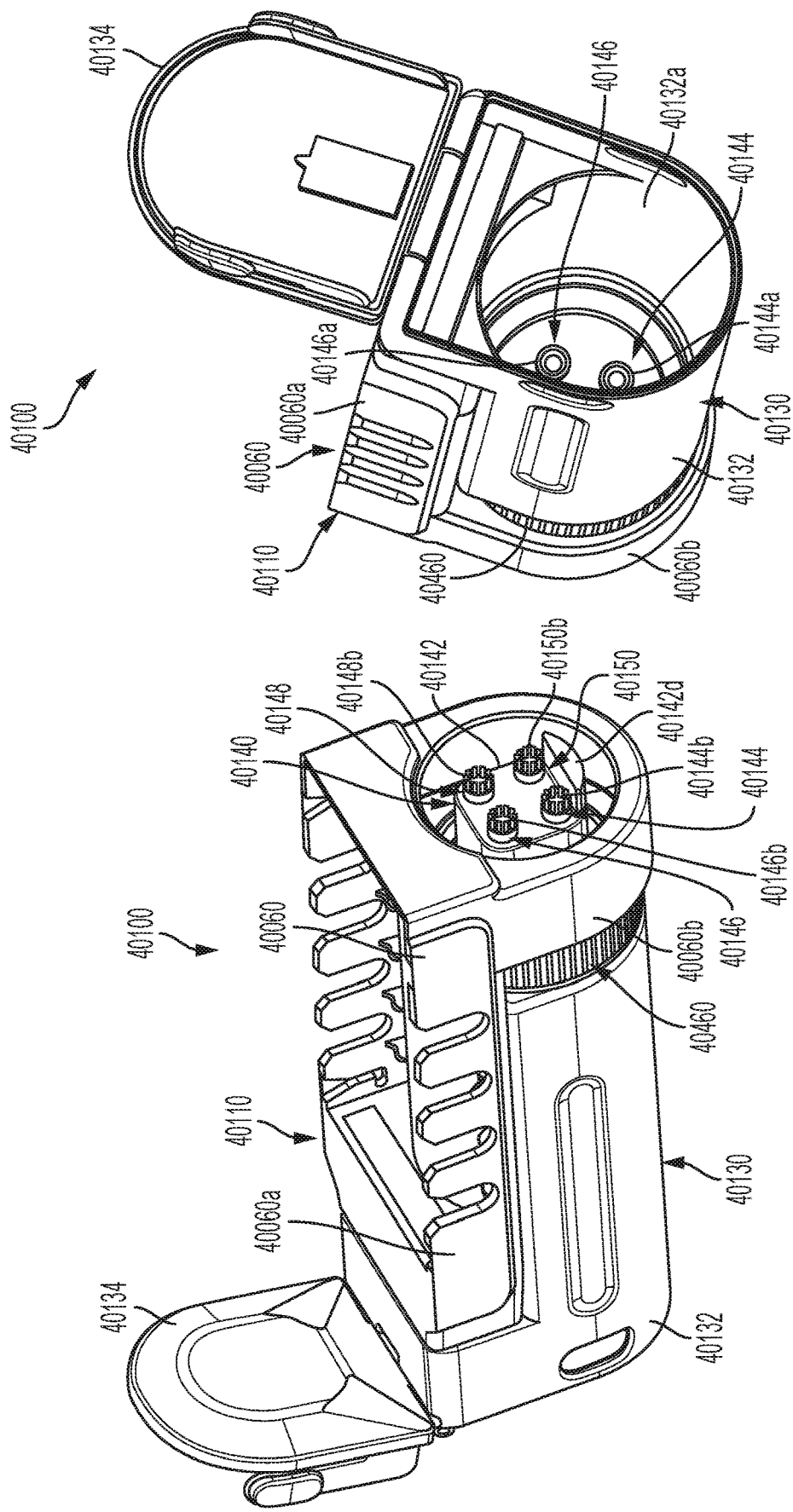

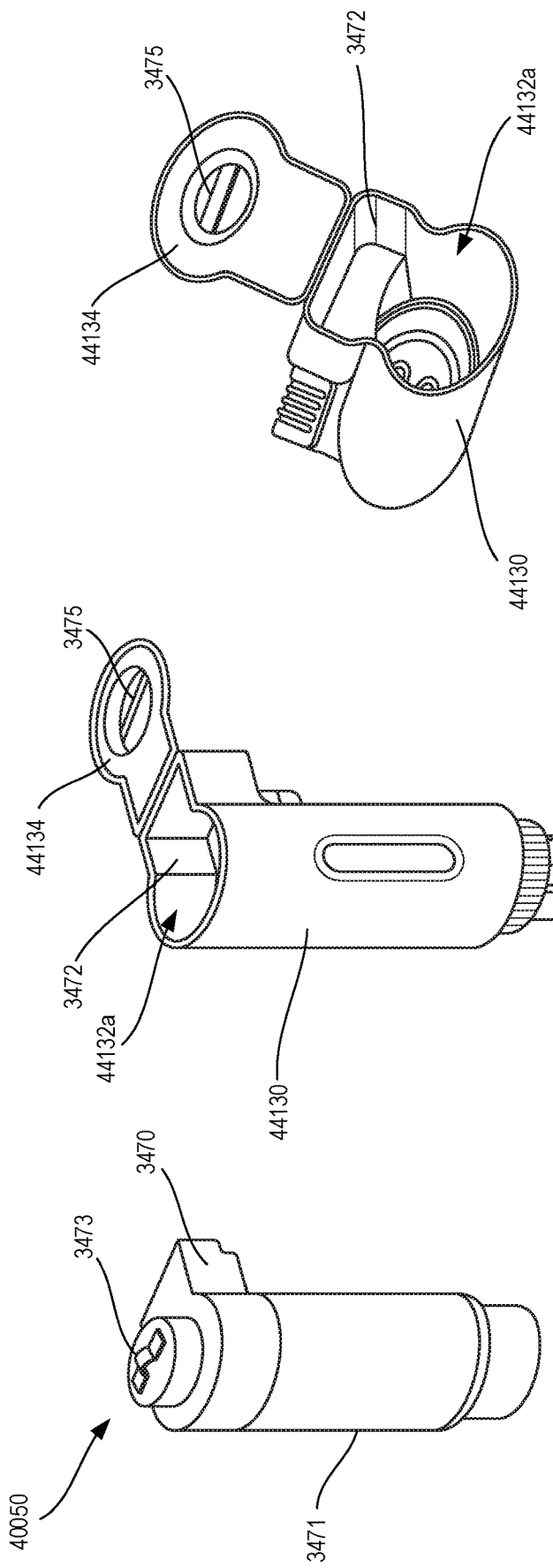

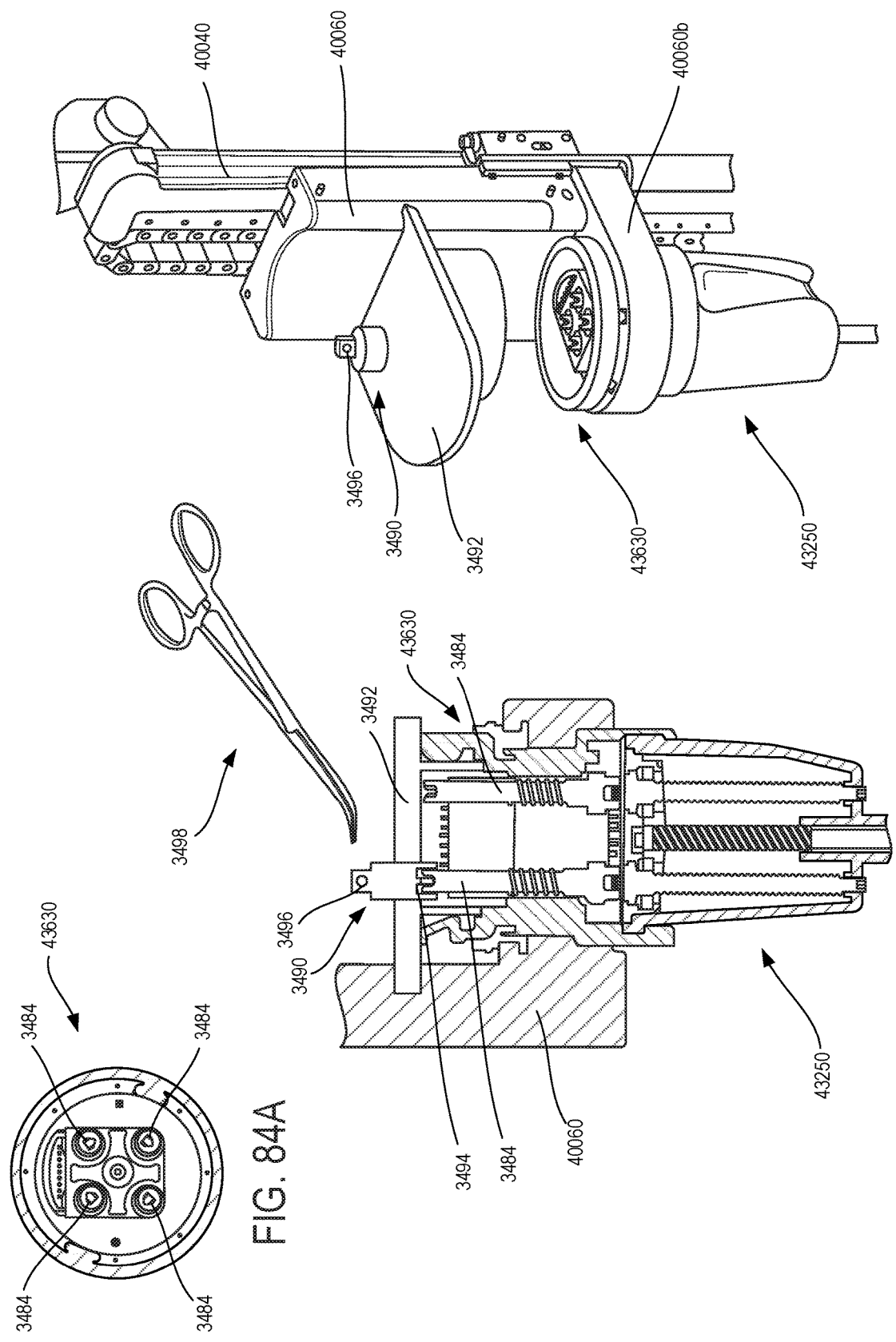

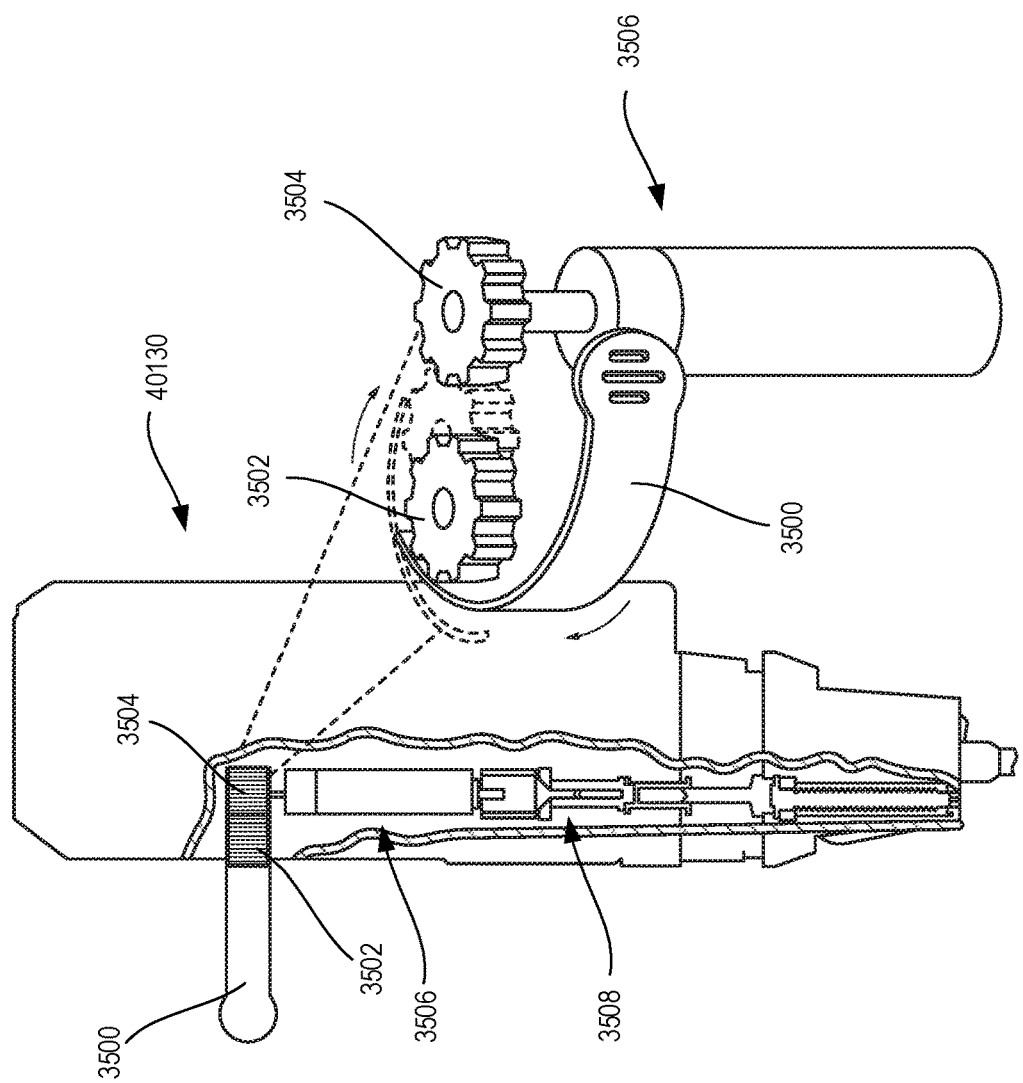
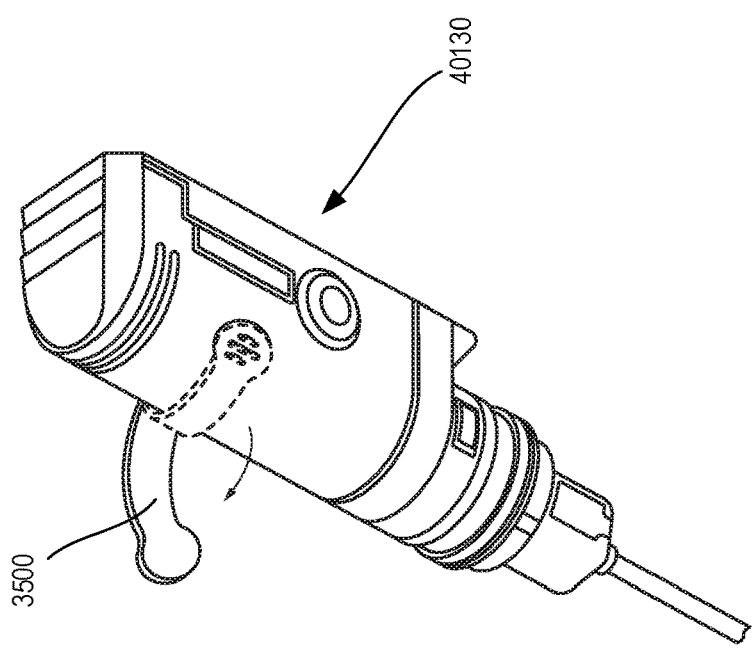
FIG. 85B
FIG. 85A

DETERMINING ROBOTIC SURGICAL ASSEMBLY COUPLING STATUS

BACKGROUND

The present disclosure relates to robotic surgical systems. Robotic surgical systems can include a central control unit, a surgeon's command console, and a robot having one or more robotic arms. Robotic surgical tools can be releasably mounted to the robotic arm(s). The number and type of robotic surgical tools can depend on the type of surgical procedure. Robotic surgical systems can be used in connection with one or more displays and/or one or more handheld surgical instruments during a surgical procedure.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 34 is a schematic view of robotic surgical assembly circuitry comprising a fluid cooling system, in accordance with at least one aspect of the present disclosure.

FIG. 37 is a perspective view of a sterile drape securable to a robotic arm, in accordance with at least one aspect of the present disclosure.

FIG. 38A is a detail view of a first attachment assembly for the sterile drape, in accordance with at least one aspect of the present disclosure.

FIG. 38B is a detail view of a second attachment assembly for the sterile drape, in accordance with at least one aspect of the present disclosure.

FIG. 39A is a perspective view of a segmented sterile drape positioned on a robotic arm, in accordance with at least one aspect of the present disclosure.

FIG. 39B is a detail view of a portion of FIG. 39A, in accordance with at least one aspect of the present disclosure.

FIG. 39C is a detail view of a portion of FIG. 39B, in accordance with at least one aspect of the present disclosure.

FIG. 41A is a perspective view of a sterile drape comprising a release cord positioned on a robotic arm, in accordance with at least one aspect of the present disclosure.

FIG. 41B is a perspective view of the sterile drape of FIG. 41A with the release cord being pulled proximally, in accordance with at least one aspect of the present disclosure.

FIG. 41C is a perspective view of the sterile drape of FIG. 41A released from the robotic arm, in accordance with at least one aspect of the present disclosure.

FIG. 41D is a perspective view of a replacement sterile drape being positioned over the robotic arm, in accordance with at least one aspect of the present disclosure.

FIG. 42A is a perspective view of a sterile drape comprising a release cord positioned on a robotic arm, in accordance with at least one aspect of the present disclosure.

FIG. 42B is a perspective view of the sterile drape of FIG. 42A being released from the robotic arm and a replacement sterile drape being deployed from the sterile drape holder, in accordance with at least one aspect of the present disclosure.

FIG. 42C is a perspective view of a replacement sterile drape being fully deployed from the sterile drape holder, in accordance with at least one aspect of the present disclosure.

FIG. 43A is a perspective view of a sterile drape comprising a support skeleton positioned on a robotic arm, in accordance with at least one aspect of the present disclosure.

FIG. 43B is a detail view of the sterile drape of FIG. 43A, in accordance with at least one aspect of the present disclosure.

FIG. 44 is a perspective view of a sterile drape comprising joint zones, in accordance with at least one aspect of the present disclosure.

FIGS. 46A-46B are detail views of a sterile drape comprising pressurized air pockets, in accordance with at least one aspect of the present disclosure.

FIGS. 46C-46D are detail views of the sterile drape of FIGS. 46A-46B, where the sterile drape has been breached, in accordance with at least one aspect of the present disclosure.

FIG. 49A is a sectional view of a self-healing sterile drape, in accordance with at least one aspect of the present disclosure.

FIG. 49B is a sectional view of the sterile drape of FIG. 49A, where the sterile drape has been breached, in accordance with at least one aspect of the present disclosure.

FIG. 49C is a sectional view of the sterile drape of FIG. 49B, where the sterile drape has healed the breach, in accordance with at least one aspect of the present disclosure.

FIG. 54A is a side elevational view of a surgical instrument being coupled to a sterile interface module, in accordance with at least one aspect of the present disclosure.

FIG. 54B is a detail view of the surgical instrument in a first uncoupled position with the sterile interface module, in accordance with at least one aspect of the present disclosure.

FIG. 54C is a detail view of the surgical instrument in a second uncoupled position with the sterile interface module, in accordance with at least one aspect of the present disclosure.

FIG. 54D is a detail view of the surgical instrument in a coupled position with the sterile interface module, in accordance with at least one aspect of the present disclosure.

FIG. 59 is an exploded view of a robotic surgical assembly comprising continuity circuits, in accordance with at least one aspect of the present disclosure.

FIG. 60 is an exploded view of a robotic surgical assembly comprising proximity sensors, in accordance with at least one aspect of the present disclosure.

FIG. 62A is a perspective view of a robotic grasper comprising a surgical instrument identification sensor assembly, in accordance with at least one aspect of the present disclosure.

FIG. 62B is an overhead elevational view of the robotic grasper of FIG. 62A grasping a surgical instrument, in accordance with at least one aspect of the present disclosure.

FIG. 63A is a perspective view of a robotic grasper comprising a surgical instrument identification sensor, in accordance with at least one aspect of the present disclosure.

FIG. 63B is a detail view of a surgical instrument comprising a first identification element, in accordance with at least one aspect of the present disclosure.

FIG. 63C is a detail view of a surgical instrument comprising a second identification element, in accordance with at least one aspect of the present disclosure.

FIG. 63D is a detail view of a surgical instrument comprising a third identification element, in accordance with at least one aspect of the present disclosure.

FIG. 67A is a side elevational view of a safety envelope defined about a patient for a robotic surgical system, in accordance with at least one aspect of the present disclosure.

FIG. 67B is an overhead elevational view of the robotic surgical system of FIG. 67A, in accordance with at least one aspect of the present disclosure.

FIG. 68 is a perspective view of a sensor tag, in accordance with at least one aspect of the present disclosure.

FIG. 69A is a schematic view of a sensor tag positioned on a patient, in accordance with at least one aspect of the present disclosure.

FIG. 69B is a schematic view of a sensor of sensor tags positioned on a patient and an operating table, in accordance with at least one aspect of the present disclosure.

FIG. 69C is a schematic view of a sensor of sensor tags positioned on a first patient and an operating table, in accordance with at least one aspect of the present disclosure.

FIG. 69D is a schematic view of a sensor of sensor tags positioned on a second patient and an operating table, in accordance with at least one aspect of the present disclosure.

FIG. 69E is a schematic view of a sensor of sensor tags positioned on a third patient and an operating table, in accordance with at least one aspect of the present disclosure.

FIG. 70 is a schematic view of a robotic surgical system comprising an image sensor to sense a robotic arm positioned within a detection zone, in accordance with at least one aspect of the present disclosure.

FIG. 71 is a perspective view of a pair of scrubs comprising a reflective material, in accordance with at least one aspect of the present disclosure.

FIG. 72 is an overhead view of a surgical staff member wearing the scrubs of FIG. 71 violating a detection zone with respect to the robotic arm, in accordance with at least one aspect of the present disclosure.

FIG. 81A is perspective view of a motor pack sterile barrier, in accordance with at least one aspect of the present disclosure.

FIG. 81B is perspective view of a motor pack sterile barrier, in accordance with at least one aspect of the present disclosure.

FIG. 82A is a perspective view of a motor pack comprising an alignment tab, in accordance with at least one aspect of the present disclosure.

FIG. 82B is a perspective view of a motor pack sterile barrier configured to receive the motor pack of FIG. 82A, in accordance with at least one aspect of the present disclosure.

FIG. 82C is a perspective view of the motor pack sterile barrier of FIG. 82B, in accordance with at least one aspect of the present disclosure.

FIG. 84A is an overhead elevational view of a sterile interface module, in accordance with at least one aspect of the present disclosure.

FIG. 84B is a sectional view of an instrument drive unit comprising an interface couplable to the drive couplers of a sterile interface module, in accordance with at least one aspect of the present disclosure.

FIG. 84C is a perspective view of the instrument drive unit of FIG. 84B, in accordance with at least one aspect of the present disclosure.

FIG. 85A is a perspective view of an instrument drive unit comprising a bailout lever, in accordance with at least one aspect of the present disclosure.

FIG. 85B is a cutaway view of the instrument drive unit of FIG. 85A, in accordance with at least one aspect of the present disclosure.

DESCRIPTION

Figure 1:
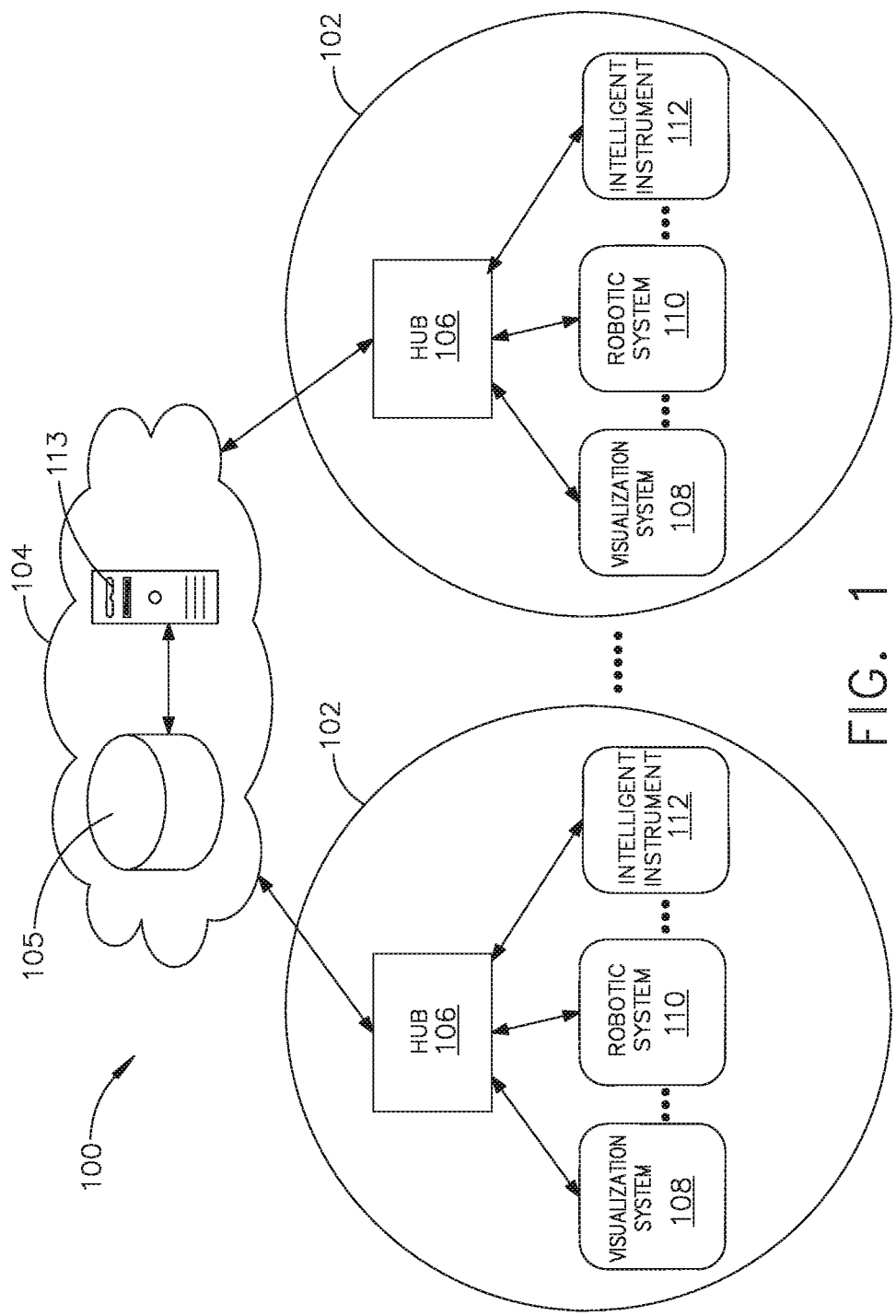
FIG. 1 is a block diagram of a computer-implemented interactive surgical system, in accordance with at least one aspect of the present disclosure.

Applicant of the present application owns the following U.S. patent applications, filed on Jun. 27, 2019, the disclosure of each of which is herein incorporated by reference in its entirety:

U.S. patent application Ser. No. 16/454,702, titled METHOD OF USING A SURGICAL MODULAR ROBOTIC ASSEMBLY, now U.S. Patent Application Publication No. 2020/0405603;

U.S. patent application Ser. No. 16/454,710, titled SURGICAL SYSTEMS WITH INTERCHANGEABLE MOTOR PACKS, now U.S. Pat. No. 11,013,569;

U.S. patent application Ser. No. 16/454,715, titled COOPERATIVE ROBOTIC SURGICAL SYSTEMS, now U.S. Patent Application Publication No. 2020/0405404;

U.S. patent application Ser. No. 16/454,740, titled HEAT EXCHANGE SYSTEMS FOR ROBOTIC SURGICAL SYSTEMS, now U.S. Patent Application Publication No. 2020/0405415;

U.S. patent application Ser. No. 16/454,780, titled ROBOTIC SURGICAL ASSEMBLY COUPLING SAFETY MECHANISMS, now U.S. Patent Application Publication No. 2020/0405408;

U.S. patent application Ser. No. 16/454,707, titled ROBOTIC SURGICAL SYSTEM WITH SAFETY AND COOPERATIVE SENSING CONTROL, now U.S. Patent Application Publication No. 2020/0405375;

U.S. patent application Ser. No. 16/454,726, titled ROBOTIC SURGICAL SYSTEM FOR CONTROLLING CLOSE OPERATION OF END-EFFECTORS, now U.S. Patent Application Publication No. 2020/0405414;

U.S. patent application Ser. No. 16/454,737, titled ROBOTIC SURGICAL SYSTEM WITH LOCAL SENSING OF FUNCTIONAL PARAMETERS BASED ON MEASUREMENTS OF MULTIPLE PHYSICAL INPUTS, now U.S. Patent Application Publication No. 16/454,737;

U.S. patent application Ser. No. 16/454,751, titled COOPERATIVE OPERATION OF ROBOTIC ARMS, now U.S. Patent Application Publication No. 2020/0405417;

U.S. patent application Ser. No. 16/454,760, titled SURGICAL INSTRUMENT DRIVE SYSTEMS, now U.S. Patent Application Publication No. 2020/0405407;

U.S. patent application Ser. No. 16/454,769, titled SURGICAL INSTRUMENT DRIVE SYSTEMS WITH CABLE-TIGHTENING SYSTEM, now U.S. Patent Application Publication No. 2020/0405422;

U.S. patent application Ser. No. 16/454,727, titled VISUALIZATION SYSTEM WITH AUTOMATIC CONTAMINATION DETECTION AND CLEANING CONTROLS, now U.S. Patent Application Publication No. 2020/0405401; and U.S. patent application Ser. No. 16/454,741, titled MULTI-ACCESS PORT FOR SURGICAL ROBOTIC SYSTEMS, now U.S. Patent Application Publication No. 2020/0405416.

Applicant of the present application owns the following U.S. patent applications, filed on Dec. 4, 2018, the disclosure of each of which is herein incorporated by reference in its entirety:

U.S. patent application Ser. No. 16/209,385, titled METHOD OF HUB COMMUNICATION, PROCESSING, STORAGE AND DISPLAY;

U.S. patent application Ser. No. 16/209,395, titled METHOD OF HUB COMMUNICATION;

U.S. patent application Ser. No. 16/209,403, titled METHOD OF CLOUD BASED DATA ANALYTICS FOR USE WITH THE HUB;

U.S. patent application Ser. No. 16/209,407, titled METHOD OF ROBOTIC HUB COMMUNICATION, DETECTION, AND CONTROL;

U.S. patent application Ser. No. 16/209,416, titled METHOD OF HUB COMMUNICATION, PROCESSING, DISPLAY, AND CLOUD ANALYTICS;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS;

U.S. patent application Ser. No. 16/209,427, titled METHOD OF USING REINFORCED FLEXIBLE CIR-

CUITS WITH MULTIPLE SENSORS TO OPTIMIZE PERFORMANCE OF RADIO FREQUENCY DEVICES;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB;

U.S. patent application Ser. No. 16/209,447, titled METHOD FOR SMOKE EVACUATION FOR SURGICAL HUB;

U.S. patent application Ser. No. 16/209,453, titled METHOD FOR CONTROLLING SMART ENERGY DEVICES;

U.S. patent application Ser. No. 16/209,458, titled METHOD FOR SMART ENERGY DEVICE INFRASTRUCTURE;

U.S. patent application Ser. No. 16/209,465, titled METHOD FOR ADAPTIVE CONTROL SCHEMES FOR SURGICAL NETWORK CONTROL AND INTERACTION;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE;

U.S. patent application Ser. No. 16/209,490, titled METHOD FOR FACILITY DATA COLLECTION AND INTERPRETATION; and U.S. patent application Ser. No. 16/209,491, titled METHOD FOR CIRCULAR STAPLER CONTROL ALGORITHM ADJUSTMENT BASED ON SITUATIONAL AWARENESS.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 3:
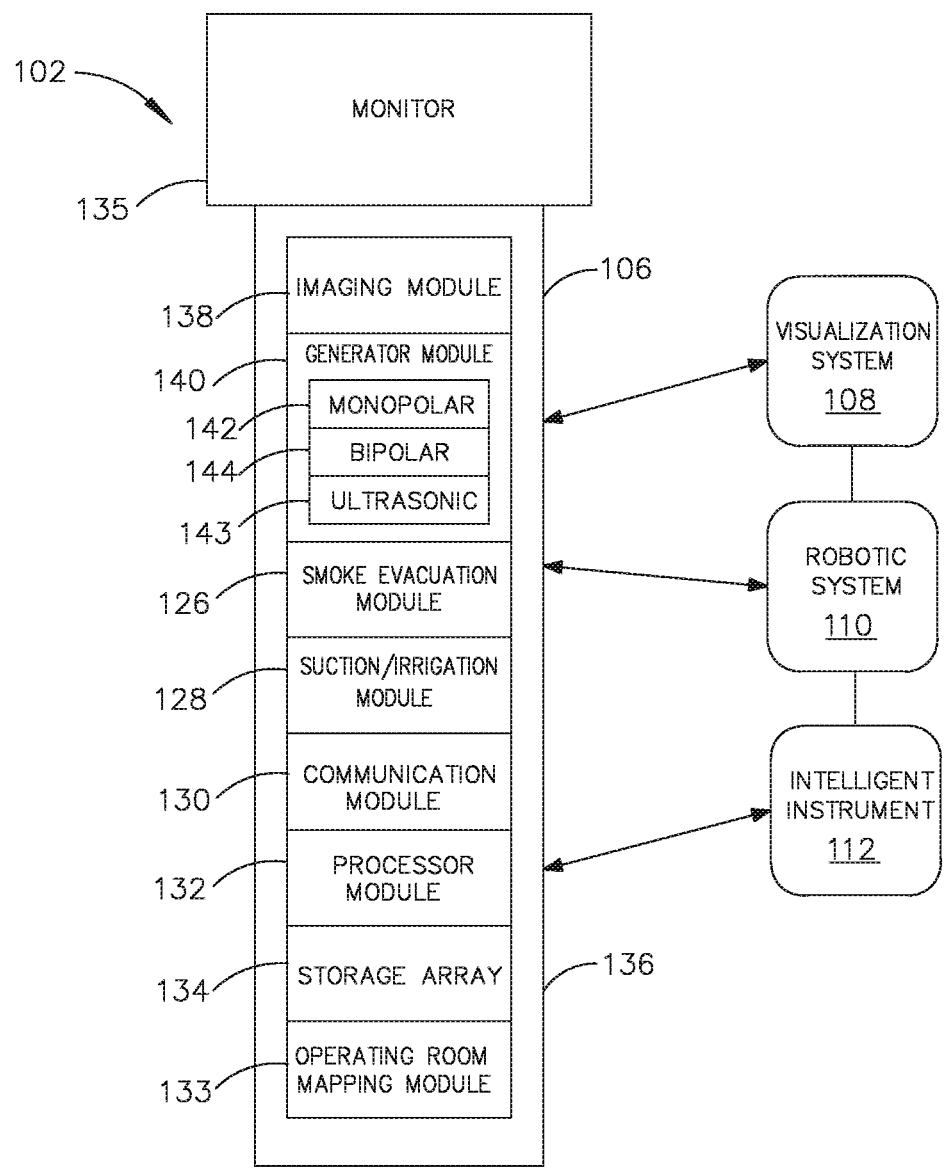
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
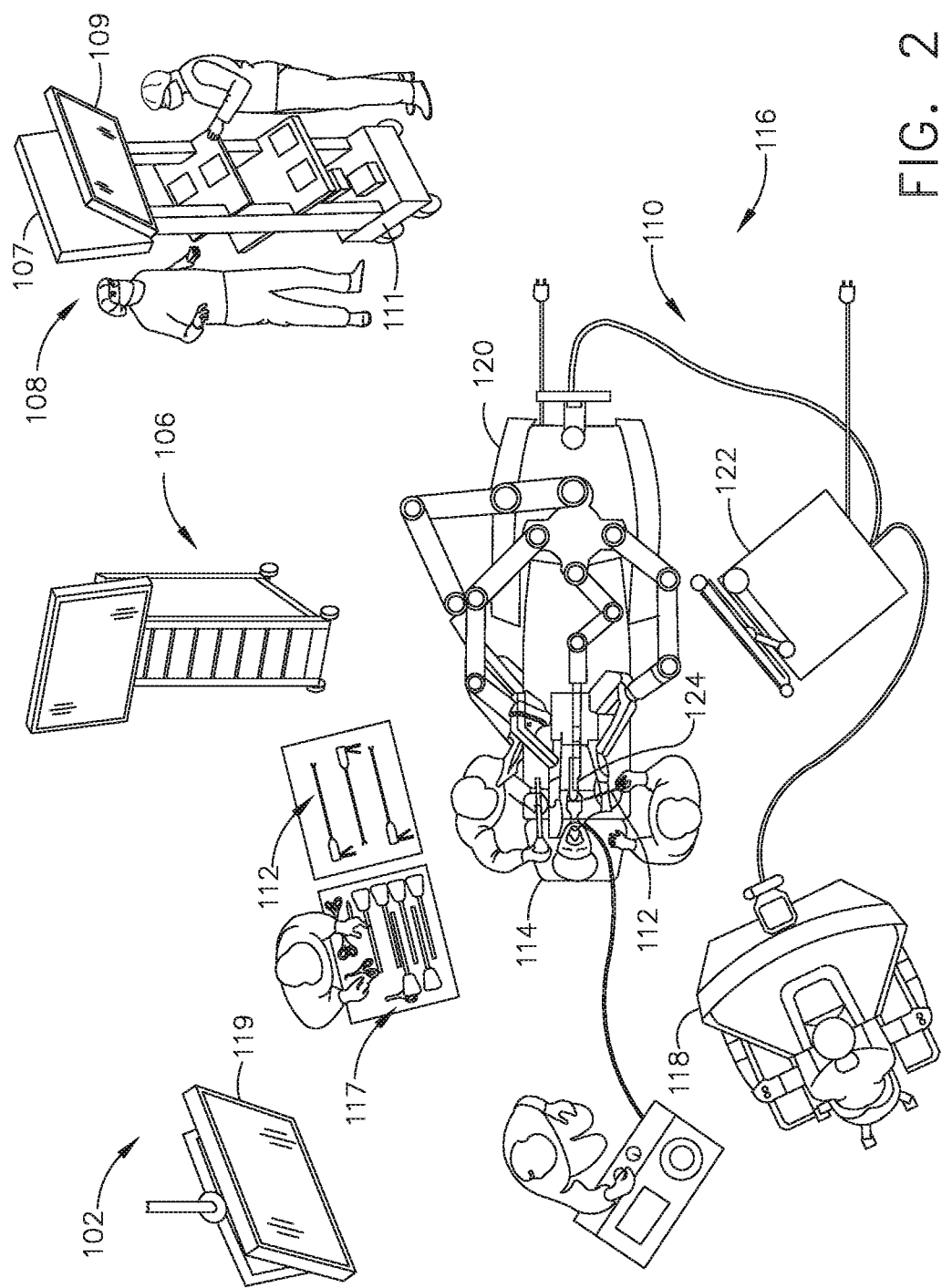
FIG. 2 is a surgical system being used to perform a surgical procedure in an operating room, in accordance with at least one aspect of the present disclosure.

In various aspects, the visualization system 108 includes one or more imaging sensors, one or more image processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snap-shot of a surgical site, as recorded by an imaging device 124, on a non-sterile display 107 or 109, while maintaining a live feed of the surgical site on the primary display 119. The snap-shot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snap-shot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts.

Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. The generator module 140 can be a generator module with integrated monopolar, bipolar, and ultrasonic components supported in a single housing unit slidably insertable into the hub modular enclosure 136. In various aspects, the hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane with external and wireless communication headers to enable the removable attachment of the modules 140, 126, 128 and interactive communication therebetween.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Robotic Surgical System

Figure 4:
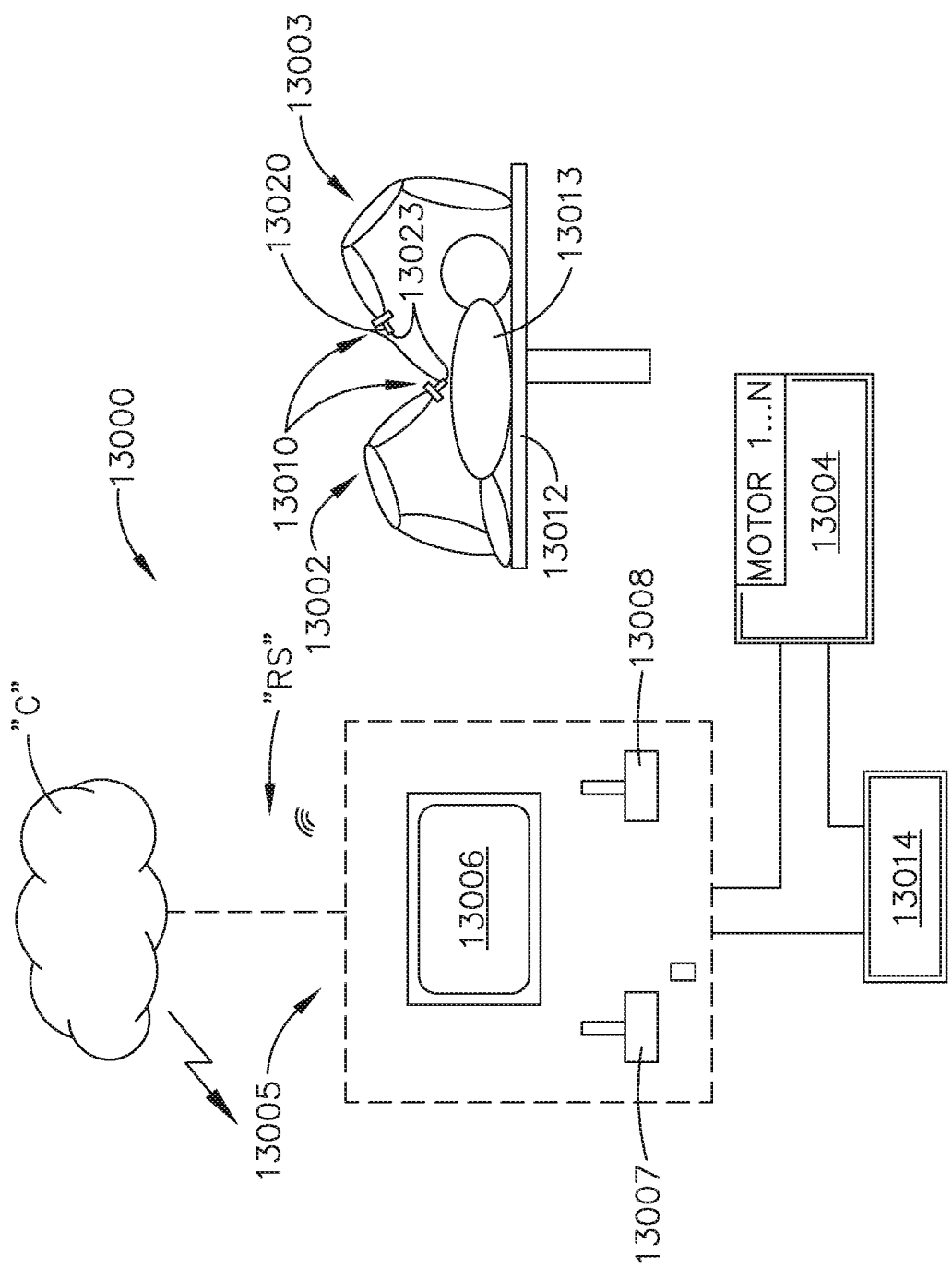
FIG. 4 is a schematic of a robotic surgical system, in accordance with at least one aspect of the present disclosure.
Figure 5:
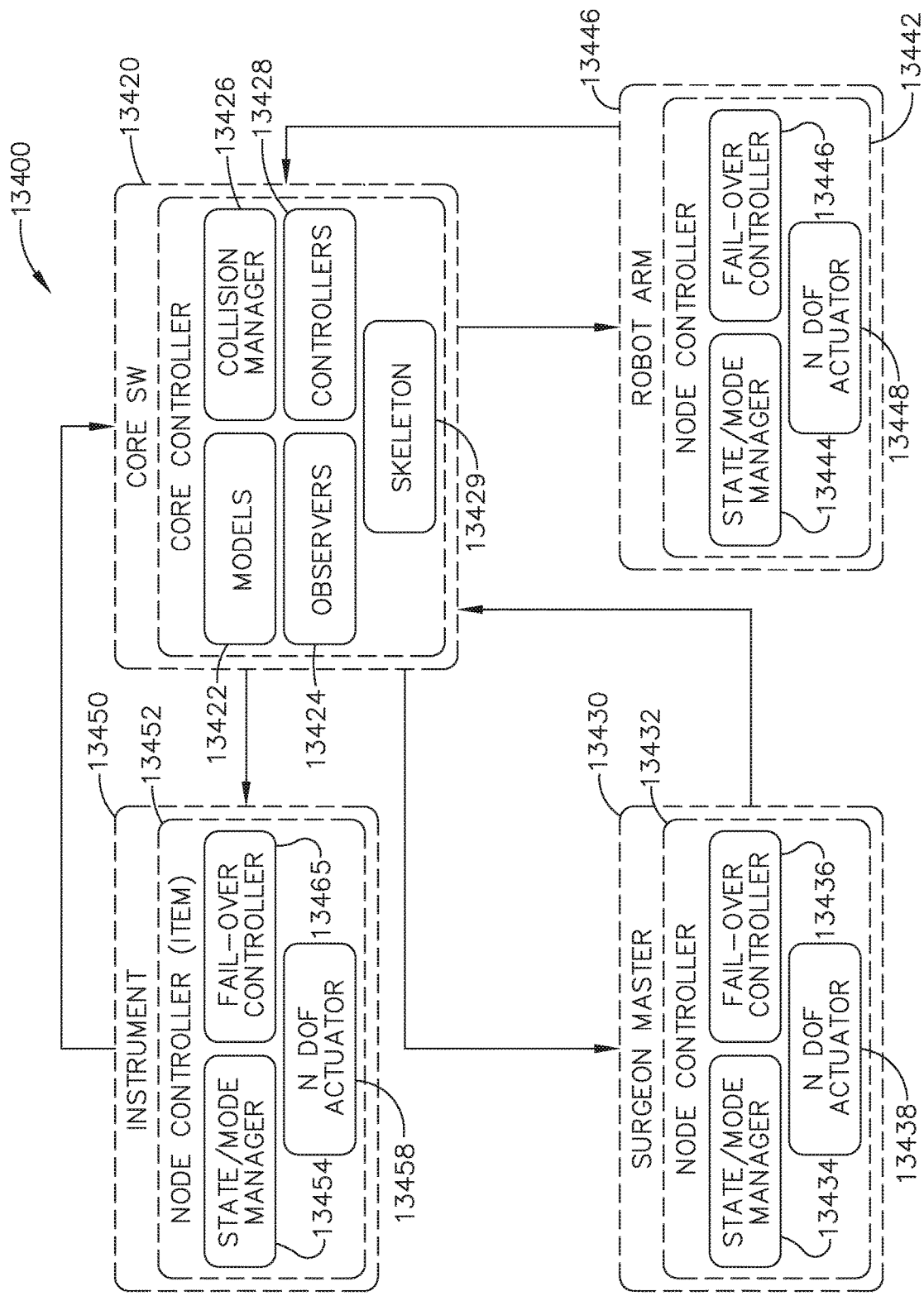
FIG. 5 is a block diagram of control components for the robotic surgical system of FIG. 4, in accordance with at least one aspect of the present disclosure.

An example robotic surgical system is depicted in FIGS. 4 and 5. With reference to FIG. 4, the robotic surgical system 13000 includes robotic arms 13002, 13003, a control device 13004, and a console 13005 coupled to the control device 13004. As illustrated in FIG. 4, the surgical system 13000 is configured for use on a patient 13013 lying on a patient table 13012 for performance of a minimally invasive surgical operation. The console 13005 includes a display device 13006 and input devices 13007, 13008. The display device 13006 is set up to display three-dimensional images, and the manual input devices 13007, 13008 are configured to allow a clinician to telemanipulate the robotic arms 13002, 13003. Controls for a surgeon's console, such as the console 13005, are further described in International Patent Publication No. WO2017/075121, filed Oct. 27, 2016, titled HAPTIC FEEDBACK FOR A ROBOTIC SURGICAL SYSTEM INTERFACE, which is herein incorporated by reference in its entirety.

Each of the robotic arms 13002, 13003 is made up of a plurality of members connected through joints and includes a surgical assembly 13010 connected to a distal end of a corresponding robotic arm 13002, 13003. Support of multiple arms is further described in U.S. Patent Application Publication No. 2017/0071693, filed Nov. 11, 2016, titled SURGICAL ROBOTIC ARM SUPPORT SYSTEMS AND METHODS OF USE, which is herein incorporated by reference in its entirety. Various robotic arm configurations are further described in International Patent Publication No. WO2017/044406, filed Sep. 6, 2016, titled ROBOTIC SURGICAL CONTROL SCHEME FOR MANIPULATING ROBOTIC END EFFECTORS, which is herein incorporated by reference in its entirety. In an exemplification, the surgical assembly 13010 includes a surgical instrument 13020 supporting an end effector 13023. Although two robotic arms 13002, 13003, are depicted, the surgical system 13000 may include a single robotic arm or more than two robotic arms 13002, 13003. Additional robotic arms are likewise connected to the control device 13004 and are telemanipulatable via the console 13005. Accordingly, one or more additional surgical assemblies 13010 and/or surgical instruments 13020 may also be attached to the additional robotic arm(s).

The robotic arms 13002, 13003 may be driven by electric drives that are connected to the control device 13004. According to an exemplification, the control device 13004 is configured to activate drives, for example, via a computer program, such that the robotic arms 13002, 13003 and the surgical assemblies 13010 and/or surgical instruments 13020 corresponding to the robotic arms 13002, 13003, execute a desired movement received through the manual input devices 13007, 13008. The control device 13004 may also be configured to regulate movement of the robotic arms 13002, 13003 and/or of the drives.

The control device 13004 may control a plurality of motors (for example, Motor 1 . . . n) with each motor configured to drive a pushing or a pulling of one or more cables, such as cables coupled to the end effector 13023 of the surgical instrument 13020. In use, as these cables are pushed and/or pulled, the one or more cables affect operation and/or movement of the end effector 13023. The control device 13004 coordinates the activation of the various motors to coordinate a pushing or a pulling motion of one or more cables in order to coordinate an operation and/or movement of one or more end effectors 13023. For example, articulation of an end effector by a robotic assembly such as the surgical assembly 13010 is further described in U.S. Patent Application Publication No. 2016/0303743, filed Jun. 6, 2016, titled WRIST AND JAW ASSEMBLIES FOR ROBOTIC SURGICAL SYSTEMS and in International Patent Publication No. WO2016/144937, filed Mar. 8, 2016, titled MEASURING HEALTH OF A CONNECTOR MEMBER OF A ROBOTIC SURGICAL SYSTEM, each of which is herein incorporated by reference in its entirety. In an exemplification, each motor is configured to actuate a drive rod or a lever arm to affect operation and/or movement of end effectors 13023 in addition to, or instead of, one or more cables.

Driver configurations for surgical instruments, such as drive arrangements for a surgical end effector, are further described in International Patent Publication No. WO2016/183054, filed May 10, 2016, titled COUPLING INSTRUMENT DRIVE UNIT AND ROBOTIC SURGICAL INSTRUMENT, International Patent Publication No. WO2016/205266, filed Jun. 15, 2016, titled ROBOTIC SURGICAL SYSTEM TORQUE TRANSDUCTION SENSING, International Patent Publication No. WO2016/205452, filed Jun. 16, 2016, titled CONTROLLING ROBOTIC SURGICAL INSTRUMENTS WITH BIDIRECTIONAL COUPLING, and International Patent Publication No. WO2017/053507, filed Sep. 22, 2016, titled ELASTIC SURGICAL INTERFACE FOR ROBOTIC SURGICAL SYSTEMS, each of which is herein incorporated by reference in its entirety. The modular attachment of surgical instruments to a driver is further described in International Patent Publication No. WO2016/209769, filed Jun. 20, 2016, titled ROBOTIC SURGICAL ASSEMBLIES, which is herein incorporated by reference in its entirety. Housing configurations for a surgical instrument driver and interface are further described in International Patent Publication No. WO2016/144998, filed Mar. 9, 2016, titled ROBOTIC SURGICAL SYSTEMS, INSTRUMENT DRIVE UNITS, AND DRIVE ASSEMBLIES, which is herein incorporated by reference in its entirety. Various surgical instrument configurations for use with the robotic arms 13002, 13003 are further described in International Patent Publication No. WO2017/053358, filed Sep. 21, 2016, titled SURGICAL ROBOTIC ASSEMBLIES AND INSTRUMENT ADAPTERS THEREOF and International Patent Publication No. WO2017/053363, filed Sep. 21, 2016, titled ROBOTIC SURGICAL ASSEMBLIES AND INSTRUMENT DRIVE CONNECTORS THEREOF, each of which is herein incorporated by reference in its entirety. Bipolar instrument configurations for use with the robotic arms 13002, 13003 are further described in International Patent Publication No. WO2017/053698, filed Sep. 23, 2016, titled ROBOTIC SURGICAL ASSEMBLIES AND ELECTROMECHANICAL INSTRUMENTS THEREOF, which is herein incorporated by reference in its entirety. Shaft arrangements for use with the robotic arms 13002, 13003 are further described in International Patent Publication No. WO2017/116793, filed Dec. 19, 2016, titled ROBOTIC SURGICAL SYSTEMS AND INSTRUMENT DRIVE ASSEMBLIES, which is herein incorporated by reference in its entirety.

The control device 13004 includes any suitable logic control circuit adapted to perform calculations and/or operate according to a set of instructions. The control device 13004 can be configured to communicate with a remote system "RS," either via a wireless (e.g., Wi-Fi, Bluetooth, LTE, etc.) and/or wired connection. The remote system "RS" can include data, instructions and/or information related to the various components, algorithms, and/or operations of system 13000. The remote system "RS" can include any suitable electronic service, database, platform, cloud "C" (see FIG. 4), or the like. The control device 13004 may include a central processing unit operably connected to memory. The memory may include transitory type memory (e.g., RAM) and/or non-transitory type memory (e.g., flash media, disk media, etc.). In some exemplifications, the memory is part of, and/or operably coupled to, the remote system "RS."

The control device 13004 can include a plurality of inputs and outputs for interfacing with the components of the system 13000, such as through a driver circuit. The control device 13004 can be configured to receive input signals and/or generate output signals to control one or more of the various components (e.g., one or more motors) of the system 13000. The output signals can include, and/or can be based upon, algorithmic instructions which may be pre-programmed and/or input by a user. The control device 13004 can be configured to accept a plurality of user inputs from a user interface (e.g., switches, buttons, touch screen, etc. of operating the console 13005) which may be coupled to remote system "RS."

A memory 13014 can be directly and/or indirectly coupled to the control device 13004 to store instructions and/or databases including pre-operative data from living being(s) and/or anatomical atlas(es). The memory 13014 can be part of, and/or or operatively coupled to, remote system "RS."

In accordance with an exemplification, the distal end of each robotic arm 13002, 13003 is configured to releasably secure the end effector 13023 (or other surgical tool) therein and may be configured to receive any number of surgical tools or instruments, such as a trocar or retractor, for example.

A simplified functional block diagram of a system architecture 13400 of the robotic surgical system 13010 is depicted in FIG. 5. The system architecture 13400 includes a core module 13420, a surgeon master module 13430, a robotic arm module 13440, and an instrument module 13450. The core module 13420 serves as a central controller for the robotic surgical system 13000 and coordinates operations of all of the other modules 13430, 13440, 13450. For example, the core module 13420 maps control devices to the arms 13002, 13003, determines current status, performs all kinematics and frame transformations, and relays resulting movement commands. In this regard, the core module 13420 receives and analyzes data from each of the other modules 13430, 13440, 13450 in order to provide instructions or commands to the other modules 13430, 13440, 13450 for execution within the robotic surgical system 13000. Although depicted as separate modules, one or more of the modules 13420, 13430, 13440, and 13450 are a single component in other exemplifications.

The core module 13420 includes models 13422, observers 13424, a collision manager 13426, controllers 13428, and a skeleton 13429. The models 13422 include units that provide abstracted representations (base classes) for controlled components, such as the motors (for example, Motor I . . . n) and/or the arms 13002, 13003. The observers 13424 create state estimates based on input and output signals received from the other modules 13430, 13440, 13450. The collision manager 13426 prevents collisions between components that have been registered within the system 13010. The skeleton 13429 tracks the system 13010 from a kinematic and dynamics point of view. For example, the kinematics item may be implemented either as forward or inverse kinematics, in an exemplification. The dynamics item may be implemented as algorithms used to model dynamics of the system's components.

The surgeon master module 13430 communicates with surgeon control devices at the console 13005 and relays inputs received from the console 13005 to the core module 13420. In accordance with an exemplification, the surgeon master module 13430 communicates button status and control device positions to the core module 13420 and includes a node controller 13432 that includes a state/mode manager 13434, a fail-over controller 13436, and a N-degree of freedom ("DOF") actuator 13438.

The robotic arm module 13440 coordinates operation of a robotic arm subsystem, an arm cart subsystem, a set up arm, and an instrument subsystem in order to control movement of a corresponding arm 13002, 13003. Although a single robotic arm module 13440 is included, it will be appreciated that the robotic arm module 13440 corresponds to and controls a single arm. As such, additional robotic arm modules 13440 are included in configurations in which the system 13010 includes multiple arms 13002, 13003. The robotic arm module 13440 includes a node controller 13442, a state/mode manager 13444, a fail-over controller 13446, and a N-degree of freedom ("DOF") actuator 13348.

The instrument module 13450 controls movement of an instrument and/or tool component attached to the arm 13002, 13003. The instrument module 13450 is configured to correspond to and control a single instrument. Thus, in configurations in which multiple instruments are included, additional instrument modules 13450 are likewise included. In an exemplification, the instrument module 13450 obtains and communicates data related to the position of the end effector or jaw assembly (which may include the pitch and yaw angle of the jaws), the width of or the angle between the jaws, and the position of an access port. The instrument module 13450 has a node controller 13452, a state/mode manager 13454, a fail-over controller 13456, and a N-degree of freedom ("DOF") actuator 13458.

The position data collected by the instrument module 13450 is used by the core module 13420 to determine when the instrument is within the surgical site, within a cannula, adjacent to an access port, or above an access port in free space. The core module 13420 can determine whether to provide instructions to open or close the jaws of the instrument based on the positioning thereof. For example, when the position of the instrument indicates that the instrument is within a cannula, instructions are provided to maintain a jaw assembly in a closed position. When the position of the instrument indicates that the instrument is outside of an access port, instructions are provided to open the jaw assembly.

Additional features and operations of a robotic surgical system, such as the surgical robot system depicted in FIGS. 4 and 5, are further described in the following references, each of which is herein incorporated by reference in its entirety:

U.S. Patent Application Publication No. 2016/0303743, filed Jun. 6, 2016, titled WRIST AND JAW ASSEMBLIES FOR ROBOTIC SURGICAL SYSTEMS;

U.S. Patent Application Publication No. 2017/0071693, filed Nov. 11, 2016, titled SURGICAL ROBOTIC ARM SUPPORT SYSTEMS AND METHODS OF USE;

International Patent Publication No. WO2016/144937, filed Mar. 8, 2016, titled MEASURING HEALTH OF A CONNECTOR MEMBER OF A ROBOTIC SURGICAL SYSTEM;

International Patent Publication No. WO2016/144998, filed Mar. 9, 2016, titled ROBOTIC SURGICAL SYSTEMS, INSTRUMENT DRIVE UNITS, AND DRIVE ASSEMBLIES;

International Patent Publication No. WO2016/183054, filed May 10, 2016, titled COUPLING INSTRUMENT DRIVE UNIT AND ROBOTIC SURGICAL INSTRUMENT;

International Patent Publication No. WO2016/205266, filed Jun. 15, 2016, titled ROBOTIC SURGICAL SYSTEM TORQUE TRANSDUCTION SENSING;

International Patent Publication No. WO2016/205452, filed Jun. 16, 2016, titled CONTROLLING ROBOTIC SURGICAL INSTRUMENTS WITH BIDIRECTIONAL COUPLING;

International Patent Publication No. WO2016/209769, filed Jun. 20, 2016, titled ROBOTIC SURGICAL ASSEMBLIES;

International Patent Publication No. WO2017/044406, filed Sep. 6, 2016, titled ROBOTIC SURGICAL CONTROL SCHEME FOR MANIPULATING ROBOTIC END EFFECTORS;

International Patent Publication No. WO2017/053358, filed Sep. 21, 2016, titled SURGICAL ROBOTIC ASSEMBLIES AND INSTRUMENT ADAPTERS THEREOF;

International Patent Publication No. WO2017/053363, filed Sep. 21, 2016, titled ROBOTIC SURGICAL ASSEMBLIES AND INSTRUMENT DRIVE CONNECTORS THEREOF;

International Patent Publication No. WO2017/053507, filed Sep. 22, 2016, titled ELASTIC SURGICAL INTERFACE FOR ROBOTIC SURGICAL SYSTEMS;

International Patent Publication No. WO2017/053698, filed Sep. 23, 2016, titled ROBOTIC SURGICAL ASSEMBLIES AND ELECTROMECHANICAL INSTRUMENTS THEREOF;

International Patent Publication No. WO2017/075121, filed Oct. 27, 2016, titled HAPTIC FEEDBACK CONTROLS FOR A ROBOTIC SURGICAL SYSTEM INTERFACE;

International Patent Publication No. WO2017/116793, filed Dec. 19, 2016, titled ROBOTIC SURGICAL SYSTEMS AND INSTRUMENT DRIVE ASSEMBLIES.

The robotic surgical systems and features disclosed herein can be employed with the robotic surgical system of FIGS. 4 and 5. The reader will further appreciate that various systems and/or features disclosed herein can also be employed with alternative surgical systems including the computer-implemented interactive surgical system 100, the computer-implemented interactive surgical system 200, the robotic surgical system 110, the robotic hub 122, and/or the robotic hub 222, for example.

In various instances, a robotic surgical system can include a robotic control tower, which can house the control unit of the system. For example, the control unit 13004 of the robotic surgical system 13000 (FIG. 4) can be housed within a robotic control tower. The robotic control tower can include a robotic hub such as the robotic hub 122 (FIG. 2) or the robotic hub 222 (FIG. 9), for example. Such a robotic hub can include a modular interface for coupling with one or more generators, such as an ultrasonic generator and/or a radio frequency generator, and/or one or more modules, such as an imaging module, suction module, an irrigation module, a smoke evacuation module, and/or a communication module.

A robotic hub can include a situational awareness module, which can be configured to synthesize data from multiple sources to determine an appropriate response to a surgical event. For example, a situational awareness module can determine the type of surgical procedure, step in the surgical procedure, type of tissue, and/or tissue characteristics, as further described herein. Moreover, such a module can recommend a particular course of action or possible choices to the robotic system based on the synthesized data. In various instances, a sensor system encompassing a plurality of sensors distributed throughout the robotic system can provide data, images, and/or other information to the situational awareness module. Such a situational awareness module can be incorporated into a control unit, such as the control unit 13004, for example. In various instances, the situational awareness module can obtain data and/or information from a non-robotic surgical hub and/or a cloud, such as the surgical hub 106 (FIG. 1), the surgical hub 206 (FIG. 10), the cloud 104 (FIG. 1), and/or the cloud 204 (FIG. 9), for example. Situational awareness of a surgical system is further disclosed herein and in U.S. Provisional Patent Application Ser. No. 62/611,341, titled INTERACTIVE SURGICAL PLATFORM, filed Dec. 28, 2017, and U.S. Provisional Patent Application Ser. No. 62/611,340, titled CLOUD-BASED MEDICAL ANALYTICS, filed Dec. 28, 2017, the disclosure of each of which is herein incorporated by reference in its entirety.

In certain instances, the activation of a surgical tool at certain times during a surgical procedure and/or for certain durations may cause tissue trauma and/or may prolong a surgical procedure. For example, a robotic surgical system can utilize an electrosurgical tool having an energy delivery surface that should only be energized when a threshold condition is met. In one example, the energy delivery surface should only be activated when the energy delivery surface is in contact with the appropriate, or targeted, tissue. As another example, a robotic surgical system can utilize a suction element that should only be activated when a threshold condition is met, such as when an appropriate volume of fluid is present. Due to visibility restrictions, evolving situations, and the multitude of moving parts during a robotic surgical procedure, it can be difficult for a clinician to determine and/or monitor certain conditions at the surgical site. For example, it can be difficult to determine if an energy delivery surface of an electrosurgical tool is in contact with tissue. It can also be difficult to determine if a particular suctioning pressure is sufficient for the volume of fluid in the proximity of the suctioning port.

Moreover, a plurality of surgical devices can be used in certain robotic surgical procedures. For example, a robotic surgical system can use one or more surgical tools during the surgical procedure. Additionally, one or more handheld instruments can also be used during the surgical procedure. One or more of the surgical devices can include a sensor. For example, multiple sensors can be positioned around the surgical site and/or the operating room. A sensor system including the one or more sensors can be configured to detect one or more conditions at the surgical site. For example, data from the sensor system can determine if a surgical tool mounted to the surgical robot is being used and/or if a feature of the surgical tool should be activated. More specifically, a sensor system can detect if an electrosurgical device is positioned in abutting contact with tissue, for example. As another example, a sensor system can detect if a suctioning element of a surgical tool is applying a sufficient suctioning force to fluid at the surgical site.

When in an automatic activation mode, the robotic surgical system can automatically activate one or more features of one or more surgical tools based on data, images, and/or other information received from the sensor system. For example, an energy delivery surface of an electrosurgical tool can be activated upon detecting that the electrosurgical tool is in use (e.g. positioned in abutting contact with tissue). As another example, a suctioning element on a surgical tool can be activated when the suction port is moved into contact with a fluid. In certain instances, the surgical tool can be adjusted based on the sensed conditions.

A robotic surgical system incorporating an automatic activation mode can automatically provide a scenario-specific result based on detected condition(s) at the surgical site. The scenario-specific result can be outcome-based, for example, and can streamline the decision-making process of the clinician. In certain instances, such an automatic activation mode can improve the efficiency and/or effectiveness of the clinician. For example, the robotic surgical system can aggregate data to compile a more complete view of the surgical site and/or the surgical procedure in order to determine the best possible course of action. Additionally or alternatively, in instances in which the clinician makes fewer decisions, the clinician can be better focused on other tasks and/or can process other information more effectively.

Figure 6:
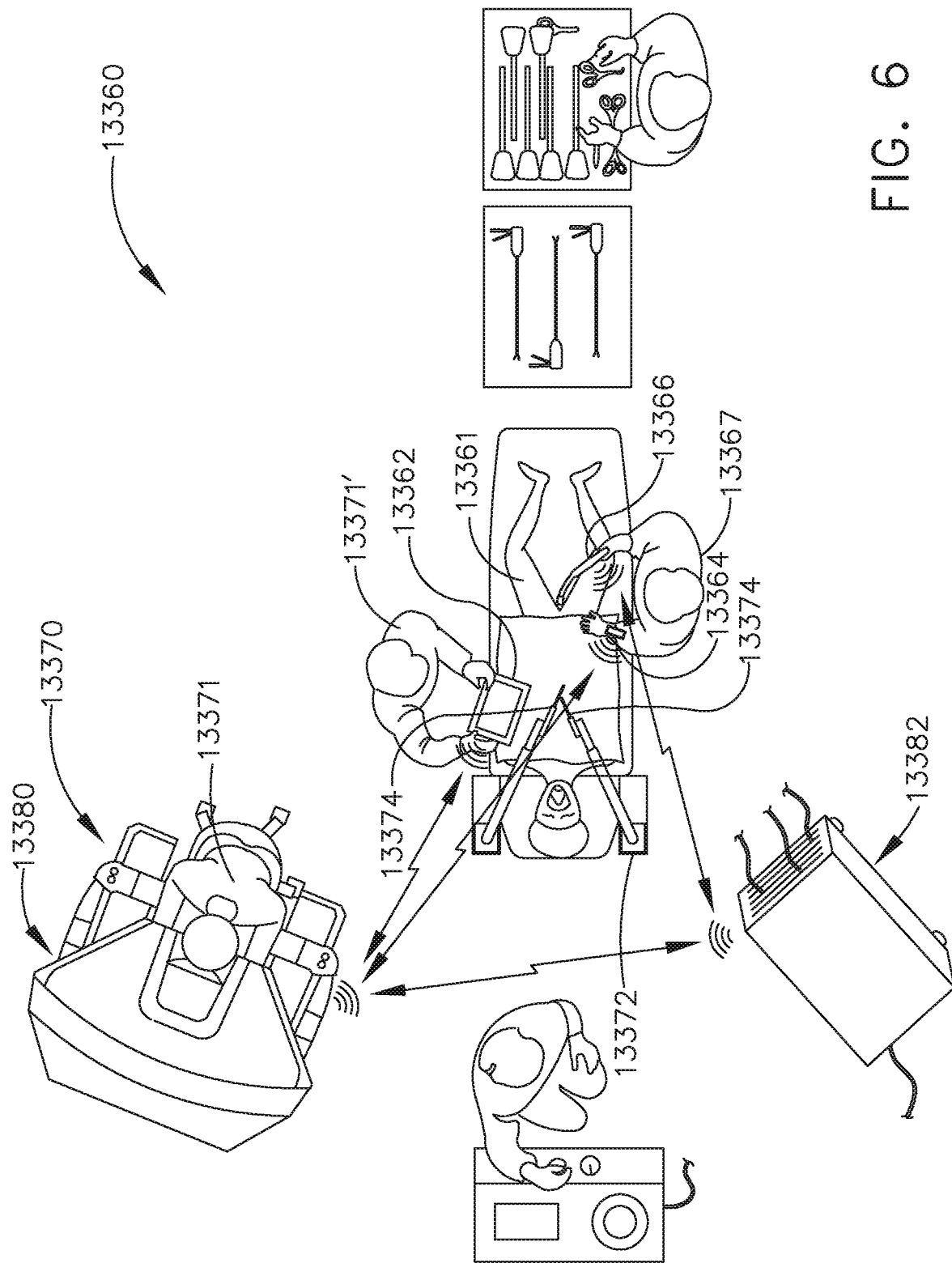
FIG. 6 is a schematic of a robotic surgical system during a surgical procedure including a plurality of hubs and interactive secondary displays, in accordance with at least one aspect of the present disclosure.
Figure 7:
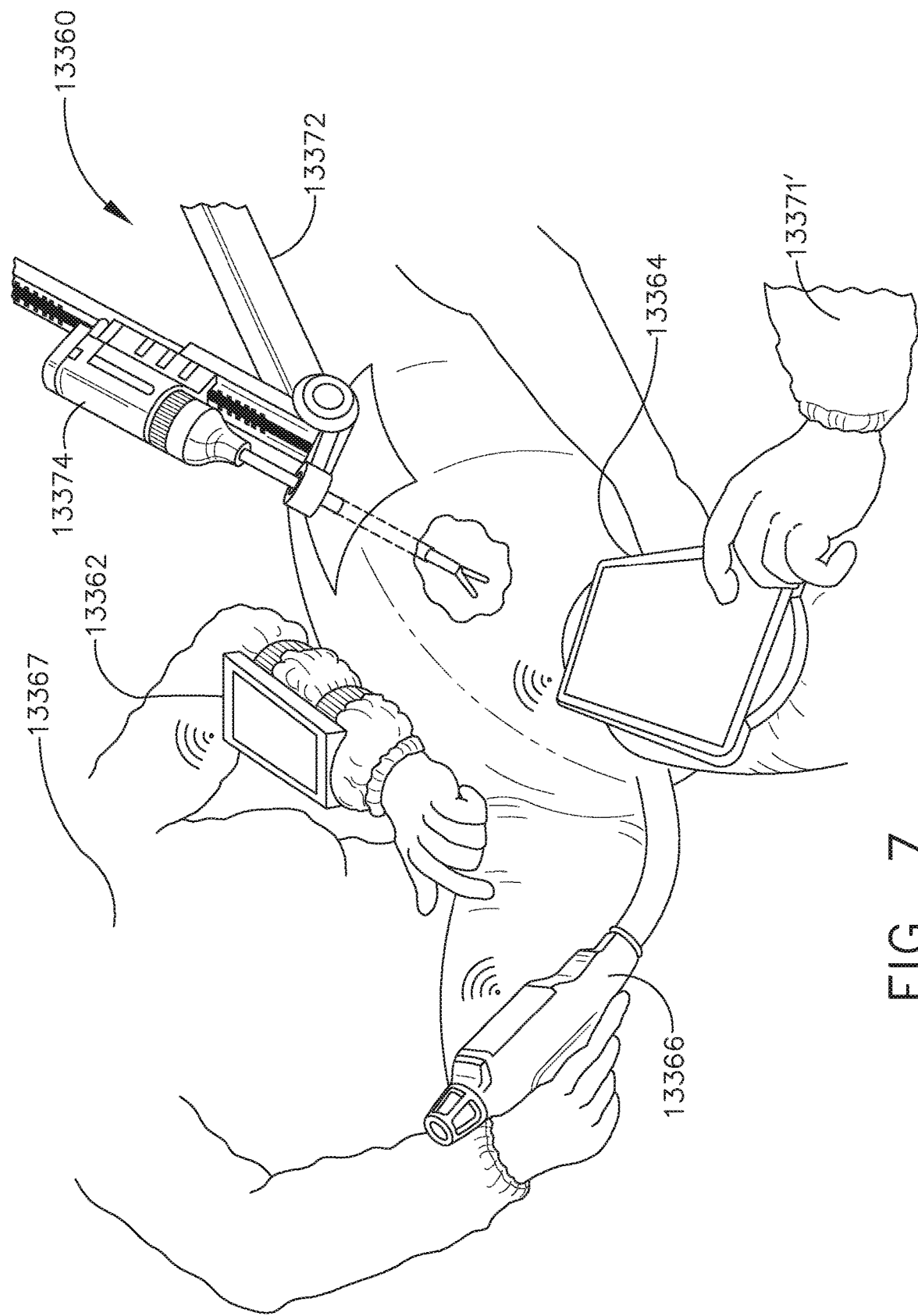
FIG. 7 is a detail view of the interactive secondary displays of FIG. 6, in accordance with at least one aspect of the present disclosure.

Referring primarily to FIGS. 6 and 7, hubs 13380, 13382 include wireless communication modules such that a wireless communication link is established between the two hubs 13380, 13382. Additionally, the robotic hub 13380 is in signal communication with the interactive secondary displays 13362, 13364 within the sterile field. The hub 13382 is in signal communication with the handheld surgical instrument 13366. If the surgeon 13371 moves over towards the patient 13361 and within the sterile field (as indicated by the reference character 13371'), the surgeon 13371 can use one of the wireless interactive displays 13362, 13364 to operate the robot 13372 away from the remote command console 13370. The plurality of secondary displays 13362, 13364 within the sterile field allows the surgeon 13371 to move away from the remote command console 13370 without losing sight of important information for the surgical procedure and controls for the robotic tools utilized therein.

The interactive secondary displays 13362, 13364 permit the clinician to step away from the remote command console 13370 and into the sterile field while maintaining control of the robot 13372. For example, the interactive secondary displays 13362, 13364 allow the clinician to maintain cooperative and/or coordinated control over the powered handheld surgical instrument(s) 13366 and the robotic surgical system at the same time. In various instances, information is communicated between the robotic surgical system, one or more powered handheld surgical instruments 13366, surgical hubs 13380, 13382, and the interactive secondary displays 13362, 13364. Such information may include, for example, the images on the display of the robotic surgical system and/or the powered handheld surgical instruments, a parameter of the robotic surgical system and/or the powered handheld surgical instruments, and/or a control command for the robotic surgical system and/or the powered handheld surgical instruments.

In various instances, the control unit of the robotic surgical system (e.g. the control unit 13113 of the robotic surgical system 13110) is configured to communicate at least one display element from the surgeon's command console (e.g. the console 13116) to an interactive secondary display (e.g. the displays 13362, 13364). In other words, a portion of the display at the surgeon's console is replicated on the display of the interactive secondary display, integrating the robot display with the interactive secondary display. The replication of the robot display on to the display of the interactive secondary display allows the clinician to step away from the remote command console without losing the visual image that is displayed there. For example, at least one of the interactive secondary displays 13362, 13364 can display information from the robot, such as information from the robot display and/or the surgeon's command console 13370.

In various instances, the interactive secondary displays 13362, 13364 are configured to control and/or adjust at least one operating parameter of the robotic surgical system. Such control can occur automatically and/or in response to a clinician input. Interacting with a touch-sensitive screen and/or buttons on the interactive secondary display(s) 13362, 13364, the clinician is able to input a command to control movement and/or functionality of the one or more robotic tools. For example, when utilizing a handheld surgical instrument 13366, the clinician may want to move the robotic tool 13374 to a different position. To control the robotic tool 13374, the clinician applies an input to the interactive secondary display(s) 13362, 13364, and the respective interactive secondary display(s) 13362, 13364 communicates the clinician input to the control unit of the robotic surgical system in the robotic hub 13380.

In various instances, a clinician positioned at the remote command console 13370 of the robotic surgical system can manually override any robot command initiated by a clinician input on the one or more interactive secondary displays 13362, 13364. For example, when a clinician input is received from the one or more interactive secondary displays 13362, 13364, a clinician positioned at the remote command console 13370 can either allow the command to be issued and the desired function performed or the clinician can override the command by interacting with the remote command console 13370 and prohibiting the command from being issued.

In certain instances, a clinician within the sterile field can be required to request permission to control the robot 13372 and/or the robotic tool 13374 mounted thereto. The surgeon 13371 at the remote command console 13370 can grant or deny the clinician's request. For example, the surgeon can receive a pop-up or other notification indicating the permission is being requested by another clinician operating a handheld surgical instrument and/or interacting with an interactive secondary display 13362, 13364.

In various instances, the processor of a robotic surgical system, such as the robotic surgical systems 13000 (FIG. 4), 13400 (FIG. 5), 13360 (FIG. 6), and/or the surgical hub 13380, 13382, for example, is programmed with pre-approved functions of the robotic surgical system. For example, if a clinician input from the interactive secondary display 13362, 13364 corresponds to a pre-approved function, the robotic surgical system allows for the interactive secondary display 13362, 13364 to control the robotic surgical system and/or does not prohibit the interactive secondary display 13362, 13364 from controlling the robotic surgical system. If a clinician input from the interactive secondary display 13362, 13364 does not correspond to a pre-approved function, the interactive secondary display 13362, 13364 is unable to command the robotic surgical system to perform the desired function. In one instances, a situational awareness module in the robotic hub 13370 and/or the surgical hub 13382 is configured to dictate and/or influence when the interactive secondary display can issue control motions to the robot surgical system.

In various instances, an interactive secondary display 13362, 13364 has control over a portion of the robotic surgical system upon making contact with the portion of the robotic surgical system. For example, when the interactive secondary display 13362, 13364 is brought into contact with the robotic tool 13374, control of the contacted robotic tool 13374 is granted to the interactive secondary display 13362, 13364. A clinician can then utilize a touch-sensitive screen and/or buttons on the interactive secondary display 13362, 13364 to input a command to control movement and/or functionality of the contacted robotic tool 13374. This control scheme allows for a clinician to reposition a robotic arm, reload a robotic tool, and/or otherwise reconfigure the robotic surgical system. In a similar manner as discussed above, the clinician 13371 positioned at the remote command console 13370 of the robotic surgical system can manually override any robot command initiated by the interactive secondary display 13362, 13364.

In one aspect, the robotic surgical system includes a processor and a memory communicatively coupled to the processor, as described herein. The memory stores instructions executable by the processor to receive a first user input from a console and to receive a second user input from a mobile wireless control module for controlling a function of a robotic surgical tool, as described herein.

In various aspects, the present disclosure provides a control circuit to receive a first user input from a console and to receive a second user input from a mobile wireless control module for controlling a function of a robotic surgical tool, as described herein. In various aspects, the present disclosure provides a non-transitory computer readable medium storing computer readable instructions which, when executed, cause a machine to receive a first user input from a console and to receive a second user input from a mobile wireless control module for controlling a function of a robotic surgical tool, as described herein.

A robotic surgical system may include multiple robotic arms that are configured to assist the clinician during a surgical procedure. Each robotic arm may be operable independently of the others. A lack of communication may exist between each of the robotic arms as they are independently operated, which may increase the risk of tissue trauma. For example, in a scenario where one robotic arm is configured to apply a force that is stronger and in a different direction than a force configured to be applied by a second robotic arm, tissue trauma can result. For example, tissue trauma and/or tearing may occur when a first robotic arm applies a strong retracting force to the tissue while a second robotic arm is configured to rigidly hold the tissue in place.

In various instances, one or more sensors are attached to each robotic arm of a robotic surgical system. The one or more sensors are configured to sense a force applied to the surrounding tissue during the operation of the robotic arm. Such forces can include, for example, a holding force, a retracting force, and/or a dragging force. The sensor from each robotic arm is configured to communicate the magnitude and direction of the detected force to a control unit of the robotic surgical system. The control unit is configured to analyze the communicated forces and set limits for maximum loads to avoid causing trauma to the tissue in a surgical site. For example, the control unit may minimize the holding force applied by a first robotic arm if the retracting or dragging force applied by a second robotic arm increases.

Figure 4A:
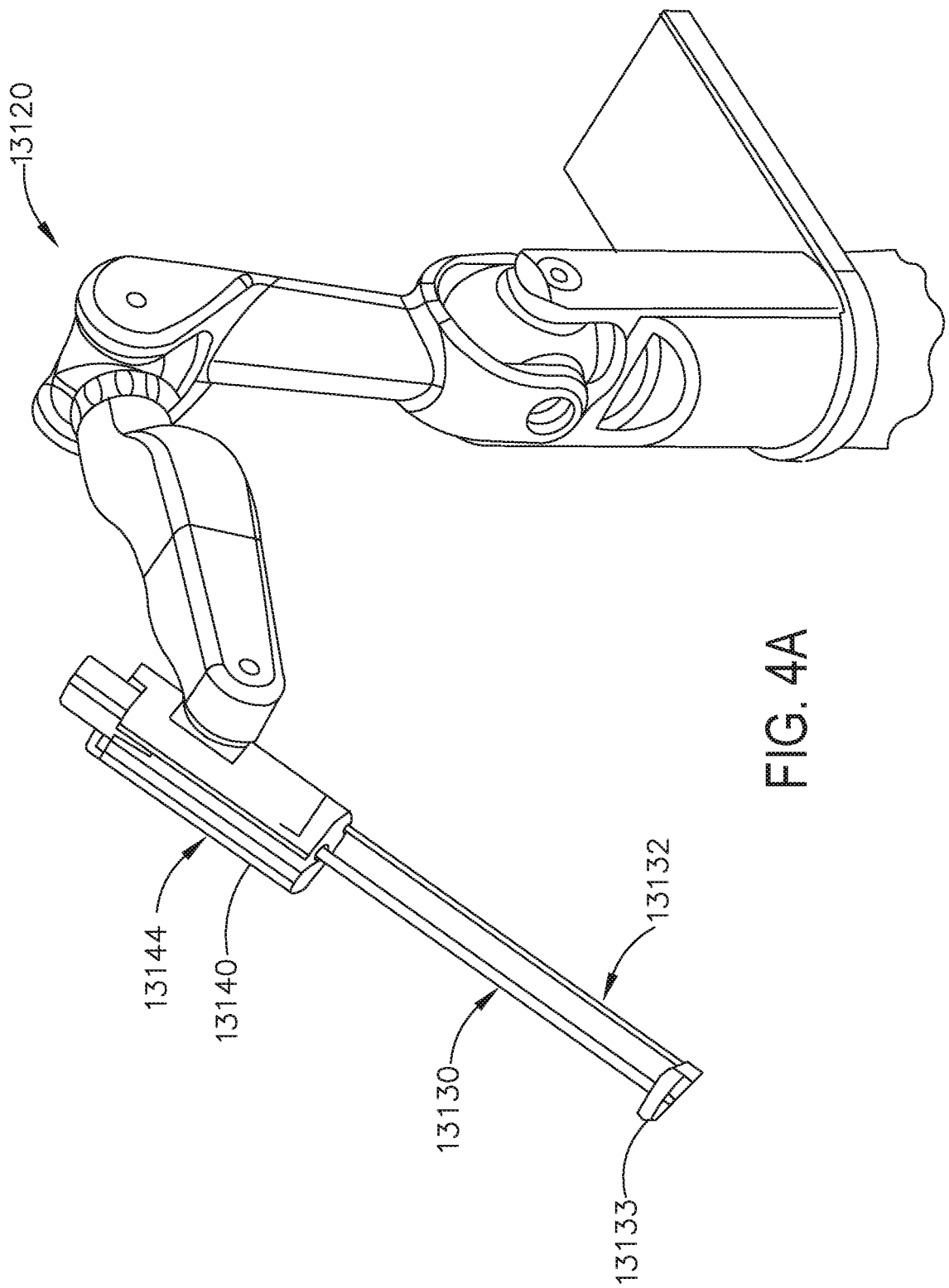
FIG. 4A illustrates another exemplification of a robotic arm and another exemplification of a tool assembly releasably coupled to the robotic arm, according to one aspect of the present disclosure.

FIG. 4a illustrates an exemplification of a robotic arm 13120 and a tool assembly 13130 releasably coupled to the robotic arm 13120. The robotic arm 13120 can support and move the associated tool assembly 13130 along one or more mechanical degrees of freedom (e.g., all six Cartesian degrees of freedom, five or fewer Cartesian degrees of freedom, etc.).

The robotic arm 13120 can include a tool driver 13140 at a distal end of the robotic arm 13120, which can assist with controlling features associated with the tool assembly 13130. The robotic arm 13120 can also include a movable tool guide 13132 that can retract and extend relative to the tool driver 13140. A shaft of the tool assembly 13130 can extend parallel to a threaded shaft of the movable tool guide 13132 and can extend through a distal end feature 13133 (e.g., a ring) of the movable tool guide 13132 and into a patient.

In order to provide a sterile operation area while using the surgical system, a barrier can be placed between the actuating portion of the surgical system (e.g., the robotic arm 13120) and the surgical instruments (e.g., the tool assembly 13130) in the sterile surgical field. A sterile component, such as an instrument sterile adapter (ISA), can also be placed at the connecting interface between the tool assembly 13130 and the robotic arm 13120, The placement of an ISA between the tool assembly 13130 and the robotic arm 13120 can ensure a sterile coupling point for the tool assembly 13130 and the robotic arm 13120. This permits removal of tool assemblies 13130 from the robotic arm 13120 to exchange with other tool assemblies 13130 during the course of a surgery without compromising the sterile surgical field.

The tool assembly 13130 can be loaded from a top side of the tool driver 13140 with the shaft of the tool assembly 13130 being positioned in a shaft-receiving channel 13144 formed along the side of the tool driver 13140. The shaft-receiving channel 13144 allows the shaft, which extends along a central axis of the tool assembly 13130, to extend along a central axis of the tool driver 13140 when the tool assembly 13130 is coupled to the tool driver 13140, In other exemplifications, the shaft can extend through on opening in the tool driver 13140, or the two components can mate in various other configurations.

As discussed above, the robotic surgical system can include one or more robotic arms with each robotic arm having a tool assembly coupled thereto. Each tool assembly can include an end effector that has one or more of a variety of features, such as one or more tools for assisting with performing a surgical procedure. For example, the end effector can include a cutting or boring tool that can be used to perforate or cut through tissue (e.g., create an incision).

Furthermore, some end effectors include one or more sensors that can sense a variety of characteristics associated with either the end effector or the tissue. Each robotic arm and end effector can be controlled by a control system to assist with creating a desired cut or bore and prevent against undesired cutting of tissue. As an alternative to (or in addition to) controlling the robotic arm, it is understood that the control system can control either the tool itself or the tool assembly.

One or more aspects associated with the movement of the robotic arm can be controlled by the control system, such as either a direction or a velocity of movement. For example, when boring through tissue, the robotic arm can be controlled to perform jackhammer-like movements with the cutting tool. Such jackhammer movements can include the robotic arm moving up and down along an axis (e.g., an axis that is approximately perpendicular to the tissue being perforated) in a rapid motion while also advancing the cutting tool in a downward direction towards the tissue to eventually perforate the tissue with the cutting tool (e.g. an ultrasonic blade). While performing such movements in a robotic surgical procedure, not only can it be difficult to see the tissue being perforated to thereby determine a relative position of the cutting tool, but it can also be difficult to determine when the cutting tool has completed perforating the tissue. Such position of the cutting tool relative to the tissue can include the cutting tool approaching or not yet in contact with the tissue, the cutting tool drilling down or cutting into the tissue, and the cutting tool extending through or having perforated the tissue. These positions can be difficult for either a user controlling the robotic arm or the robotic surgical system to determine which can result in potential harm to the patient due to over or under-penetrating the tissue, as well as result in longer procedure times. As such, in order to reduce procedure time and surgical errors, the robotic surgical system includes a control system that communicates with at least one sensor assembly configured to sense a force applied at a distal end of the end effector or cutting tool. The control system can thereby determine and control, based on such sensed forces, one or more appropriate aspects associated with the movement of the robotic arm, such as when boring or cutting into tissue, as will be described in greater detail below.

Although a cutting tool for perforating tissue is described in detail herein, the sensor assembly of the present disclosure that is in communication with the control system can be implemented in any number of robotic surgical systems for detecting any number of a variety of tools and/or end effectors used for performing any number of a variety of procedures without departing from the scope of this disclosure. Furthermore, any number of movements can be performed by the robotic arm to perforate or cut tissue using the robotic surgical system including the sensor assembly and control system described herein and is not limited to the jackhammering or boring of tissue.

FIG. 4a and additional exemplifications are further described in U.S. patent application Ser. No. 15/237,753, entitled CONTROL OF ADVANCEMENT RATE AND APPLICATION FORCE BASED ON MEASURED FORCES, filed Aug. 16, 2016, the entire disclosure of which is incorporated by reference herein.

The entire disclosures of:

U.S. Pat. No. 9,072,535, filed May 27, 2011, entitled SURGICAL STAPLING INSTRUMENTS WITH ROTATABLE STAPLE DEPLOYMENT ARRANGEMENTS, which issued Jul. 7, 2015;

U.S. Pat. No. 9,072,536, filed Jun. 28, 2012, entitled DIFFERENTIAL LOCKING ARRANGEMENTS FOR ROTARY POWERED SURGICAL INSTRUMENTS, which issued Jul. 7, 2015;

U.S. Pat. No. 9,204,879, filed Jun. 28, 2012, entitled FLEXIBLE DRIVE MEMBER, which issued on Dec. 8, 2015;

U.S. Pat. No. 9,561,038, filed Jun. 28, 2012, entitled INTERCHANGEABLE CLIP APPLIER, which issued on Feb. 7, 2017;

U.S. Pat. No. 9,757,128, filed Sep. 5, 2014, entitled MULTIPLE SENSORS WITH ONE SENSOR AFFECTING A SECOND SENSOR'S OUTPUT OR INTERPRETATION, which issued on Sep. 12, 2017;

U.S. patent application Ser. No. 14/640,935, entitled OVERLAID MULTI SENSOR RADIO FREQUENCY (RF) ELECTRODE SYSTEM TO MEASURE TISSUE COMPRESSION, filed Mar. 6, 2015, now U.S. Patent Application Publication No. 2016/0256071;

U.S. patent application Ser. No. 15/382,238, entitled MODULAR BATTERY POWERED HANDHELD SURGICAL INSTRUMENT WITH SELECTIVE APPLICATION OF ENERGY BASED ON TISSUE CHARACTERIZATION, filed Dec. 16, 2016, now U.S. Patent Application Publication No. 2017/0202591; and U.S. patent application Ser. No. 15/237,753, entitled CONTROL OF ADVANCEMENT RATE AND APPLICATION FORCE BASED ON MEASURED FORCES, filed Aug. 16, 2016 are hereby incorporated by reference herein in their respective entireties.

The surgical devices, systems, and methods disclosed herein can be implemented with a variety of different robotic surgical systems and surgical devices. Surgical devices include robotic surgical tools and handheld surgical instruments. The reader will readily appreciate that certain devices, systems, and methods disclosed herein are not limited to applications within a robotic surgical system. For example, certain systems, devices, and methods for communicating, detecting, and/or control a surgical device can be implemented without a robotic surgical system.

Surgical Network

Figure 8:
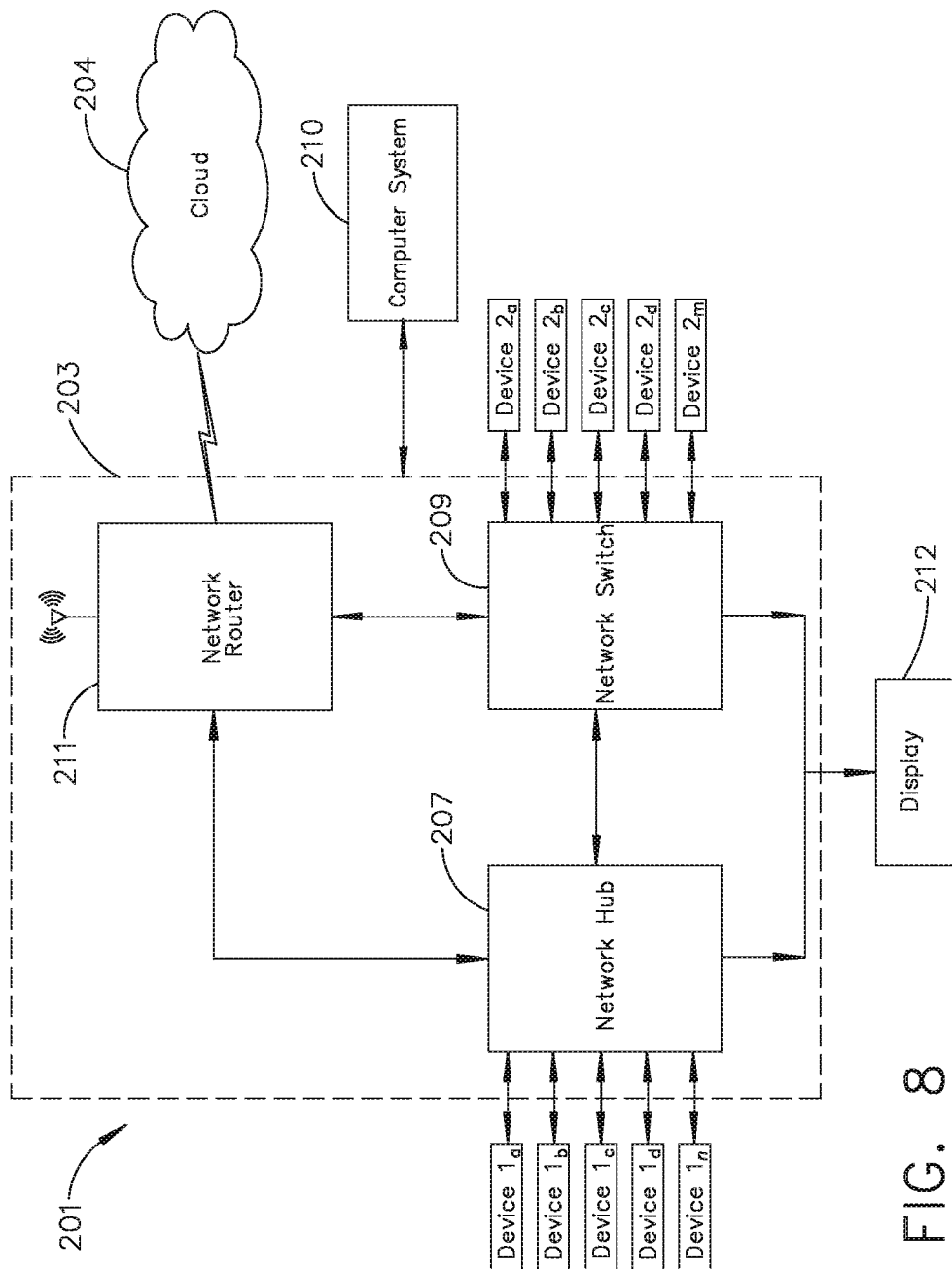
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/internet protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
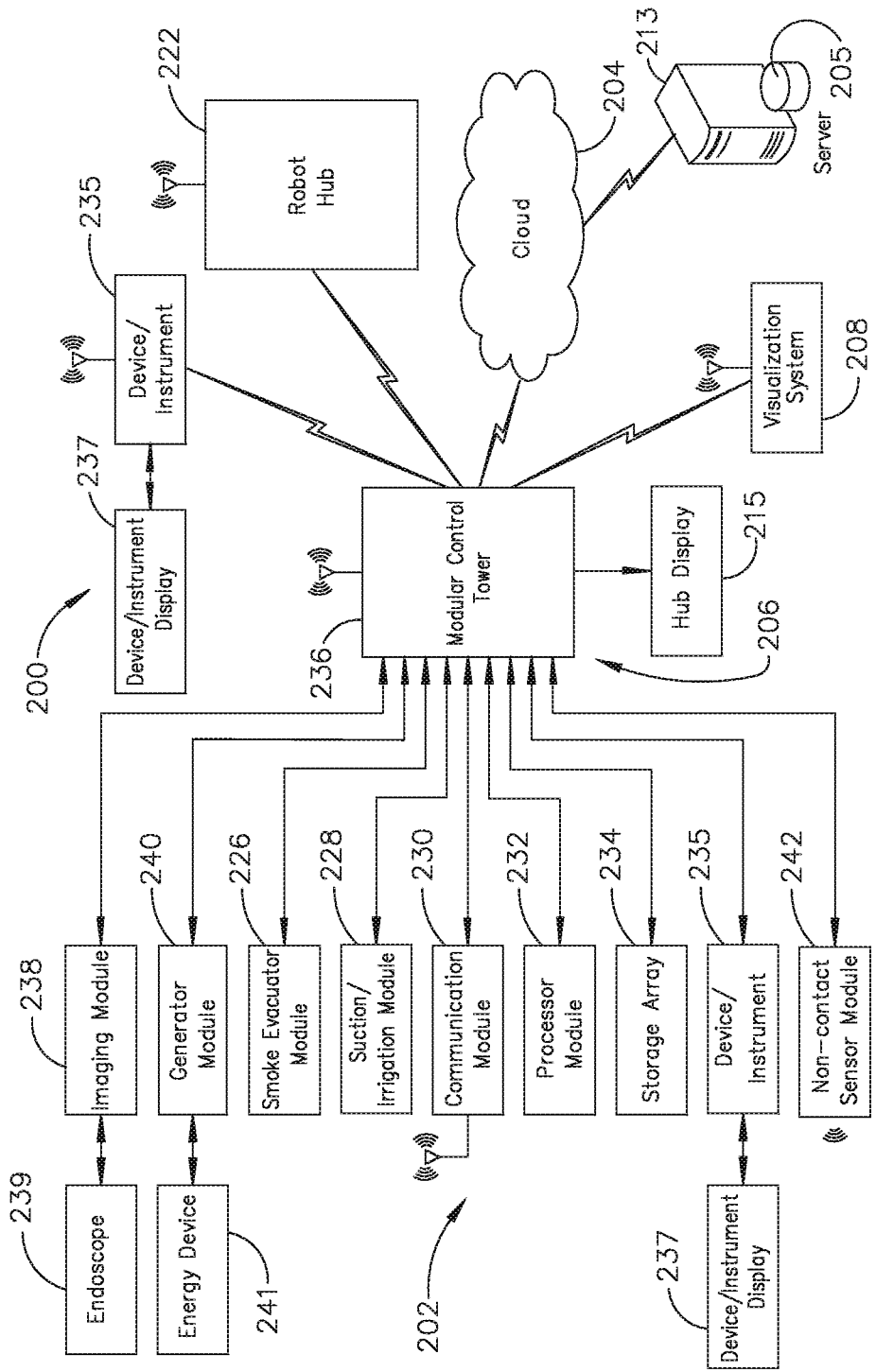
FIG. 9 illustrates a computer-implemented interactive surgical system, in accordance with at least one aspect of the present disclosure.
Figure 10:
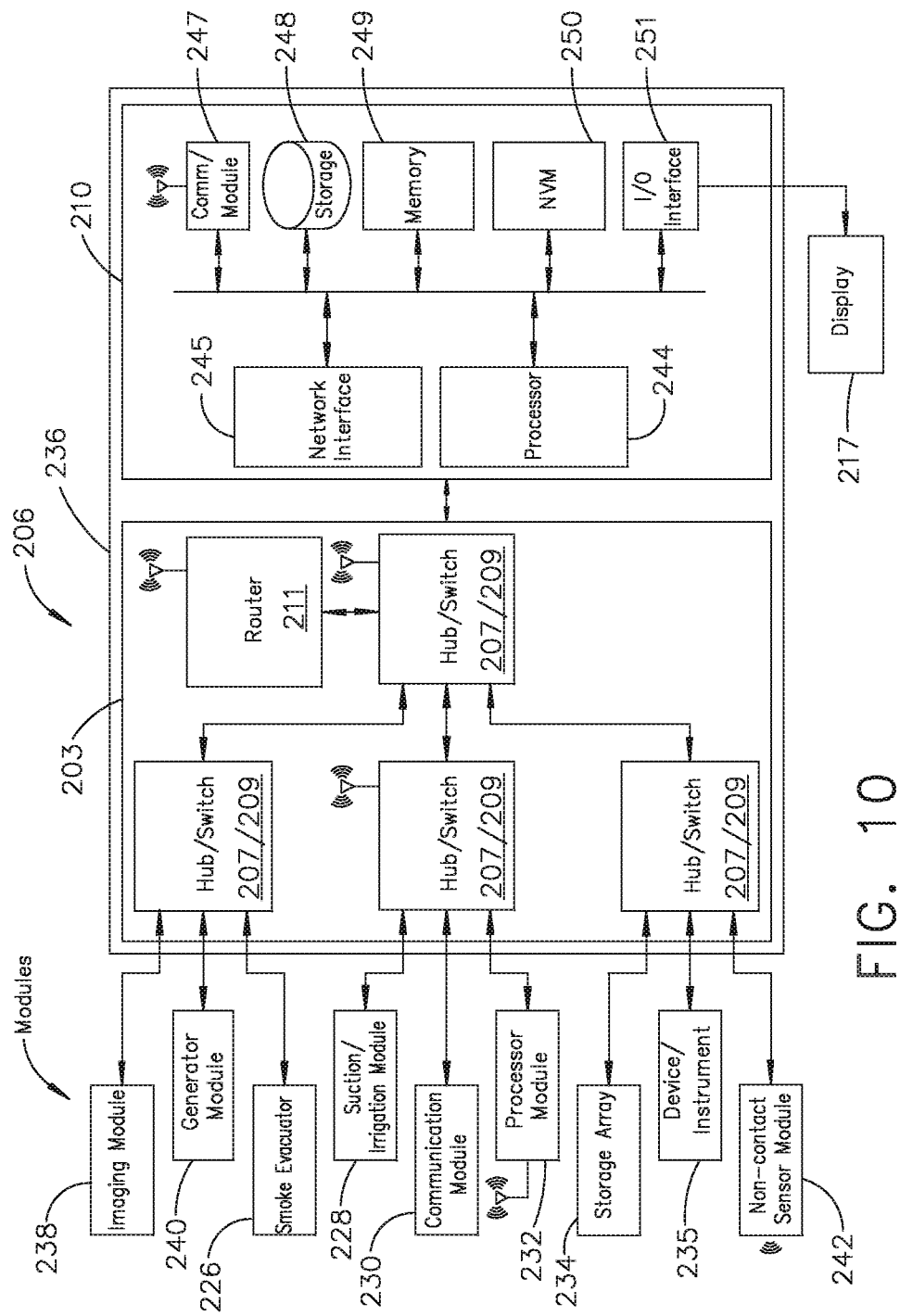
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, the disclosure of which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
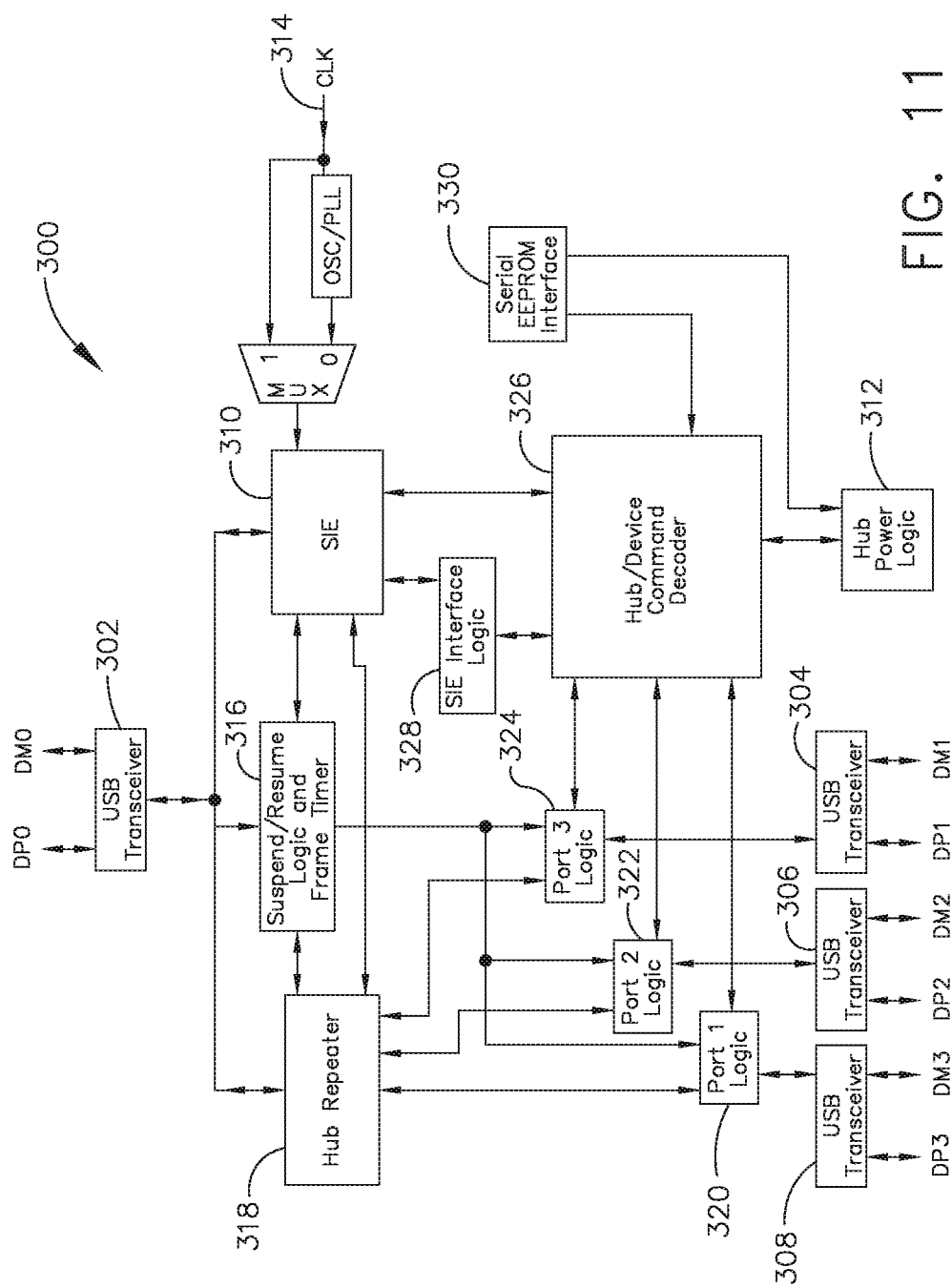
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, according to one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
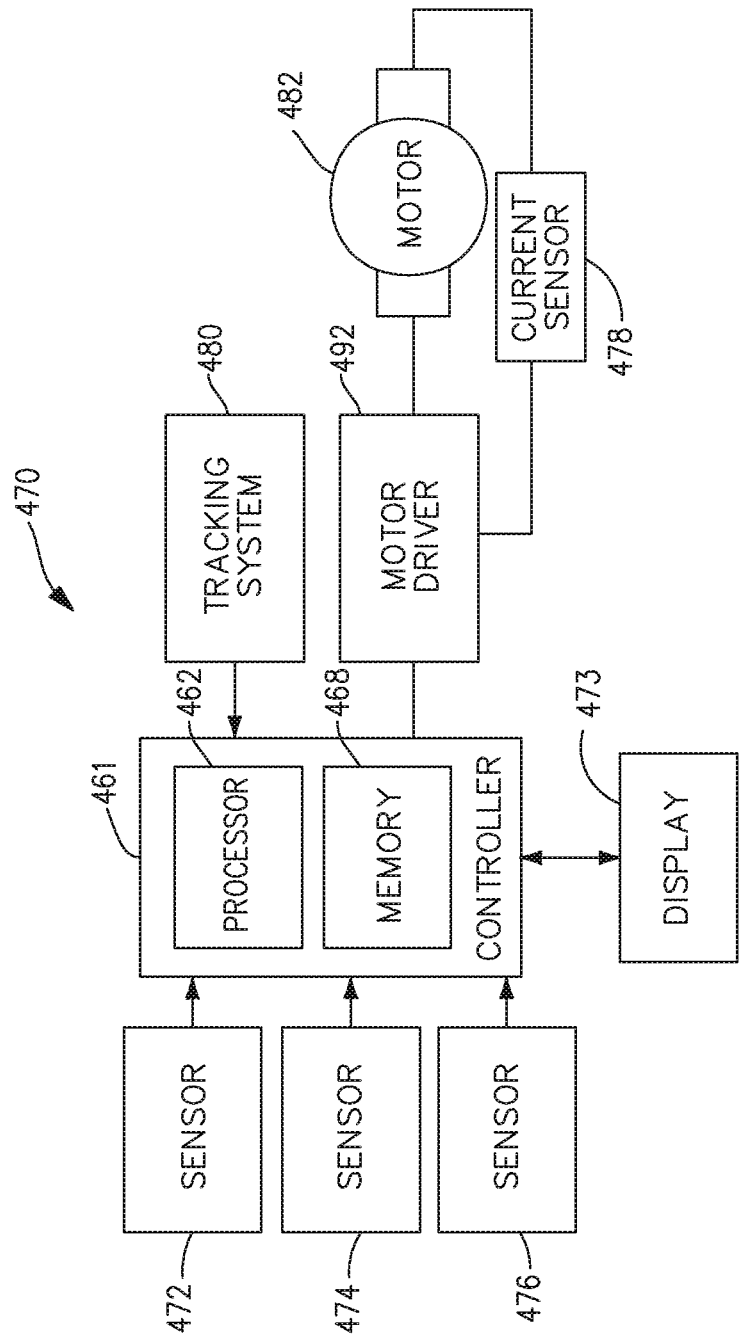
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 is configured to determine the position of the longitudinally movable displacement member. The position information is provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an !-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue.

The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
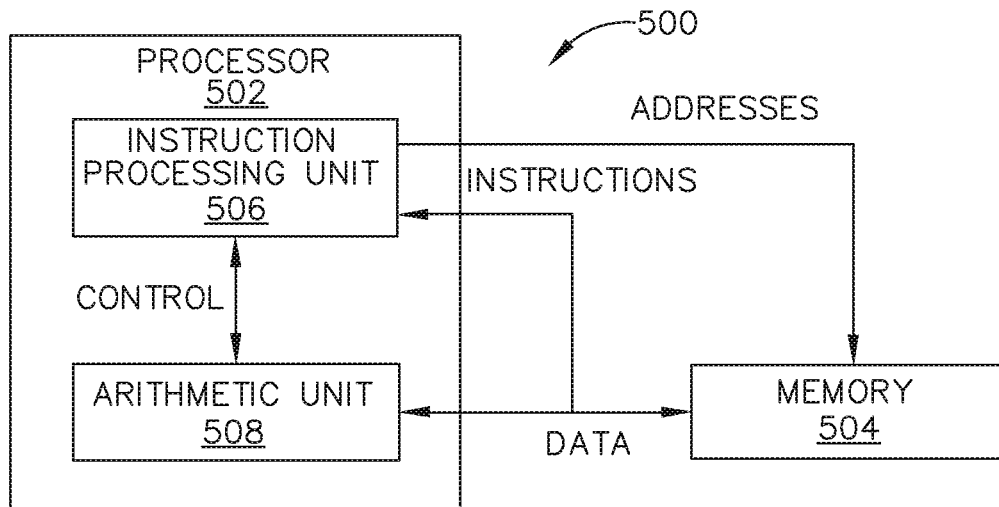
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
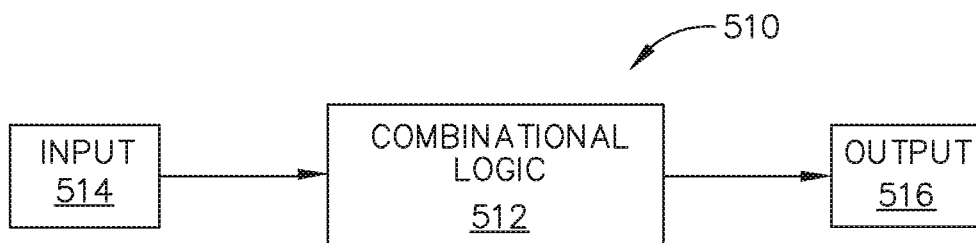
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
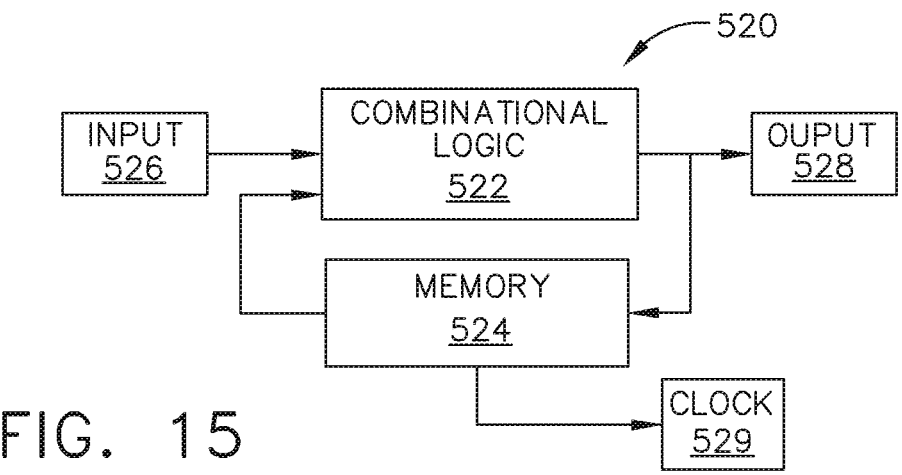
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
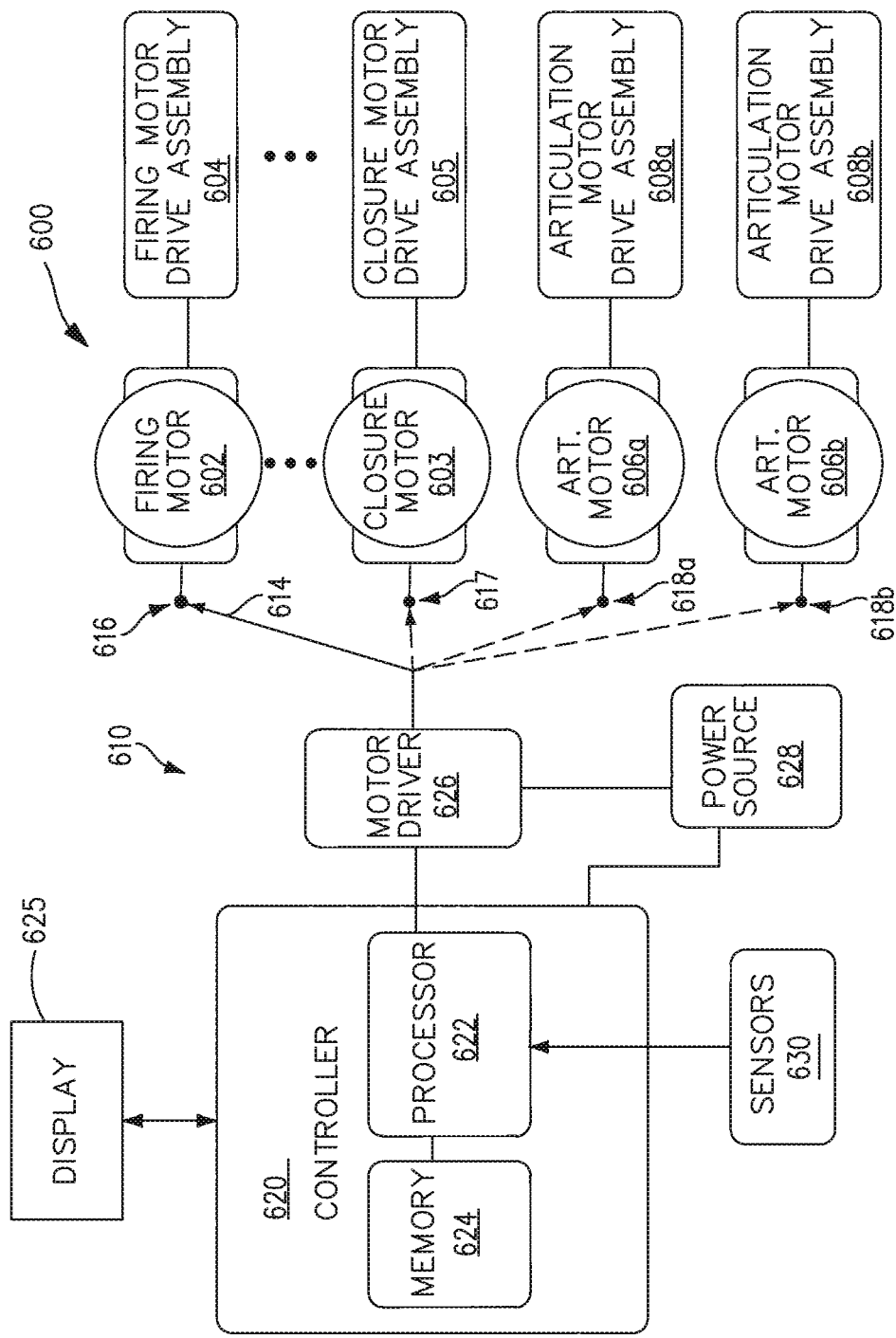
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
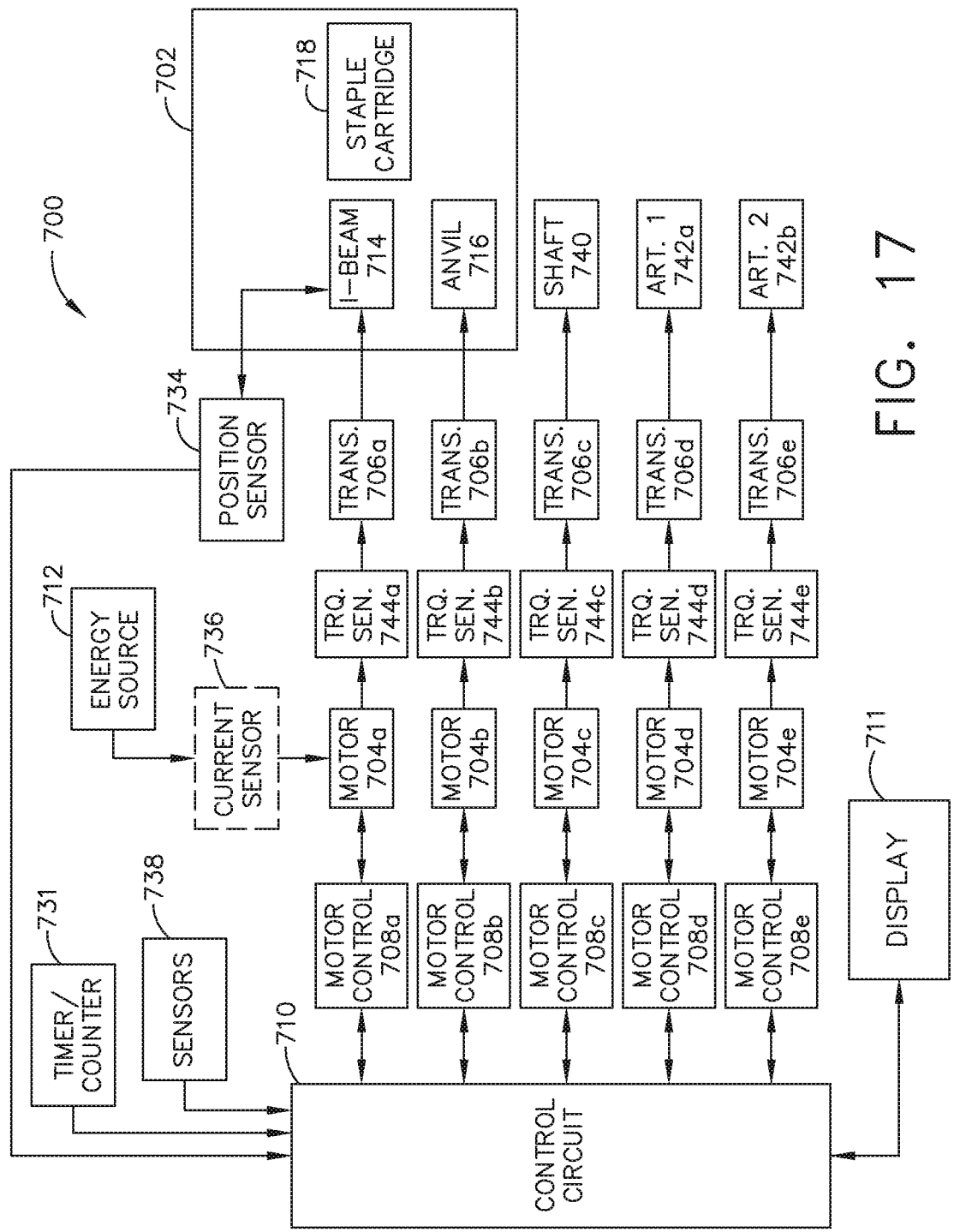
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members.

In one aspect, the robotic surgical instrument 700 comprises a control circuit 710 configured to control an anvil 716 and an I-beam 714 (including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the I-beam 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the I-beam 714 as determined by the position sensor 734 with the output of the timer/counter 731 such that the control circuit 710 can determine the position of the I-beam 714 at a specific time (t) relative to a starting position or the time (t) when the I-beam 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the I-beam 714, anvil 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the I-beam 714. The position sensor 734 may be or include any type of sensor that is capable of generating position data that indicate a position of the I-beam 714. In some examples, the position sensor 734 may include an encoder configured to provide a series of pulses to the control circuit 710 as the I-beam 714 translates distally and proximally. The control circuit 710 may track the pulses to determine the position of the I-beam 714. Other suitable position sensors may be used, including, for example, a proximity sensor. Other types of position sensors may provide other signals indicating motion of the I-beam 714. Also, in some examples, the position sensor 734 may be omitted. Where any of the motors 704a-704e is a stepper motor, the control circuit 710 may track the position of the I-beam 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the I-beam 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the I-beam 714. The transmission 706a comprises movable mechanical elements such as rotating elements and a firing member to control the movement of the I-beam 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the I-beam 714. A position sensor 734 may be configured to provide the position of the I-beam 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, an I-beam 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the anvil 716. The transmission 706b comprises movable mechanical elements such as rotating elements and a closure member to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it, and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704a-704e. The force required to advance any of the movable mechanical elements such as the I-beam 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move an I-beam 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 18:
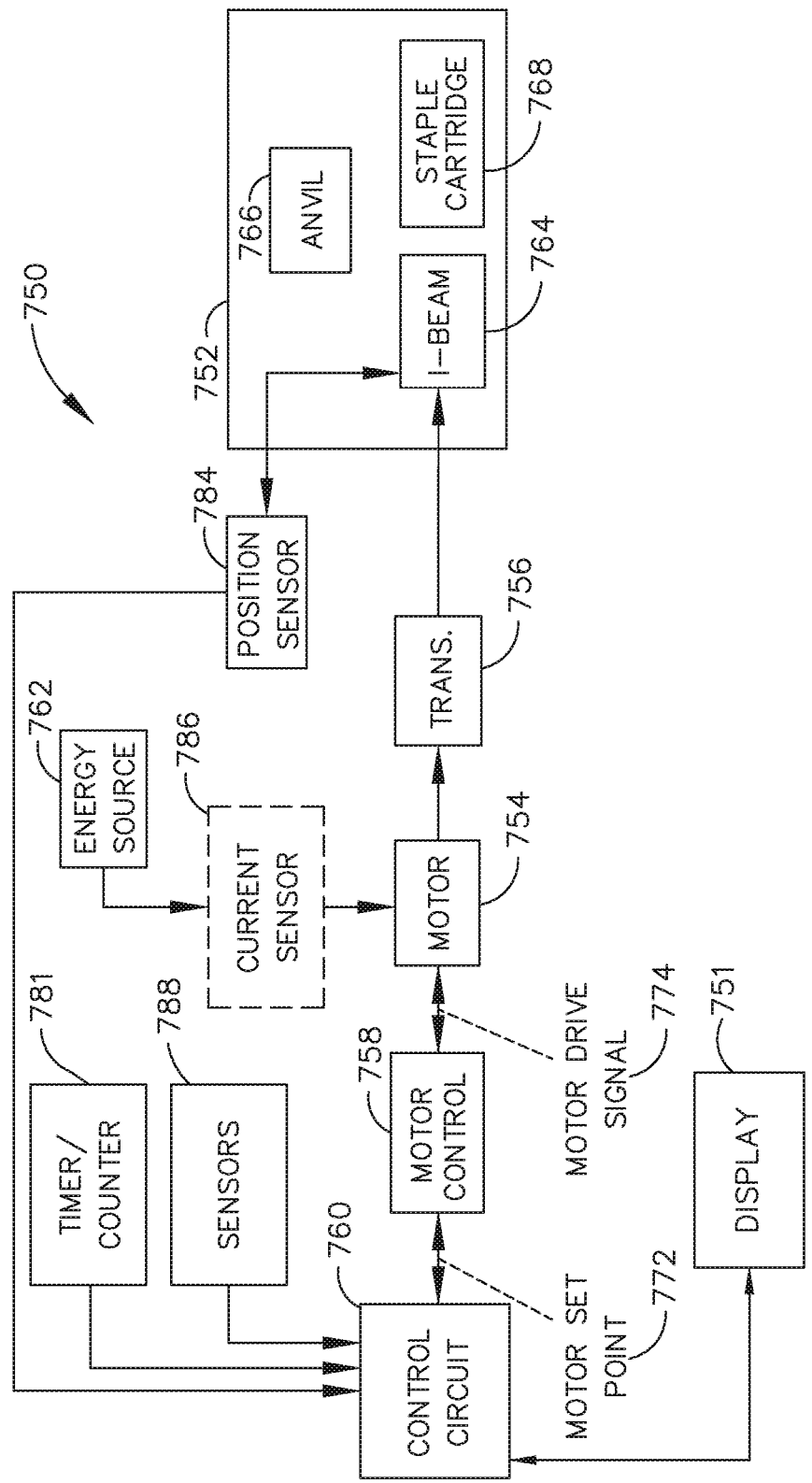
FIG. 18 illustrates a block diagram of a surgical instrument programmed to control the distal translation of a displacement member, in accordance with at least one aspect of the present disclosure.

FIG. 18 illustrates a block diagram of a surgical instrument 750 programmed to control the distal translation of a displacement member according to one aspect of this disclosure. In one aspect, the surgical instrument 750 is programmed to control the distal translation of a displacement member such as the I-beam 764. The surgical instrument 750 comprises an end effector 752 that may comprise an anvil 766, an !-beam 764 (including a sharp cutting edge), and a removable staple cartridge 768.

The position, movement, displacement, and/or translation of a linear displacement member, such as the I-beam 764, can be measured by an absolute positioning system, sensor arrangement, and position sensor 784. Because the I-beam 764 is coupled to a longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the !-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move an I-beam 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or I-beam 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, an I-beam 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the I-beam 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
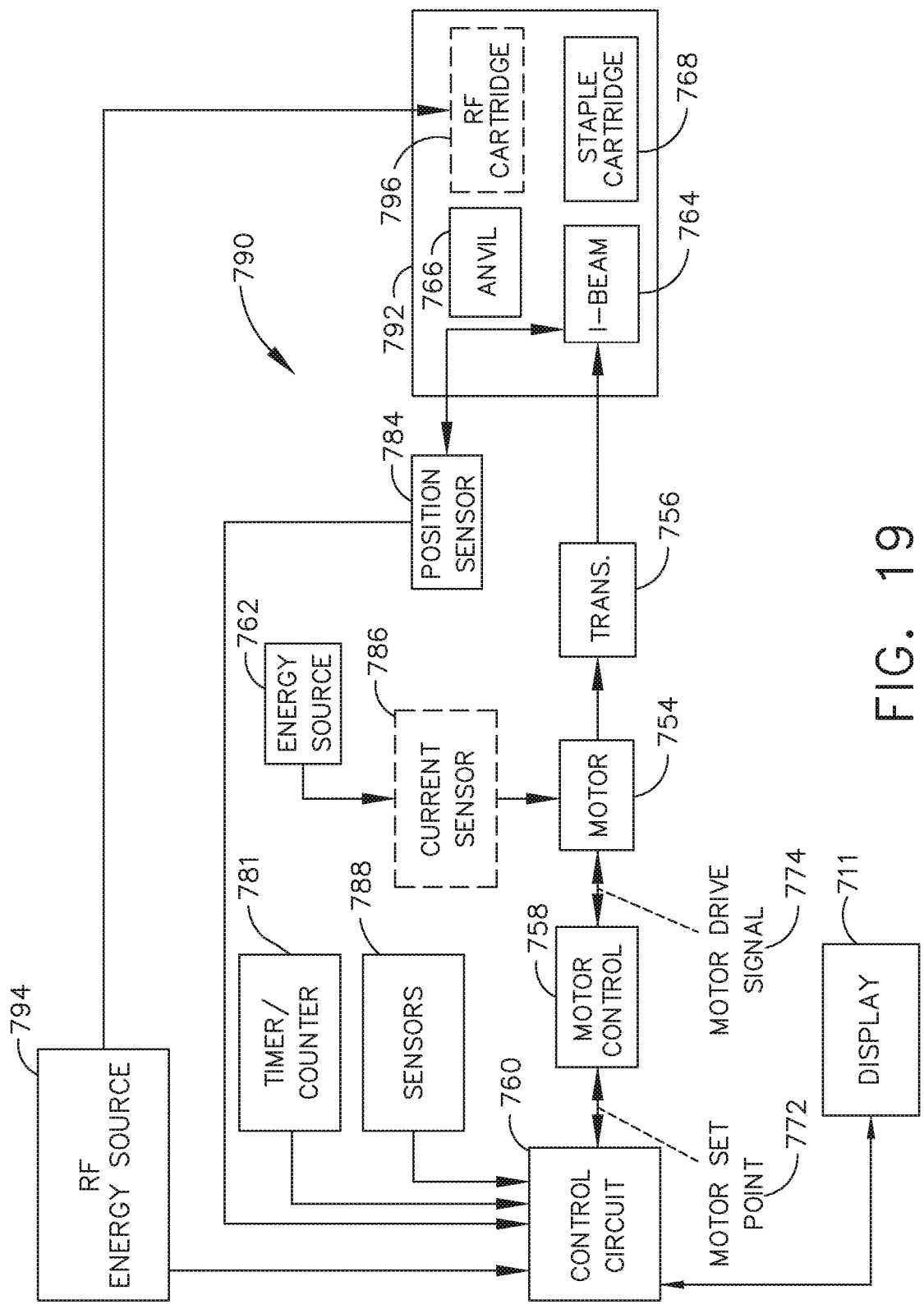
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the I-beam 764. The surgical instrument 790 comprises an end effector 792 that may comprise an anvil 766, an I-beam 764, and a removable staple cartridge 768 which may be interchanged with an RF cartridge 796 (shown in dashed line).

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the I-beam 764 may be implemented as a knife member comprising a knife body that operably supports a tissue cutting blade thereon and may further include anvil engagement tabs or features and channel engagement features or a foot. In one aspect, the staple cartridge 768 may be implemented as a standard (mechanical) surgical fastener cartridge. In one aspect, the RF cartridge 796 may be implemented as an RF cartridge. These and other sensors arrangements are described in commonly owned U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety.

The position, movement, displacement, and/or translation of a linear displacement member, such as the I-beam 764, can be measured by an absolute positioning system, sensor arrangement, and position sensor represented as position sensor 784. Because the I-beam 764 is coupled to the longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764, as described herein. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the !-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by the closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor portion of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

An RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Figure 20:
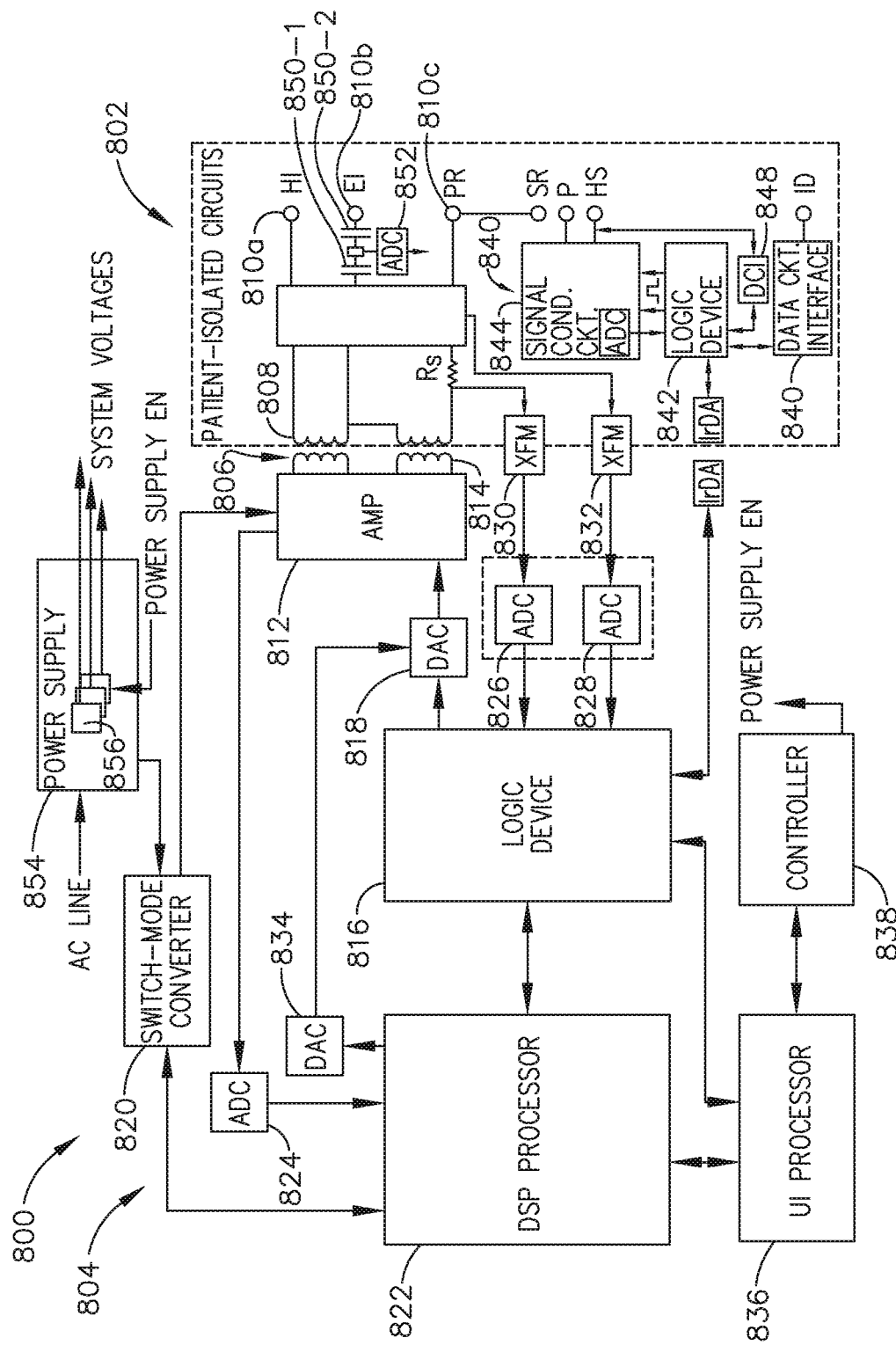
FIG. 20 is a simplified block diagram of a generator configured to provide inductorless tuning, among other benefits, in accordance with at least one aspect of the present disclosure.

FIG. 20 is a simplified block diagram of a generator 800 configured to provide inductorless tuning, among other benefits. Additional details of the generator 800 are described in U.S. Pat. No. 9,060,775, titled SURGICAL GENERATOR FOR ULTRASONIC AND ELECTROSURGICAL DEVICES, which issued on Jun. 23, 2015, which is herein incorporated by reference in its entirety. The generator 800 may comprise a patient isolated stage 802 in communication with a non-isolated stage 804 via a power transformer 806. A secondary winding 808 of the power transformer 806 is contained in the isolated stage 802 and may comprise a tapped configuration (e.g., a center-tapped or a non-center-tapped configuration) to define drive signal outputs 810a, 810b, 810c for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, drive signal outputs 810a, 810c may output an ultrasonic drive signal (e.g., a 420V root-mean-square (RMS) drive signal) to an ultrasonic surgical instrument, and drive signal outputs 810b, 810c may output an RF electrosurgical drive signal (e.g., a 100V RMS drive signal) to an RF electrosurgical instrument, with the drive signal output 810b corresponding to the center tap of the power transformer 806.

In certain forms, the ultrasonic and electrosurgical drive signals may be provided simultaneously to distinct surgical instruments and/or to a single surgical instrument, such as the multifunction surgical instrument, having the capability to deliver both ultrasonic and electrosurgical energy to tissue. It will be appreciated that the electrosurgical signal, provided either to a dedicated electrosurgical instrument and/or to a combined multifunction ultrasonic/electrosurgical instrument may be either a therapeutic or sub-therapeutic level signal where the sub-therapeutic signal can be used, for example, to monitor tissue or instrument conditions and provide feedback to the generator. For example, the ultrasonic and RF signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue, while the electrosurgical RF energy may be employed for vessel sealing.

The non-isolated stage 804 may comprise a power amplifier 812 having an output connected to a primary winding 814 of the power transformer 806. In certain forms, the power amplifier 812 may comprise a push-pull amplifier. For example, the non-isolated stage 804 may further comprise a logic device 816 for supplying a digital output to a digital-to-analog converter (DAC) circuit 818, which in turn supplies a corresponding analog signal to an input of the power amplifier 812. In certain forms, the logic device 816 may comprise a programmable gate array (PGA), a FPGA, programmable logic device (PLD), among other logic circuits, for example. The logic device 816, by virtue of controlling the input of the power amplifier 812 via the DAC circuit 818, may therefore control any of a number of parameters (e.g., frequency, waveform shape, waveform amplitude) of drive signals appearing at the drive signal outputs 810a, 810b, 810c. In certain forms and as discussed below, the logic device 816, in conjunction with a processor (e.g., a DSP discussed below), may implement a number of DSP-based and/or other control algorithms to control parameters of the drive signals output by the generator 800.

Power may be supplied to a power rail of the power amplifier 812 by a switch-mode regulator 820, e.g., a power converter. In certain forms, the switch-mode regulator 820 may comprise an adjustable buck regulator, for example. The non-isolated stage 804 may further comprise a first processor 822, which in one form may comprise a DSP processor such as an Analog Devices ADSP-21469 SHARC DSP, available from Analog Devices, Norwood, Mass., for example, although in various forms any suitable processor may be employed. In certain forms the DSP processor 822 may control the operation of the switch-mode regulator 820 responsive to voltage feedback data received from the power amplifier 812 by the DSP processor 822 via an ADC circuit 824. In one form, for example, the DSP processor 822 may receive as input, via the ADC circuit 824, the waveform envelope of a signal (e.g., an RF signal) being amplified by the power amplifier 812. The DSP processor 822 may then control the switch-mode regulator 820 (e.g., via a PWM output) such that the rail voltage supplied to the power amplifier 812 tracks the waveform envelope of the amplified signal. By dynamically modulating the rail voltage of the power amplifier 812 based on the waveform envelope, the efficiency of the power amplifier 812 may be significantly improved relative to a fixed rail voltage amplifier schemes.

In certain forms, the logic device 816, in conjunction with the DSP processor 822, may implement a digital synthesis circuit such as a direct digital synthesizer control scheme to control the waveform shape, frequency, and/or amplitude of drive signals output by the generator 800. In one form, for example, the logic device 816 may implement a DDS control algorithm by recalling waveform samples stored in a dynamically updated lookup table (LUT), such as a RAM LUT, which may be embedded in an FPGA. This control algorithm is particularly useful for ultrasonic applications in which an ultrasonic transducer, such as an ultrasonic transducer, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 800 is impacted by various sources of distortion present in the output drive circuit (e.g., the power transformer 806, the power amplifier 812), voltage and current feedback data based on the drive signal may be input into an algorithm, such as an error control algorithm implemented by the DSP processor 822, which compensates for distortion by suitably pre-distorting or modifying the waveform samples stored in the LUT on a dynamic, ongoing basis (e.g., in real time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 804 may further comprise a first ADC circuit 826 and a second ADC circuit 828 coupled to the output of the power transformer 806 via respective isolation transformers 830, 832 for respectively sampling the voltage and current of drive signals output by the generator 800. In certain forms, the ADC circuits 826, 828 may be configured to sample at high speeds (e.g., 80 mega samples per second (MSPS)) to enable oversampling of the drive signals. In one form, for example, the sampling speed of the ADC circuits 826, 828 may enable approximately 200× (depending on frequency) oversampling of the drive signals. In certain forms, the sampling operations of the ADC circuit 826, 828 may be performed by a single ADC circuit receiving input voltage and current signals via a two-way multiplexer. The use of high-speed sampling in forms of the generator 800 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADC circuits 826, 828 may be received and processed (e.g., first-in-first-out (FIFO) buffer, multiplexer) by the logic device 816 and stored in data memory for subsequent retrieval by, for example, the DSP processor 822. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 816 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the DSP processor 822, for example, with the frequency control signal being supplied as input to a DDS control algorithm implemented by the logic device 816.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 822. Variables controlled by the control algorithm to suitably control the current amplitude of the drive signal may include, for example, the scaling of the LUT waveform samples stored in the logic device 816 and/or the full-scale output voltage of the DAC circuit 818 (which supplies the input to the power amplifier 812) via a DAC circuit 834.

The non-isolated stage 804 may further comprise a second processor 836 for providing, among other things user interface (UI) functionality. In one form, the UI processor 836 may comprise an Atmel AT91SAM9263 processor having an ARM 926EJ-S core, available from Atmel Corporation, San Jose, Calif., for example. Examples of UI functionality supported by the UI processor 836 may include audible and visual user feedback, communication with peripheral devices (e.g., via a USB interface), communication with a foot switch, communication with an input device (e.g., a touch screen display) and communication with an output device (e.g., a speaker). The UI processor 836 may communicate with the DSP processor 822 and the logic device 816 (e.g., via SPI buses). Although the UI processor 836 may primarily support UI functionality, it may also coordinate with the DSP processor 822 to implement hazard mitigation in certain forms. For example, the UI processor 836 may be programmed to monitor various aspects of user input and/or other inputs (e.g., touch screen inputs, foot switch inputs, temperature sensor inputs) and may disable the drive output of the generator 800 when an erroneous condition is detected.

In certain forms, both the DSP processor 822 and the UI processor 836, for example, may determine and monitor the operating state of the generator 800. For the DSP processor 822, the operating state of the generator 800 may dictate, for example, which control and/or diagnostic processes are implemented by the DSP processor 822. For the UI processor 836, the operating state of the generator 800 may dictate, for example, which elements of a UI (e.g., display screens, sounds) are presented to a user. The respective DSP and UI processors 822, 836 may independently maintain the current operating state of the generator 800 and recognize and evaluate possible transitions out of the current operating state. The DSP processor 822 may function as the master in this relationship and determine when transitions between operating states are to occur. The UI processor 836 may be aware of valid transitions between operating states and may confirm if a particular transition is appropriate. For example, when the DSP processor 822 instructs the UI processor 836 to transition to a specific state, the UI processor 836 may verify that requested transition is valid. In the event that a requested transition between states is determined to be invalid by the UI processor 836, the UI processor 836 may cause the generator 800 to enter a failure mode.

The non-isolated stage 804 may further comprise a controller 838 for monitoring input devices (e.g., a capacitive touch sensor used for turning the generator 800 on and off, a capacitive touch screen). In certain forms, the controller 838 may comprise at least one processor and/or other controller device in communication with the UI processor 836. In one form, for example, the controller 838 may comprise a processor (e.g., a Meg168 8-bit controller available from Atmel) configured to monitor user input provided via one or more capacitive touch sensors. In one form, the controller 838 may comprise a touch screen controller (e.g., a QT5480 touch screen controller available from Atmel) to control and manage the acquisition of touch data from a capacitive touch screen.

In certain forms, when the generator 800 is in a "power off" state, the controller 838 may continue to receive operating power (e.g., via a line from a power supply of the generator 800, such as the power supply 854 discussed below). In this way, the controller 838 may continue to monitor an input device (e.g., a capacitive touch sensor located on a front panel of the generator 800) for turning the generator 800 on and off. When the generator 800 is in the power off state, the controller 838 may wake the power supply (e.g., enable operation of one or more DC/DC voltage converters 856 of the power supply 854) if activation of the "on/off" input device by a user is detected. The controller 838 may therefore initiate a sequence for transitioning the generator 800 to a "power on" state. Conversely, the controller 838 may initiate a sequence for transitioning the generator 800 to the power off state if activation of the "on/off" input device is detected when the generator 800 is in the power on state. In certain forms, for example, the controller 838 may report activation of the "on/off" input device to the UI processor 836, which in turn implements the necessary process sequence for transitioning the generator 800 to the power off state. In such forms, the controller 838 may have no independent ability for causing the removal of power from the generator 800 after its power on state has been established.

In certain forms, the controller 838 may cause the generator 800 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 802 may comprise an instrument interface circuit 840 to, for example, provide a communication interface between a control circuit of a surgical instrument (e.g., a control circuit comprising handpiece switches) and components of the non-isolated stage 804, such as, for example, the logic device 816, the DSP processor 822, and/or the UI processor 836. The instrument interface circuit 840 may exchange information with components of the non-isolated stage 804 via a communication link that maintains a suitable degree of electrical isolation between the isolated and non-isolated stages 802, 804, such as, for example, an IR-based communication link. Power may be supplied to the instrument interface circuit 840 using, for example, a low-dropout voltage regulator powered by an isolation transformer driven from the non-isolated stage 804.

In one form, the instrument interface circuit 840 may comprise a logic circuit 842 (e.g., logic circuit, programmable logic circuit, PGA, FPGA, PLD) in communication with a signal conditioning circuit 844. The signal conditioning circuit 844 may be configured to receive a periodic signal from the logic circuit 842 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 800 to the surgical instrument) and monitored to determine a state or configuration of the control circuit. The control circuit may comprise a number of switches, resistors, and/or diodes to modify one or more characteristics (e.g., amplitude, rectification) of the interrogation signal such that a state or configuration of the control circuit is uniquely discernable based on the one or more characteristics. In one form, for example, the signal conditioning circuit 844 may comprise an ADC circuit for generating samples of a voltage signal appearing across inputs of the control circuit resulting from passage of interrogation signal therethrough. The logic circuit 842 (or a component of the non-isolated stage 804) may then determine the state or configuration of the control circuit based on the ADC circuit samples.

In one form, the instrument interface circuit 840 may comprise a first data circuit interface 846 to enable information exchange between the logic circuit 842 (or other element of the instrument interface circuit 840) and a first data circuit disposed in or otherwise associated with a surgical instrument. In certain forms, for example, a first data circuit may be disposed in a cable integrally attached to a surgical instrument handpiece or in an adaptor for interfacing a specific surgical instrument type or model with the generator 800. The first data circuit may be implemented in any suitable manner and may communicate with the generator according to any suitable protocol, including, for example, as described herein with respect to the first data circuit. In certain forms, the first data circuit may comprise a non-volatile storage device, such as an EEPROM device. In certain forms, the first data circuit interface 846 may be implemented separately from the logic circuit 842 and comprise suitable circuitry (e.g., discrete logic devices, a processor) to enable communication between the logic circuit 842 and the first data circuit. In other forms, the first data circuit interface 846 may be integral with the logic circuit 842.

In certain forms, the first data circuit may store information pertaining to the particular surgical instrument with which it is associated. Such information may include, for example, a model number, a serial number, a number of operations in which the surgical instrument has been used, and/or any other type of information. This information may be read by the instrument interface circuit 840 (e.g., by the logic circuit 842), transferred to a component of the non-isolated stage 804 (e.g., to logic device 816, DSP processor 822, and/or UI processor 836) for presentation to a user via an output device and/or for controlling a function or operation of the generator 800. Additionally, any type of information may be communicated to the first data circuit for storage therein via the first data circuit interface 846 (e.g., using the logic circuit 842). Such information may comprise, for example, an updated number of operations in which the surgical instrument has been used and/or dates and/or times of its usage.

As discussed previously, a surgical instrument may be detachable from a handpiece (e.g., the multifunction surgical instrument may be detachable from the handpiece) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical instruments with current generator platforms.

Additionally, forms of the generator 800 may enable communication with instrument-based data circuits. For example, the generator 800 may be configured to communicate with a second data circuit contained in an instrument (e.g., the multifunction surgical instrument). In some forms, the second data circuit may be implemented in a many similar to that of the first data circuit described herein. The instrument interface circuit 840 may comprise a second data circuit interface 848 to enable this communication. In one form, the second data circuit interface 848 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit may store information about the electrical and/or ultrasonic properties of an associated ultrasonic transducer, end effector, or ultrasonic drive system. For example, the first data circuit may indicate a burn-in frequency slope, as described herein. Additionally or alternatively, any type of information may be communicated to second data circuit for storage therein via the second data circuit interface 848 (e.g., using the logic circuit 842). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 800 and provide an indication to a user (e.g., a light emitting diode indication or other visible indication) based on the received data.

In certain forms, the second data circuit and the second data circuit interface 848 may be configured such that communication between the logic circuit 842 and the second data circuit can be effected without the need to provide additional conductors for this purpose (e.g., dedicated conductors of a cable connecting a handpiece to the generator 800). In one form, for example, information may be communicated to and from the second data circuit using a one-wire bus communication scheme implemented on existing cabling, such as one of the conductors used transmit interrogation signals from the signal conditioning circuit 844 to a control circuit in a handpiece. In this way, design changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 802 may comprise at least one blocking capacitor 850-1 connected to the drive signal output 810b to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 850-2 may be provided in series with the blocking capacitor 850-1, with current leakage from a point between the blocking capacitors 850-1, 850-2 being monitored by, for example, an ADC circuit 852 for sampling a voltage induced by leakage current. The samples may be received by the logic circuit 842, for example. Based changes in the leakage current (as indicated by the voltage samples), the generator 800 may determine when at least one of the blocking capacitors 850-1, 850-2 has failed, thus providing a benefit over single-capacitor designs having a single point of failure.

In certain forms, the non-isolated stage 804 may comprise a power supply 854 for delivering DC power at a suitable voltage and current. The power supply may comprise, for example, a 400 W power supply for delivering a 48 VDC system voltage. The power supply 854 may further comprise one or more DC/DC voltage converters 856 for receiving the output of the power supply to generate DC outputs at the voltages and currents required by the various components of the generator 800. As discussed above in connection with the controller 838, one or more of the DC/DC voltage converters 856 may receive an input from the controller 838 when activation of the "on/off" input device by a user is detected by the controller 838 to enable operation of, or wake, the DC/DC voltage converters 856.

Figure 21:
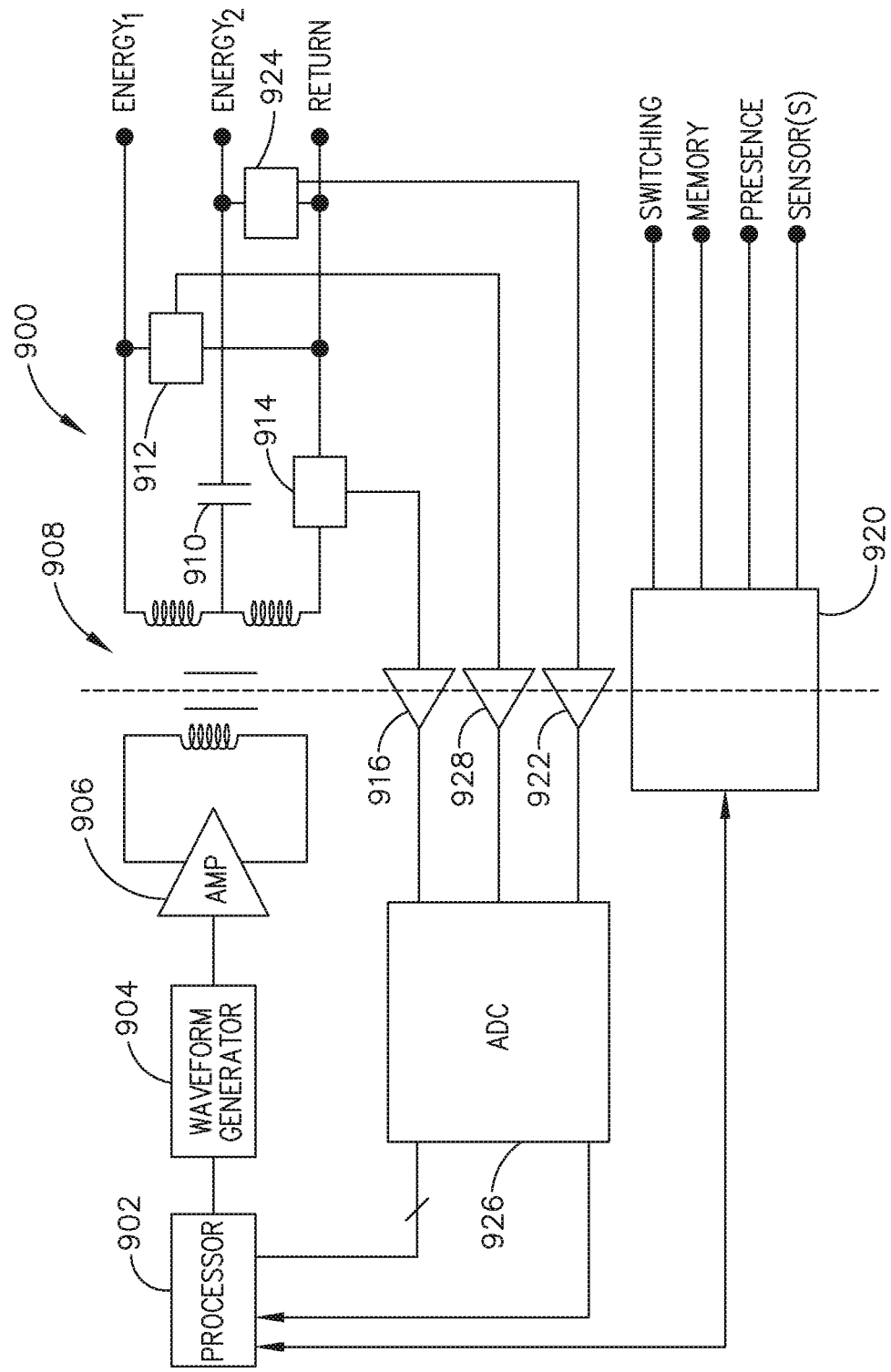
FIG. 21 illustrates an example of a generator, which is one form of the generator of FIG. 20, in accordance with at least one aspect of the present disclosure.

FIG. 21 illustrates an example of a generator 900, which is one form of the generator 800 (FIG. 21). The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue.

The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY1 and RETURN. A second signal of a second energy modality is coupled across a capacitor 910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 912 is coupled across the terminals labeled ENERGY1 and the RETURN path to measure the output voltage therebetween. A second voltage sensing circuit 924 is coupled across the terminals labeled ENERGY2 and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY1/RETURN or the second voltage sensing circuit 924 coupled across the terminals labeled ENERGY2/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY1 and RETURN as shown in FIG. 21. In one example, a connection of RF bipolar electrodes to the generator 900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

Robotic surgical systems can be used in minimally invasive medical procedures. During such medical procedures, a patient can be placed on a platform adjacent to a robotic surgical system, and a surgeon can be positioned at a console that is remote from the platform and/or from the robot. For example, the surgeon can be positioned outside the sterile field that surrounds the surgical site. The surgeon provides input to a user interface via an input device at the console to manipulate a surgical tool coupled to an arm of the robotic system. The input device can be a mechanical input devices such as control handles or joysticks, for example, or contactless input devices such as optical gesture sensors, for example.

The robotic surgical system can include a robot tower supporting one or more robotic arms. At least one surgical tool (e.g. an end effector and/or endoscope) can be mounted to the robotic arm. The surgical tool(s) can be configured to articulate relative to the respective robotic arm via an articulating wrist assembly and/or to translate relative to the robotic arm via a linear slide mechanism, for example. During the surgical procedure, the surgical tool can be inserted into a small incision in a patient via a cannula or trocar, for example, or into a natural orifice of the patient to position the distal end of the surgical tool at the surgical site within the body of the patient. Additionally or alternatively, the robotic surgical system can be employed in an open surgical procedure in certain instances.

Figure 22:
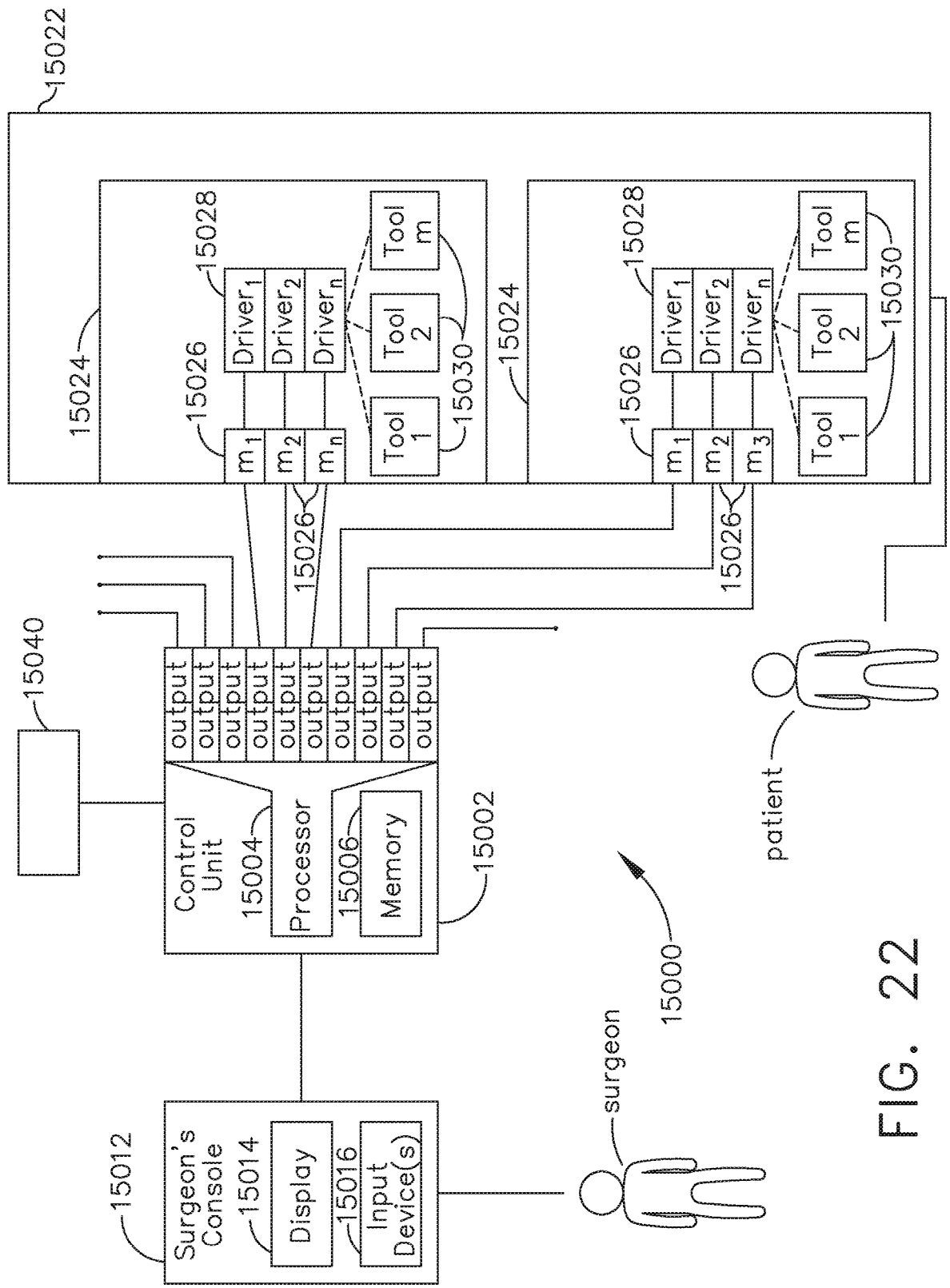
FIG. 22 is a schematic of a robotic surgical system, in accordance with one aspect of the present disclosure.

A schematic of a robotic surgical system 15000 is depicted in FIG. 22. The robotic surgical system 15000 includes a central control unit 15002, a surgeon's console 15012, a robot 15022 including one or more robotic arms 15024, and a primary display 15040 operably coupled to the control unit 15002. The surgeon's console 15012 includes a display 15014 and at least one manual input device 15016 (e.g., switches, buttons, touch screens, joysticks, gimbals, etc.) that allow the surgeon to telemanipulate the robotic arms 15024 of the robot 15022. The reader will appreciate that additional and alternative input devices can be employed.

The central control unit 15002 includes a processor 15004 operably coupled to a memory 15006. The processor 15004 includes a plurality of inputs and outputs for interfacing with the components of the robotic surgical system 15000. The processor 15004 can be configured to receive input signals and/or generate output signals to control one or more of the various components (e.g., one or more motors, sensors, and/or displays) of the robotic surgical system 15000. The output signals can include, and/or can be based upon, algorithmic instructions which may be pre-programmed and/or input by the surgeon or another clinician. The processor 15004 can be configured to accept a plurality of inputs from a user, such as the surgeon at the console 15012, and/or may interface with a remote system. The memory 15006 can be directly and/or indirectly coupled to the processor 15004 to store instructions and/or databases.

The robot 15022 includes one or more robotic arms 15024. Each robotic arm 15024 includes one or more motors 15026 and each motor 15026 is coupled to one or more motor drivers 15028. For example, the motors 15026, which can be assigned to different drivers and/or mechanisms, can be housed in a carriage assembly or housing. In certain instances, a transmission intermediate a motor 15026 and one or more drivers 15028 can permit coupling and decoupling of the motor 15026 to one or more drivers 15028. The drivers 15028 can be configured to implement one or more surgical functions. For example, one or more drivers 15028 can be tasked with moving a robotic arm 15024 by rotating the robotic arm 15024 and/or a linkage and/or joint thereof. Additionally, one or more drivers 15028 can be coupled to a surgical tool 15030 and can implement articulating, rotating, clamping, sealing, stapling, energizing, firing, cutting, and/or opening, for example. In certain instances, the surgical tools 15030 can be interchangeable and/or replaceable. Examples of robotic surgical systems and surgical tools are further described herein.

The reader will readily appreciate that the computer-implemented interactive surgical system 100 (FIG. 1) and the computer-implemented interactive surgical system 200 (FIG. 9) can incorporate the robotic surgical system 15000. Additionally or alternatively, the robotic surgical system 15000 can include various features and/or components of the computer-implemented interactive surgical systems 100 and 200.

In one exemplification, the robotic surgical system 15000 can encompass the robotic system 110 (FIG. 2), which includes the surgeon's console 118, the surgical robot 120, and the robotic hub 122. Additionally or alternatively, the robotic surgical system 15000 can communicate with another hub, such as the surgical hub 106, for example. In one instance, the robotic surgical system 15000 can be incorporated into a surgical system, such as the computer-implemented interactive surgical system 100 (FIG. 1) or the computer-implemented interactive surgical system 200 (FIG. 9), for example. In such instances, the robotic surgical system 15000 may interact with the cloud 104 or the cloud 204, respectively, and the surgical hub 106 or the surgical hub 206, respectively. In certain instances, a robotic hub or a surgical hub can include the central control unit 15002 and/or the central control unit 15002 can communicate with a cloud. In other instances, a surgical hub can embody a discrete unit that is separate from the central control unit 15002 and which can communicate with the central control unit 15002.

Robotic Surgical Assembly

Turning now to FIGS. 23-25 and 27, the robotic surgical assembly 40100 is connectable to an interface panel or carriage 40042, which is slidably mounted onto the rail 40040. The carriage 40042 supports or houses a motor "M" (FIG. 26) that receives controls and power from the control device 13004 (FIG. 4). The carriage 40042 may be moved along the rail 40040 via a motor driven chain or belt 40041 or the like. Alternatively, the carriage 40042 may be moved along the rail 40040 via a threaded rod/nut arrangement. For example, the carriage 40042 may support a threaded nut or collar, which receives a threaded rod therethrough. In use, as the threaded rod is rotated, the threaded collar, and in turn, the carriage 40042 are caused to be translated along the rail 40040. A coupling, or the like, is connected to a drive shaft of the motor M, and may be rotated clockwise or counter clockwise upon an actuation of the motor M. While a chain/belt 40041 or threaded rod and collar arrangement are described, it is contemplated that any other systems capable of achieving the intended function may be used (e.g., cable drives, pulleys, friction wheels, rack and pinion arrangements, etc.).

The carriage 40042 includes a coupling flange 40043 extending or projecting from a rear panel thereof and from the rail 40040. The coupling flange 40043 of the carriage 40042 defines an opening or bore 40043a therethrough and rotatably supports an instrument rotation gear or pulley 40048. The pulley 40048 has ring-shaped, non-circular, transverse cross-sectional profile passage or opening therethrough (e.g., substantially D-shaped, or the like) which defines a key-way for non-rotational receipt of a drive transfer assembly 40140 of the sterile barrier housing 40130. The pulley 40048 is rotatably supported in the coupling flange 40043 by journal bearings or the like.

A sterile shell or barrier 40060 is provided, which shrouds or covers the carriage 40042. Shell 40060 includes a rear shell portion 40060a configured and adapted to cover the rear panel of the carriage 40042 and an annular shell portion 40060b extending from rear shell portion 40060a and configured to cover the coupling flange 40043 of the carriage 40042. The annular shell portion 40060b of the shell 40060 defines an opening 40060c in registration with a passage or opening 40048a of the pulley 40048 having a non-circular, transverse cross-sectional profile (e.g., substantially D-shaped, or the like). A sterile drape 40061 or the like may be secured or adhered to the shell 40060 and may be pulled over the rail 40040 and the robotic arms 13002, 13003 (FIG. 4) to establish and maintain a sterile barrier between the patient 13013 (FIG. 4), the surgical field, and/or the robotic surgical system 13000 (FIG. 4).

The robotic surgical assembly 40100 includes a sterile barrier housing 40130 configured to mate with or otherwise connect to the shell 40060. The sterile barrier housing 40130 includes a hollow shell or body 40132 defining a cavity therein. The sterile barrier housing 40130 pivotally or hingedly supports a proximal cap or cover 40134 configured and adapted to selectively close a proximal end of the body 40132. The sterile barrier housing 40130 further includes a drive transfer assembly 40140 supported on, or connected to, a distal end of the body 40132.

The cavity of the body 40132 of the sterile barrier housing 40130 is configured to slidably receive a motor pack 40050 or the like therein. The motor pack 40050 may include four motors 40052, 40054, 40056, 40058 arranged in a rectangular formation such that respective drive shafts 40052a, 40054a, 40056a, 40058a thereof are all parallel to one another and all extend in a common direction. The drive shaft 40052a, 40054a, 40056a, 40058a of each motor 40052, 40054, 40056, 40058, respectively, may operatively interface with a respective drive coupler (of which only driver coupler 44144a is shown in FIG. 81B) of the drive transfer assembly 44140 (FIG. 81A) of the sterile barrier housing 40130. The motor pack 40050 may include four canister motors or the like, each having a drive shaft having a non-circular transverse cross-sectional profile (e.g., substantially D-shaped, or the like).

For an exemplary motor pack 40050 for use in the robotic surgical assembly 40100, reference may be made to U.S. Provisional Patent Application Ser. No. 62/181,817, filed on Jun. 19, 2015, entitled "Robotic Surgical Assemblies," the entire contents of which are incorporated by reference herein.

The motor couplers 40052b, 40054b, 40056b, 40058b may be non-rotatably connected to a respective drive shaft 40052a, 40054a, 40056a, 40058a of each motor 40052, 40054, 40056, and 40058, respectively. Each motor coupler 40052b, 40054b, 40056b, 40058b may have a substantially tubular configuration defining a lumen therethrough having a non-circular, transverse cross-sectional profile. The lumen of each motor coupler 40052b, 40054b, 40056b, 40058b is configured to non-rotatably engage and/or receive respective drive shaft 40052a, 40054a, 40056a, 40058a of each motor 40052, 40054, 40056, 40058, respectively, wherein the lumens may have a substantially D-shaped, transverse cross-sectional profile.

Each motor coupler 40052b, 40054b, 40056b, 40058b includes one or more distally extending tab 40052c, 40054c, 40056c, 40058c, which is/are configured to engage a respective mating feature or slot of the drive couplers (e.g., drive coupler 44144a) of the drive transfer shafts 44144, 44146, 44148, 44150 (FIG. 81A) of the sterile barrier housing 40130 to transmit rotational forces from the motors 40052, 40054, 40056, 40058 to respective drive transfer shafts 44144, 44146, 44148, 44150 of the drive transfer assembly 44140 in the manner of an "Oldham coupling." This Oldham-type coupling limits backlash and enables autocorrecting when components thereof are slightly misaligned with one another. In some embodiments, one or more of these tabs and/or slots may have complementary V-shaped configurations. It is contemplated that any rotational force transmitting feature may be provided at the distal end of the motor couplers 40052b, 40054b, 40056b, 40058b. In use, as any one of the motors 40052, 40054, 40056, 40058 is activated to rotate a respective drive shaft 40052a, 40054a, 40056a, 40058a, the particular drive shaft drive shaft 40052a, 40054a, 40056a, 40058a transmits the rotation to the respective motor coupler 40052b, 40054b, 40056b, 40058b, which in turn, transmits the rotation (via tabs 40052c, 40054c, 40056c, 40058c) to the respective drive couplers (e.g., drive coupler 44144a) of the drive transfer shafts 44144, 44146, 44148, 44150 of the drive transfer assembly 400140. Such an arrangement and coupling permit a degree of flotation of the motor couplers 40052b, 40054b, 40056b, 40058b and the drive couplers (e.g., drive coupler 44144a) in any radial direction relative to a longitudinal axis thereof.

The robotic surgical assembly 40100 includes a lock ring or collar 40160 rotatably supported on the distal end of the body 40132 of the sterile barrier housing 40130. The lock collar 40160 projects distally from the body 40132 of the sterile barrier housing 40130 and defines an internal thread configured for threadable connection to a proximal ring connector 40171 of the sterile barrier collar assembly 40170, which is described below.

The robotic surgical assembly 40100 includes a sterile barrier collar assembly 40170 connectable to the annular shell 40060b of the shell 40060 and extendable through the D-shaped passage or opening of the pulley 40048. Specifically, the sterile barrier collar assembly 40170 includes a tubular sleeve body 40172 having a non-circular, transverse cross-sectional outer profile (e.g., substantially D-shaped, or the like) and an inner bore 40172a having a complementary non-circular, transverse cross-sectional profile (e.g., substantially D-shaped, or the like).

The sterile barrier collar assembly 40170 further includes a semi-annular coupling cuff 40176 supported on or otherwise secured to a distal end of the tubular sleeve body 40172. The coupling cuff 40176 includes a U-shaped body portion having an open side edge or instrument opening that opens distally and laterally and a pair of opposed side arms. Each side arm of the body portion includes a ramp surface formed in or projecting from an inner juxtaposed surface thereof. Each ramp increases in height from a distal end (near the open side edge) to a proximal end (near a back span of the body portion). It is contemplated that each ramp may be angled at approximately 10° relative to a planar distal surface of the coupling cuff 40176. Each side arm of the body portion further includes a recess or channel formed in a surface thereof that is configured to slidably receive a respective arm or tab of a distal floating plate that is connected to or otherwise extending from a distal end of the tubular sleeve body 40172.

Figure 26:
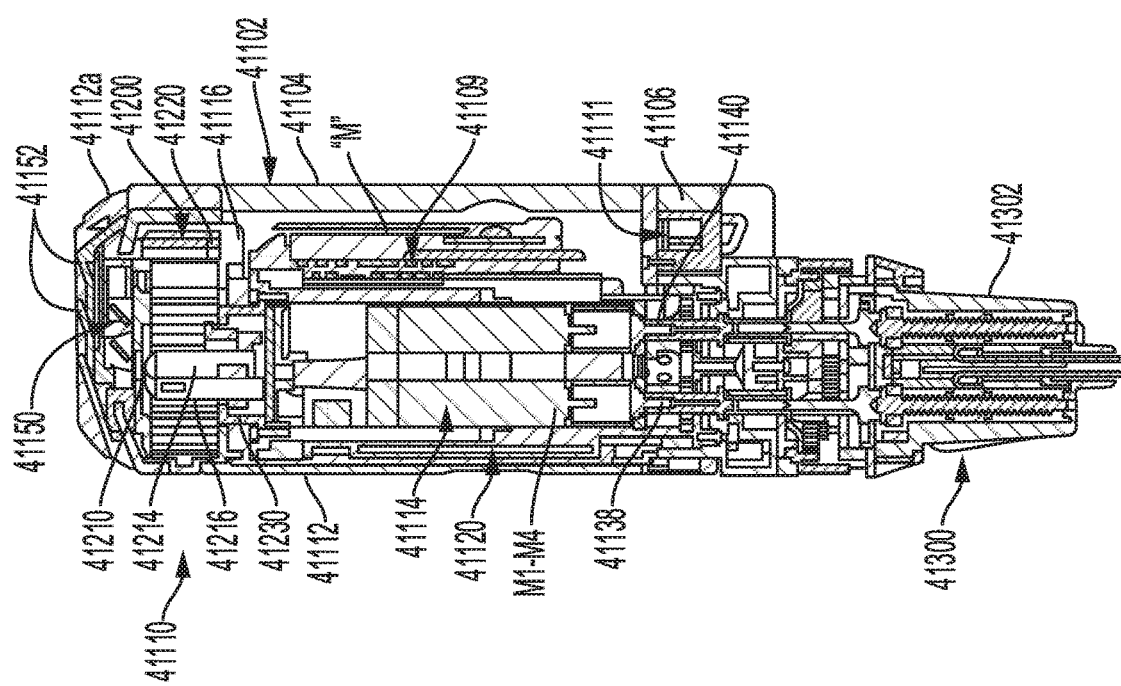
FIG. 26 is a sectional view of an instrument drive unit, in accordance with at least one aspect of the present disclosure.
Figure 28:
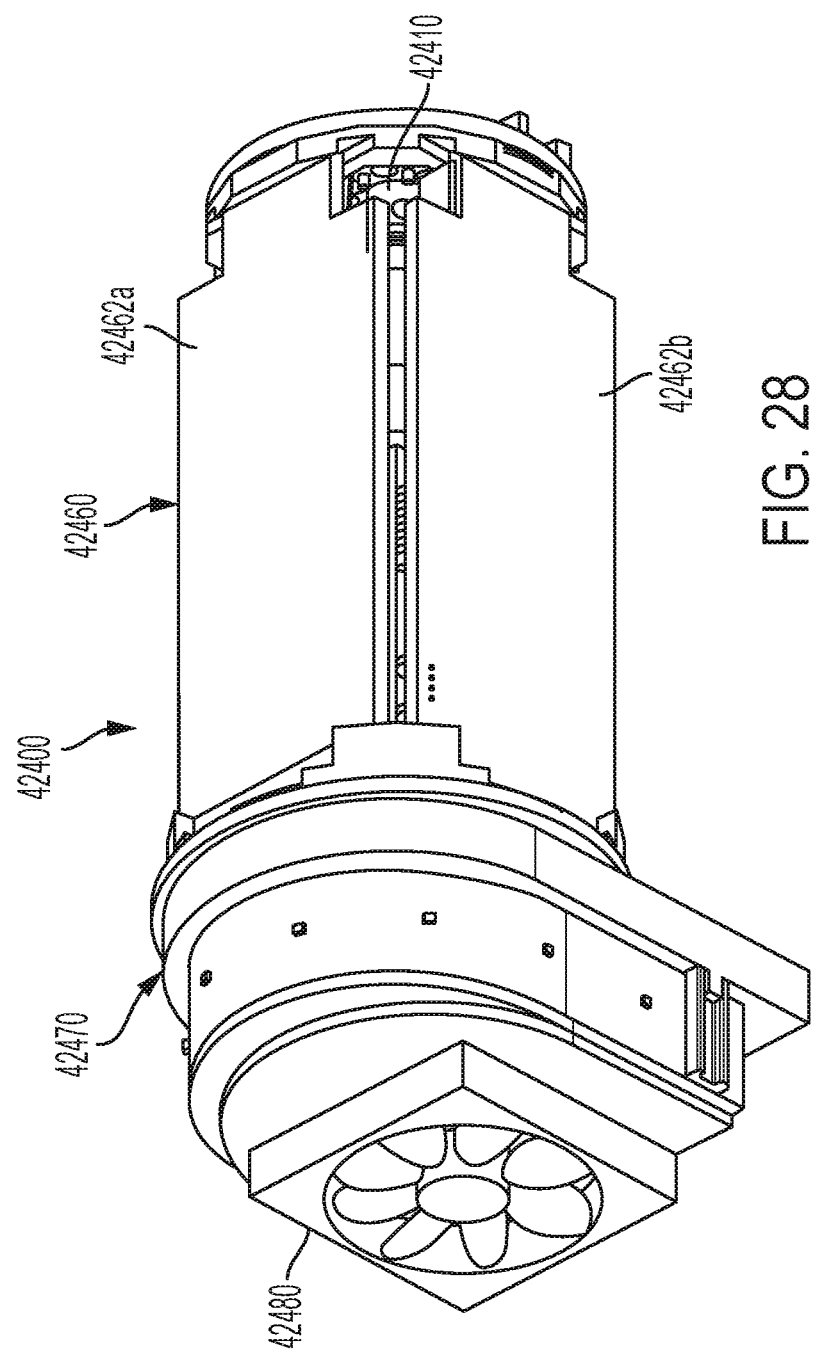
FIG. 28 is a perspective view of an instrument drive unit comprising a cooling unit, in accordance with at least one aspect of the present disclosure.
Figure 29:
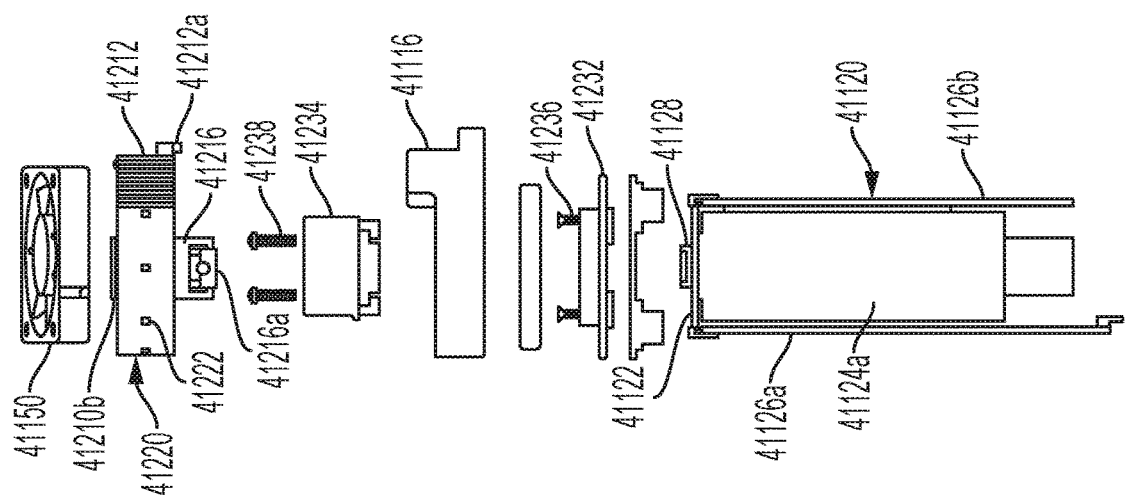
FIG. 29 is an exploded view of an instrument drive unit comprising a cooling unit, in accordance with at least one aspect of the present disclosure.

Turning now to FIGS. 26 and 28-29, various views of a robotic surgical assembly, also referred to as an instrument drive unit (IDU) 41110, are shown. As described above, the IDU 41110 transfers power and actuation forces from its motors to driven members (not shown) of electromechanical surgical instrument 41300 to ultimately drive movement of components of the end effector of electromechanical surgical instrument 41300, for example, a movement of a knife blade (not shown) and/or a closing and opening of jaw members of the end effector, the actuation or firing of a stapler, and/or the activation or firing of an electrosurgical energy-based instrument, or the like. The motor assembly 41114 of the IDU 41110 is rotated by a motor "M" supported in the IDU holder 41102 and transfers its rotational motion to electromechanical surgical instrument 41300.

The IDU holder 41102 of surgical assembly 41100 functions both to actuate a rotation of motor assembly 41114 of the IDU 41110 and to effect axial translation of IDU 41110 along the rail 40040 (FIG. 24) of the robotic arms 13002, 13003 (FIG. 4). The IDU holder 41102 includes a back member or carriage 41104 and an outer member or outer housing 14106, also referred to as a sterile shell or barrier 40060 (FIG. 23), extending laterally (e.g., perpendicularly) from a distal end 41107 of carriage 41104. In some embodiments, the housing 41106 may extend at various angles relative to carriage 41104 and from various portions of carriage 41104. The carriage 41104 has a first side and a second side, opposite the first side. The first side of the carriage 41104 is detachably connectable to the rail 40040 of the robotic arms 13002, 13003 to enable the IDU holder 41102 to slide or translate along rail 40040 of the robotic arms 13002, 13003. The second side of the carriage 41104 is configured to support a housing 41112 or the like of the IDU 41110.

The carriage 41104 of the IDU holder 41102 supports or houses a motor, such as, for example, canister motor "M" therein. Motor "M" receives controls and power from control device 13004 (FIG. 4) to ultimately rotate internal motor assembly 41114 of IDU 41110. Carriage 41104 includes a printed circuit board 41109 in electrical communication with motor "M" of carriage 41104 to control an operation of motor "M" of carriage 41104. Carriage 41104 further includes a belt or gear drive mechanism 41111 that extends distally from motor "M." Drive mechanism 41111 is configured to operably interface with motor assembly 41114 of IDU 41110 to effect a rotation of motor assembly 41114 upon actuation of motor "M" of carriage 41104.

The housing 41112 of IDU 41110 is engaged to the second side of carriage 41104 of IDU holder 41102 so as to shroud, cover, and protect the inner components of IDU 41110 and carriage 41104. Housing 41112 of IDU 41110 may have a generally cylindrical configuration, but in some embodiments, housing 41112 may assume a variety of configurations, such as, for example, squared, triangular, elongate, curved, semi-cylindrical, or the like. As mentioned above, housing 41112 protects or shields various components of IDU 41110 including motor assembly 41114 and a flex spool assembly 41200 for transferring power and data to components of IDU 41110. Housing 41112 also provides a platform 41116 on which the inner components of IDU 41110 are attached.

IDU 41110 includes a fan 41150 disposed within a top portion thereof and is located above flex spool assembly 41200. Fan 41150 is connected to flex spool assembly 41200 via a connector (not explicitly shown) to provide adjustable power to fan 41150. A top portion 41112a of housing 41112 may define a plurality of vents or slits 41152 therein to allow for air to transfer out of IDU 41110. Fan 41150 is configured to draw air through flex spool assembly 41200 and out of top portion 41112a of housing 41112 through slits 41152 to cool electronics during operation thereof and to maintain a negative pressure through IDU 41110. The flex spool assembly 41200 is configured to adjust the amount of power delivered to fan 41150 based on the temperature within IDU 41110. Speed controllers (not shown) associated with flex spool assembly 41200 and/or integrated circuit 41120 may be provided to control a speed of fan 41150 to adjust a cooling rate. For example, the speed control may adjust the electrical current that is delivered to fan 41150 to adjust a speed thereof.

The IDU 41110 includes the integrated circuit 41120 and the motor assembly 41114 each rotatably disposed therewithin. In some embodiments, IDU 41110 may include brackets and/or stops configured to compensate for loads directed on motor assembly 41114 and/or integrated circuit 41120 in a direction that is perpendicular or transverse to the longitudinal axis defined by IDU 41110. Integrated circuit 41120 includes a top rigid printed circuit board or *nexus* and four elongate rigid printed circuit boards 41124a, 41124b, 41126a, 41126b that extend perpendicularly from top printed circuit board 41122. Top printed circuit board 41122 has one or more male electrical connectors 41128 for coupling to one or more female electrical connectors 41216a of flex spool assembly 41200.

The elongate printed circuit boards 41124a, 41124b, 41126a, 41126b are parallel with one another and are disposed along a longitudinal axis of IDU 41110. Elongate printed circuit boards 41124a, 41124b, 41126a, 41126b include a first pair of elongate printed circuit boards 41124a, 41124b that oppose one another and a second pair of elongate printed circuit boards 41126a, 41126b that oppose one another. Elongate printed circuit boards 41124a, 41124b, 41126a, 41126b cooperatively form a rectangular configuration and define a cavity therein configured for slidable receipt of motor assembly 41114. It should be appreciated that circuit boards 41124a, 41124b, 41126a, 41126b and nexus 41122 of integrated circuit 41122 may be configured in any number of structural combinations, such as, for example, first, second, third, and fourth circuit boards

41124*a*, 41124*b*, 41126*a*, 41126*b* being coupled, side-by-side, where one of first, second, third, or fourth circuit board 41124*a*, 41124*b*, 41126*a*, 41126*b* is further coupled to one side of a first, second, third, or fourth side of nexus 41122. In some embodiments, integrated circuit 41120 may have various connectors, flex cables, or wires used to interconnect elongate printed circuit boards 41124*a*, 41124*b*, 41126*a*, 41126*b* to one another and/or to nexus 41122.

First pair of elongate printed circuit boards 41124*a*, 41124*b* have a first end portion in electrical communication with nexus 41122 and a second end portion in electrical communication with motor assembly 41114 to transfer power from printed circuit assembly 41200 to motor assembly 41114, as will be described in detail below. Second pair of elongate printed circuit boards 41126*a*, 41126*b* have a first end portion in electrical communication with nexus 41122 and a distal end in electrical communication with various electrical components of IDU 41110 and/or surgical instrument 41300 to transfer communication signals and/or power to the various electrical components of IDU 41110 and surgical instrument 41300.

The electrical components of IDU 41110 may include, but are not limited to, transducers, encoders, gyroscopes, magnetometers, distal limit sensors, pressure sensors, torsional sensors, load cells, optical sensors, position sensors, heat sensors, illumination elements, cameras, speakers, audible emission components, motor controllers, LED components, microprocessors, sense resistors, accelerometers, switches to monitor, limit and control positional limits, etc. In some embodiments, each of these electrical components may be incorporated into flex spool assembly 41200 of IDU 41110.

Motor assembly 41114 of IDU 41110 is non-rotatably disposed within the cavity of integrated circuit 41120. Motor assembly 41114 may include four motors "M1-M4," for example, canister motors or the like, each having a drive shaft 41138, 41140 (only drive shafts of two motors of motors "M1-M4" being shown in FIG. 26) having a non-circular, transverse cross-sectional profile (e.g., substantially D-shaped, or the like), as is described above. The four motors "M1-M4" are arranged in a rectangular formation such that respective drive shafts 41138, 41140 thereof are all parallel to one another and all extending in a common direction. As the motors "M1-M4" of the motor assembly 41114 are actuated, rotation of the respective drive shafts 41138, 41140 of the motors "M1-M4" is transferred to gears or couplers of drive assemblies of surgical instrument 41300 via respective drive transfer shafts to actuate various functions of surgical instrument 41300.

Flex spool assembly 41200 of IDU 41110 is configured to transfer power and information (e.g., signals that direct actuation of certain functions of IDU 41110 and surgical instrument 41300) from control device 13004 to an integrated circuit 41120 of IDU 41110. Flex spool assembly 41200 generally includes a first flex circuit 41210 and a second flex circuit 41220. First flex circuit 41210 is configured to electrically interconnect control device 13004 and a plurality of electrical components (e.g., motors, various sensors, transducers, etc.) of IDU 41110 and/or surgical instrument 41300.

IDU 41110 further includes a spindle assembly 41230 for transferring rotational motion from motor assembly 41114 to first flex circuit 41210. Spindle assembly 41230 includes an outer annular member 41232, and an inner annular member or ring member 41234. Outer annular member 41232 is fastened to a proximal end portion of motor assembly 41114 via fasteners 41236. Inner annular member 41234 is fastened to outer annular member 41232 via fasteners 41238 and is rotatable relative to platform 41116 such that outer annular member 41234 rotates relative to platform 41116. In embodiments, outer and inner annular members 41232, 41234 of spindle assembly 41230 may be of a single integral construction. A lubricious coating may be applied to surfaces of spindle assembly 41230 that contact platform 41116 or to the surfaces of platform 41116 that contact spindle assembly 41230, such that spindle assembly 41230 rotates relative to platform with limited friction. Accordingly, the lubricious coating may include any suitable material, such as, for example, ultra-high molecular weight polyethylene, nylon, acetal, or polytetrafluoroethylene.

Robotic Surgical Assembly Cooling

Cooling the IDU 40110 (FIG. 23) of a robotic surgical assembly 41100 (FIG. 23) for a robotic surgical system 13000 (FIG. 4) can be challenging because of the fact that the instrument drive unit can be located at least partially within the sterile field during the course of a surgical procedure. As described above, the IDU 40110 can include a fan 41150 (FIGS. 26 and 28-29) to promote air transfer out of the IDU 40110 for cooling the IDU 40110 during use; however, this can create two issues. First, if the air intake of the fan 41150 is from outside of the sterile field and the fan 41150 releases the circulated air into the sterile field, then the fan 41150 can be releasing nonsterile air into the sterile field, which can result in contamination of the sterile field. Second, if the air intake of the fan 41150 is from inside of the sterile field, then the fan 41150 could potentially intake a contaminant from the sterile field and then cause that contaminant to be proliferated through the surgical theater, outside of the bounds of the sterile field. Therefore, there is a need for robotic surgical assembly cooling systems that address these and other issues.

In various aspects, contamination of the surgical site, sterile field, and/or surgical theater by air-circulating cooling systems can be prevented by controlling heat transfer and air circulation within the robotic surgical system 13000 and/or IDU 40110. For example, an air filter (e.g., an ultra-low particular air (ULPA) filter) can be integrated into or otherwise positioned at the air intake manifold to ensure that air exhausted from the robotic surgical system 13000 is sterile. As another example, the robotic surgical system 13000 can include a circulation path where the air intake and the exhaust are both directed to an area of the robotic surgical system 13000 outside of the sterile surgical area. In one aspect, the air circulation path could be directed towards or connected to the smoke evacuation system in order to leverage the smoke evacuation system's integral, high-quality air filters. As yet another example, the robotic surgical system 13000 can be configured to ionically collect particulates from air that is drawn into or exposed to the cooling system. In one aspect, the robotic surgical system 13000 can include an ionizing air filter configured to capture particulates within the air drawn into the cooling system. The ionizing air filter can include plates that are configured to collect charged particles that are drawn into the device. The removable charged plates could be cleaned and reused. Further, the charged plates could permit testing and identification of particulates captured from the indrawn air. The charged plates could have the capability of actively attracting a variety of different contaminants and particulates from the air passing through the ionizing air filter, including bacterial contaminants. These systems and other examples will be discussed in greater detail below.

In such aspects, dedicated heat management systems can be implemented within or in conjunction with the sterile barrier, such as by integrating a cooling apparatus within the air circulation flow path or coupling the cooling apparatus to the IDU 40110. For example, the cooling system can be in thermal cooperation with the IDU 40110 and/or components thereof (including, for example, the motor assembly), but the cooling air circulation path can be isolated from the internal air of the IDU 40110. As another example, the cooling system can include a cooling circulation system that can include fluid and/or vaporous aspects in order to transfer heat from the IDU 40110 to a location for venting to the atmosphere remote from the robotic arm 13120. As another example, the cooling system can include a Peltier cooling element to extract heat from the IDU 40110 and other heat-generating components of the robotic surgical system 13000 for transfer to other surfaces exposed to convection from dedicated air-flow pathways.

Figure 23:
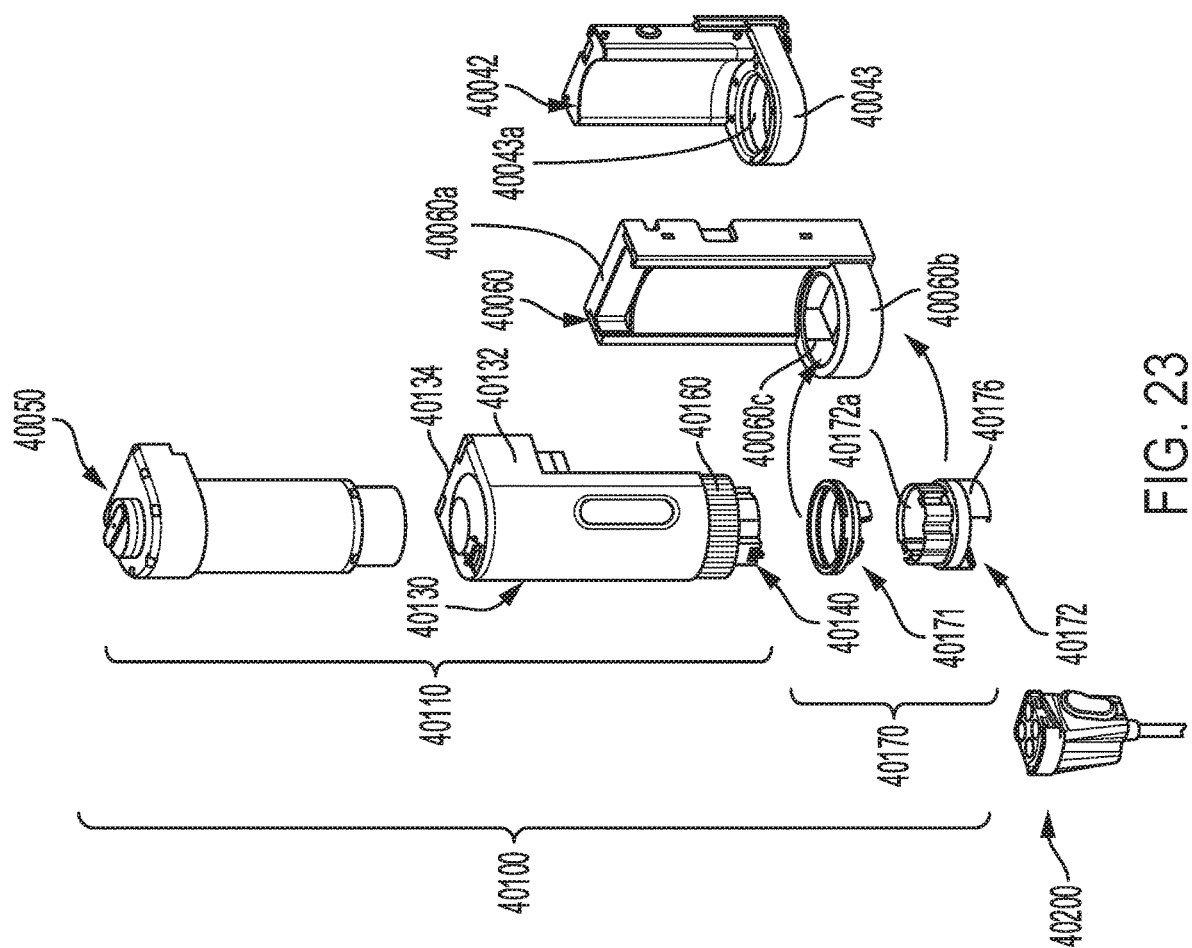
FIG. 23 is an exploded view of a robotic surgical assembly, in accordance with at least one aspect of the present disclosure.
Figure 24:
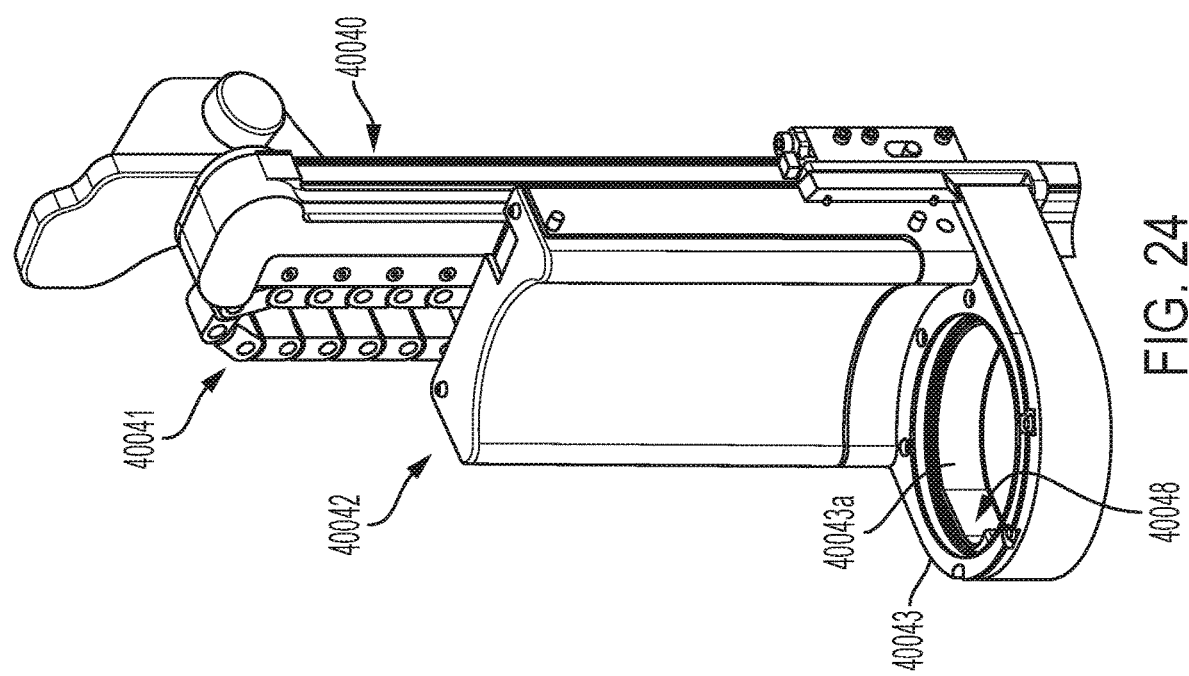
FIG. 24 is a perspective view of a carriage and a slide rail of a robotic surgical assembly, in accordance with at least one aspect of the present disclosure.
Figure 25:
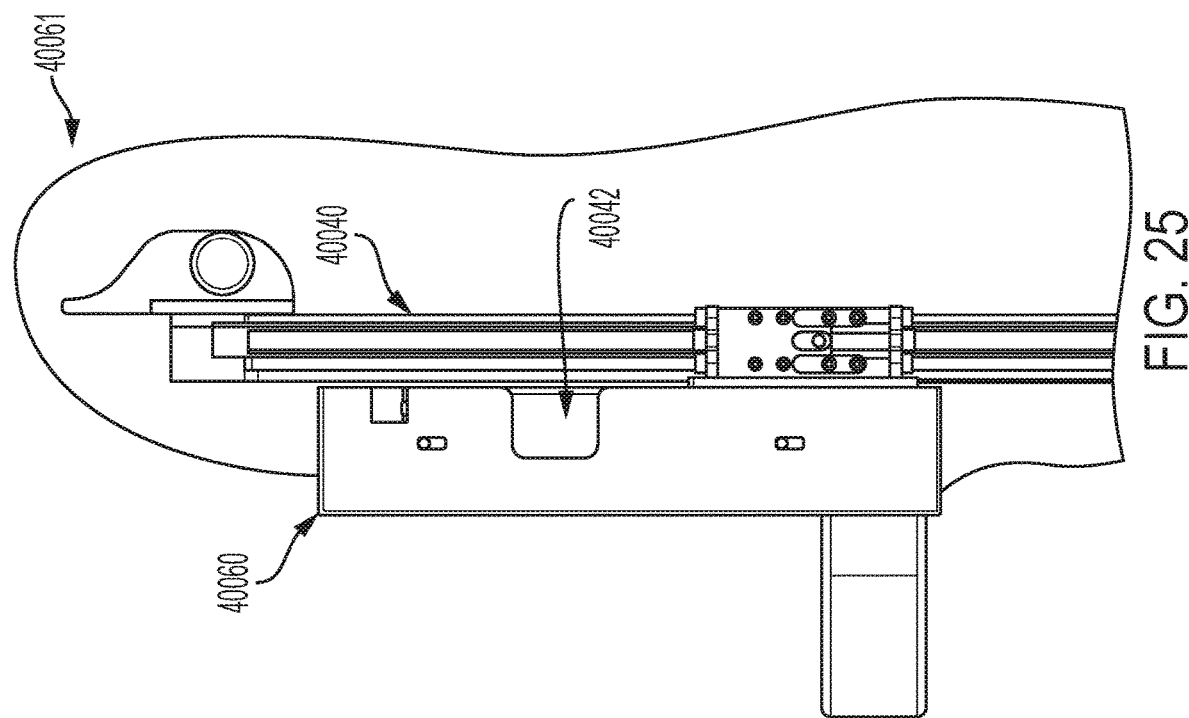
FIG. 25 is a side elevational view of a carriage and a slide rail of a robotic surgical system, in accordance with at least one aspect of the present disclosure.
Figure 31:
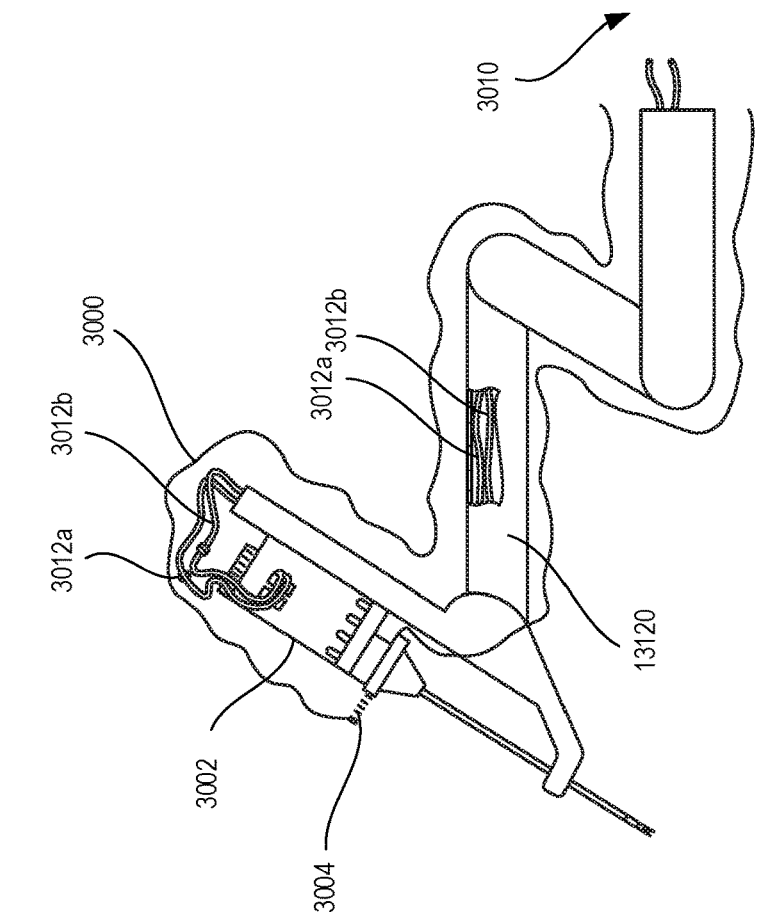
FIG. 31 is a side elevational view of a robotic arm comprising a fluid-based cooling system for an instrument drive unit, in accordance with at least one aspect of the present disclosure.
Figure 30:
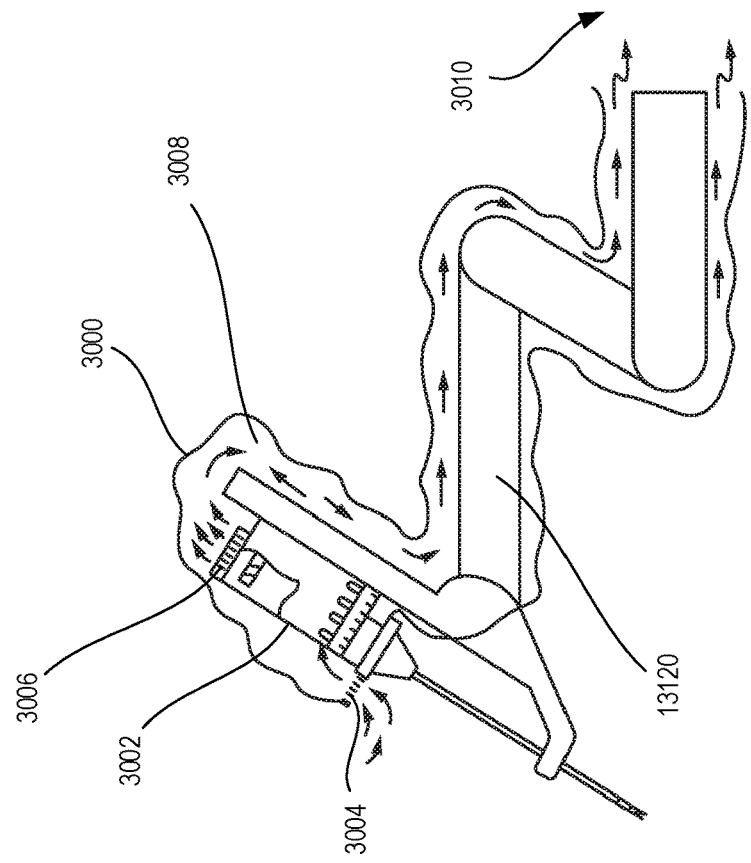
FIG. 30 is a side elevational view of a robotic arm comprising an air-based cooling system for an instrument drive unit, in accordance with at least one aspect of the present disclosure.

Referring now to FIGS. 30 and 31, in some aspects the sterile drape 3000 can be dimensioned or configured to cover the IDU 3002 when affixed to the robotic arm 13120, as opposed to the IDU 3002 being exposed to the sterile field, as shown in FIGS. 23-25. For example, FIG. 30 is a side elevational view of a robotic arm 13120 comprising an air-based cooling system for an IDU 3002 positioned within the sterile drape 3000. In this aspect, the sterile drape 3000 includes an air intake filter 3004 through which ambient air (e.g., air from the sterile field) is indrawn into the interior 3008 of the sterile barrier 3000. The filter 3004 can include, for example, an ULPA filter or an ionizing air filter. The filter 3004 is configured to remove contaminants and other particulates from the indrawn ambient air. Once it has been drawn through the filter 3004, the air can pass into the IDU 3002 (e.g., through a port thereon) at which point it is heated by the electronics, motors, and other interior components of the IDU 3002 and then exhausted by the IDU fan 3006 (e.g., the fan 41150 from FIGS. 26, 28, and 29) into the interior 3008 of the sterile drape 3000, carrying thermal energy away from the IDU 3002. The heated air is then drawn through the interior 3008 of the sterile drape 3000 and exhausted into or at a secondary location 3010 remote from the robotic surgical arm 13120. The secondary location 3010 can include, for example, an enclosure. In one aspect, the secondary location 3010 can include a smoke evacuation system to which the interior 3008 of the sterile drape 3000 is fluidically coupled. In another aspect, the secondary location 3010 can include atmosphere within a room or another such enclosure.

In addition to air-based cooling systems, the robotic surgical system 13000 could also include fluid-based cooling systems. For example, FIG. 31 is a side elevational view of a robotic arm 13120 comprising a fluid-based cooling system for an IDU 3002 positioned within the sterile drape 3000. In this aspect, the robotic surgical system 13000 can define a fluid circulation path coupled to the IDU 3002 and that extends at least partially through the robotic arm 13120. The fluid circulation path can include a first tube 3012a configured to transport a cooling fluid (e.g., water) to the IDU 3002 and/or a heat exchanger coupled to the IDU 3002 and a second tube 3012b configured to transport the fluid heated by the IDU 3002 to a secondary location 3010, as described above.

Figure 32:
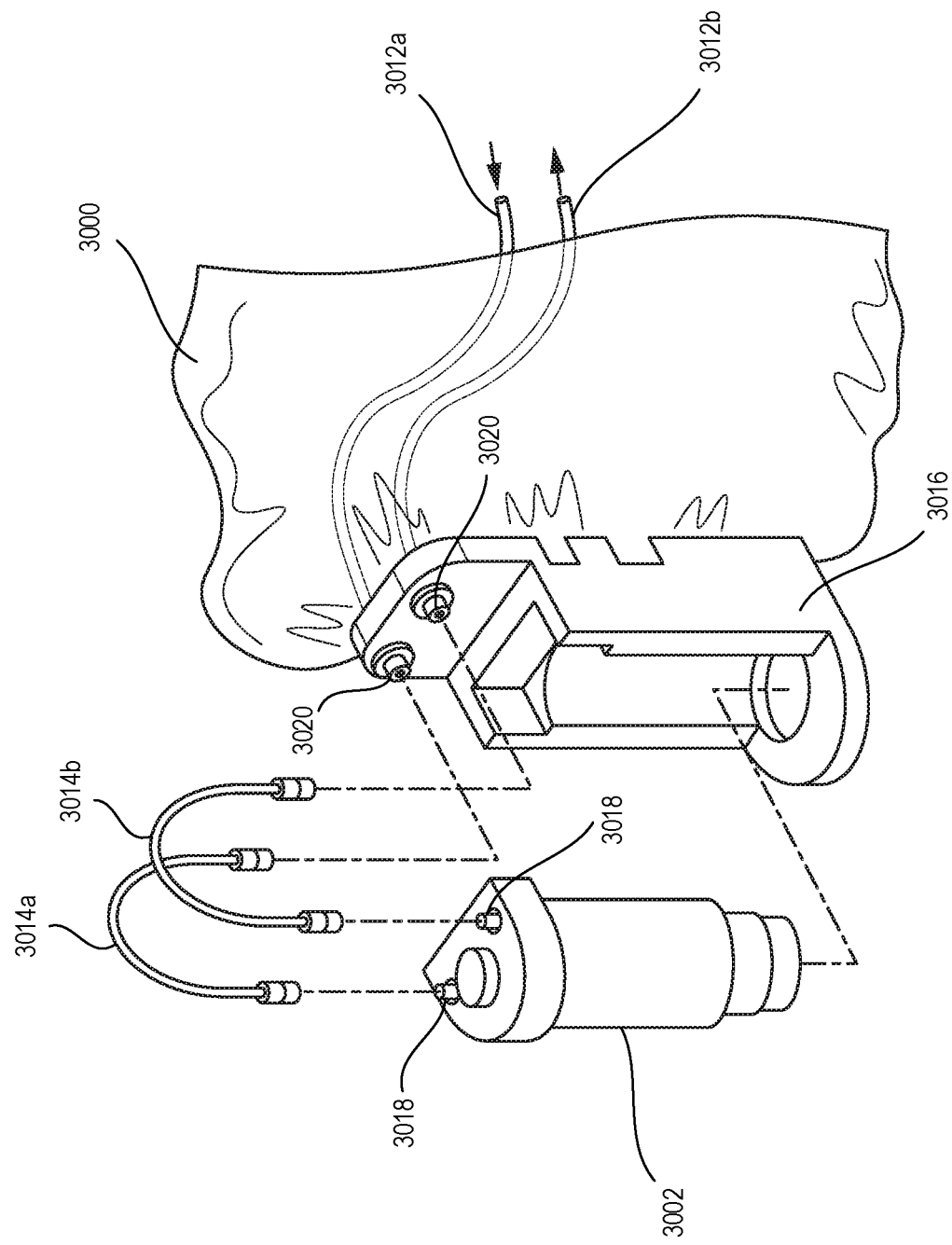
FIG. 32 is a perspective view of a fluid-based, enclosed cooling system for an instrument drive unit, in accordance with at least one aspect of the present disclosure.

In other aspects, the IDU 3002 can be positioned externally to the sterile drape 3000 and can be configured to include a sealed cooling system enclosed from the sterile field. For example, FIG. 32 is a perspective view of a fluid-based, enclosed cooling system for an IDU 3002 positioned externally to the sterile drape 3000. In this aspect, the first tube 3012a and the second tube 3012b are fluidically coupled to a pair of connectors 3020 disposed on the carriage 3016 (or the sterile barrier thereof) that is configured to receive and secure the IDU 3002. Further, the IDU 3002 likewise includes a pair of connectors 3018 disposed thereon. The IDU connectors 3018 can be fluidically coupled to the carriage connectors 3020 via a first connector tube 3014a and a second connector tube 3014b, in order to fluidically couple the first tube 3012a and the second tube 3012b to the IDU 3002 for providing cooling fluid thereto and removing heated fluid therefrom for cooling the IDU 3002. In operation, the first tube 3012a can transport cooling liquid through the sterile drape 3000 to the first connector tube 3014a via a carriage connector 3020, which in turn transports the cooling liquid to the IDU 3002 through the corresponding IDU connector 3018. The cooling fluid is then passed through a heat exchanger or other assembly for transferring thermal energy from the motors, electronics, and/or other components of the IDU 3002 to the cooling liquid. At that point, the heated liquid is transported to the second connector tube 3014b via the corresponding IDU connector 3018, which in turn transports the heated liquid to the second tube 3012b via the corresponding carriage connector 3020. The second tube 3012b then carries then heated liquid to the secondary location 3010, as described above. The cooling system can thus be entirely fluidically isolated from the sterile environment.

In various aspects, the robotic surgical system 1300 could also be configured to include cooling air inlets and outlets within the robotic surgical assembly 40100 that are oriented to mitigate the intake of contaminants from the sterile field. For example, the air inlets and outlets can be oriented so that the air drawn into the cooling system is directed either obliquely relative to or away from the surgical site so as to not create a substantial air differential within the sterile field, reducing the intake of fluids or aerosols that may be present within the sterile field.

Figure 33:
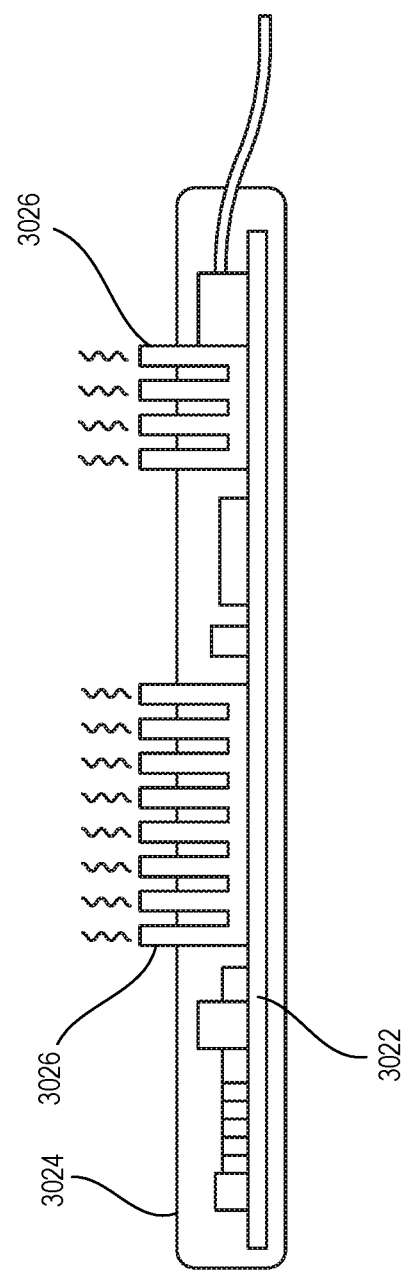
FIG. 33 is a schematic view of robotic surgical assembly circuitry comprising a heat sink assembly, in accordance with at least one aspect of the present disclosure.

In various aspects, contamination of the surgical site, sterile field, and/or surgical theater by air-circulating cooling systems can be prevented by integrating thermal management elements within the electronics systems of the robotic surgical system 13000 and/or IDU 3002 that are sealed and/or isolated from the sterile field. Referring now to FIGS. 33 and 34, the electronics 3022 of the IDU 3002 (e.g., the integrated circuit 41120 in FIG. 26) can be fluidically sealed to prevent contamination and/or exposure to particulates from air and/or fluid circulated through the IDU 3002 for cooling. In various aspects, a sealing layer 3024 can thus be defined about the IDU electronics 3022. The sealing layer 3024 can include, for example, epoxy, acrylate, ultraviolet-curable adhesive, polyurethane, polysulfide (or other solidifying resin), silicone, fluorosilicone (or other suitable polymers or elastomers), or combinations thereof. The materials of the sealing layer 3024 can be deposited via potting or encapsulation techniques, for example. Sealing the electronics 3022 can inhibit cooling and/or exacerbate thermal buildup; therefore, the IDU 3002 can include various cooling elements to mitigate these deleterious effects.

As one example, FIG. 33 illustrates an aspect including heat sink fins 3026 in thermal communication with the electronics 3022 and extending through the sealing layer 3024 for dispersing heat generated from the electronics 3022. The heat radiated by the fins can then be dispersed from the IDU 3002 via air- or fluid-based cooling systems, as described above. In one aspect, the illustrated assembly could be fabricated by adhesively bonding the heat sink fins 3026 to the electronics 3022 via a thermally conductive material (in order to promote thermal communication between the electronics 3022 and the heat sink fins 3026) and the sealing layer 3024 can then be applied thereover to cover the electronics 3022 to create a fluid and air barrier, while still enabling the heat sink fins 3026 to be placed into an air- or fluid-based circulation path to allow for thermal transfer from the electronics 3022. In one aspect, the heat sink fins 3026 can be positioned at or adjacent to a particular structure or set of structures for which additional cooling is desired. In yet another aspect, the heat sink fins 3026 can be positioned at or adjacent to components of the IDU 3002 other than or in addition to the electronics 3022. For example, the heat sink fins 3026 could be integrated into the housing of the motor pack 40050 such that they are in thermal communication with the motors 41052, 41054, 41056, 41056 (FIG. 27), or other components of the motor assembly 41114 (FIG. 26).

As another example, FIG. 34 illustrates as aspect including one or more conduits 3028 extending through the sealing layer 3024 and in thermal communication with the electronics 3022. The conduits 3028 can be part of the circulation path of the cooling system and thus be fed cooling fluid from an inlet 3030 (e.g., coupled to the first tube 3012a) and remove the heated fluid via an outlet 3032 (e.g., coupled to the second tube 3012b). The conduits 3028 can extend through the sealing layer 3024 such that at least a portion of the walls of the conduits 3028 are in contact or thermal communication with the electronics 3022. Accordingly, as the cooling fluid travels through the conduits 3028, thermal energy is transferred from the electronics 3022 to the fluid, which is then removed from the IDU 3002 via the outlet 3032. In one aspect, a cleaning solution can be introduced through the conduits 3028 to clean and sterilize the air or fluid circulation path of the cooling system, without contacting the electronics 3022, motor assembly 41114, and/or other components of the IDU 3002.

In any of the aspects described above where the cooling systems include air or fluid circulated through the IDU 3002, the cooling systems can additionally include pumps, blowers, tubing, and other components necessary for driving the air or fluid through the circulation path. The pumps, blowers, and other such components can be located locally with respect to the robotic arm 13120 or positioned remotely therefrom.

As another example, a Peltier cooling element could be integrated into the sealing layer 3024. In one aspect, the Peltier cooling element could be positioned in proximity to a critical structure within the IDU 3002 for which it was especially desirable or difficult (e.g., due to engineering constraints) to cool. Thus, the Peltier cooling element could be used to extract heat from the critical structure and transfer the heat to areas, either within the IDU 3002 and/or outside of the IDU 3002, with a higher convective heat transfer rate than the area at or around the critical structure.

Figure 36:
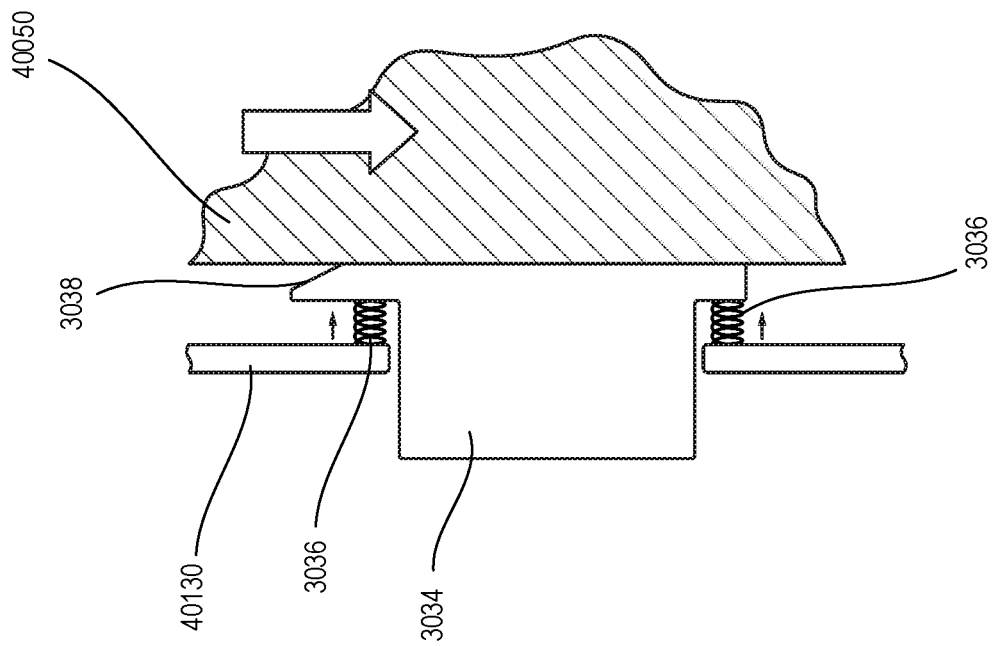
FIG. 36 is a sectional view of the instrument drive unit and heat sink assembly of FIG. 35, in accordance with at least one aspect of the present disclosure.
Figure 35:
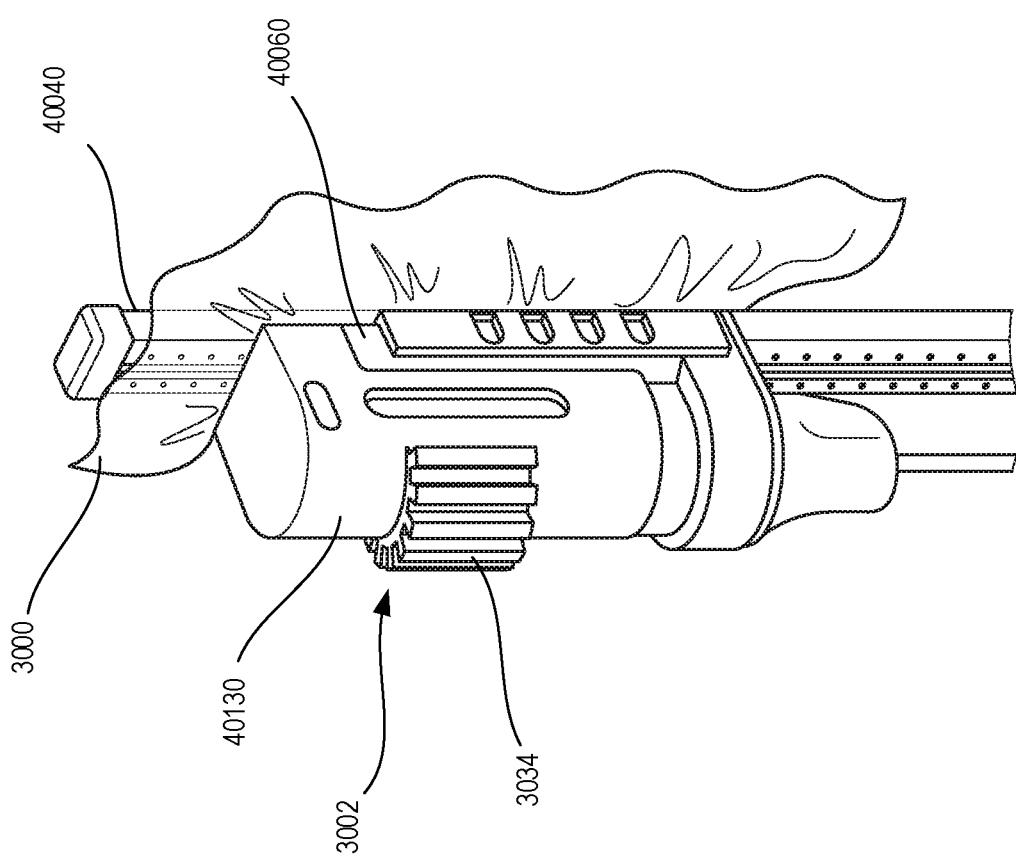
FIG. 35 is a perspective view of an instrument drive unit comprising a heat sink assembly, in accordance with at least one aspect of the present disclosure.

In other aspects, cooling systems for the IDU 3002 can be integrated into the sterile barrier components of the robotic surgical assembly 40100 for cooling the nonsterile components housed thereby. For example, in an aspect illustrated in FIGS. 35 and 36 the sterile barrier housing 40130 configured to receive a motor pack 40050 can include one or more heat sink fins 3034 that extend through the wall of the sterile barrier housing 40130 and contact the motor pack 40050 (when the motor pack 40050 is positioned therein) for dispersing heat generated by the motor pack 40050. In one aspect, the heat sink fins 3034 can further be biased towards the interior of the sterile barrier housing 40130 via, for example, springs 3036. The biasing of the heat sink fins 3034 ensures that they physically contact, and are thus in thermal communication with, the motor pack 40050 to maintain heat conduction from the motor pack 40050 to the heat sink fins 3034. The portion of the heat sink fins 3034 interior to the sterile barrier housing 40130 can further include a chamfered edge 3038 in order to slidably direct the motor pack 40050 into position within the sterile barrier housing 40130 as the motor pack 40050 is received thereby. Due to the physical contact between the heat sink fins 3034 and the motor pack 40050, the heat sink fins 3034 absorb heat generated by the motor pack 40050 and then convectively disperse the absorb heat into the surrounding environment (e.g., the surgical theater) to cool the motor pack 40050 and the IDU 3002 as a whole.

Sterile Drape

As described above, a sterile drape 3000 may be utilized in conjunction with the robotic arm 13120 and/or robotic surgical assembly 40100 (FIG. 26) to establish and maintain a sterile barrier between the patient 13013 (FIG. 4), the surgical field, and/or the robotic surgical system 13000 (FIG. 4). The sterile drape 3000 can be deployable in a variety of different manners for enshrouding the robotic arm 13120 and/or various components of the robotic surgical assembly 40100. Furthermore, the sterile drape 3000 can include a variety of different materials and structures for communicating information to the surgical staff, such as whether the sterile drape 3000 has suffered a breach (due to, e.g., a puncture or abrasion).

In one aspect illustrated in FIG. 37, a sterile drape 3000 can include one or more first connectors 3040 positioned along a first edge 3039 and one or more second connectors 3042, which are configured to removably engage the first connectors 3040, positioned along an opposing second edge 3041. The first connectors 3040 can include male connectors and the second connectors 3042 can include corresponding female connectors, or vice versa, for example. The first connectors 3040 and the second connectors 3042 can be arranged such that, when they are joined together, the sterile drape 3000 can form a generally tubular structure that is shaped and dimensioned to enshroud a robotic arm 13120 and/or other component(s) of the robotic surgical assembly 40100. The removable connectors 3040, 3042 can thereby allow the sterile drape 3000 to be secured about the robotic arm 13120 and/or robotic surgical assembly 40100 after the sterile components of the robotic surgical assembly 40100 (i.e., the sterile barrier housing 40130 for the motor pack 40050 and the sterile shell or barrier 40060 for the carriage 40042) are secured in place. The connectors 3040, 3042 can include a variety of different types and configurations of connectors or closure elements. For example, in the aspect illustrated in FIG. 38A, the connectors 3040, 3042 can define a single, inter-meshable closure positioned longitudinally along the edges 3039, 3041 of the sterile drape 3000 that is joinable in the manner of a zip fastener. As another example, in the aspect illustrated in FIG. 38A, the connectors 3040, 3042 can define corresponding male and female snap features that are positioned at discrete locations along the edges 3039, 3041 of the sterile drape 3000.

In one aspect, the sterile drape 3000 can further include an adhesive layer positioned along at last one of the edges 3039, 3041 of the sterile drape 3000. In operation, the adhesive layer could be exposed and then adhered over the connectors 3040, 3042 to provide additional securement to the line of connection of the sterile drape 3000. In another aspect, the sterile drape 3000 can further include protuberances or grips located at or adjacent to the connectors 3040, 3042 in order to assist users in bringing the opposing edges 3039, 3041 of the sterile drape 3000 together and aligning the respective connectors 3040, 3042 while maintaining sterile technique.

In one aspect, the sterile drape 3000 can include a plurality of interlocking segments that are detachably connectable together to conform to a robotic arm 13120. Such combinations of interlocking segments can allow a robotic arm 13120 to be progressively barriered off, for example. For example, FIGS. 39A and 39B illustrate a sterile barrier 3000 that includes a first segment 3000a, a second segment 3000b, a third segment 3000c, and a fourth segment 3000d that are detachably connectable together at connection points 3044. Each of the segments 3000a, 3000b, 3000c, 3000d of the sterile drape 3000 can be dimensioned or otherwise configured to conform to a specific portion or component of the robotic arm assembly. Further, although the sterile drape 3000 is illustrated as including four segments 3000a, 3000b, 3000c, 3000d in FIGS. 39A-39C, this is simply for illustrative purposes and the sterile drape 3000 can, in various aspects, have any number of segments 3000a, 3000b, 3000c, 3000d. In one aspect, the corresponding segments can be connected both to each other and the robotic arm 13120 at the connection points 3044. For example, the robotic arm 13120 can include a first connector 3046 (e.g., a male connector) that is configured to engage with a corresponding second connector 3048 (e.g., a female connector) disposed on one of the sterile drape segments (which is the second segment 3000b in the detail view shown in FIG. 39B). That sterile drape segment can then also include a third connector 3050 (e.g., a male connector) that is configured to engage with a corresponding fourth connector (e.g., a female connector) disposed on the corresponding sterile drape segment (which is the first segment 3000a in the detail view shown in FIG. 39B). Further, the sterile drape segments can be constructed in different manners. For example, some of the sterile drape segments could include tubular structures (e.g., the first segment 3000a and the third segment 3000b), whereas other sterile drape segments could include flat structures that are folded over and sealed together (e.g., the second segment 3000b could include a flat segment that with opposing ends that are sealed around the Y-shaped junction between opposing members of the robotic arm 13120).

In other aspects, the sterile barrier 3000 can include segments having elastic sleeves at their the open ends, which enable a tight fit around the robotic arm 13120 in the regions where the sterile drape segments overlap and allow for attachment to hard plastic barrier component. The hard plastic barrier component(s) could include a circular groove that could serve as an attachment point for the elastic sleeve portion and would prevent slippage of the elastic sleeve with respect thereto. In still other aspects, the sterile barrier 3000 can include segments having accordion-like folds at joint and elbow locations, which can provide flexibility to the sterile drape 3000 without stretching or potentially damaging the sterile drape 3000.

In one aspect, one or more sterile drape modules can be detachably connected to the sterile drape 3000 for supplementing or augmenting the sterile drape 3000. For example, FIGS. 39A and 39C illustrate a module 3054 including a blower 3056 that is configured to transport air from a first location (e.g., within the sterile barrier 3000) to a second location via an outlet 3058. The module 3054 can be configured to facilitate air movement through the sterile barrier 3000 for cooling of the robotic surgical assembly, for example.

Figure 40:
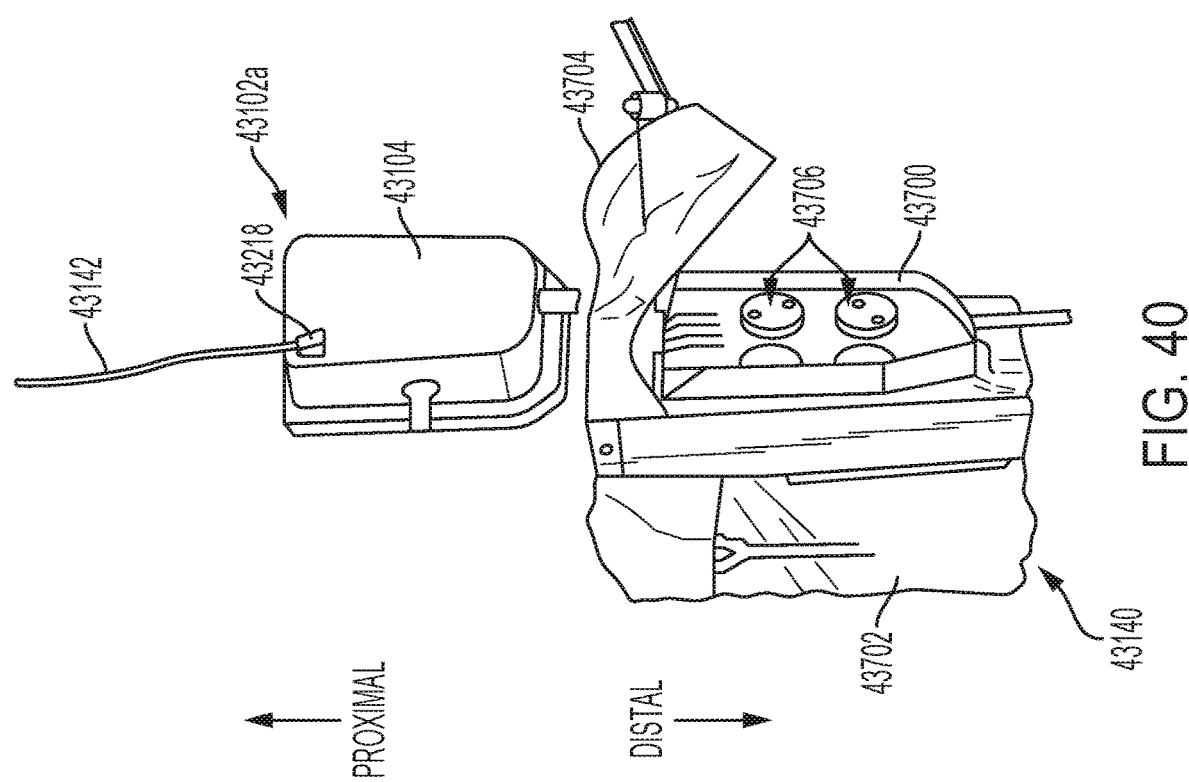
FIG. 40 is a perspective view of an adapter interface for a sterile drape, in accordance with at least one aspect of the present disclosure.

The sterile barrier 3000 can include a variety of different modules and attachment points for facilitating the attachment of devices thereto. For example, in one aspect illustrated in FIG. 40, the sterile drape 43704 may be provided between a patient side cart (not shown), particularly over the manipulator arms 43140, and the surgical instrument (not shown) in order to create a sterile boundary between the sterile field, which may include a sterile adapter 43700 of the actuation interface assembly 43706 to which a sterile surgical instrument is attached, and the non-sterile patient side cart. The sterile adapter 43700 of the sterile drape 43704 can include actuation interface assemblies 43706 that are configured to engage with transmission mechanisms provided at a proximal end of the surgical instruments. The surgical instrument and the actuation interface assembly 43706 may be mechanically and electrically connected to be able to operate the instrument.

In one aspect illustrated in FIGS. 41A-41D, multiple sterile drapes 3000 can be provided as a set that are detachably connected to each other at their proximal ends 3066 via, for example, perforated edges, zip fasteners, and other connectors or lines of connection. Accordingly, users can deploy a sterile drape 3000 on a robotic arm 13120 by drawing one of sterile drapes 3000 from the set over the robotic arm 13120 and then detaching the deployed sterile drape 3000 from the remaining members of the set, as is shown in FIGS. 41B-41D. The sterile drape 3000 can further include a rip cord 3060 coupled to a line of connection 3062 extending longitudinally along the sterile drape 3000. The rip cord 3060 can be configured to release the line of connection 3062 (as shown in FIG. 41B), opening the sterile drape 3000 lengthwise and thereby allowing the sterile drape 3000 to be released from the robotic arm 13120 on which it is deployed (as shown in FIG. 41C) in a convenient manner. Thereafter, a replacement sterile drape 3000 can be deployed along the robotic arm 13120 (as shown in FIG. 41D).

In one aspect illustrated in FIGS. 42A-42C, the sterile drape 3000 can be deployable from a container 3064 or cartridge that is positionable at the base of the robotic arm 13120 or is integral to the robotic arm 13120. In this aspect, the container 3064 can house a set of sterile drapes 3000 that are detachably connected to each other at their proximal ends 3066 via, for example, perforated edges, zip fasteners, a rip cord (such as the rip cord 3060 described above), and other connectors or lines of connection. Accordingly, users can replace a sterile drape 3000 deployed on a robotic arm 13120 by withdrawing a new sterile drape 3000 from the container 3064 after or as the currently deployed sterile drape 3000 is removed, as is shown in FIGS. 42B and 42C. The sterile drape 3000 can further include a rip cord 3060, as described above in connection with FIGS. 41A-41D.

In one aspect illustrated in FIGS. 43A and 43B, the sterile drape 3000 a skeleton 3068 configured to structurally reinforce the sterile drape 3000. The skeleton 3068 can include structures that are positioned along an interior surface, along an exterior surface, and/or positioned between layers of the sterile drape 3000. In the illustrated aspect, the skeleton 3068 includes a rigid or semi-rigid helical structure oriented coaxially with the sterile drape 3000. The helical structure can be circular, ellipsoidal, rectangular, or any other shape in cross-section that conforms to the profile of the robotic arm 13120 with which the sterile drape 3000 is to be utilized. The skeleton 3068 can be beneficial in order to, for example, make the sterile drape 3000 easier to snake around joints than sterile drapes 3000 lacking the skeleton 3068. Further, in aspects where the skeleton 3068 is utilized in conjunction with a segmented sterile barrier (e.g., such as the sterile barrier 3000 illustrated in FIG. 39A), the shape, structure, and/or configuration of the skeleton 3068 can be customized for the particular section of the robotic arm 13120 and/or robotic surgical assembly 40100 over which that section is to be deployed.

In one aspect illustrated in FIG. 44, the sterile barrier 3000 can include one or more joint sections 3070. The joint sections 3070 can be constructed from a material, have a particular arrangement or structure, or otherwise be configured to promote bending of the sterile drape 3000 at their locations as compared to the remaining portions of the sterile drape 3000. For example, the joint sections 3070 can define gaps or a lack of the presence of a skeleton 3068. Further, the joint sections 3070 can be positioned at regular or irregular intervals along the length of the sterile drape 3000, for example. In one aspect, the joint sections 3070 can be positioned at locations corresponding to the locations of the joints of the robotic arm 13120 for which the sterile drape 3000 is intended to be utilized, thereby allowing the sterile drape 3000 to closely conform to the arrangement of the arm sections of the robotic arm 13120.

Figure 45B:
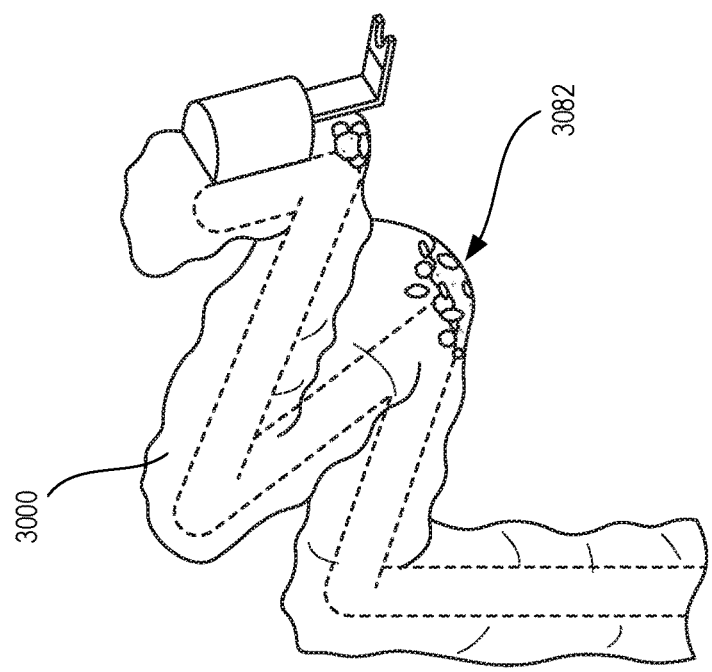
FIG. 45B is a perspective view of the sterile drape of FIG. 45A positioned on a robotic arm, where the sterile drape has been breached, in accordance with at least one aspect of the present disclosure.
Figure 45A:
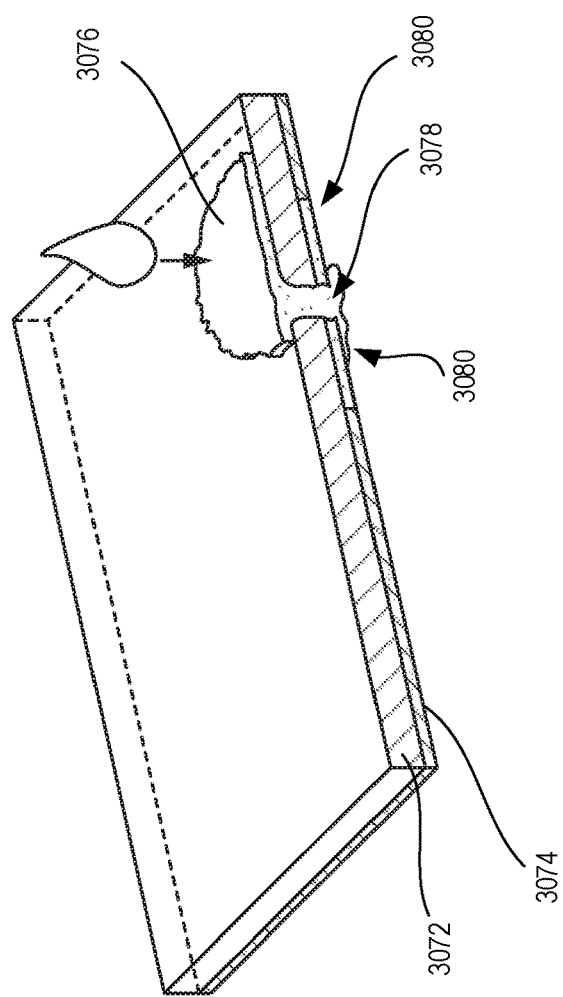
FIG. 45A is a detail view of a sterile drape comprising a moisture-detecting layer, in accordance with at least one aspect of the present disclosure.

In one aspect illustrated in FIGS. 45A and 45B, the sterile barrier 3000 can be configured to indicate when a liquid 3076 (e.g., body fluid) has breached the sterile barrier 3000. In the illustrated example, the sterile barrier 3000 includes a first or exterior layer 3072 and a second or interior layer 3074. The exterior layer 3072 can include a clear or translucent material. The interior layer 3074 can be configured to change color upon contact with moisture. For example, the interior layer 3074 can include a moisture-detecting dye. Accordingly, when a breach 3078 has formed in at least the exterior layer 3072 and liquid 3076 has come in contact with the interior layer 3074, the portions 3080 of the interior layer 3074 coming in contact with the liquid 3076 are configured to change color. Therefore, the sterile barrier 3000 creates a visual indication 3082 that the sterile barrier 3000 has been breached and potentially contaminated by a liquid 3076 so that users can take corrective action (e.g., sealing the breach or having the robotic arm 13120 and/or other components of the robotic surgical system 13000 cleaned).

In one aspect illustrated in FIGS. 46A-46D, the sterile barrier 3000 can be configured to visually indicate when a breach 3088 has occurred in the sterile barrier 3000 or the surface of the sterile barrier 3000 has otherwise been physically disturbed. In the illustrated example, the sterile barrier 3000 includes a plurality of air- or fluid-filled pockets 3084 positioned along a surface 3086 of the sterile barrier 3000. The pockets 3084 can include, for example, regularly spaced, protruding, air-filled hemispheres. Accordingly, when a breach 3088 has formed in the sterile barrier 3000, the pockets 3084 deflate or collapse and thereby create a visual indication that the sterile barrier 300 has been breached so that users can take corrective action.

Figure 47C:
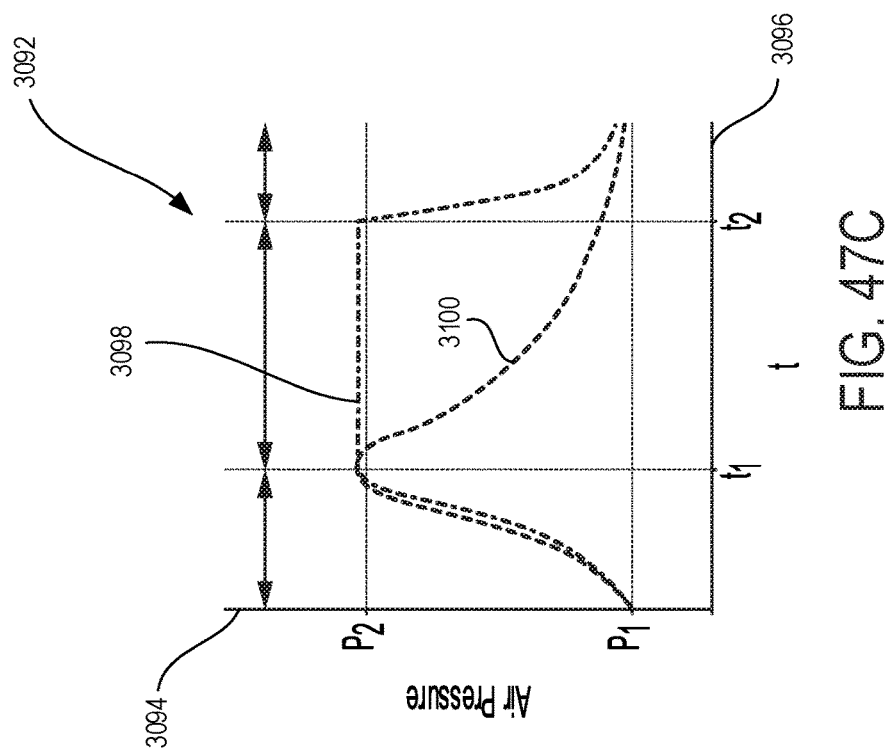
FIG. 47C is a graph of sterile drape air pressure verse time for breached and non-breached sterile drapes, in accordance with at least one aspect of the present disclosure.
Figure 47B:
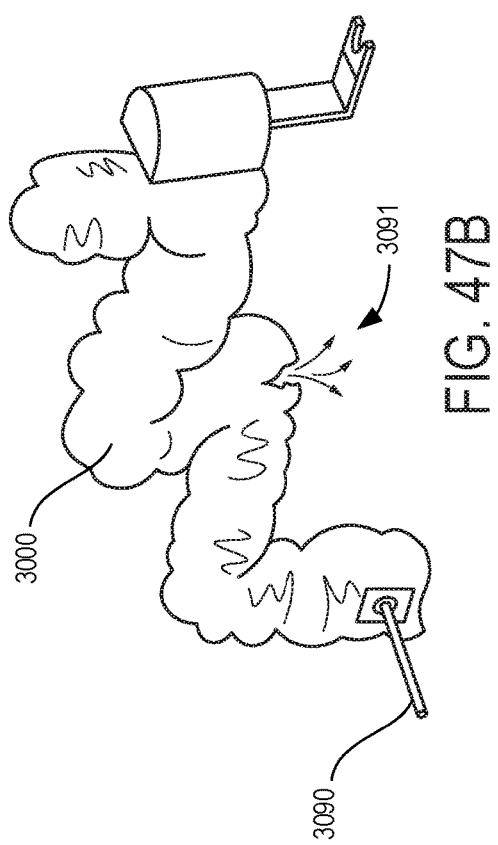
FIG. 47B is a perspective view of the sterile drape of FIG. 47A, where the sterile drape has been breached, in accordance with at least one aspect of the present disclosure.
Figure 47A:
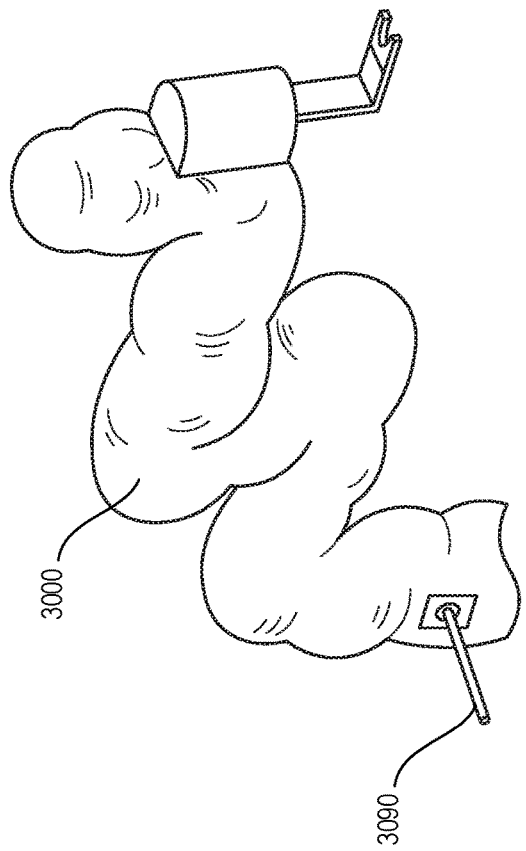
FIG. 47A is a perspective view of a pressurized sterile drape positioned on a robotic arm, in accordance with at least one aspect of the present disclosure.

In one aspect illustrated in FIGS. 47A-47C, the sterile barrier 3000 can be configured to be pressurized or inflated from an air source 3090 in order to indicate when a breach 3091 has occurred in the sterile barrier 3000. In the illustrated example, the sterile barrier 3000 can be configured to be airtight (or substantially airtight) when deployed on a robotic arm 13120 and can be pressurized via an air source 3090 that is fluidically couplable to the sterile barrier 3000. In various aspects, the air source 3090, sterile barrier 3000, robotic arm 13120, and/or another component of the robotic surgical system 13000 can include an air pressure sensor for sensing the internal air pressure of the sterile barrier 3000. Accordingly, when a breach 3091 has formed in the sterile barrier 3000, the sterile barrier 3000 can be depressurized and at least partially deflate, as illustrated in FIG. 47B. The robotic surgical system 13000 can be configured to sense this depressurization based on the sensed air pressure profile of the sterile barrier. In one aspect, the control device 13004 (FIG. 4) can be communicably connected to the air pressure sensor for receiving air pressure data therefrom. For example, FIG. 47C illustrates a prophetic graph 3092 where the vertical axis 3094 represents air pressure and the horizontal axis 3096 represents time. A first line 3098 indicates a surgical procedure where the sterile barrier 3000 was inflated from an initial pressure $P_1$ until it reached an operating pressure $P_2$ at $t_1$. As can be seen, the first line 3098 maintains a flat profile until the sterile barrier 3000 begins being deflated at $t_2$ (which can represent the completion of the surgical procedure, for example). Therefore, it can be determined that the sterile barrier 3000 did not suffer a breach during the surgical procedure. Conversely, a second line 3100 indicates a surgical procedure where the sterile barrier 3000 was inflated to an operating pressure $P_2$, but then suffered a breach at a point after $t_1$, resulting in the air pressure of the sterile barrier 3000 decreasing prematurely. Therefore, it can be determined that the sterile barrier 3000 did suffer a breach 3091 during the surgical procedure. In this way, monitoring the internal air pressure of a pressurized sterile barrier 3000 can be utilized to monitor for breaches 3091. Once a breach 3091 has been detected, the robotic surgical system 13000 (or a control device 13004 thereof) can be configured to provide a notification to the users (e.g., via a display device 13006 (FIG. 4)) or take some other corrective action (e.g., increase the air-flow rate provided by the air source 3090 to attempt to compensate for the breach 3091).

Figure 48A:
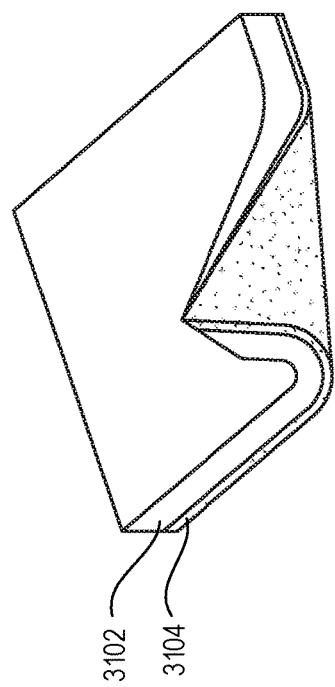
FIG. 48A is a detail view of a sterile drape comprising a color-changing layer, in accordance with at least one aspect of the present disclosure.
Figure 48B:
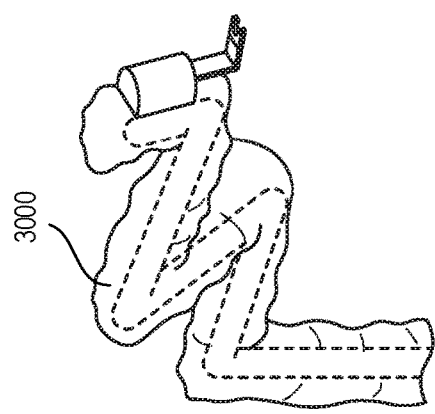
FIG. 48B is a perspective view of the sterile drape of FIG. 48A, where the sterile drape has not been experienced a temperature above a threshold temperature, in accordance with at least one aspect of the present disclosure.
Figure 48C:
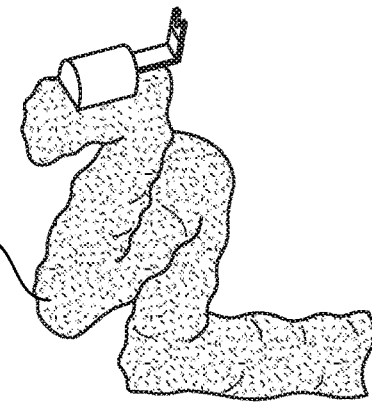
FIG. 48C is a perspective view of the sterile drape of FIG. 48A, where the sterile drape has been experienced a temperature above a threshold temperature, in accordance with at least one aspect of the present disclosure.
Figure 48D:
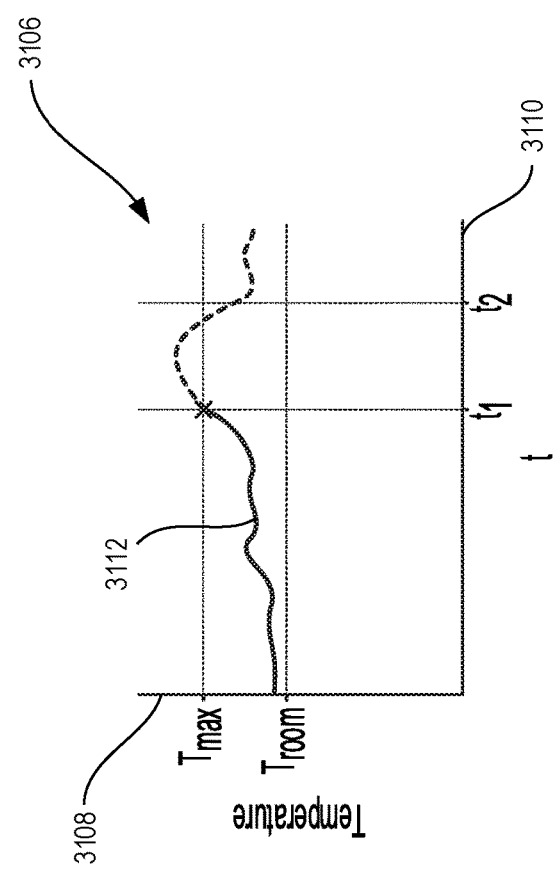
FIG. 48D is a graph of temperature verse time for a color-changing sterile drape, in accordance with at least one aspect of the present disclosure.

In one aspect illustrated in FIGS. 48A-48D, the sterile barrier 3000 can be configured to indicate whether a threshold temperature was reached or exceeded. In the illustrated example, the sterile barrier 3000 includes a first or exterior layer 3102 and a second or interior layer 3104. The exterior layer 3102 can include a clear or translucent material. The interior layer 3104 can be configured to change color upon reaching or exceeding a threshold temperature $T_{max}$. For example, the interior layer 3074 can include a thermosensitive or thermochromic dye that is configured to change color upon reaching the threshold temperature $T_{max}$. The thermochromic dye can be applied to the interior layer 3074 in the form of microcapsules, for example. In one aspect, the thermosensitive dye can be configured to permanently change color upon reaching the threshold temperature $T_{max}$ to visually alert users as to whether the sterile shield 3000 has ever been exposed to a temperature reaching the threshold temperature $T_{max}$. For example, FIG. 48D illustrates a prophetic graph 9106 where the vertical axis 3108 represents the temperature experienced by the sterile barrier 3000 and the horizontal axis 3110 represents time. A line 3112 indicates the temperature experienced by the sterile barrier 3000 during the course of a particular surgical procedure. At time $t_1$ the temperature reaches or exceeds the temperature threshold $T_{max}$, thereby causing the sterile barrier 3000 to transition from a first color (or translucent), as shown in FIG. 48B, to a second color, as shown in FIG. 48C. The color change can visually indicate that the sterile barrier 3000 has been exposed to temperatures outside of its acceptable operating range so that users can, for example, take corrective action.

In one aspect illustrated in FIGS. 49A-48C, the sterile barrier 3000 can be configured to self-heal breaches 3120. In the illustrated example, the sterile barrier 3000 includes a first or interior layer 3114, a third or exterior layer 3118, and a second layer 3116 sandwiched between the first and third layers 3114, 3118. The second layer 3116 can include a material that is configured to heal breaches 3120, such as a liquid or gel polymer that is configured to crosslink and solidify when exposed to air. Accordingly, when a breach 3120 has formed in at least one of the first or second layers 3114, 3118 of the sterile barrier 3000 (as shown in FIG. 49B), the material from the second layer 3116 advances into the space opened by the breach 3120, at which point it is exposed to air and forms a plug 3122 and thereby heals the breach 3120 (as shown in FIG. 49C). It can be useful for sterile barriers 3000 to include some type of self-healing mechanism in order to prevent or mitigate contamination of components enshrouded by the sterile barrier 3000 when a breach 3120 has occurred.

Figure 50:
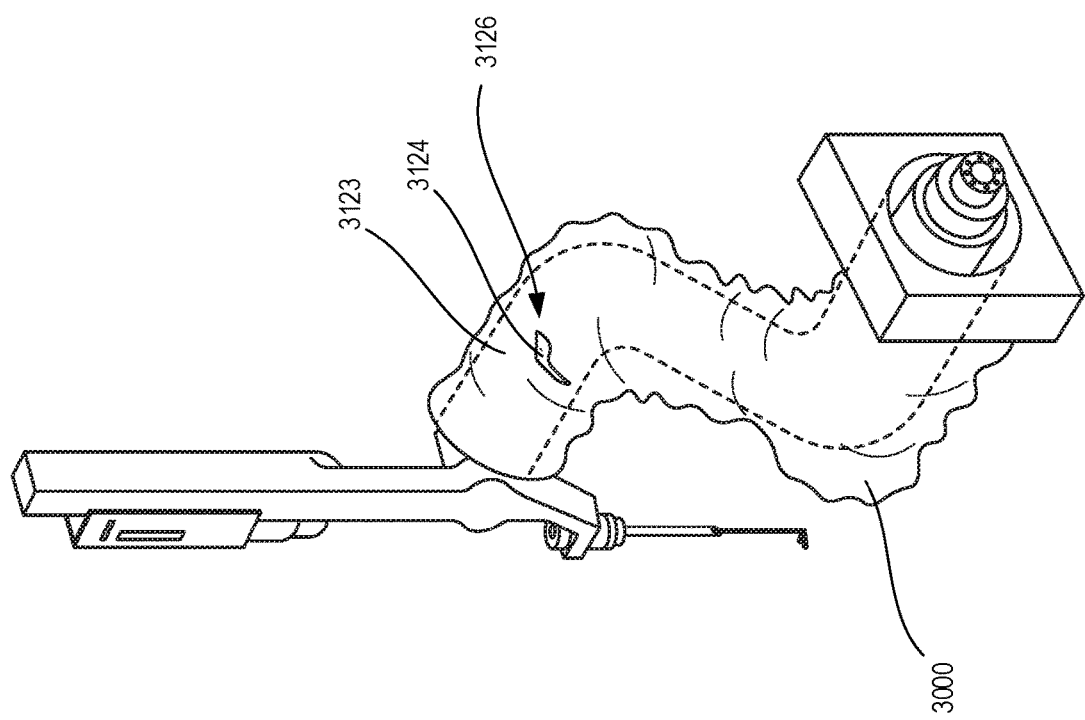
FIG. 50 is a perspective view of a sterile drape comprising a colored underlayer, in accordance with at least one aspect of the present disclosure.

In one aspect illustrated in FIG. 50, the sterile barrier 3000 can be configured to visually indicate when a breach 3126 has occurred in the sterile barrier 3000. In the illustrated example, the sterile barrier 3000 can include a first or exterior layer 3123 that is a first color and a second or interior layer 3124 that is a second color. The exterior layer 3123 can additionally be constructed from an opaque material such that the interior layer 3124 is not visible unless a breach 3126 is formed in the exterior layer 3123. Accordingly, when the sterile barrier 3000 suffers a breach 3126, the interior layer 3124, which is a different color from the exterior layer 3123, is revealed, visually indicating the presence of the breach 3126. In one aspect, the color of the interior layer 3124 can be selected such that it highly contrasts or is especially visible against the color of the exterior layer 3123.

Robotic Surgical Attachment Assemblies

Figure 51:
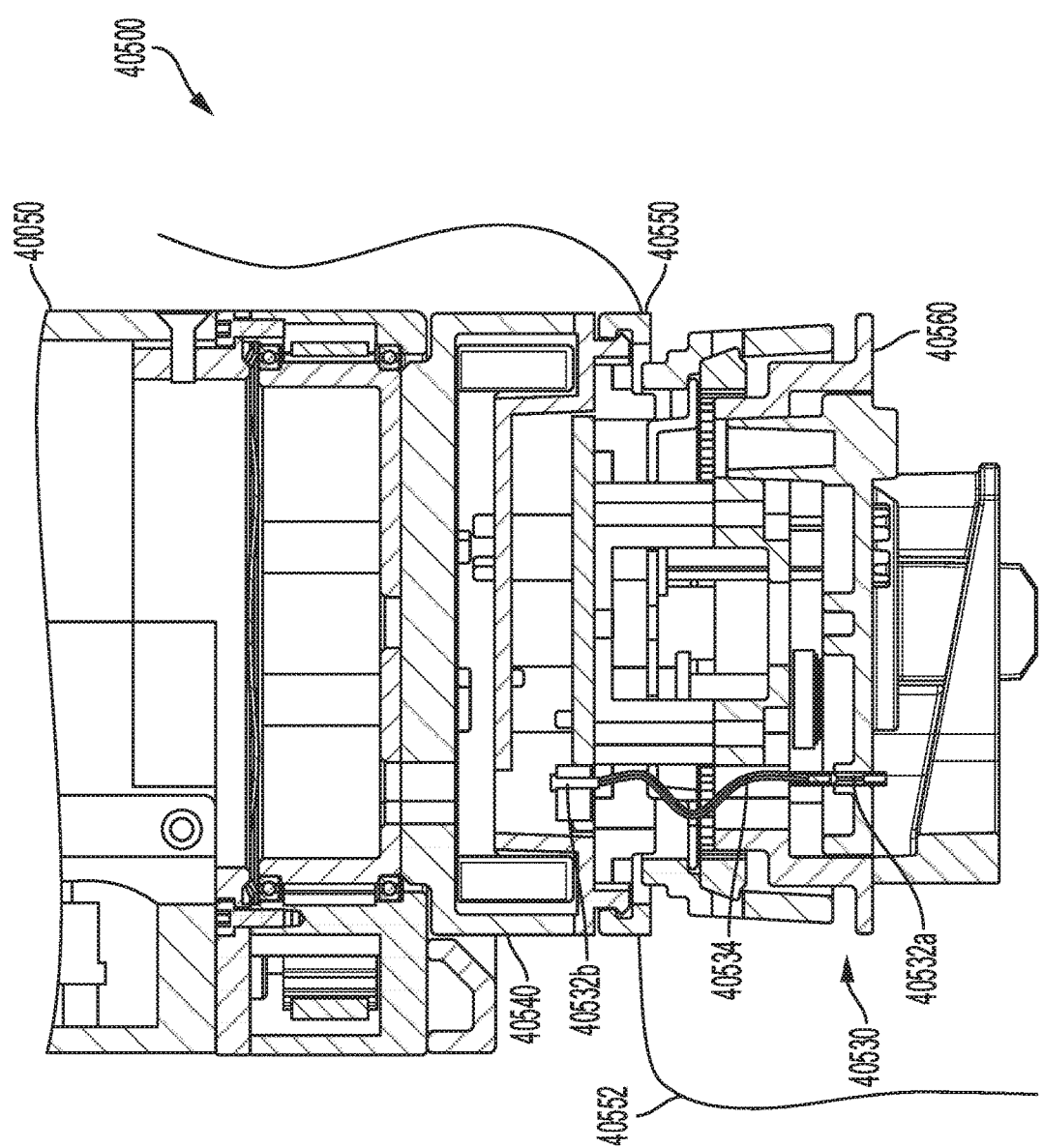
FIG. 51 is a sectional view of a portion of a robotic surgical assembly, in accordance with at least one aspect of the present disclosure.
Figure 52:
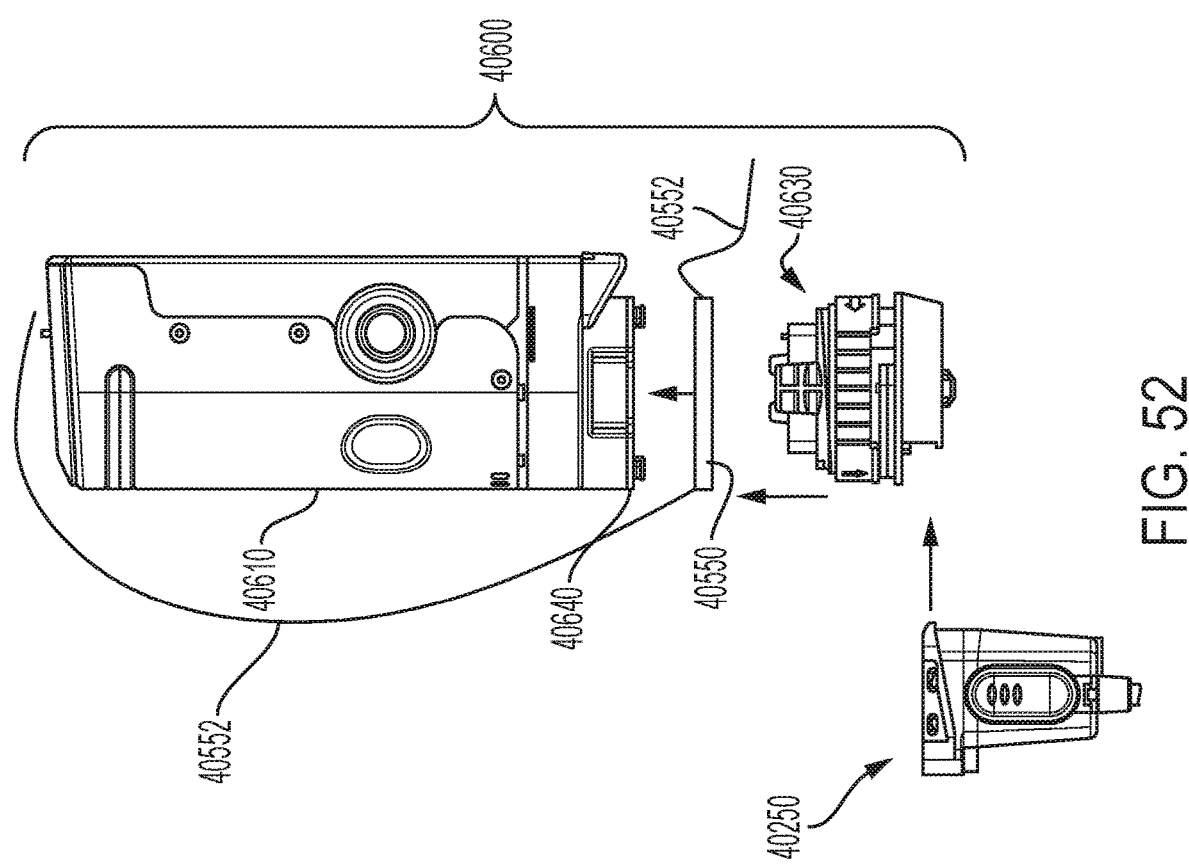
FIG. 52 is an exploded view of a robotic surgical assembly, in accordance with at least one aspect of the present disclosure.
Figure 53:
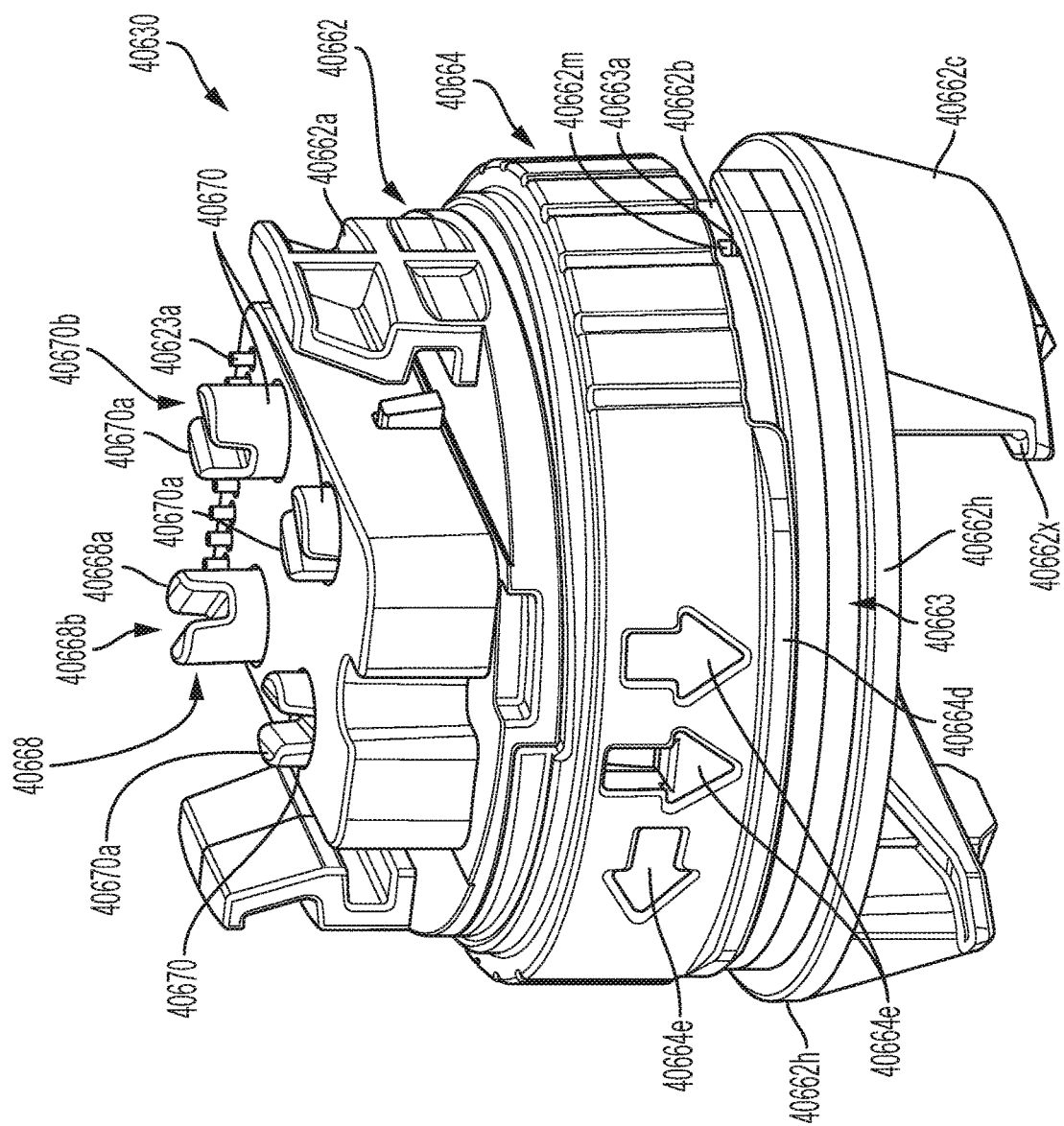
FIG. 53 is a perspective view of a sterile interface module of a robotic surgical assembly, in accordance with at least one aspect of the present disclosure.

Turning now to FIGS. 51-53, the robotic surgical assembly 43600 of the robotic surgical system 13000 (FIG. 4) includes an instrument drive unit or housing 43610 supporting a motor assembly or motor pack 43050, as described above under the heading ROBOTIC SURGICAL ASSEMBLY. The housing 43610 of the robotic surgical assembly 43600 includes a connector assembly 43540.

A collar assembly or sterile interface module 43630 is provided for selectively interconnecting the robotic surgical assembly 43600 and an electromechanical surgical instruments 43250. In general, the sterile interface module 43630 functions to provide an interface between the instrument drive unit or housing 43610 and an electromechanical surgical instrument 43250. This sterile interface module 43250 advantageously maintains sterility, provides a means to transmit electrical communication between the robotic surgical assembly 43600 and the electromechanical surgical instrument 43250, provides a means for transferring rotational force from the robotic surgical assembly 43600 to the electromechanical surgical instrument 43250 for performing a function with the electromechanical surgical instrument 43250, and/or provides a means to selectively attach/remove the electromechanical surgical instrument 43250 to the robotic surgical assembly 43600 (e.g., for rapid instrument exchange).

The collar assembly or sterile interface module 43630 includes electrical connectors 43532a, 43532b and an electrical ribbon 43534 coupled between the electrical connectors 43532a, 43532b to provide electrical communication between the robotic surgical assembly 43600 and any electromechanical surgical instrument, such as electromechanical surgical instrument 43250, coupled thereto.

Ring member 43550 is configured for rotatable attachment to a distal end of the connector assembly 43640 (e.g., via snap fit) of the IDU or housing 43610. The sterile drape 43552 can be arranged as desired about the housing 43610, the robotic surgical assembly 43600 and the robotic arms 13002, 13003 (FIG. 4) to provide a sterile barrier between the various aforementioned components and/or the surgical site/fluids and the electromechanical surgical instruments 43250, as is described above.

The first and second drive transfer assemblies 43668, 43670 of the sterile interface module 43630 include respective drive couplers 43668a, 43670a defining coupling ends 43668b, 43670b engagable with coupling ends 41052c, 41054c, 41056c, 41058c (FIG. 27) of respective motor couplers 41052b, 41054b, 41056b, 41058b (FIG. 27) of the motor assembly 41114 (FIG. 26) supported within the housing 43610. The first and second drive transfer assemblies 43668, 43670 further include transfer shafts (not shown) that extend to a respective instrument engagement end (e.g., a gear or the like with distally extending teeth) at a distal end thereof for transmitting drive motions from the motor assembly 41114 to the electromechanical surgical instrument 43250 for driving various functions thereof.

Additional detail regarding coupling arrangements for robotic surgical assemblies and/or IDUs can be found in U.S. International Patent Application No. PCT/US2017/033899, published as WO2017205308A1, titled ROBOTIC SURGICAL ASSEMBLIES, which is incorporated by reference herein in its entirety.

As can be seen, the surgical system 13000 includes a number of different connection points between components of the robotic surgical assembly 43600 and between the electromechanical surgical instrument 43250 and the robotic surgical assembly 43600. If any one of these components is not fully connected or seated to the corresponding component or components to which it is connectable, such incomplete connections can cause failures of the surgical system 13000 and unsafe operational conditions. Therefore, it can be desirable for various attachment assemblies of the robotic surgical assembly 43600 to promote connections between the components, only permit activation of the robotic arm 13120 or other powered components of the surgical system 13000 until all of the components are properly connected together, and otherwise ensure that each of the components and/or the electromechanical surgical instrument 43250 are fully connected together.

In one aspect, the various components of the robotic surgical assembly 43600 and/or surgical instrument 43250 can include connectors biased to resist connection between the corresponding connectable components (i.e., driving the components apart) up to a point at which the bias reverses, biasing the components into complete coupling between each other. For example, the aspect illustrated in FIGS. 54A-54D demonstrates a biased coupling arrangement between the sterile interface module 43630 and the surgical instrument 43250. In this example, the sterile interface module 43630 includes a ramped surface 2300 that is dimensioned to receive a corresponding ramped surface 2302 of the surgical instrument 43250. Further, the module ramped surface 2300 includes a biasing element 3204 and the instrument ramped surface 3202 includes a corresponding recess 3206 that is configured to receive and retain the biasing element 3204 therein when the surgical instrument 43250 is fully seated to the sterile interface module 43630. It should be noted that in other aspects, the positions of the biasing element 3204 and the recess 3206 can be interchanged with each other. Accordingly, as the instrument ramped surface 3202 begins to be slid into position relative to the module ramped surface 3200 (as shown in FIG. 54B), the biasing element 3204 is configured to bear against a portion of the instrument ramped surface 3202 and provide a physical resistance to the continued insertion of the instrument ramped surface 3202 (as shown in FIG. 54C). However, as the biasing element 3204 gives way under an increased load from the insertion of the instrument ramped surface 3202, the instrument ramped surface 3202 reaches a point at which it can be slid further past the module ramped surface 3200 without restriction from the biasing element 3204. At that point, the biasing element 3204 snaps into engagement with the recess 3206 and thereby securely holds the surgical instrument 43250 in firm engagement with the sterile interface module 43630 (as shown in FIG. 54D). In one aspect, the position at which the biasing element 3204 securely engages the recess 3206 of the surgical instrument 43250 can correspond to the position at which the module electrical contacts 3210 are aligned and communicatively coupled to the corresponding instrument electrical contacts 3212 to ensure proper data and signal transmission between the sterile interface module 43630 and the surgical instrument 43250. It should be noted that although this example depicts a biased coupling arrangement between the sterile interface module 43630 and the surgical instrument 43250, this example was simply for illustrative purposes and the above concepts apply equally to coupling arrangements between any other components of the robotic surgical assembly 43600.

In one aspect, the various components of the robotic surgical assembly 43600 and/or surgical instrument 43250 can include connectors having electronic or electrical lockouts for detecting when components are fully connected together. For example, the aspect illustrated in FIGS. 55A-55C demonstrates a biased coupling arrangement between the sterile interface module 43630 and the surgical instrument 43250. In this example, the surgical instrument 43250 includes a first electrical contact 3214 disposed at its module engagement end and the sterile interface module 43630 includes a second electrode contact 3216 positioned such that it physically contacts the first electrical contact 3214 only when the surgical instrument 43250 is fully seated to the sterile interface module 43630. In one aspect, one or more of the electrical contacts 3214, 3216 can be biased to make contact with the opposing electrical contact 3214, 3216. In another aspect, the electrical contacts 3214, 3216 can be oriented such that they are the last electrical connection that is made between the components being coupled together (in this case, the sterile interface module 43630 and the surgical instrument 43250) during the attachment process. Therefore, as soon as the electrical circuit between the electrical contacts 3214, 3216 is completed, the robotic surgical system 13000 can be assured that the surgical instrument 43250 is fully seated on the sterile interface module 43630. In one aspect, an ID chip or control circuit of the surgical instrument 43250 can be powered on by the contact between the electrical contacts 3214, 3216 and the control device 13004 of the robotic surgical system 13000 can be configured to transmit a query for response by the ID chip. Accordingly, once the control device 13004 receives a response to its query, the control device 13004 can be assured that the surgical instrument 43250 is fully seated on the sterile interface module 43630. The control device 13004 can thereafter permit the robotic surgical system 13000 to be fully activated or operated. In another aspect, the surgical instrument 43250 can include a control program and/or set of parameters defining how the surgical instrument 43250 is to be operated by the robotic surgical system 13000. The control program and/or set of parameters can be required for operation of the surgical instrument 43250, for example. Since transmission of the control program and/or set of parameters is/are required to operate the surgical instrument 43250 in this example, the control device 13004 can therefore prevent the surgical system 13000 from being activated or operated until the electrical circuit between the electrical contacts 3214, 3216 is completed. Once the control program and/or set of parameters is/are received, then the control device 13004 can customize the motor controllers for the surgical instrument 43250 as dictated by the control program and/or set of parameters and then permit the activation or operation of the robotic surgical system 13000. It should be noted that although this example depicts a lockout coupling arrangement between the sterile interface module 43630 and the surgical instrument 43250, this example was simply for illustrative purposes and the above concepts apply equally to coupling arrangements between any other components of the robotic surgical assembly 43600.

Figure 56:
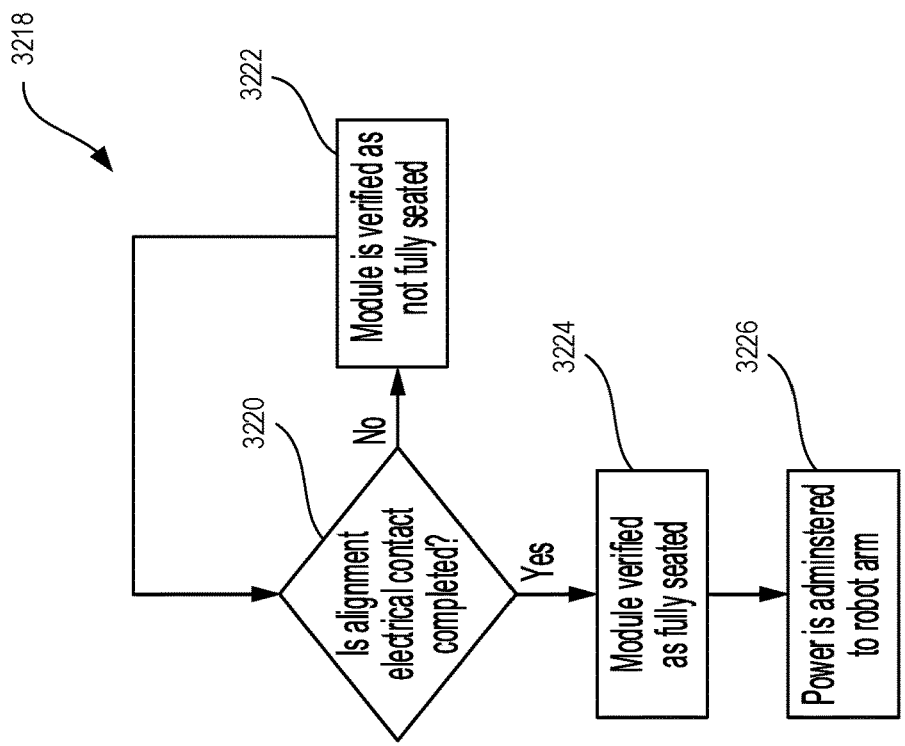
FIG. 56 is a logic flow diagram of a process for verifying that a surgical instrument is fully coupled to the robotic surgical assembly, in accordance with at least one aspect of the present disclosure.
Figure 55A:
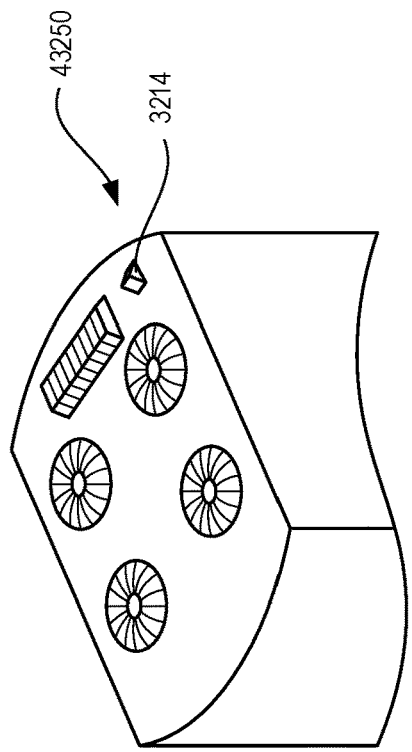
FIG. 55A is a perspective view of a proximal end of a surgical instrument comprising an alignment electrical contact, in accordance with at least one aspect of the present disclosure.
Figure 55B:
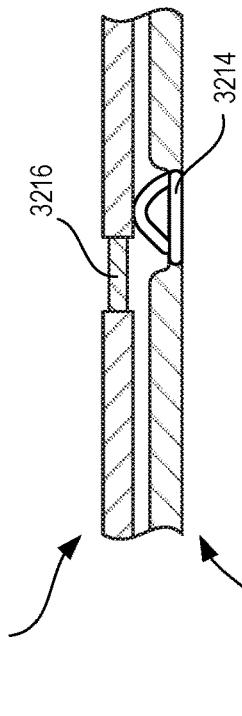
FIG. 55B is a sectional view of the surgical instrument of FIG. 55A uncoupled to a sterile interface module, in accordance with at least one aspect of the present disclosure.
Figure 55C:
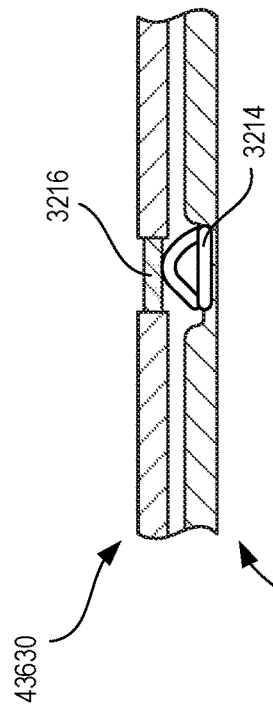
FIG. 55C is a sectional view of the surgical instrument of FIG. 55A coupled to a sterile interface module, in accordance with at least one aspect of the present disclosure.

A control circuit, such as the processor 15004 of the robotic surgical system 15000 illustrated in FIG. 22, can be configured to monitor an attachment assembly, such as the attachment assembly illustrated in FIGS. 55A-55C, for connecting two modules and control power to the robotic arm 13120 accordingly. The modules monitored by the control circuit can include any combination of components of the surgical robotic assembly 43600 and/or a surgical instrument 43250. For example, the processor 15004 can be configured to execute the process 3218 illustrated in FIG. 56. The process 3218 can be embodied as, for example, instructions stored in a memory 15006 coupled to the processor 15004 that, when executed by the processor 15004, cause the robotic surgical system 15000 to perform the process 3218.

Accordingly, the processor 15004 executing the process 3218 can determine whether alignment of the electrical contact(s) has been completed. For example, the processor 15004 can determine whether a circuit has been completed by opposing electrical contacts 3214, 3216 or whether a module (e.g., a surgical instrument 43250) is responsive to a query generated by the processor 15004, as described above. If the electrical contacts have not been aligned, then the process 3218 proceeds along the NO branch and the processor 15004 determines 3222 that the module is not fully seated and then continues monitoring for alignment of the electrical contacts. If the electrical contacts have been aligned, then the process 3218 proceeds along the YES branch and the processor 15004 determines 3224 that the module is fully seated. Accordingly, the processor 15004 then administers power 3226 to the robotic arm 13120 or otherwise permits the robotic arm 13120 to be operated by a user.

Robotic Surgical Detection Assemblies

As noted above with respect to FIGS. 51-53, the robotic surgical system 13000 includes a number of different connection points between components of the robotic surgical assembly 43600 and between the electromechanical surgical instrument 43250 and the robotic surgical assembly 43600. Each of these connection points represents a potential failure point if a component of the robotic surgical system 13000 or the surgical instrument 43250 is improperly connected or misaligned. Improperly connected or misaligned components can cause failures of the surgical system 13000 and unsafe operational conditions. Therefore, it can be desirable for the robotic surgical system 13000 to include detection systems to ensure proper connections and alignment of components. In response to detecting an improper or misaligned connection, the robotic surgical system 13000 can take various actions, including providing alerts or prompts to users or preventing the robotic surgical system 13000 (or components thereof) from being activated until all components or the relevant components of the robotic surgical system 13000 are properly connected together. For example, the robotic surgical system 13000 can prevent the motor pack 40050 from activating until the electromechanical surgical instrument 43250 is properly connected to the robotic surgical assembly 43600. The robotic surgical system 13000 can, in various aspects, be configured to detect coupling between corresponding components based upon detecting the presence of the components with respect to each other, detecting an actual coupling between components (e.g., via a continuity circuit, as described below), or a combination thereof. In one aspect, the robotic surgical system 13000 can control the components and/or provide alerts based on the detection of proper coupling between the components and knowledge of at least one more piece of information, such as firing status, cartridge authentication, cartridge identification, analysis for suitability of cartridge selection (e.g., based on situational awareness, as is described above), and so on.

In one aspect, the various components of the robotic surgical assembly 43600 and/or surgical instrument 43250 can include sensors configured to detect proximity and physical mating between corresponding components thereof. For example, in the aspect illustrated in FIGS. 57A and 57B, the sterile shell or barrier 40060 can include a sensor assembly configured to detect whether a corresponding detection element is within a threshold proximity to the sensor assembly (or a particular sensor thereof). In the illustrated aspect, the sterile shell 40060 comprises a set of four sensors 3230a, 3230b, 3230c, 3230d. This aspect further includes a corresponding detection element assembly that is configured to be detected by the sensor assembly. In the illustrated aspect, the IDU 43610 includes a first detection element 3228a, the ring member 43550 includes a second detection element 3228b, the sterile interface module 43630 includes a third detection element 3228c, and the surgical instrument 43250 includes a fourth detection element 3228d disposed thereon. The first sensor 3230a is configured to detect the first detection element 3228a, the second sensor 3230b is configured to detect the second detection element 3228b, and so on. It should be understood that the sensor assembly is not limited to this particular number and arrangement of the sensors 3230a, 3230b, 3230c, 3230d and/or detection elements 3228a, 3228b, 3228c, 3228d as this aspect is simply for purposes of illustrating the concepts discussed herein. The sensors 3230a, 3230b, 3230c, 3230d can include any type of sensor configured to detect the presence of a corresponding detection element within a threshold proximity thereof. For example, the sensors 3230a, 3230b, 3230c, 3230d can include Hall effect sensors and the detection elements 3228a, 3228b, 3228c, 3228d can include magnets. As another example, the sensors 3230a, 3230b, 3230c, 3230d can include RFID readers and the detection elements 3228a, 3228b, 3228c, 3228d can include (passive or active) RFID tags. In certain examples, the sensors may comprise proximity sensors (e.g., ultrasonic, IR, inductive, capacitive, photoelectric, hall effect senor, etc.). In certain examples the sensors comprise pressure sensors such as, for example, piezoresistive, capacitive, strain gauges, or any other suitable sensor type, including combinations thereof.

Figure 57B:
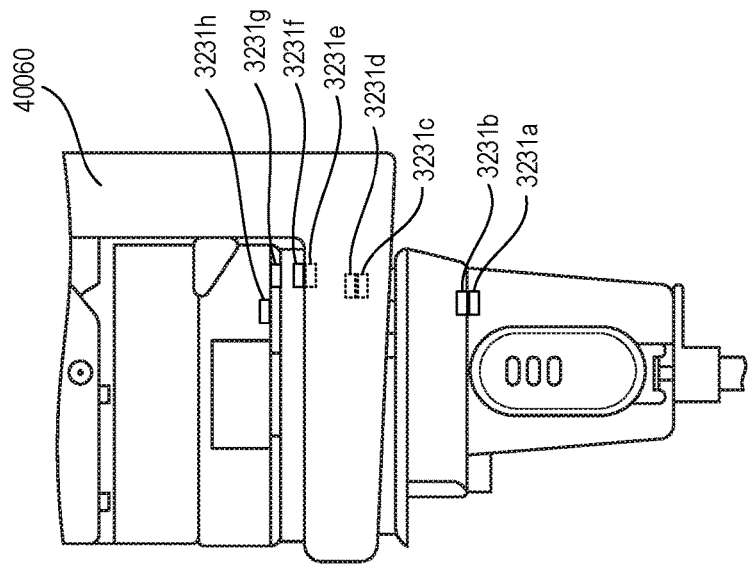
FIG. 57B is a side elevational view of a surgical instrument coupled to the robotic surgical assembly of FIG. 57A, in accordance with at least one aspect of the present disclosure.

Further, the components of the robotic surgical assembly 43600 and/or surgical instrument 43250 can include corresponding sets of electrical contacts 3231a-3231h are properly paired that are configured to detect proper mating and alignment between the components described above in connection with FIGS. 55A-55C. As illustrated in FIG. 57B, for example, proper pairing is achieved between the electrical contacts 3231a, 3231b, between the electrical contacts 3231c, 3231d, and between the electrical contacts 3231e, 3231f, but not the electrical contacts 3231g, 3231h. In various aspects, proper pairing, or lack of proper pairing, between corresponding ones of the electrical contacts 3231a-3231h can be detected by applying a voltage to electrical circuits that are formed by proper pairing of the electrical contacts 3231a-3231h, and detecting current through the electrical circuits. Other suitable techniques for detecting proper pairing of the electrical contacts 3231a-3231h are contemplated by the present disclosure.

In one aspect, the interfaces between the surgical instrument 43250 and/or the robotic surgical assembly 40100 can be temperature-dependent. For example, the electrical contacts 3231a-3231h can include conductive rings disposed on the surgical instrument 43250 and/or the components of the robotic surgical assembly 40100. The conductive rings can be separated by a gap, but electrically coupled with a shape memory alloy that is configured to operate within a certain operating temperature, for example. If the component on which the conductive rings are disposed is heated beyond the operating temperature of the shape memory alloy, the shape memory alloy changes shape, thereby breaking the electrical coupling between the components and disengaging the components from each other.

In one aspect, the electrical contacts 3231a-3231h can include a series of springs configured to contact the corresponding components of the robotic surgical assembly 40100 and/or the surgical instrument 43250 and inductance can be measured on the springs to determine proper coupling of the components. In particular, when the components are properly coupled, the components can compresses the springs, thereby changing the inductance, which can be measured by a control circuit coupled to the electrical contacts 3231a-3231h. Accordingly, the control circuit can compare the change in inductance between the various springs of the electrical contacts 3231a-3231h and then control could various components of the robotic surgical system 13000 based on whether an inductance change for a spring or set of springs differs from the average of the springs and/or a baseline or threshold change in value. For example, the control circuit could determine or measure the inductance associated with a given spring for an electrical contact, compare the determined inductance to a threshold, and then enable or disable the motor pack 40050 according to the comparison between the determined inductance and the threshold. In this way, the springs could serve as switches to enable or disable the motor pack 40050.

Figure 57A:
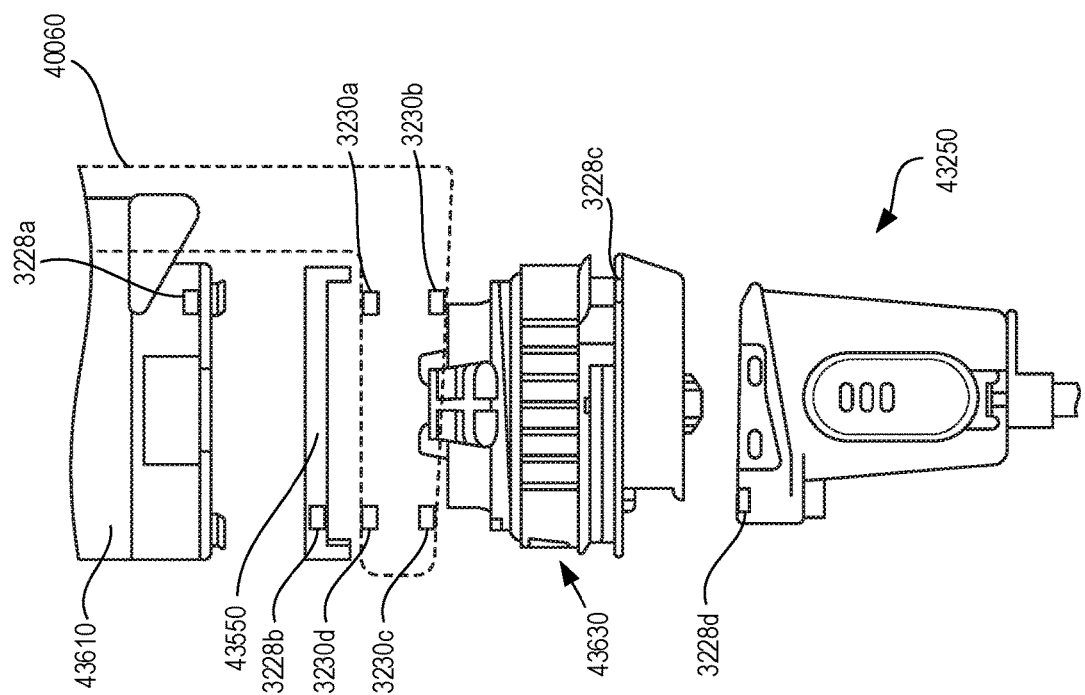
FIG. 57A is an exploded view of a robotic surgical assembly and surgical instrument comprising coupling sensors, in accordance with at least one aspect of the present disclosure.
Figure 58:
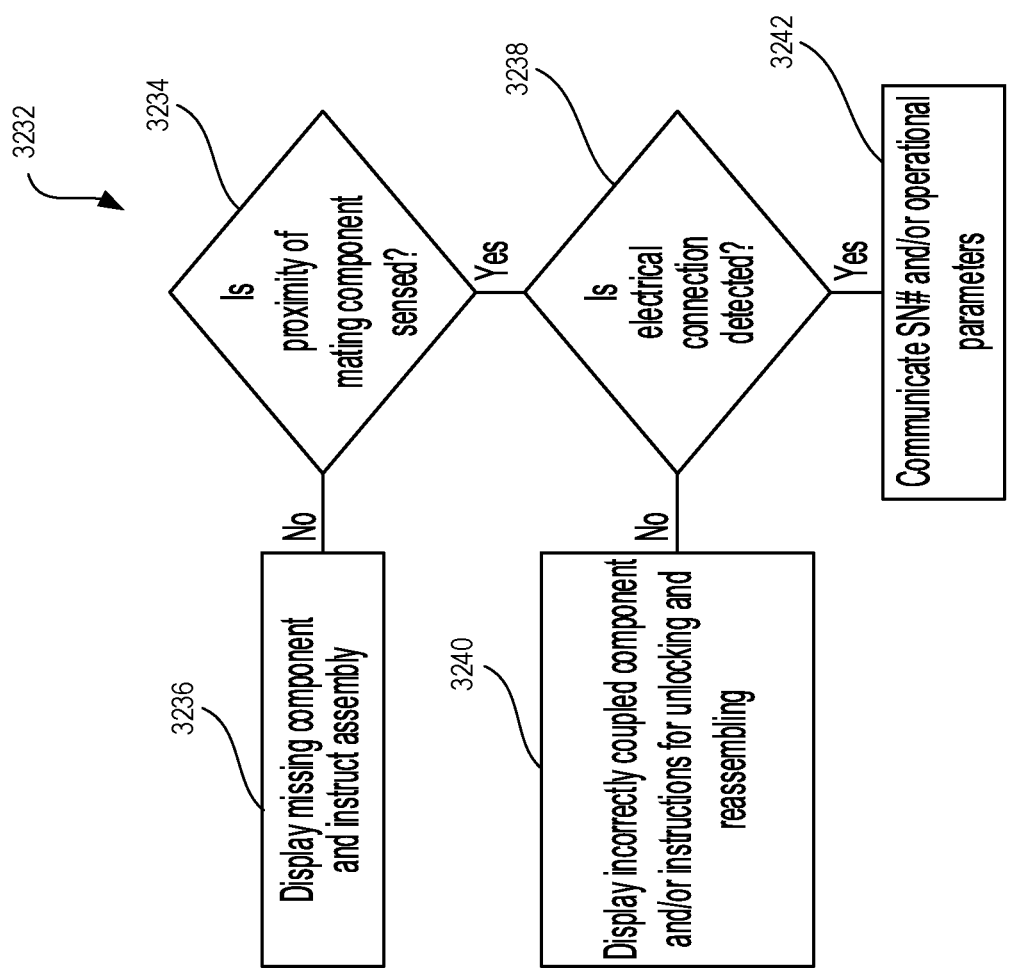
FIG. 58 is a logic flow diagram of a process for verifying that a surgical instrument is fully coupled to the robotic surgical assembly, in accordance with at least one aspect of the present disclosure.

A control circuit, such as the processor 15004 of the robotic surgical system 15000 illustrated in FIG. 22, can be configured to monitor a detection assembly, such as the detection assembly illustrated in FIGS. 57A and 57B. For example, the processor 15004 can be communicatively coupled to the sensors 3230a, 3230b, 3230c, 3230d described above. The modules monitored by the control circuit can include any combination of components of the surgical robotic assembly 43600 and/or a surgical instrument 43250. For example, the processor 15004 can be configured to execute the process 3232 illustrated in FIG. 58. The process 3232 can be embodied as, for example, instructions stored in a memory 15006 coupled to the processor 15004 that, when executed by the processor 15004, cause the robotic surgical system 15000 to perform the process 3232.

Accordingly, the processor 15004 executing the process 3232 can determine 3234 whether mating components (e.g., the IDU 43610, ring member 43550, sterile interface module 43630, or surgical instrument 43250) are within a sensed proximity to one another based on signals from the sensors 3230*a*, 3230*b*, 3230*c*, 3230*d*. If proximity of mating components is not sensed, then the process 3232 proceeds along the NO branch and the processor 15004 causes 3236 a display (e.g., a surgeon console's display 15014 (FIG. 22)) to display that the component is missing and/or instructions for assembling the robotic surgical system 13000.

If proximity of mating components is sensed, then the process 3232 proceeds along the YES branch and the processor 15004 determines 3238 whether an electrical connection is detected by determining whether electrical connections 3231*a*-3231*h* are properly paired. The processor 15004 can make this determination via the attachment assembly described in FIGS. 55A-55C, for example. If an electrical connection is not detect, but proximity of mating components is sensed, the process concludes that the components are improperly connected, and the process 3232 proceeds along the NO branch causing 3240 a display to alert a user that the component is incorrectly coupled and/or instructions for unlocking and reassembling the components. If an electrical connection is detected, then the process 3232 proceeds along the YES branch and the processor 15004 receives 3242 the serial number and/or operational parameters from the surgical instrument 43250 for the operation of the surgical instrument 43250 by the surgical system 13000.

In one aspect, various components of the robotic surgical assembly 43600 and/or surgical instrument 43250 can include a continuity circuit to determine when the components of the robotic surgical assembly 43600 and/or surgical instrument 43250 are coupled together. For example, the aspect of the robotic surgical assembly 40100 illustrated in FIG. 59 includes a continuity circuit assembly configured to detect when the carriage shell 40060 is seated to the carriage 40042, the ring connector 40171 (or another component of the sterile barrier collar assembly 40170 illustrated in FIG. 23 or the collar assembly 43630 illustrated in FIGS. 51-53) is seated to the carriage shell 40060, the sterile barrier housing 40130 is seated to the ring connector 40171, and the cap 40134 of the sterile barrier housing 40130 is closed.

In the example illustrated in FIG. 59, the carriage 40042 includes a first continuity circuit portion 3250; the carriage shell 40060 includes second, third, and fourth continuity circuit portions 3252, 3254, 3256; the ring connector 40171 includes a fifth continuity circuit portion 3258; and the sterile barrier housing 40130 includes sixth, seventh, eighth, and ninth continuity circuit portions 3260, 3262, 3264, 3266. The second, third, and fourth continuity circuit portions 3252, 3254, 3256 of the carriage shell 40060 are electrically coupled together. In one aspect, the second, third, and fourth continuity circuit portions 3252, 3254, 3256 can be different portions of a single continuity circuit extending through the carriage shell 40060. Likewise, the sixth, seventh, and eighth continuity circuit portions 3260, 3262, 3264 of the sterile barrier housing 40130 are electrically coupled together. In one aspect, the sixth, seventh, and eighth continuity circuit portions 3260, 3262, 3264 can be different portions of a single continuity circuit extending through the sterile barrier housing 40130.

The first continuity circuit portion 3250 is positioned to contact and electrically connect to the second continuity circuit portion 3252 disposed on the carriage shell 40060 when the carriage shell 40060 is seated on the carriage 40042. The third continuity circuit portion 3254 is positioned to contact and electrically connect to the fifth continuity circuit portion 3258 disposed on the ring connect 40171 when the ring connect 40171 is seated on the carriage shell 40060. The fourth continuity circuit portion 3256 is positioned to contact and electrically connect to the seventh continuity circuit portion 3262 disposed on the sterile barrier housing 40130 when the sterile barrier housing 40130 is seated on the carriage shell 40060. The fifth continuity circuit portion 3258 is positioned to contact and electrically connect to the sixth continuity circuit portion 3260 disposed on the sterile barrier housing 40130 when the sterile barrier housing 40130 is seated on the ring connector 40171. The eighth continuity circuit portion 3264 is positioned to contact and electrically connect to a ninth continuity circuit portion 3266 disposed on the cap 40134 of the sterile barrier housing 40130 when the cap 40134 is in the closed position. Accordingly, when each of the illustrated components of the robotic surgical assembly 40100 are properly seated together and the cap 40134 of the sterile barrier housing 40130 is in the closed position, the various circuit portions form a continuous electrical connection.

Accordingly, in one aspect, a control circuit coupled to the illustrated continuity circuit assembly can be configured to transmit a signal through the continuity circuit assembly at a first point and then control the robotic surgical system 15000 according to whether the signal is received at a second point. If the control circuit does not receive the input signal, that would indicate that one or more components of the robotic surgical assembly 40100 are not properly seated to each other and/or that the cap 40134 of the sterile barrier housing 40130 is open. If the control circuit does receive the input signal, that would indicate that all of the components of the robotic surgical assembly 40100 are properly connected and the cap 40134 is closed. In another aspect, the control circuit can be configured to apply a voltage to the continuity circuit assembly and determine whether the continuity circuit assembly is an open circuit or a closed circuit. An open circuit would indicate that one or more components of the robotic surgical assembly 40100 are not properly seated to each other and/or that the cap 40134 of the sterile barrier housing 40130 is open. A closed circuit would indicate that all of the components of the robotic surgical assembly 40100 are properly connected and the cap 40134 is closed. The control circuit can then control the robotic surgical system 15000 according to the engagement status between the components of the robotic surgical assembly 40100. For example, the control circuit could prevent the robotic arm to which the robotic surgical assembly 40100 is coupled from activating or moving unless it determines that all of the components of the robotic surgical assembly 40100 are properly connected together.

In various examples, each of the continuity circuit portions described above comprises a unique resistive element with a different resistance, which can be connected in parallel or in series circuit. The resistive elements are configured to form a part of the continuity circuit only when their respective components of the robotic surgical assembly 40100 are properly connected. Accordingly, the resistive elements form a series of interruptible interconnections that provide a different detected value depending on which portion of the series is interrupted. A control circuit can determine which control circuit portion is interrupted based on the detected value. In at least one example, the detected value can be a current value. A predetermined voltage can be applied to the continuity circuit, and a current value can be measured to determine which, if any, of the components of the robotic surgical assembly 40100 is not properly connected thereby causing its control circuit portion to be interrupted.

In various examples, the continuity circuit portions are interrupted when their respective components of the robotic surgical assembly 40100 are properly connected. In other examples, the continuity circuit portions are interrupted when their respective components of the robotic surgical assembly 40100 are improperly connected.

In one aspect, various components of the robotic surgical assembly 43600 and/or surgical instrument 43250 can include one or more detection elements that are detectable by a sensor assembly 3270 to determine the location and orientation of each component. For example, the aspect of the robotic surgical assembly 40100 illustrated in FIG. 60 includes a first detection element 3274 disposed on the carriage 40042 (or the sterile shell thereof), a second detection element 3276 disposed on the IDU 40110 (e.g., the motor pack assembly), a third detection element disposed on the sterile barrier collar assembly 40170 (which can include the collar assembly 40170 illustrated in FIG. 23 or the collar assembly 43630 illustrated in FIGS. 51-53), and a set of detection elements 3280, 3282, 3284 disposed on the surgical instrument 40200. In the particular example shown in FIG. 60, the surgical instrument 40200 is a trocar 3273. The same or different detection element assemblies or arrangements can be utilized in connection with other trocars 3273 or different surgical instruments 40200. In particular, the trocar 3273 can include a fourth detection element 3280 disposed adjacently to its proximal engagement end, a fifth detection element 3282 disposed at its collar at which it is gripped by the grasper 3272 of the robotic arm 13120, and a sixth detection element 3284 likewise disposed at its collar. Further, in this aspect the sensor assembly 3270 is located on the robotic arm 13120. The sensor assembly 3270 can include a set of sensors configured to sense the detection elements disposed on the robotic surgical assembly 43600 and/or surgical instrument 43250. In this particular aspect, the sensor assembly 3270 includes a first set of sensors 3270a, 3270b that are configured to detect the detection elements 3274, 3276, 3278 disposed on the robotic surgical assembly 40100 and a second set of sensors 3271a, 3271b that are configured to detect the detection elements 3280, 3282, 3284 disposed on the surgical instrument 40200. The first set of sensors 3270a, 3270b can be positioned at or adjacently to the position on the robotic arm 13120 near which the carriage is secured 40042, for example. The second set of sensors 3271a, 3271b can be positioned at or adjacently to the grasper 3272 for holding the surgical instrument 40200, for example. The sensor assembly 3270 can include any type of sensor configured to detect the presence of a corresponding detection element within a threshold proximity thereof. For example, the sensors 3270a, 3270b, 3271a, 3271b can include RFID readers and the detection elements 3274, 3276, 3278, 3280, 3282, 3284 can include (passive or active) RFID tags.

In certain examples, the sensors of the sensor assembly 3270 comprise limited detection ranges that are capable of detecting their corresponding detection elements only when their respective components of the robotic surgical assembly 40100 are in properly assembled, or at least partially assembled, configurations. In other words, placing the components of the robotic surgical assembly 40100 in properly assembled configurations causes the detection elements of such components to be in the detectable ranges of their corresponding sensors of the sensor assembly 3270. In certain examples, the signals from RFID tags are detected by the RFID readers at predetermined signal strengths in the properly assembled configurations of their respective components of the robotic surgical assembly 40100. Accordingly, a control circuit coupled to the RFID readers can assess proper assembly of the robotic surgical assembly 40100 by comparing signal strength of the signals transmitted from the RFID tags to predetermined signal strengths associated with properly assembled configurations of corresponding components of the robotic surgical assembly 40100.

Figure 61C:
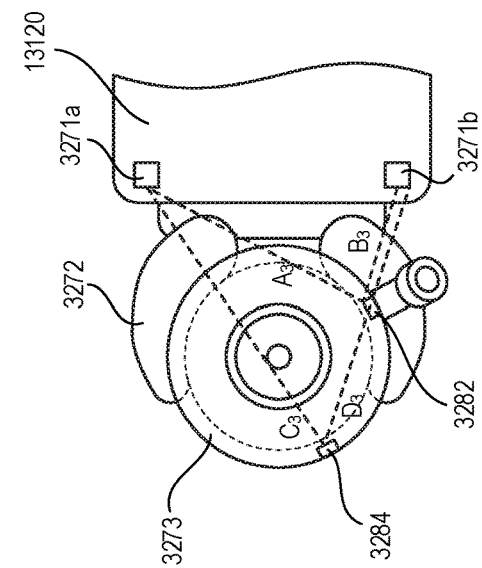
FIG. 61C is an overhead elevational view of the robotic surgical assembly of FIG. 60, where the surgical instrument is in a third orientation, in accordance with at least one aspect of the present disclosure.
Figure 61B:
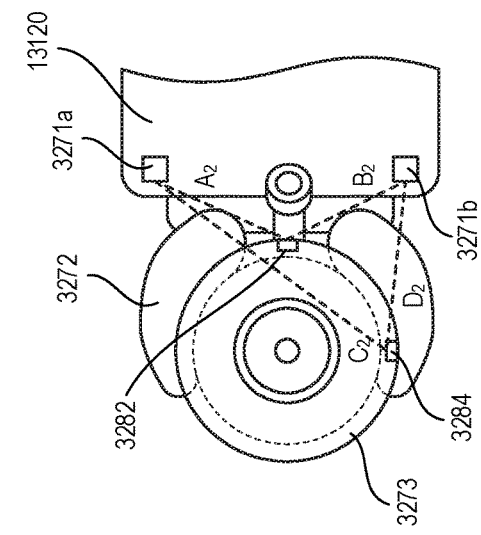
FIG. 61B is an overhead elevational view of the robotic surgical assembly of FIG. 60, where the surgical instrument is in a second orientation, in accordance with at least one aspect of the present disclosure.
Figure 61A:
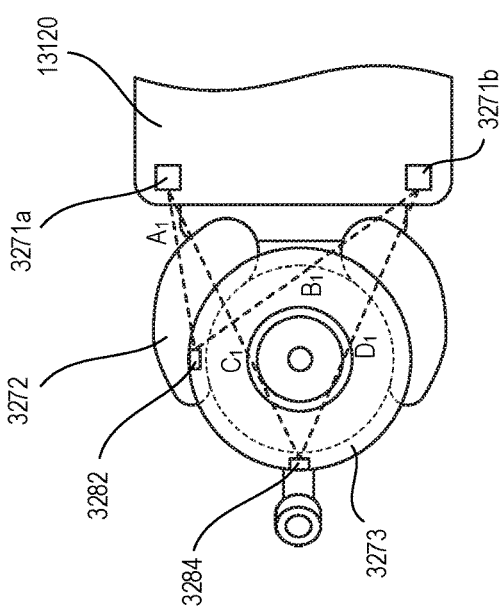
FIG. 61A is an overhead elevational view of the robotic surgical assembly of FIG. 60, where the surgical instrument is in a first orientation, in accordance with at least one aspect of the present disclosure.

Accordingly, the sensor assembly 3270 can detect the presence of each of the components of the robotic surgical assembly 40100 and the surgical instrument 40200 based on whether the corresponding detection element(s) for the component are within detection range of the sensor assembly 3270. However, as is illustrated in FIGS. 61A-61C, the sensor assembly 3270 can also detect the orientation or arrangement of the components of the robotic surgical assembly 40100 and the surgical instrument 40200 based on the locations of the detection elements with respect to one or more sensors within the sensor assembly 3270. For example, FIG. 61A illustrates the trocar 3273 in a first orientation where the distance from the third sensor 3271a and the fourth sensor 3271b to the fifth detection element 3282 is $A_1$ and $B_1$, respectively. Further, the distance from the third sensor 3271a and the fourth sensor 3271b to the sixth detection element 3284 is $C_1$ and $D_1$, respectively. By comparing the values for $A_1$ and $B_1$, a control circuit coupled to the sensor assembly 3270 can triangulate the location of the fifth detection element 3282 and accordingly determine the orientation of the portion of the trocar 3273 to which the fifth detection element 3282 is attached. Likewise, by comparing the values for $C_1$ and $D_1$, a control circuit coupled to the sensor assembly 3270 can triangulate the location of the sixth detection element 3284 and accordingly determine the orientation of the portion of the trocar 3273 to which the sixth detection element 3284 is attached (which, in the illustrated aspect, is the insufflation port attachment point). Therefore, the control circuit can determine that the trocar 3273 is in the first orientation. Further, FIGS. 61B and 61C illustrate the trocar 3273 in a second orientation and third orientation, respectively, and the corresponding detectable distances between the sensors 3271a, 3271b and the detection elements 3282, 3284. By detecting the distances, the control circuit can differentiate between these different orientations and thereby determine whether the trocar 3273 is oriented correctly with respect to the robotic arm 13120.

The sensor assembly 3270 can be communicably coupled to a control circuit, such as the processor 15004 of the robotic surgical system 15000 illustrated in FIG. 22, for receiving the sensor data from the sensor assembly 3270. The control circuit can monitor the presence and orientation of the components of the robotic surgical assembly 40100 and the surgical instrument 40200 and control the robotic surgical system 15000 accordingly, such as by providing warnings and/or instructions to the users or only permitting the activation or operation of the robotic arm 13120 in the event that each of the components is connected and oriented correctly.

In one aspect, a surgical instrument 40200 (e.g., a trocar 3273) can include an electrical continuity circuit for detecting the orientation of the surgical instrument 40200. For example, the grasper 3272 of the robotic arm 13120 could include one or more sensors that senses contact with the surgical instrument 40200. The grasper 3272 could seek to establish electrical continuity from a first point on the surgical instrument 40200 to a second point on the surgical instrument 40200 via the current passing from the grasper 3272, through the surgical instrument 40200, and then back to the grasper 3272. For example, in the aspect illustrated in FIGS. 62A and 62B, the grasper 3272 includes a sensor 3290 configured to detect the presence of the trocar 3273 and a pair of electrical contacts 3292 disposed at a first location and a second location. The sensor 3290 can include an image sensor configured to read a detection element (e.g., a barcode or QR code) disposed on the trocar 3273 for identifying the trocar 3273, for example. Further, the trocar 3273 can include an electrical contact 3296 that is sized and dimensioned to be contacted by both of the grasper electrical contacts 3292 when trocar 3273 is oriented correctly within the grasper 3272 when gripped thereby. Accordingly, when the trocar 3273 is oriented correctly within the grasper 3272, the trocar electrical contact 3296 and the grasper electrical contacts 3292 establish electrical continuity, which can be detected via a control circuit coupled thereto, for example. When the trocar 3273 is not oriented correctly within the grasper 3272, at least one of the grasper electrical contacts 3292 will not physically contact the trocar electrical contact 3296 and thus electrical continuity will not be established (which can likewise be detected via the control circuit).

The sensor 3290 can be communicably coupled to a control circuit, such as the processor 15004 of the robotic surgical system 15000 illustrated in FIG. 22, for receiving the sensor data from the sensor 3290 via, e.g., a first connection 3300. Likewise, the electrical contacts 3292 can be coupled to the control circuit via, e.g., a second connection 3298 for transmitting a signal therethrough. If the control signal can receive the transmitted signal, then it can determine that there is electrical continuity between the trocar electrical contact 3296 and the grasper electrical contacts 3292 and that the trocar 3273 is therefore oriented correctly within the grasper 3272. The control circuit can monitor the presence and orientation of a surgical instrument 40200 (or any other components of the robotic surgical assembly 40100 that are gripped by a grasper 3272) and control the robotic surgical system 15000 accordingly, such as by providing warnings and/or instructions to the users or only permitting the activation or operation of the robotic arm 13120 in the event that the surgical instrument 40200 is connected and oriented correctly.

In one aspect, a surgical instrument 40200 (e.g., a trocar 3273) can include detection elements 3304 that indicate the identity or type of the surgical instrument 40200. For example, in the aspect illustrated in FIG. 63A, the grasper 3272 can include a sensor 3302 that is configured to sense the detection element 3304 disposed on the trocar 3273 when the trocar 3273 is grasped by or within a proximity to the grasper 3272. The particular arrangement or type of the detection element 3304 can be configure to identify the type or identity of the trocar 3273. Further, the detection element 3304 can be positioned or configured such that it is only detectable by the sensor 3302 when the trocar 3273 is oriented correctly within the grasper 3272. In one aspect, the sensor 3302 can include a Hall effect sensor and the detection element 3304 can include one or more magnets that create a magnetic signature detectable by the Hall effect sensor, for example. In another aspect, the sensor 3302 can include an image sensor and the detection element 3304 can include a set of markings, barcode, or QR code that is visually distinguishable by the image sensor. For example, FIG. 63B illustrates a detection element 3304 in a first configuration, FIG. 63C illustrates a detection element 3304 in a second configuration, and FIG. 63D illustrates a detection element 3304 in a third configuration. The first configuration of the detection element 3304 can indicate that the trocar 3273 is an 8 mm trocar with a stop cock, the second configuration of the detection element 3304 can indicate that the trocar 3273 is an 8 mm trocar without a stop cock, and the third configuration of the detection element 3304 can indicate that the trocar 3273 is a 5 mm trocar without a stop cock, for example. Further, if the detection element 3304 is not detectable by the sensor 3302, then that can indicate that an incompatible trocar 3273 is being utilized or that the trocar 3273 is not oriented correctly within the grasper 3272. Accordingly, a control circuit communicably coupled to the sensor 3302, such as the processor 15004 of the robotic surgical system 15000 illustrated in FIG. 22, can monitor the presence of a surgical instrument 40200 (or any other components of the robotic surgical assembly 40100 that are gripped by a grasper 3272) and control the robotic surgical system 15000 accordingly, such as by providing warnings and/or instructions to the users or only permitting the activation or operation of the robotic arm 13120 in the event that the surgical instrument 40200 is connected and oriented correctly.

Figure 64:
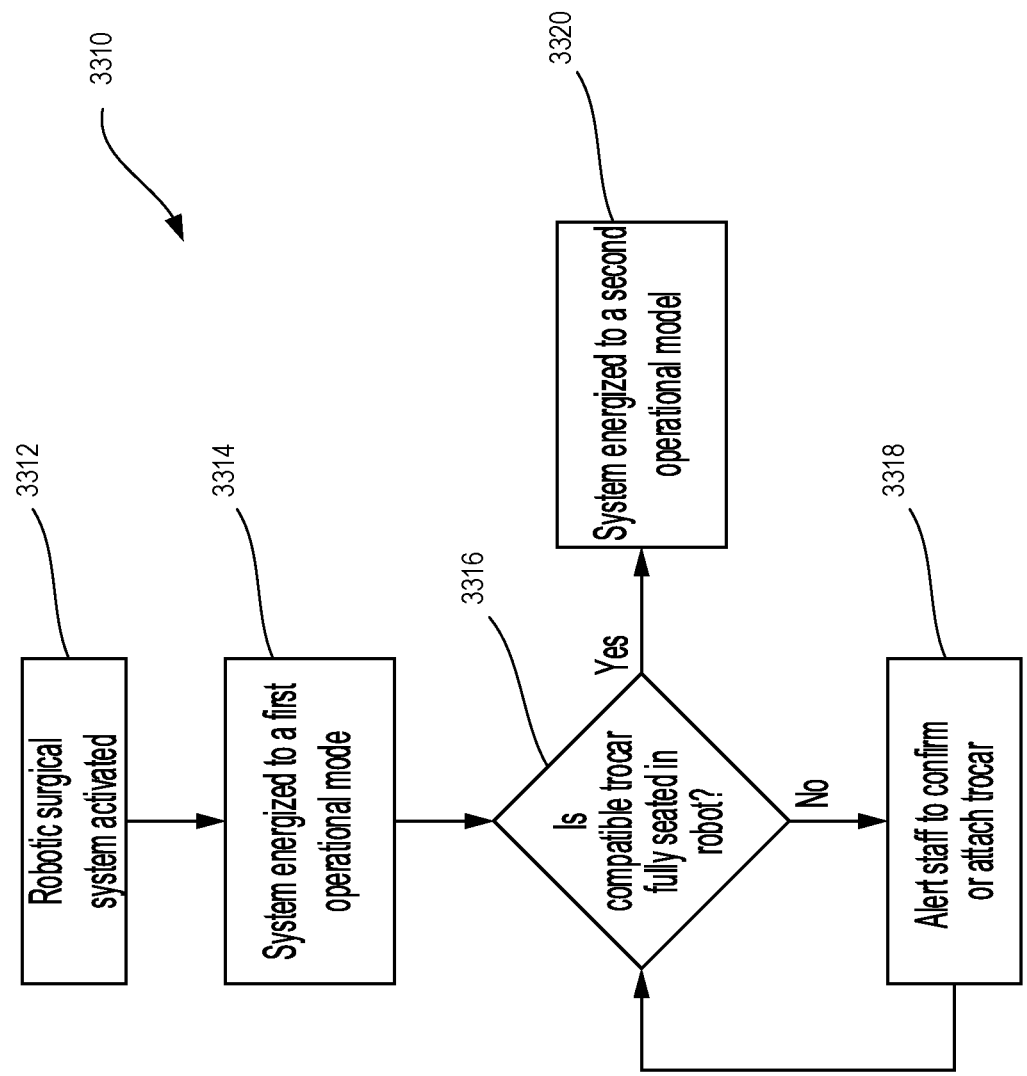
FIG. 64 is a logic flow diagram of a process for determining whether a compatible trocar is coupled to the robotic surgical assembly, in accordance with at least one aspect of the present disclosure.

In various aspects discussed above and below, a control circuit can be configured to take various actions in response to detecting the presence and orientation of a surgical instrument 40200 and/or components of a robotic surgical system 40100, such as providing instructions to users or only permitting activation or operation of the robotic surgical system 15000 when all components are properly connected together. In another aspect, a control circuit, such as the processor 15004 of the robotic surgical system 15000 illustrated in FIG. 22, can operate the robotic surgical system 15000 in different modes according to whether a compatible surgical instrument 40200 (e.g., a trocar) are connected to the robotic surgical system 15000 by, for example, executing the process 3310 illustrated in FIG. 64.

Accordingly, a processor 15004 executing the process 3310 can determine 3312 that the robotic surgical system 15000 has been activated and then energize 3314 or operate the robotic surgical system 15000 in an initial or first operational mode. Accordingly, the processor 15004 can determine 3316 whether a compatible surgical instrument 40200, such as a trocar, is seated within the robotic surgical system 15000. The processor 15004 can make this determination by reading a barcode or QR code via an image sensor as described in connection with FIGS. 62A and 62B, identifying detection elements via a sensor as described in connection with FIGS. 63A-63D, and so on, and then determining whether those elements correspond to a compatible surgical instrument 40200. If the surgical instrument 40200 is compatible, then the process 3310 proceeds along the YES branch and the processor 15004 energizes 3320 the robotic surgical system 15000 to a second operational mode. In the second operational mode, the processor 15004 can control the surgical instrument 40200 according to parameters (e.g., grip strength or expected grip stroke) specific to the identified surgical instrument 40200, for example. If the surgical instrument 40200 is not compatible or the processor 15004 is not able to determine whether the surgical instrument is compatible 40200 (e.g., due to the instrument being improperly oriented with respect to the robotic arm 13120, causing the detection elements to not be identifiable), then the process 3310 proceeds along the NO branch and the processor 15004 alerts 3318 the surgical staff to attach the surgical instrument 40200 or confirm that the surgical instrument 40200 is attached properly. The processor 15004 can provide the alert via the surgeon console's display 15014, for example. The processor 15004 can thereafter continue monitoring to determine 3316 whether the surgical instrument 40200 is fully seated and respond accordingly.

Figure 65:
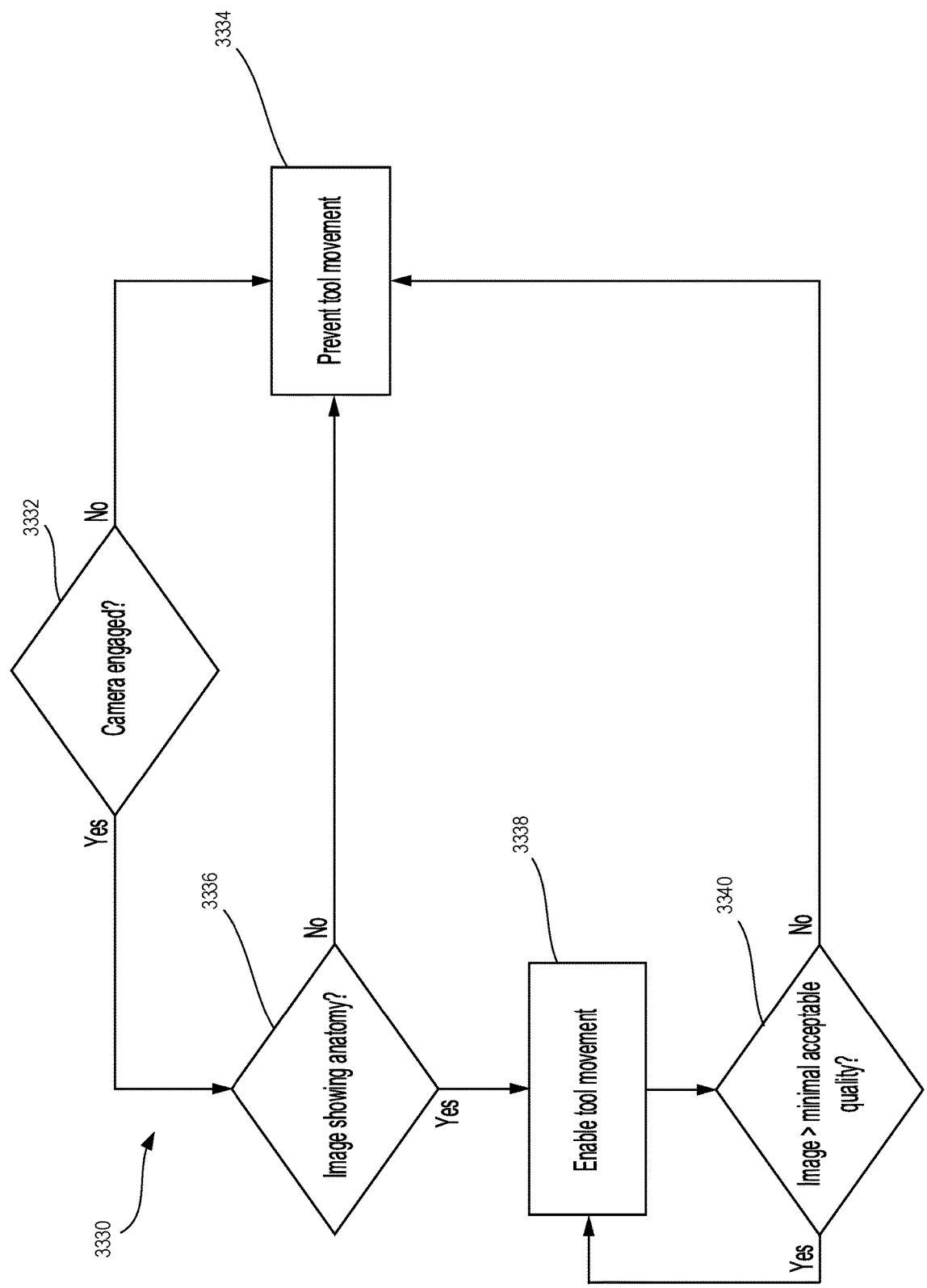
FIG. 65 is a logic flow diagram of a process for controlling surgical tool movement according to scope visualization, in accordance with at least one aspect of the present disclosure.

In addition to controlling the robotic surgical system 15000 according to the presence, position, orientation, and/or type of surgical instrument 40200 connected to the robotic surgical system 15000, the robotic surgical system 15000 could also be controlled according to whether a camera (i.e., a scope, such as an endoscope 239 as shown in FIG. 9) is engaged, what is being viewed by the camera, and/or image quality of the video feed provided by the camera. Controlling the robotic surgical system 15000 according to the camera status can be beneficial because insufficient visualization (i.e., no camera being attached or the camera having poor image quality) is indicative of situations where it would be desirable to prevent surgical instruments 40200 (or other components of the robotic surgical system 15000) from moving inadvertently. For example, a camera having poor image quality can indicate that the camera is being cleaned, either internally within the patient during a surgical procedure or externally to the patient. As another example, a camera not being connected to the robotic surgical system 15000 can indicate that the camera has been detached for cleaning or that the initial setup process for the robotic surgical system 15000 is ongoing. In any of these cases, it should not be necessary for the surgical instrument 40200, robotic arm, or other components of the robotic surgical system 15000 to move. Therefore, it can be desirable to prevent movement of the robotic surgical system 15000 in these instances by locking out users from moving the surgical instruments 40200 and/or robotic arms until the camera status is resolved and sufficient image quality within the body of the patient has been (re)established. In one aspect, a control circuit, such as the processor 15004 of the robotic surgical system 15000 illustrated in FIG. 22, can operate the robotic surgical system 15000 according to what is being viewed by the camera by, for example, executing the process 3330 illustrated in FIG. 65. In one aspect, the control circuit could be coupled to a proximity sensor configured to detect the position of the camera and/or the robotic arm on which the camera is supported. In another aspect, the control circuit can be configured to execute various image processing algorithms for determining image quality and/or performing image recognition.

Accordingly, a processor 15004 executing the process 3330 can determine 3332 whether a camera is engaged to the robotic surgical system 15000. The processor 15004 can make this determination by monitoring whether the robotic surgical system 15000 is actively receiving a video feed, by sensing for the presence of a camera using various detection arrangements (e.g., as described in connection with FIGS. 62A-63D), and so on. If a camera is not engaged, then the process 3330 proceeds along the NO branch and the processor 15004 prevents 3334 movement of a surgical tool, such as a surgical instrument 40200, coupled to the robotic surgical system 15000. If a camera is engaged, then the process 3330 proceeds along the YES branch and the processor 15004 determines whether the image or video feed from the camera are showing anatomy. The processor 15004 can identify anatomical structures using a variety of image recognition techniques, such as image overlay. If the image or video feed from the camera is not showing anatomy, then the process 3330 proceeds along the NO branch and the processor 150004 prevents 3334 movement of a surgical tool. If the image or video feed is showing anatomy, then the process 3330 proceeds along the YES branch and the processor 15004 enables 3338 movement of the coupled surgical tool. Thereafter, the processor 15004 monitors the quality of the image or video feed to ensure that it is maintained within acceptable bounds. Accordingly, the processor 15004 determines 3340 whether the image quality meets or exceeds a threshold image quality. The processor 15004 can make this determination by, for example, algorithmically analyzing the image or video feed data to ascertain the degree or noise or blur present in the data and then comparing the calculated noise or blur relative to a threshold. If the image quality does not satisfy the threshold, then the process 3330 proceeds along the NO branch and the processor 15004 prevents 3334 movement of a surgical tool. If the image quality does satisfy the threshold, then the process 3330 proceeds along the YES branch and the processor 15004 continues to enable 3338 movement of the surgical tool. In sum, this process 3330 only permits a surgical tool to be operated via the robotic surgical system 15000 when a camera is engaged and showing anatomy with an appropriate image quality. Therefore, this process 3330 prevents the surgical tool from being operated outside of the scope of the surgical procedure, during when there should be no or little reasons to operate the surgical tool.

In one aspect, a surgical instrument 40200 (e.g., a trocar 3273) can include a grip surface 3342 configured to cause differential vacuum pressure depending upon the orientation of the surgical instrument 40200 within a grasper 3272. For example, in the aspect illustrated in FIGS. 66A-66C, the grasper 3272 and/or robotic arm 13120 includes a vacuum source 3344 that is configured to cooperate with a grip surface 3342 of a trocar 3273 to generate a vacuum pressure when the trocar 3273 is gripped by the grasper 3272. The vacuum source 3344 can include an opening that is configured to sealingly engage with the grip surface 3342 of the trocar 3273. The grip surface 3342 can be irregular or non-uniform such that the grip surface 3342 causes different vacuum pressures to be generated depending upon the orientation of the trocar 3273. For example, the grip surface 3342 can include a roughened portion 3342a that is not configured to create an air-tight seal with the vacuum source 3344 and a smooth portion 3342a that is configured to create an air-tight (or substantially air tight) seal with the vacuum source 3344. To demonstrate these concepts, in FIG. 66B the roughened portion 3342a of the grip surface 3342 overlaps partially with the opening of the vacuum source 3344, causing a pressure $V_1$ to be generated. Correspondingly, in FIG. 66C the smooth portion 3342b of the grip surface 3342 is aligned with the opening of the vacuum source 3344, with no overlap from the roughened portion 3342a, which thus causes a pressure $V_2$ to be generated. These pressures can be detected by a control circuit coupled to the vacuum source 3344 and/or a pressure source configured to detect the air pressure generated at the interface between the grip surface 3342 and the vacuum source 3344 to identify the orientation of the trocar 3273 relative to the grasper 3272.

Figure 66A:
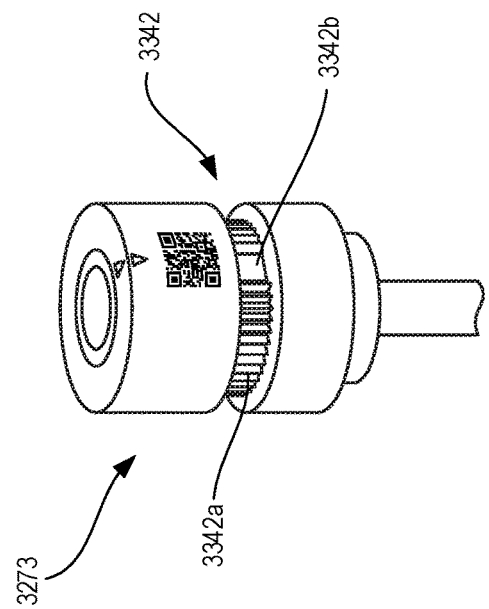
FIG. 66A is a perspective view of a surgical instrument comprising an irregular gripping interface, in accordance with at least one aspect of the present disclosure.
Figure 66B:
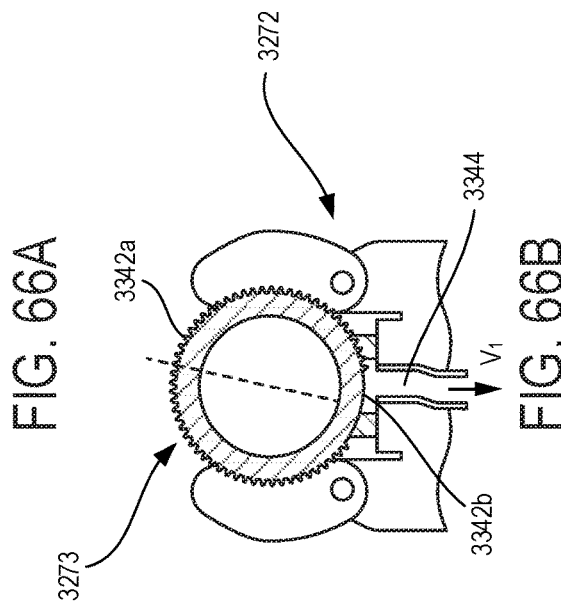
FIG. 66B is an overhead elevational view of a robotic grasper comprising a vacuum source grasping the surgical instrument of FIG. 66A, where the surgical instrument is not properly aligned, in accordance with at least one aspect of the present disclosure.
Figure 66D:
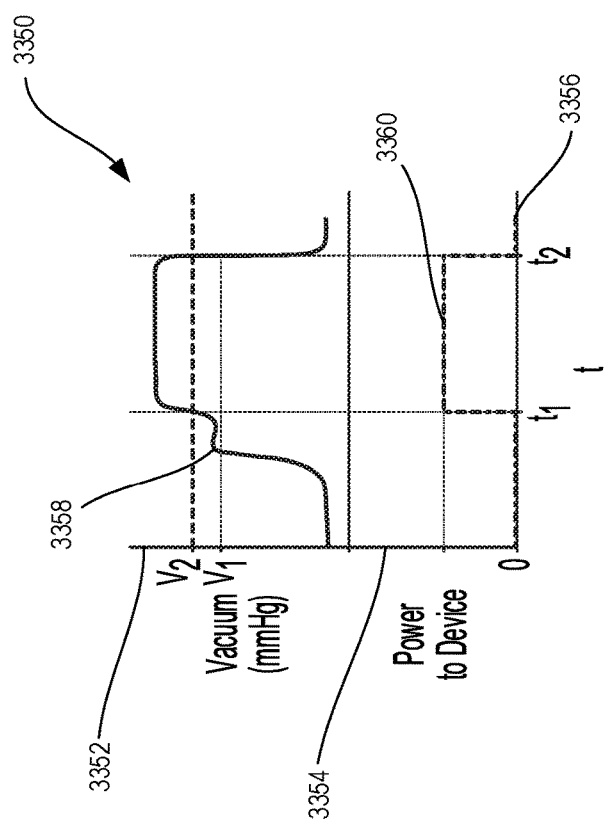
FIG. 66D is a graph of vacuum pressure and device power verse time for a robotic surgical system configured to control device power according to surgical instrument alignment, in accordance with at least one aspect of the present disclosure.
Figure 66C:
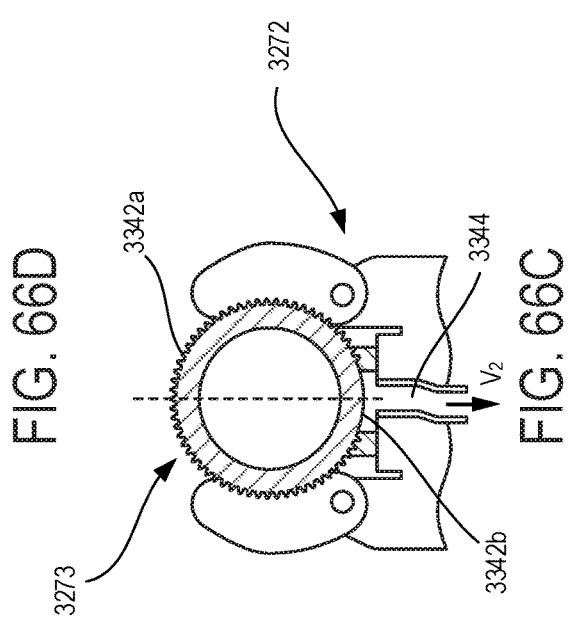
FIG. 66C is an overhead elevational view of a robotic grasper comprising a vacuum source grasping the surgical instrument of FIG. 66A, where the surgical instrument is properly aligned, in accordance with at least one aspect of the present disclosure.
Figure 73:
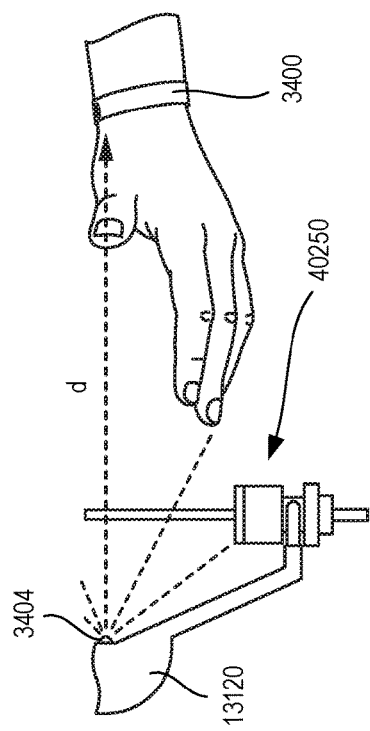
FIG. 73 is a schematic view of a robotic surgical system comprising a sensor to sense an identifier position, in accordance with at least one aspect of the present disclosure.

FIG. 66D further illustrates a prophetic set of graphs 3350 indicating control of the robotic surgical system 15000 via a control circuit monitoring vacuum pressure from the aspect illustrated in FIGS. 66A-66C. The graphs 3350 include a first vertical axis 3352 representing vacuum pressure and a second vertical axis 3354 representing power to a device coupled to or a component of the robotic surgical system 15000 (e.g., a surgical instrument or a robotic arm). Further, the graphs 335 include a horizontal axis 3356 representing time. A first line 3358 represents the vacuum pressure over time and a second line 3360 represents device power over time. In this example, a pressure value of $V_2$ indicates that the trocar 3273 (or other surgical instrument) is oriented properly within the grasper 3272 (as shown in FIG. 66C) and thus can serve as a threshold for powering the device. As indicated by the first line 3358, the vacuum pressure initially increases to a first peak at or near $V_1$, which indicates that the trocar 3273 is not correctly oriented at that time (as shown in FIG. 66B). Accordingly, the control circuit coupled to the vacuum source 3344 and/or pressure sensor can identify that the trocar 3273 is not oriented properly and present an alert or instructions to the surgical staff, for example. As further indicated by the first line 3358, the surgical staff correct the orientation of the trocar 3273 and at time $t_1$ the vacuum pressure reaches or exceeds the pressure threshold $V_2$ indicative of the trocar 3273 being oriented correctly. Accordingly, the control circuit can activate, energize, or otherwise permit operation of the device controlled thereby, as indicated by the second line 3360 increasing from zero to a define value at time $t_1$. The control circuit continues energizing the device until, at time $t_2$, the vacuum pressure drops steeply (potentially indicating that the trocar 3273 has been disconnected from the grasper 3272). Accordingly, the control circuit deactivates the device, as indicated by the second line 3360 decreasing from the defined value to zero at time $t_2$. In this way, a control circuit can control the operation of a surgical instrument and/or a component of the robotic surgical system 15000 according to detected vacuum pressure indicative of the orientation of a surgical tool, such as a trocar 3273.

Robotic Detection Zones and Safety Thresholds

In various aspects, the movement and functions of the robotic surgical systems can be controlled based on the proximity of components of the robotic surgical systems to individuals or objects located within the operating room or the presence of individuals or objects located within the operating room within detection or safety zones defined within the operating room. For example, FIGS. 67A-74 illustrate a variety of different illustrative detection arrangements for monitoring the position of surgical staff members, the patient 3380, components of the robotic surgical systems 3370, and/or surgical tools and controlling the robotic surgical systems 3370 accordingly. Further, each of these aspects can be utilized in conjunction with situationally aware systems, which are described above under the heading ROBOTIC SURGICAL SYSTEM.

In other aspects, various other activities occurring within the operating room can be visually monitored to provide additional information to the robotic surgical system regarding the placement and location of individuals and objects within the operating room. For example, the functional or operational workspace over or about the patient could be monitored by a camera or series of cameras positioned outside the patient's body (e.g., on the robotic arm(s) or throughout the operating room space). Further, the cameras configured to record the activities occurring outside the patient's body could be synchronized with the image or video feed from scopes positioned within the patient's body. By synchronizing the video feeds, the external cameras could provide the robotic surgical system with situational awareness regarding activities occurring in preparation for the next surgical task, tools being changed, or other devices used in tandem with the robot tools. Still further, the external cameras could be configured to track non-robotic instruments (e.g., handheld surgical instruments) utilized by the surgical staff during the course of the surgical procedure. The external cameras could also establish a detection zone or safety envelope around the surgical staff with respect to the range of motion of the robotic arm(s) and ensure the robotic arms never violate this space. The safety envelope can be updated real time (e.g., with a safety threshold) to ensure safety of the staff. Sensors or specialized equipment may be worn by the surgical staff to identify themselves and aid in their detection by the robotic surgical system.

In other aspects, various non-camera sensors can be utilized to detect and monitor the detection zones. For example, an alternative to optical mapping of the operating room and/or individuals within the operating room could include RF, acoustic, or millimeter radar detection mediums. For example, the functional or operational workspace could be acoustically mapped by generating a baseline acoustical map and then monitoring to detect changes in the acoustical characteristics of the mapped area, which could indicate the proximity of individuals or objects within the mapped area. As another example, antennae could be positioned at specific locations of the surgical tools, components of the robotic surgical system, and other devices. The antennae can be connected to fixed frequency oscillators in an LC circuit, for example. Accordingly, if an object is sufficiently distant from the given antenna, the inductive and capacitive reactance match, and the voltage through the inductor is at maximum. Moving a grounded object closer to the antenna (such as a person moving closer to the antenna) changes the capacitance, which lowers the voltage through the inductor. The change in voltage can be used to drive an amplifier and thus be utilized to detect the movement of individuals or objects through the operating room. A control circuit could then control the movement of the robotic arms and other components or the robotic surgical system accordingly.

In one aspect, a detection zone can be defined with respect to the operating table. For example, FIGS. 67A and 67B illustrate a robotic surgical system 3370 including a sensor 3271 actuated by a robotic arm 13120. In one aspect, the sensor 3271 can be positioned adjacently to a surgical tool coupled to the robotic arm 13120. The sensor 3271 is configured to detect a set of detection elements 3374 positioned at the corners of an operating table 3378. The sensor 3271 can include any sensor type capable of identifying and determining the relative position or location of the corresponding detection elements 3274. For example, the sensor 3271 can include an image sensor and the detection elements 3374 can include visually identifiable elements, for example. As another example, the sensor 3271 can include an RFID reader and the detection elements 3374 can include RFID tags, for example. In other examples, the sensor 3271 can include a Hall effect sensor and the detection elements 3274 can include magnets. In various other examples, the sensor 3271 can include a reed sensor, an ultra-high frequency RF sensor, and so on and the detection elements 3274 can include corresponding elements.

Further, the robotic surgical system 3370 can define a detection zone 3376 based on the position of the detection elements 3274 detected by the sensor 3271. In one aspect, the detection zone 3376 can be coextensive with the detected boundary of the operating table 3378 as delineated by the detection elements 3274. In other aspects, such as the aspect illustrated in FIGS. 67A and 67B, the detection zone 3376 can be non-coextensive with the operating table. For example, the detection zone 3376 can be defined as extending a distance p from the detected boundary of the operating table 3378 and a height h thereabove. The detection zone 3376 can define a volume about the operating table 3378 and/or patient 3380 in which the robotic surgical system 3370 monitors for the presence of objects and/or individuals and then controls the surgical tools or components of the robotic surgical system 3370 accordingly. For example, if an individual (other than the patient 3380) is detected as being present within the detection zone 3376, a control circuit coupled to the sensor 3271 can cause the robotic arm 13120 to cease movement, thereby preventing the robotic arm 13120 and/or a surgical tool coupled thereto from contacting the individual. As another example, if a surgical tool is detected as being present within the detection zone 3376, the control circuit can slow the movement of the robotic arm 13120 or decrease the maximum allowable movement speed of the robotic arm 13120, thereby seeking to mitigate the risk of the surgical tool being inadvertently brought into contact against the patient 3380.

In one aspect, a detection zone can be defined with respect to removably attachable tags, thereby allowing users to freely define the scope and bounds of the detection zone. For example, FIG. 68 illustrates a tag 3384 detectable by a sensor, as described above. The tags 3384 can be utilized to identify the space occupied by the patient 3380 or to establish other safety thresholds to ensure that the components of the robotic surgical system 3370 and/or surgical tools supported thereby do not violate that space or function differently within that space. The tags 3384 can be disposable or reusable. In operation, the tags 3384 could be placed by the user (e.g., a surgeon or nurse) on or around the patient 3380 to provide feedback to the robotic surgical system 3370 regarding the patient location or a desired safety zone (which may not necessarily be limited to a space defined by the patient's location). Accordingly, users can flag the operating table 3378, the patient 3380, the limbs or other body parts of the patient 3380, and/or other critical or interfering objects within the operating envelope. In one aspect, the tags 3384 can include a detection element 3374 coupled to an attachment surface 3386, such as an adhesive surface, affixable to the patient or objects. As shown in FIG. 69A, a sensor 3382 supported by a robotic arm 13120 adjacently to the surgical tool (e.g., a trocar 3273) can detect the detection elements 3374 of the tags 3384 as they are positioned on the patient 3380 or other objects. Further, as shown in FIGS. 69B-69D, the tags 3384 can be utilized to identify a detection zone or safety thresholds with respect to patients 3380 of different body dimensions. Such customizable detection zones or safety thresholds can be much safer than statically defined detection zones due to the inherent variation in patients' 3380 anatomy.

In one aspect, a detection zone can be defined with respect to a component of the robotic surgical system itself, such as a robotic arm 13120. For example, in FIG. 70 the robotic surgical system includes a sensor 3388 (e.g., an image sensor) that is configured to detect the position of a surgical instrument 40250 or another surgical tool supported by a robotic arm 13120 with respect to a detection zone 3390 corresponding to the range of movement of the surgical instrument 40250. In various aspects, the sensor 3388 can be mounted to the robotic arm 13120 or positioned at another location within the operating room. In one aspect, the scrubs 3394 provided to the surgical staff members can include reflective material 3393 to assist the camera 3388 or other image sensor in visually distinguishing the surgical staff members from the surrounding environment and thereby detecting when they are present within a detection zone 3390.

In one aspect, the robotic surgical system can be configured to define multiple detection zones that delineate different manners in which the robotic arm 13120, surgical instrument 40250, or other components of the robotic surgical system are controlled. For example, FIG. 72 illustrates an example where the sensor 3388 is configured to monitor both a first detection zone 3390 (which is also shown in FIG. 70) and a second detection zone 3396 defined about the first detection zone 3390. The first detection zone 3390 can correspond to the range of movement of the surgical instrument 40250 supported by the robotic arm 1310 and the second detection zone 3396 can correspond to a threshold distance about the first detection zone 3390, for example. However, the various detection zones 3390, 3396 do not necessarily be defined in relation to each other and, in some aspects, can instead be separately defined from each other or defined according to separate locations, objects, or individuals. Further, as noted above, the robotic arm 13120 could be controlled differently depending upon which of the detection zones 3390, 3396 an individual is present within. For example, the sensor 3388 does not detect an individual in either of the detection zones 3390, 3396, then a control circuit coupled to the sensor 3388 can permit the robotic arm 13120 and/or surgical instrument 40250 to operate normally. If the sensor 3388 detects an individual present within the second detection zone 3396, but not the first detection zone 3390, the control circuit can take a first action, such as slowing or limiting the maximum movement speed of the robotic arm 13120. Finally, if the sensor 3388 detects an individual present within the first detection zone 3390, the control circuit can take a second action, such as deactivating or preventing movement of the robotic arm 13120 and/or the surgical instrument 40250. Therefore, the robotic surgical system can dictate its behavior based on the position of the surgical staff relative to the detection zones 3390, 3396.

In another aspect, the robotic surgical system can be configured to detect an object or reference worn by surgical staff members during a surgical procedure. For example, the robotic surgical system in FIG. 73 can include a sensor 3404 to sense the location and/or presence of a band 3400 worn by the surgical staff in the operating room and then control the robotic arm 13120 and/or the surgical instrument 40250 accordingly. The bands 3400 can include an elastomeric material, for example, and could be worn on the wrist, forearm, bicep, and so on. Further, the bands 3400 could be disposable or reusable. In one aspect, the sensor 3404 can include a thermal camera and the band 3400 can include a thermal band that is configured to emit thermal energy or has been heated to a particular temperature, for example. The thermal band can be set to a predefined temperature, such as 99° F. Having the bands 3400 set to a predefined temperature could be beneficial because it would allow the sensor 3404 to be calibrated to detect objects specifically at that temperature, thereby improving detection accuracy. On benefit of utilizing thermal data is that the operating room is often dimmed or dark during setup for a surgical procedure, which can interfere with the function of image sensors configured to work within the visual light spectrum. In another aspect, the sensor 3404 can include a magnetic or RF sensor and the band 3400 can include a magnetic or RF band, respectively. As noted above with respect to the robotic surgical system including a thermal camera for detecting a thermal band, such magnetic or RF detection mediums can be beneficial in situations where the room is darkened or dim.

In various other aspects, the robotic surgical system could also be configured to utilize multi-spectral imaging, passive IR, visual light, multi-spectral RF, and/or ultrasound and other detection mediums to monitor the operating room and its inhabitants and surgical tools. Such sensor data could also be utilized by the robotic surgical system to complement or augment contact sensor data (e.g., as described in connection with FIGS. 54A-66D).

Figure 74:
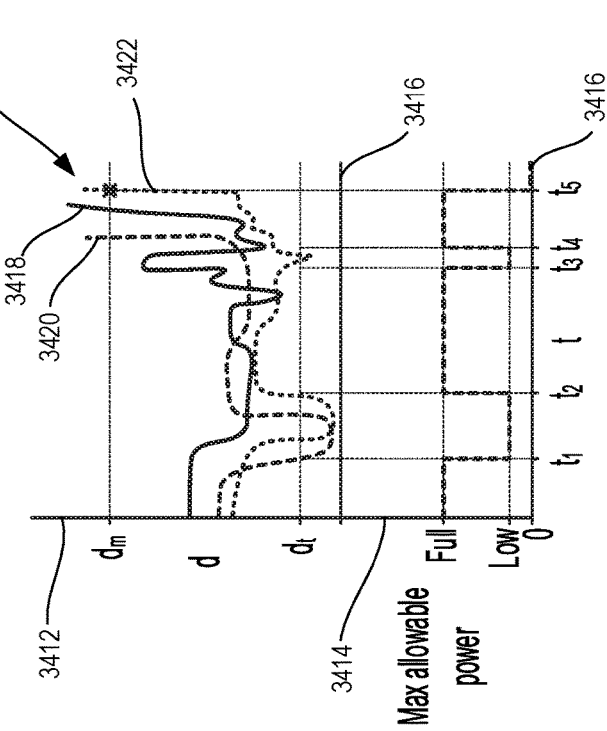
FIG. 74 is a graph of object distance and robotic surgical system power verse time, in accordance with at least one aspect of the present disclosure.

As noted above, a control circuit coupled to the various described sensor assemblies can control the actions or operations of the robotic surgical system or surgical instruments coupled to the robotic surgical system in a variety of different manners. Such control circuits can include the processor 15004 of the robotic surgical system 15000 illustrated in FIG. 22, for example. Accordingly, the control of one such control algorithm executed by a control circuit is illustrated by FIG. 74, which is a set of graphs 3410. The graphs 3410 include a first vertical axis 3412 representing distance between the detected object and a reference (e.g., the distance between a thermal band 3400 and a thermal camera 3404 or the distance between a surgical staff member and a defined detection zone), a second vertical axis 3414 representing power provided to the robotic surgical system, and a horizontal axis 3416 representing time. In this particular prophetic example, the relative position of three objects within the operating room are being monitored, one of which is represented by each of the first line 3418, the second line 3420, and the third line 3422. In this implementation, the control circuit is configured to modulate the maximum allowable power providable to the robotic surgical system according to the relative positions of the objects. The distance $d_m$ represents the maximum detection distance for the robotic surgical system and the distance $d_t$ represents the safety or threshold distance between the monitored objects and the reference. As can be seen by the first line 3418, the first object never violates the distance $d_t$. As can be seen by the second line 3420, the second object is detected as being within the threshold distance $d_t$ at time $t_1$ (i.e., is within a safety zone or safety envelope defined with respect to the reference). Accordingly, the control circuit reduces the maximum allowable power to the robot from the "full" to the "low" value. As can be seen by the third line 3422, the third object likewise moves within the distance $d_t$ after $t_1$ and both of the second and third objects are within the distance $d_t$ for a time period, prior to the second object moving away by at least the distance $d_t$. However, at the time that the second object moves away by at least the distance $d_t$, the third object is nonetheless still within the threshold distance $d_t$ from the reference; therefore, the control circuit maintains the maximum allowable power at the "low" value. However, at time $t_2$, the second object likewise moves away from the reference by at least the threshold distance $d_t$. As there are no objects violating the threshold distance $d_t$, the control circuit increases the maximum allowable power to the "full" value. The third object once again violates the threshold distance $d_t$ between time $t_3$ and $t_4$. In response, the control circuit once again decreases the maximum allowable power to the robotic surgical system to the "low" period during that time period. Further, at time $t_5$, all three objects have moved past the maximum detection distance $d_m$. Accordingly, the control circuit can determine that the surgical procedure has been completed and deactivates the robotic surgical system (as indicated by the maximum allowable power being decreased to zero). In sum, one or more functions of the robotic surgical system (e.g., the maximum allowable power) can be controlled according to the presence of one or more objects or individuals within particular zones or within particular proximities defined according to various reference objects.

Motor Pack Assemblies

Referring back to FIGS. 23 and 25-27, the robotic surgical assembly 40100 can include a motor pack 40050 configured to be received within the sterile barrier housing 40130. The motor pack 40050 may include four motors 40052, 40054, 40056, 40058 with respective drive shafts 40052*a*, 40054*a*, 40056*a*, 40058*a* for driving various operations of a surgical instrument 40100 coupled to the robotic surgical assembly 40100. Various alternative motor packs 40050 are described herebelow.

Figure 75:
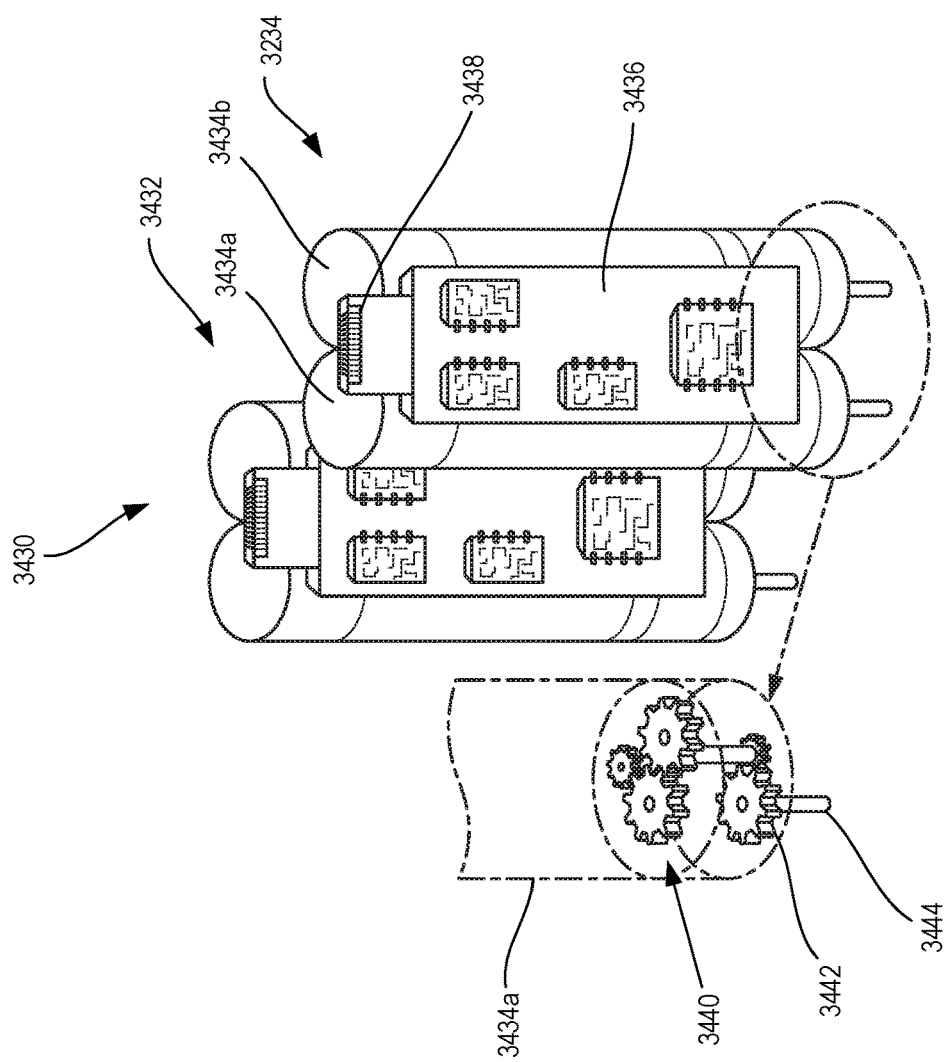
FIG. 75 is a schematic view of a motor pack comprising interchangeable motor assemblies, in accordance with at least one aspect of the present disclosure.

In one aspect, the motors of the motor pack 40050 may be reconfigurable or interchangeable. For example, FIG. 75 illustrates a motor assembly 3430 supportable within a motor pack 40050, wherein the motor assembly 3430 includes a set of modular motor units 3432. In this aspect, the motor pack 40050 can be configured to support sets of modular motor units 3432, as opposed to a singular set of motors, where each of the modular motor units 3432 could be individually swapped out of the motor pack 40050. In the illustrated example, the modular motor units 3432 include a first motor 3434*a* and a second motor 3434*b* coupled to control circuitry 3436 and electrical connector 3438 for receiving control signals. However, the modular motor units 3432 can include any number of motors. Configuring the motor assembly 3430 as a collection of modular motor units 3432 provides several benefits compared to utilizing a singular, integral motor assembly, including improving the modularity of the motor pack 40050, improving the ease with repairs can be performed on the motor pack 40050, and permitting new or updated technologies to be integrated into previous versions of the motor pack 40050. For example, the modular motor units 3432 could be swapped between a handheld surgical instrument (e.g., the surgical instrument shown in FIGS. 79-80) and a robotically controlled surgical instrument (e.g., the surgical instruments 400200, 400250 shown in FIG. 23 or 52). As another example, if there is a failure with one of the motors or the control circuitry of the motor pack 40050, then the malfunctioning modular motor unit 3432 can be removed and repaired, without necessitating that the entire motor pack 40050 be disassembled or serviced. As yet another example, because each of the interchangeable modular motor units 3432 includes its own control circuitry 3436, the control circuitry 3436 could include the necessary logic for controlling the modular motor unit 3432 and thus new versions of modular motor units 3432 could be integrated into prior versions of motor packs 40050 without requiring any further hardware upgrades to the robotic surgical system. Therefore, motors that are more efficient (e.g., requiring less power or providing more torque for the same amount of power), provide more torque, have higher hold loads, quieter drives, have longer operational lifespans, generate higher output speeds, have smaller external footprints, generate less heat, have improved water tight configurations, and so on could be integrated into prior versions of motor packs 40050 as these updated motor configurations are developed, without requiring any other hardware updates or other changes to the robotic surgical system architecture. Further, modular motor units 3432 from different manufacturers or even containing different types of motors could be swapped into a motor pack 40050.

Figure 76:
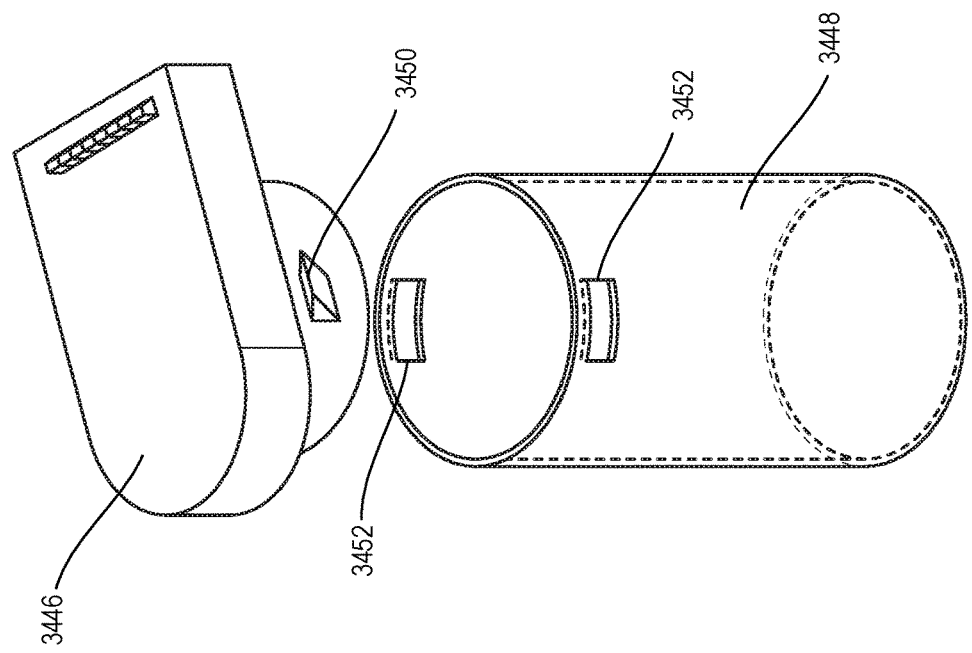
FIG. 76 is a perspective view of a motor pack housing comprising a removable cap, in accordance with at least one aspect of the present disclosure.

In one aspect, the motor pack 40050 can further be configured to assist in swapping out or servicing the modular motor units 3432. For example, FIG. 76 illustrates a motor pack 40050 that includes a body 3448 configured to receive a motor assembly therein, such as a motor assembly 3430 including one or more modular motor units 3432 as shown in FIG. 75 or the motor assembly shown in FIG. 27, and a lid 3446 that is removably affixable to the body 3448. Accordingly, users could remove the lid 3446 from the body 3448, replace and/or service any modular motor units 3432 or other motor assemblies therein, and then replace the lid 3446. The lid 3446 can be removably connectable to the body 3448 via one or more detents 3450 that are configured to engage corresponding slots 3452 disposed on the body 3448, for example.

Figure 27:
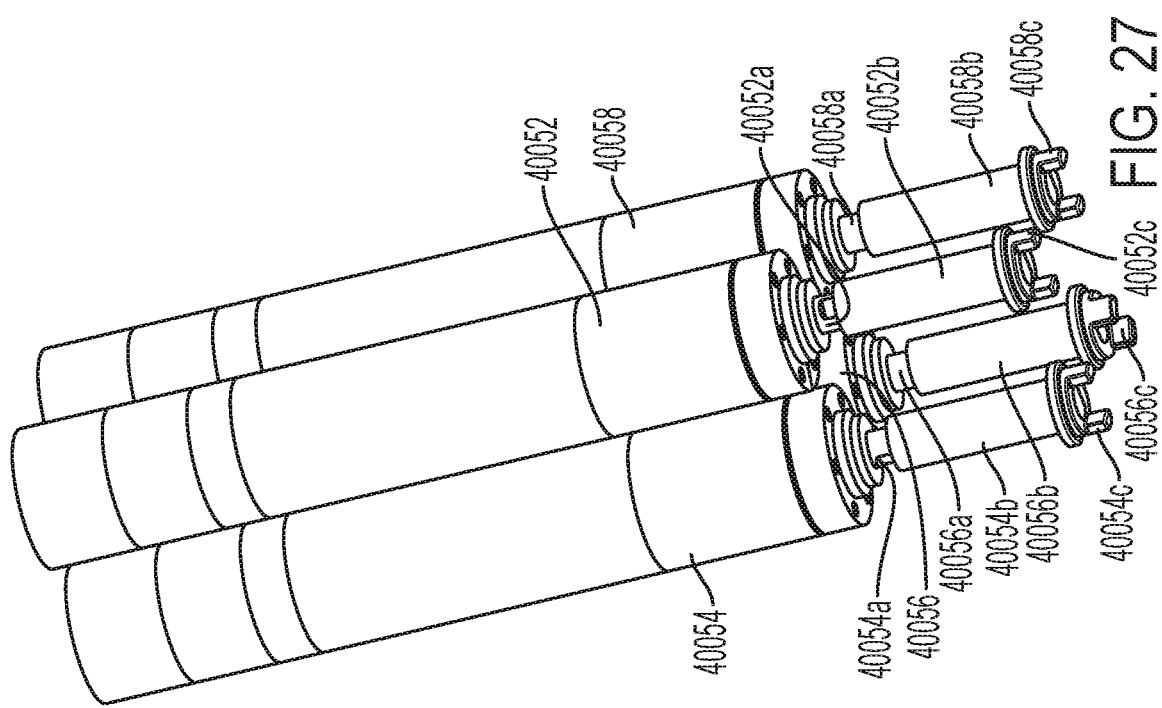
FIG. 27 is a perspective view of motors and respective motor couplers of a motor pack, in accordance with at least one aspect of the present disclosure.

In another aspect, the motors of the motor pack 40050 may be re-orientable or reconfigurable into different configurations. For example, the motors can be swapped between a first configuration or a second configuration, which can in turn cause the motor to produce different effects or provide different functions. Referring again to FIG. 75, one of the motors (e.g., the first motor 3434a) within a modular motor unit 3432 can include a gear drive 3440 wherein the last stage 3442 drives an output shaft 3444 (e.g., a drive shaft 52a, 54a, 56a, and 58a as illustrated in FIG. 27) that is offset from or not aligned with the longitudinal axis of the motor 3434a. Accordingly, the output shaft 3444 of the motor 3434a can positioned a first orientation or a second orientation with respect to the motor pack 40050 depending upon the orientation of the modular motor unit 3432 within the motor pack 40050. In various aspects, one or multiple of the motors within a motor pack 40050 and/or a modular motor unit 3432 can be reconfigurable in this manner. Such reconfigurable motors could be utilized to, for example, allow users to configure which drive disk or sterile shell drive coupler (such as the drive coupler 44144a shown in FIG. 81B) is coupled to which modular motor unit 3432, which would in turn change which function of the surgical instrument each motor was driving. Further, the use of reconfigurable motor packs 40500 within the IDU 40110 (FIG. 23) would allow users to customize the IDU 40110 for different, more advance, and/or new surgical tools. Further, the motors within the motor pack 40500 could be constructed to have different sizes and/or different power outputs. Therefore, reconfigurable motors within the motor pack 40500 could allow users to align the differently sized motors with particular drive couplers depending upon the type of surgical instrument being coupled to the IDU 40110. Having differently sized motors could be beneficial because not all surgical instrument functions require the same torque thresholds. Therefore, the motor within the motor pack 40050 could be constructed so that some of the motors were larger to produce higher output power/torque and some motors were smaller to produce lower output power/torque, without altering the overall size of the motor pack 40050. During use, the motor pack 40050 could then be reconfigured to align the motors based on the particular desired or required output power/torque for the surgical instrument. In another aspect, for motor packs 40050 that include differentially sized motors or motors have offset output shafts 3444, the motor pack 40050 could additionally include a gearing assembly that engages with the differentially aligned output shafts of the motors and places the output of the motor pack 40050 back on the centerline of the motors.

Figure 77:
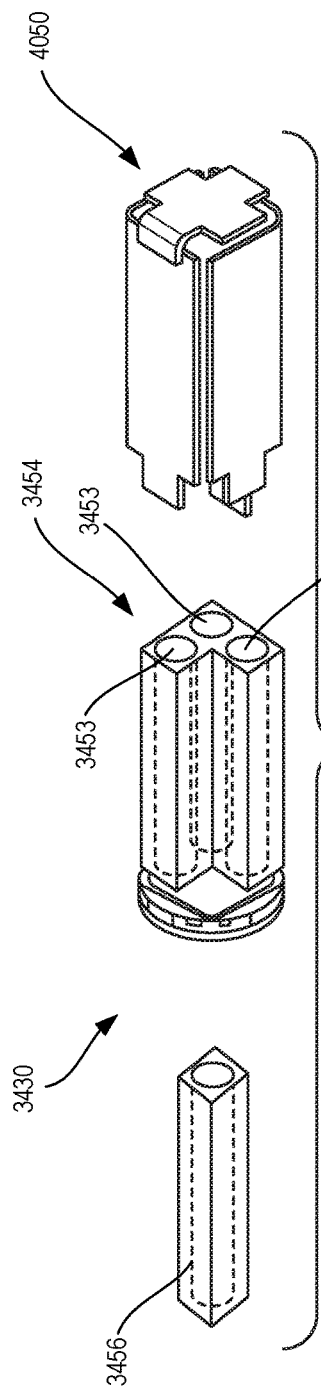
FIG. 77 is an exploded view of a motor pack assembly comprising a removable motor, in accordance with at least one aspect of the present disclosure.
Figure 78:
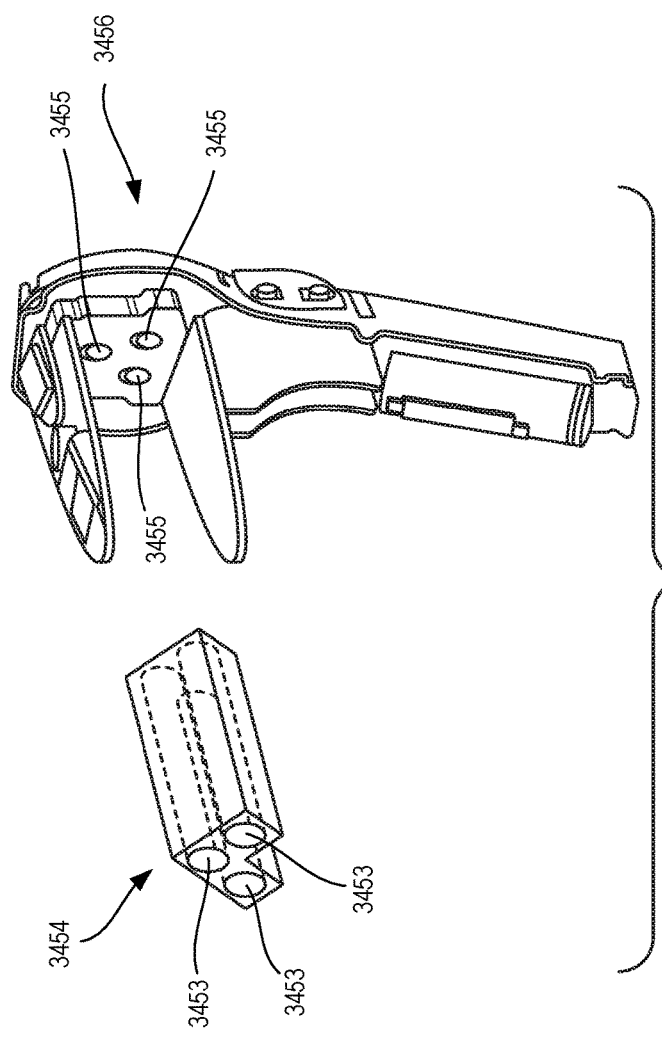
FIG. 78 is an exploded view of the motor pack assembly of FIG. 77 being coupled to a surgical instrument handle, in accordance with at least one aspect of the present disclosure.
Figures 79, 80:
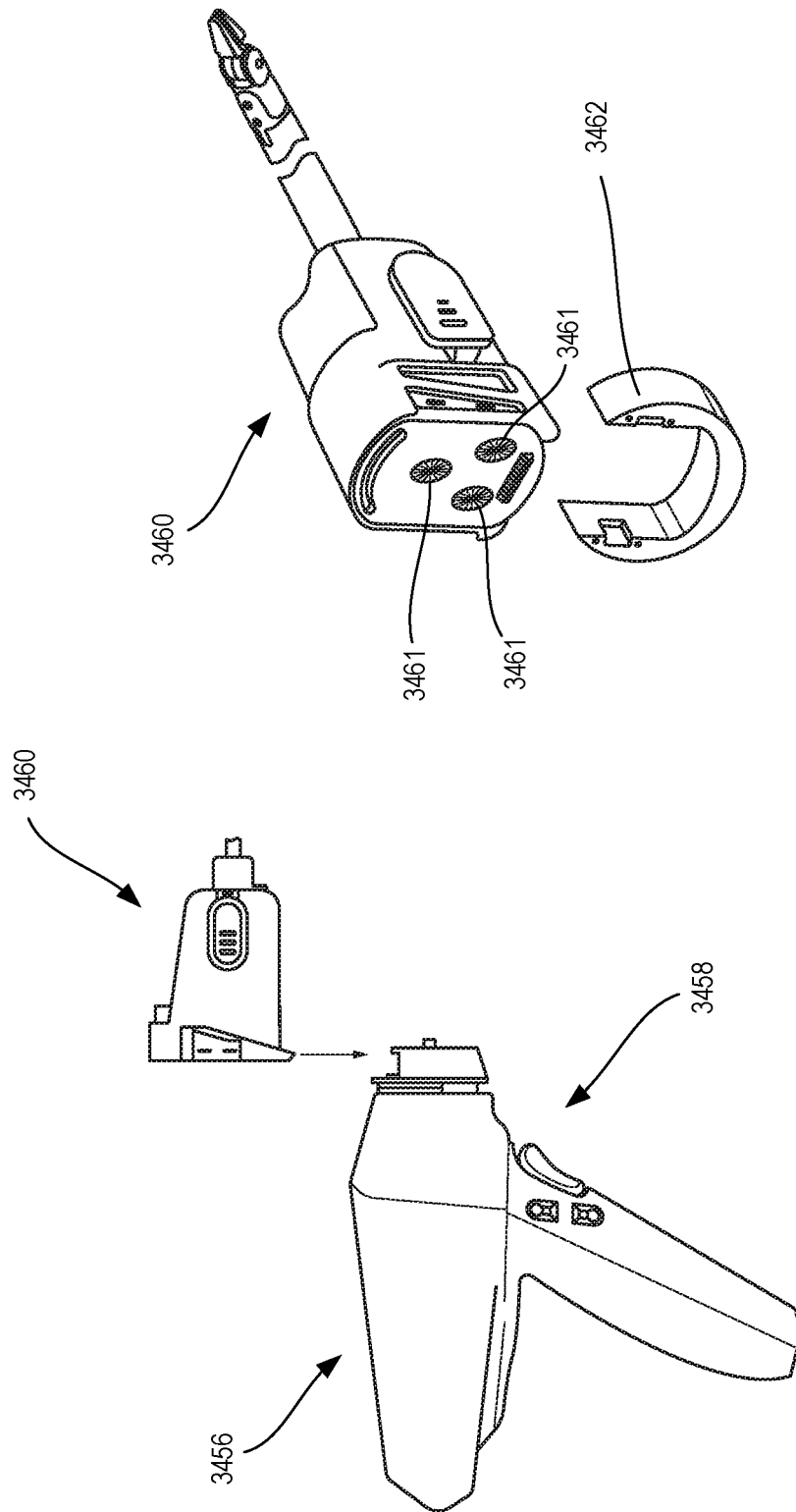
FIG. 79 is an exploded view of the surgical instrument handle of FIG. 78 being coupled to an end effector assembly of FIG. 80, in accordance with at least one aspect of the present disclosure.
FIG. 80 is a perspective view of an end effector assembly drivable via a three motor system, in accordance with at least one aspect of the present disclosure.

Generally speaking, the motor pack 40500 for a robotic surgical system includes a four-motor configuration (see, e.g., FIG. 27), whereas a motor assembly for a handheld surgical instrument is driven by a three-motor configuration. Therefore, motor assemblies for robotic surgical systems and handheld surgical instruments can be incompatible with each other. However, in one aspect, the motor assembly 3430 can be reconfigurable for use in connection with a robotic surgical system 13000 or a handheld surgical instrument. For example, FIG. 77 illustrates a motor assembly 3430 supportable within a motor pack 40050, wherein the motor assembly 3430 includes a first modular motor unit 3456 including a single motor and a second modular motor unit 3454 including three motors 3453. In this example, the motor assembly 3430 can be provided in a first configuration where the first modular motor unit 3456 is utilized in conjunction with the second modular motor unit 3456 and a second configuration where the first modular motor unit 3456 is removed and the second modular motor unit 3454 is utilized alone. When in the first configuration, the motor assembly 3430 can be utilized to drive a robotic surgical system, for example. When in the second configuration, the motor assembly 3430 can be utilized to drive a handheld surgical instrument 3458, as illustrated in FIG. 79, for example. In particular, the second modular unit 3454 can be arranged such that its motors 3453 are aligned with corresponding connectors 3455 or drive shafts of a handpiece 3457 for receiving and/or coupling the handpiece 3457 to the motors 3453. Correspondingly, the motors 3453 of the second modular unit 3454 can be configured to engage and drive the proximal couplers 3461 of the drive assemblies of an electromechanical surgical instrument 3460, as illustrated in FIG. 80, when the electromechanical surgical instrument 3460 is coupled to the handpiece 3457 (e.g., via a coupling collar 3462). Accordingly, depending upon which configuration the motor assembly 3430 is in (i.e., whether the first modular motor unit 3456 is present or remove), the motor assembly 3430 can interchangeably drive either a robotic surgical system or a handheld surgical instrument 3458.

In another aspect, a handheld surgical instrument 3458 could be configured to have a single a non-replaceable, permanent, or integral motor and be configured to receive a modular motor unit containing two motors, such as the modular motor unit 3432 illustrated in FIG. 75. Accordingly, a modular motor units 3432 could interchangeably drive a handheld surgical instrument 3458 in combination with its integral motor or drive a robotic surgical system in combination with a second modular motor unit 3432. The non-replaceable motor for the handheld surgical instrument 3458 could be utilized to drive a particular selected function for the handheld surgical instrument 3458, such as rotation of the instrument's shaft. Further, the motors 3434a, 3434b of the modular motor unit 3432 could be higher capacity (i.e., capable of producing higher output powers or torques) and could therefore be utilized to drive the surgical functions of the handheld surgical instrument 3458. In yet another aspect, a handheld surgical instrument 3458 could be configured to receive a motor pack 40050 comprising four motors, but lock out or not engage one of the motors that is unneeded. Alternatively, a handheld surgical instrument 3458 that is normally driven by three motors, but includes some manual function (e.g., manual rotation of the instrument's shaft), could engage all four motors of the motor pack 40050 and then convert the manual operation to a motor-driven operation. This aspect could include various adapters and/or additional controls for controlling the motor-driven operation.

Referring now to FIGS. 81A and 81B, the robotic surgical assembly 44100 includes a sterile barrier housing 40130 configured to mate with or otherwise connect to the shell 44060. The sterile barrier housing 40130 includes a hollow shell or body 44132 defining a cavity 44132a therein. The sterile barrier housing 40130 pivotally or hingedly supports a proximal cap or cover 40134 configured and adapted to selectively close a proximal end of the body 44132. The sterile barrier housing 40130 further includes a drive transfer assembly 44140 supported on, or connected to, a distal end of the body 44132. The cavity of the body 44132 of the sterile barrier housing 40130 is configured to slidably receive a motor pack 40050 (FIG. 23) or the like therein.

The drive transfer assembly 44140 of the sterile barrier housing 40130 includes a body portion 44142 extending from the distal end of the body 44132. The body portion 44142 of the drive transfer assembly 44140 has a non-circular form (e.g., substantially D-shaped, as illustrated) outer profile for keyed receipt within a complementary non-circular (e.g., D-shaped, as illustrated) passage or opening of the pulley 40048 (FIG. 23) of the carriage 40042 (FIG. 23). While a D-shaped, transverse cross-sectional profile is shown and described, any non-circular, transverse cross-sectional profile may be used to provide a keyed connection, including and not limited to hex, Allen, star, cross, double "D", "T", torx, val, phillips, helix profiles.

The drive transfer assembly 44140 rotatably supports at least one, and as shown in FIGS. 81A and 81B, four drive transfer shafts 44144, 44146, 44148, 44150. As illustrated, a proximal end of each drive transfer shaft 44144, 44146, 44148, 44150 non-rotatably supports a respective drive coupler (of which only driver coupler 44144*a* is shown in FIG. 81B) that, via the motor couplers 41052*b*, 41054*b*, etc. (FIG. 27), are configured and adapted for non-rotatable connection to a drive shaft 41052*a*, 41054*a*, 41056*a*, 41058*a* (FIG. 27) of a respective motor 41052, 41054, 41056, 41058 (FIG. 27) of motor pack 40050. In particular, each drive coupler is translatably supported on respective drive transfer shaft 44144, 44146, 44148, 44150 via a pin-slot arrangement such that the couplers may float on respective drive transfer shaft 44144, 44146, 44148, 44150. Each drive coupler defines a respective mating feature configured to receive and transmit rotational forces from respective drive shafts 41052*a*, 41054*a*, 41056*a*, 41058*a* of the motors 41052, 41054, 41056, 41058 of the motor pack 40050. A distal end of each drive transfer shaft 44144, 44146, 44148, 44150 supports a respective drive coupler 44144*b*, 44146*b*, 44148*b*, 44150*b*, which are configured and adapted for non-rotatable connection to proximal couplers 3461 (FIG. 80) of the drive assemblies of the electromechanical surgical instrument (e.g., the surgical instrument 40200 illustrated in FIG. 23, the surgical instrument 43250 illustrated in FIG. 57A, or the surgical instrument 3460 illustrated in FIG. 80). It is contemplated that each drive coupler 44144*b*, 44146*b*, 44148*b*, 44150*b* may resemble a crown gear or the like.

The motor pack 40050 and the sterile barrier housing 40130 can have different shapes and configurations than those illustrated in FIGS. 81A and 81B, however. In one aspect, the motor pack 40050 and/or sterile barrier housing 40130 can be dimensioned or include alignment features configured to urge the motor pack 40050 into proper alignment with the sterile barrier housing 40130 when the motor pack 40050 is being inserted into the sterile barrier housing 40130 and/or when the sterile barrier housing 40130 is being closed, as opposed to the cavity 132*a* of the sterile barrier housing 40130 having a cylindrical profile as illustrated in FIGS. 81A and 81B. For example, FIGS. 82A-82C illustrate a motor pack 40050 and a corresponding sterile barrier housing 40130 including a variety of characteristics to promote the alignment of the motor pack 40050 within the sterile barrier housing 40130.

In one aspect, the body 3471 of the motor pack 40050 and the cavity 44132*a* of the sterile barrier housing 40130 can have a complementary non-radially symmetric shape, such as an oval. The protrusion body 3471 and/or cavity 44132*a* can have a symmetric profile or may be tapered, for example, to improve ease of use by allowing for the keyed interaction between the protrusion body 3471 and the cavity 44132*a* to get tighter the farther the motor pack 40050 is inserted into the sterile barrier housing 40130.

In another aspect, the motor pack 40050 can include a protrusion 3470 or alignment feature extending from its body 3471 and the sterile barrier housing 40130 can include a corresponding recess 3472 that is configured or keyed to receive the protrusion 3470. The protrusion 3470 can be dimensioned to physically prevent the motor pack 40050 from being inserted into the sterile barrier housing 40130 in any orientation except where the protrusion 3470 is aligned with the keyed recess 3472. The protrusion 3470 and/or recess 3472 can have a symmetric profile or may be tapered, for example, to improve ease of use by allow for the keyed interaction between the protrusion 3470 and the recess 3472 to get tighter the farther the motor pack 40050 is inserted into the sterile barrier housing 40130.

In another aspect, the motor pack 40050 can include a protrusion 3473 or alignment feature extending from its body 3471 and the cap 40134 of the sterile barrier housing 40130 can include a corresponding recess 3475 configured or keyed to receive the protrusion 3473 when the motor pack 40050 is positioned within the sterile barrier housing 40130 and the cap 40134 is being closed. The recess 3475 could thus be configured to physically interact with the protrusion 3473 of the motor pack 40050 as the cap 40134 is closed, aligning or seating the motor pack 40050 within the sterile barrier housing 40130. In one further aspect, the protrusion 3473 can include an electrical connector and the recess 3475 can include a corresponding electrical connector configured to electrically and communicably couple the motor pack 40050 to the sterile barrier housing 40130 when the cap 40134 is closed, thereby allowing electrical signals and other controls signals to be transmitted to the motor pack 40050 through the corresponding electrical connectors.

Although the particular example illustrated in FIGS. 82A-82C includes all three of the aforementioned aspects, this example is merely for illustrative purposes and the motor pack 40050 and/or sterile barrier housing 40130 can include any combination of one or multiple of these aspects.

In various aspects, the motors of the various motor assemblies described herein can be inline or offline from the surgical tool, the IDU 40110, and/or any other component of the robotic surgical system. In one aspect, if a particular type of motor pack 40500 is incapable of driving a desired function of a robotic surgical system and/or a handheld surgical instrument, then the motor pack 40500 could be supplemented with more than one motor operating in parallel to one another to increase the capabilities of the motor pack 40500. Accordingly, a motor and/or motor pack 40500 could be configured to piggyback another primary motor pack 40500 being utilized to drive a robotic surgical system, allowing the robotic surgical system 40100 to operate inline from the macro perspective of the overall system and the motor pack 40500 relative to the surgical tool, but allow the offset motor and/or motor pack 40500 to boost the primary drive motor pack 40500 to which it is coupled and thereby preform at a level beyond the standard output configuration of that size and type of motor pack 40500. Various inline motor assembly configurations are described in connection with PCT Application Publication No. WO2017/210516, titled ROBOTIC SURGICAL ASSEMBLIES AND INSTRUMENT DRIVE UNITS THEREOF; PCT Application Publication No. WO2017/205308, titled ROBOTIC SURGICAL ASSEMBLIES; and U.S. Patent Application Publication No. US2018/0168748, titled ROBOTIC SURGICAL ASSEMBLIES, each of which is hereby incorporated by reference herein in its entirety. Various offline motor assembly configurations are described in connection with PCT Application Publication No. WO2016/183054, titled COUPLING INSTRUMENT DRIVE UNIT AND ROBOTIC SURGICAL INSTRUMENT; U.S. Patent Application Publication No. US2018/0153628, titled OFFSET INSTRUMENT DRIVE UNIT; and PCT Patent Application Publication No. WO2016/043845, titled ROBOTICALLY CONTROLLING SURGICAL ASSEMBLIES, each of which is hereby incorporated by reference herein in its entirety.

Robotic Surgical Assembly Adapter and Bailout Assemblies

Referring back to FIGS. 23-27, the robotic surgical assembly 40100 can include an IDU 40110 that is drivingly couplable to a sterile barrier collar assembly 40170 (or the sterile barrier collar assembly 43630 described in connection with FIGS. 51-53), a carriage 40042 (or a sterile shell 40060 situated thereover), and an electromechanical surgical instrument 40200 for driving the various functions of the surgical instrument 40200 via a motor assembly supported within the IDU 40110. The robotic surgical assembly 40100 described above can additionally include various integrated adapters, bailouts, or other mechanisms for limiting damage to the robotic surgical assembly 40100 and/or robotic surgical system 15000 (FIG. 22), returning a damaged surgical instrument 40200 to a removal state, and performing various other functions.

In one aspect, the robotic surgical assembly 40100 can include motor torque fuses that are configured to limit the maximum force exertable from the motor pack 40050 on the surgical instrument 40200. For example, the sterile barrier collar assembly 43630 could be configured to function as both a coupling mechanism (e.g., between the IDU 40100 and the surgical instrument 40200) and a fuse to prevent over torqueing of an attached surgical instrument 40200. In particular, one or both of the drive transfer assemblies 43668, 43670 of the sterile interface module 43630 could have reduced cross-section along their length that would encourage the drive transfer assemblies 43668, 43670 to fusably fail before either the motor gear train of the motor pack 40050 or the drive train of the surgical instrument 40200 in the event that a high torque condition occurs. Accordingly, this would reduce the possibility of damage to the reusable components of the robotic surgical assembly 40100 and the surgical instrument 40200. Preventing damage to the surgical instrument 40200 in the event that a high torque condition occurs is especially desirable because if the drive train of the surgical instrument 40200 is damaged or jams during a surgical procedure, the surgical instrument 40200 could cause damage to any tissue grasped or being treated by the surgical instrument 40200. Therefore, having the sterile barrier collar assembly 43630 or a component thereof fail is a much more desirable alternative.

Figure 83B:
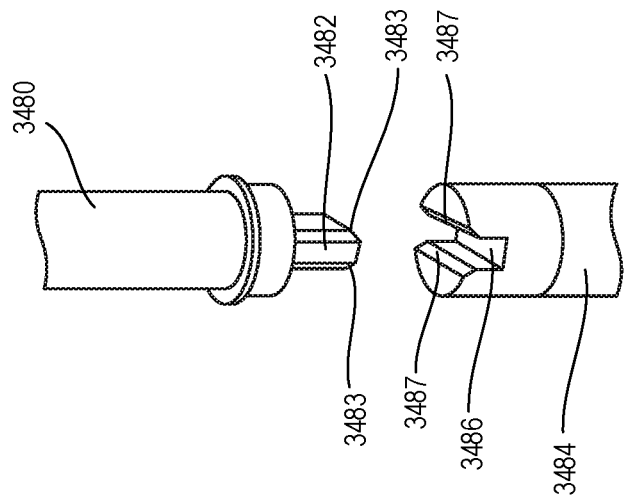
FIG. 83B is a detail view of portion C of FIG. 83A, in accordance with at least one aspect of the present disclosure.
Figure 83A:
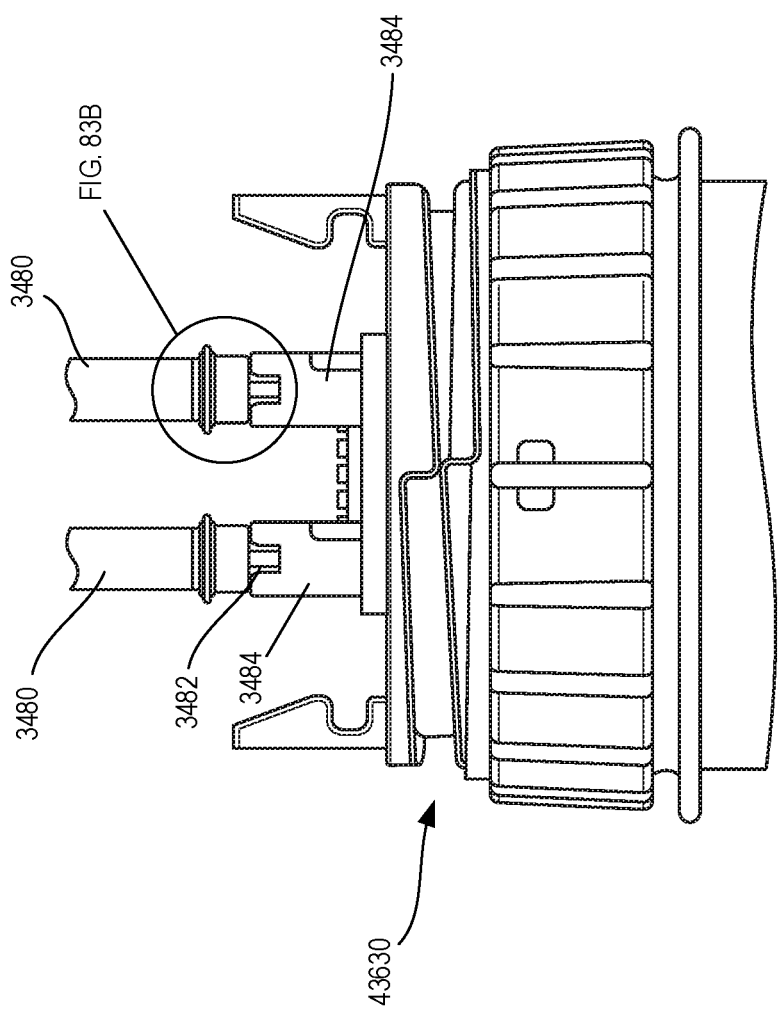
FIG. 83A is a side elevational view of a sterile interface module of a robotic surgical system, in accordance with at least one aspect of the present disclosure.

In one aspect, the drive transfer assemblies 43668, 43670 of the sterile barrier collar assembly 43630 could be configured to reduce or eliminate built-up torque in the rotary driver due to the motor pack 40050. For example, FIGS. 83A and 83B illustrate a sterile barrier collar assembly 43630 engaged with the rotary drivers 3480 from the motor pack 40050 (e.g., drive shafts 41052a, 41054a, 41056a, 41058a illustrated in FIG. 27) or sterile barrier housing 40130 (e.g., the drive transfer shafts 44144, 44146, 44148, 44150 of the drive transfer assembly 44140 illustrated in FIG. 81A). In this aspect, the rotary drivers 3480 each include a tab 3482 having a tapered profile with beveled edges 3483. Further, the drive couplers 3484 each include a recess 3486 and that is configured or keyed to receive the tab 3482 from a corresponding rotary driver 3480 and likewise includes beveled edges 3487. This profile of the tabs 3482 of the rotary drivers 3480 and the corresponding recesses 3486 of the drive couplers 3484 allows for the reduction of built-up pressure in the robotic surgical assembly 40100 if the motor pack 40500 were to fail when the sterile barrier collar assembly 43630 is released from the driver carriage of the surgical instrument 40200. In particular, the illustrated profile allows for complete engagement between the rotary drivers 3480 and the drive couplers 3484 when there is no force driving them apart, thereby allowing the rotary drivers 3480 and the drive couplers 3484 to function as normal. However, when the sterile barrier collar assembly 43630 is released from the surgical instrument 40200, the distally slidable motion allows built up torque to be released from the coupling between the rotary drivers 3480 and the drive couplers 3484 because the tabs 3482 partially disengage from the corresponding recesses 3486 and the beveled edges 3483, 3487 allow for the rotary drivers 3480 and/or drive couplers 3484 to slip or move with respect to each other. The slippage thereby allows for the release of any built-up torque, which in turn allows for easy removal of the components of the robotic surgical assembly 40100.

In one aspect, the robotic surgical assembly 40100 can include a mechanism for physically actuating or manipulating a surgical instrument 40100 coupled to the robotic surgical assembly 40100 (or a portion thereof) during the operation thereof. In some situations, the motor pack 40050 can become jammed or suffer an electrical or mechanical failure that results in the surgical instrument 40200 not responding to the surgeon's controls, which can be especially problematic when the surgical instrument 40200 is inserted within a patient during a surgical procedure. In one aspect, the motor pack 40050 can be disengaged from the sterile interface module 43630, leaving the sterile interface module 43630 connected to the surgical instrument 40200 such that the drive couplers 3484 (which are normally driven by the motor pack 40500) are visible and able to be accessed. When exposed, the drive couplers 3484 could be manually drivable to actuate the surgical instrument 40200 connected thereto. For example, in FIGS. 84A-84C the robotic surgical assembly 40100 can further include an interface module 3492 that is configured to engage with the drive couplers 3484 of the sterile interface module 43630 and allow the drive couplers 3484 to be manually driven by standard sterile OR tools (e.g., hemostats 3498) to manually actuate various functions of the surgical instrument 40200, including allowing the surgical instrument 40200 to be manipulated such that it can be extracted from the patient. In one aspect, the interface module 3492 includes a driver 3490 that is configured to be manually actuatable drive a drive coupler 3484 that is coupled to the interface module 3492. In the illustrated example, the driver 3490 includes a first end 3494 that is configured to engage with a corresponding mating portion of a driver coupler 3484 (e.g., the recess 3486 of the drive coupler 3484 as illustrated in FIGS. 83A and 83B) and a second end 3496 that is configured to extend to be manually grippable to actuatable by tools. The second end 3496 can include a tab or projection. In one aspect, the driver 3490 is positioned on the interface module 3492 to engage with a particular driver coupler 3484 of the sterile interface module 43630. For example, the driver 3490 can be positioned in the interface module 3492 to engage with the drive coupler 3484 that is configured to control a critical function of the surgical instrument 43250, such as the driver coupler 3484 that controls the I-beam shaft for a surgical stapling and cutting instrument. Although illustrated as including a single driver 3490, in other aspects the sterile interface module 3492 can include multiple drivers 3490.

In one aspect, the robotic surgical assembly 40100 can include a mechanism for manually bailing out the robotic surgical assembly 40100 during operation. For example, the robotic surgical assembly 40100 could include a bailout lever that, when actuated, either interrupts the drive train between the motor pack 40500 and the sterile collar assembly 43630 or causes the motor pack 40500 and the sterile collar assembly 43630 to counter-rotate. On such example is illustrated in FIGS. 85A and 85B, which shows a sterile barrier housing 40130 including a bailout lever 3500 that is actuatable between a first position that permits normal operation of the robotic surgical assembly 40100 and a second position that interrupts the operation of the robotic surgical assembly 40100. In particular, the bailout lever 3500 is coupled to a first or bailout gear 3502 that is transitioned from a first position that is disengaged from the drive train 3508 between the motor pack 40500 and the sterile collar assembly 43630 and a second position that is engaged with the drive train 3508 such that the operation of the drive train 3508 is interrupted as the bailout lever 3500 is actuated from its first position to its second position. As the bailout gear 3502 is transitioned to the second position, the bailout gear 3502 engages with a corresponding second or motor gear 3504, as shown in FIG. 85B. The engagement between the bailout gear 3502 and the motor gear 3504 locks the motor gear 3504, which in turn prevents actuation or operation of the motor 3506 to which the motor gear 3504 is coupled and/or the motor assembly 41114 (FIG. 26) as a whole.

In one aspect, the bailout lever 3500 could be configured such that actuating the bailout lever 3500 (i.e., transitioning the bailout lever 3500 to the second position) could permanently deform or otherwise render the sterile barrier housing 40130 no longer usable. In another aspect, the bailout lever 3500 could include a resetable feature that allows the bailout lever 3500 to be reset (and the sterile barrier housing 40130 utilized again) after it has been actuated, unless an excessive load was imparted upon the bailout gear 3502 when engaged with the motor gear 3504 and/or drive train 3508. In one aspect, the bailout lever 3500 could have ergonomic features that are easily gripped. In another aspect, the bailout lever 3500 could include a connector that is configured to engage with a second lever member that allows the second lever member to be attached to the bailout lever 3500 to extend the length of the bailout lever 3500 and thereby provide an improved mechanical advantage. In one aspect, the bailout lever 3500 could include a unidirectional mechanism (e.g., a ratchet mechanism) that is configured to prevent the bailout lever 3500 from being actuated in the incorrect direction. The unidirectional mechanism could be engaged or disengaged according to the type of drive train 3508 to which the bailout lever 3500 is coupled (e.g., a drive train for articulating a surgical instrument 40200 or a drive train for actuating the jaw(s) of a surgical instrument). Further, the unidirectional mechanism could be configured selectably constrain counter-rotating movement of the drive train 3508 (or a component thereof). For example, in robotic surgical assemblies 40100 that permit manual actuation (e.g., for resetting the robotic surgical assembly 40100, as illustrated in FIGS. 84A-84C), the unidirectional mechanism could be configured to constrain counter-rotating movement in the direction in which the robotic surgical assembly 40100 is manually actuatable.

In one aspect, the robotic surgical assembly 40100 can include interchangeable or replaceable bailout systems to allow for jammed or broken components of the robotic surgical assembly 40100 to be reset. The interchangeable bailout assemblies could be couplable to the sterile collar assembly 43630, for example. In use, users could disconnect the sterile collar assembly 43630 from the IDU 41110, couple an interchangeably bailout assembly to the sterile collar assembly 43630, and then manually actuate the bailout assembly to reset the sterile collar assembly 43630 and/or a surgical instrument 40200 coupled thereto to a particular position (e.g., full retraction or centering of the drive assembly of the sterile collar assembly 43630). In one aspect, the bailout assembly could be configured to actuate all of the drive assembly members to their home positions simultaneously. In one aspect, the bailout assembly could include a return or resetting lever that is selectively couplable to a specific drive member, thereby allowing the user to individually actuate or retract each drive member to its home state. In one aspect, the bailout assembly could include a sensor configured to sense a parameter of the bailout assembly to know where the home position is of the drive assemblies are and controllably retract to the drive assemblies to their home positions, preventing and over-retraction or centering of the drive assemblies. In one aspect, the bailout assembly could include a control circuit configured to communicably connect to the surgical instrument 40200 when coupled to the robotic surgical assembly 40100 (e.g., through electrical contacts disposed on surgical instrument 40200 and the components of the robotic surgical assembly 40100). The control circuit could be configured to identify the surgical instrument 40200 and then control the bailout assembly according to the surgical instrument type (i.e., configure its parameters to return the drive assemblies to the home positions particular for that surgical instrument type). The control circuit could also be configured to mark the surgical instrument 40200 as damaged to prevent reuse of the surgical instrument 40200. For example, the control circuit could write to a value to an EEPROM within the surgical instrument 40200 that marks the surgical instrument 40200 as damaged and thereby prevents the surgical instrument 40200 from operating thereafter. In one aspect, the bailout assembly could include a motor or other powered system for automatically actuating the drive assembly to which it is connected to its home position, rather than requiring that users manually actuate the bailout assembly to reset the robotic surgical assembly 40100. Further, the bailout assembly could include controls or be communicably coupled to controls, such that users can cause the bailout assembly to reset the robotic surgical assembly 40100 to the desired position via actuation of the controls.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A carriage assembly configured to be coupled to a robotic arm of a robotic surgical system and a surgical instrument, the carriage assembly comprising:
    a carriage comprising a first interface;
    a housing configured to receive a motor pack for driving the surgical instrument, the housing comprising:
        a second interface configured to engage the first interface to removably secure the housing to the carriage; and
        a third interface configured to engage a fourth interface of the surgical instrument to removably secure the surgical instrument to the carriage assembly; and
    a control circuit configured to:
        receive a first input indicative of a first full engagement status of the first interface with the second interface; and
        receive a second input indicative of a second full engagement status of the third interface with the fourth interface, wherein the second input is different than the first input; and wherein:
    the first interface comprises a first electrical contact;
    the second interface comprises a second electrical contact configured to contact the first electrical contact in the first full engagement status;
    the third interface comprises a third electrical contact; and
    the fourth interface comprises a fourth electrical contact configured to contact the third electrical contact in the second full engagement status.

2. A robotic surgical assembly configured to be coupled to a robotic arm of a robotic surgical system and a surgical instrument, the robotic surgical assembly comprising:
    a carriage;
    a carriage housing releasably connectable to the carriage;
    a motor housing configured to house a motor pack for driving the surgical instrument, wherein the motor housing is releasable connectable to the carriage housing;
    an interface module configured to releasably secure the robotic surgical assembly to the surgical instrument;
    a series of interconnections defined by mating portions of the carriage, the carriage housing, the motor housing, and the interface module; and
    a control circuit configured to detect a fully engaged configuration of the mating portions based on the interconnections.

3. The surgical robotic assembly of claim 2, wherein the interconnections form a complete circuit in the fully engaged configuration.

4. The surgical robotic assembly of claim 3, wherein the control circuit is further configured to detect an operational parameter of the surgical instrument in the fully engaged configuration.

5. The surgical robotic assembly of claim 2, wherein the control circuit is further configured to cause an alert to be issued, wherein the alert is regarding an improperly assembled pair of the mating portions.

6. The robotic surgical assembly of claim 5, wherein the alert comprises an error message displayed on a surgeon's console of the robotic surgical system.

7. The robotic surgical assembly of claim 2, wherein the interconnections are defined by electrical contacts on the mating portions.

8. A surgical robot, comprising
    a robotic arm; and
    a carriage assembly configured to be coupled to the robotic arm and a surgical instrument, the carriage assembly comprising:
        a carriage comprising a first interface;
        a housing configured to receive a motor pack for driving the surgical instrument, the housing comprising:
            a second interface configured to engage the first interface to removably secure the housing to the carriage; and
            a third interface configured to engage a fourth interface of the surgical instrument to removably secure the surgical instrument to the carriage assembly; and
        a control circuit configured to:
            receive a first input indicative of a first full engagement status of the first interface with the second interface; and
            receive a second input indicative of a second full engagement status of the third interface with the fourth interface, wherein the second input is different than the first input; and wherein:
    the first interface comprises a first electrical contact;
    the second interface comprises a second electrical contact configured to contact the first electrical contact in the first full engagement status;
    the third interface comprises a third electrical contact; and
    the fourth interface comprises a fourth electrical contact configured to contact the third electrical contact in the second full engagement status.

9. A surgical robot, comprising
    a robotic arm; and
    a robotic surgical assembly configured to be coupled to the robotic arm and a surgical instrument, the robotic surgical assembly comprising:
        a carriage;
        a carriage housing releasably connectable to the carriage;
        a motor housing configured to house a motor pack for driving the surgical instrument, wherein the motor housing is releasable connectable to the carriage housing;
        an interface module configured to releasably secure the robotic surgical assembly to the surgical instrument;
        interconnections defined by interfacing portions of the carriage, the carriage housing, the motor housing, and the interface module; and
        a control circuit configured to detect a fully engaged configuration of the interfacing portions based on the interconnections.

* * * * *